US008436008B2

(12) United States Patent
Zhang et al.

(10) Patent No.: US 8,436,008 B2
(45) Date of Patent: May 7, 2013

(54) SUBSTITUTED HETEROCYCLIC COMPOUNDS

(75) Inventors: Colin Zhang, Ambler, PA (US);
Ding-quan Qian, Newark, DE (US);
Jincong Zhuo, Garnet Valley, PA (US);
Wenqing Yao, Kennett Square, PA (US)

(73) Assignee: Incyte Corporation, Wilmington, DE (US)

( * ) Notice: Subject to any disclaimer, the term of this patent is extended or adjusted under 35 U.S.C. 154(b) by 133 days.

(21) Appl. No.: 12/643,739

(22) Filed: Dec. 21, 2009

(65) Prior Publication Data
US 2010/0173901 A1 Jul. 8, 2010

Related U.S. Application Data

(60) Provisional application No. 61/139,896, filed on Dec. 22, 2008.

(51) Int. Cl.
*C07D 401/14* (2006.01)
*C07D 413/14* (2006.01)
*A61K 31/538* (2006.01)
*A61K 31/506* (2006.01)

(52) U.S. Cl.
USPC .......................................... 514/275; 544/297

(58) Field of Classification Search .................. 544/297; 514/275
See application file for complete search history.

(56) References Cited

U.S. PATENT DOCUMENTS

| 6,919,484 B2 | 7/2005 | Dolbier, Jr. et al. |
| 2007/0185075 A1 | 8/2007 | Bell et al. |

FOREIGN PATENT DOCUMENTS

| EP | 1505064 | 2/2005 |
| WO | 0200196 | 1/2002 |
| WO | 2005014579 | 2/2005 |
| WO | 2005054239 | 6/2005 |
| WO | 2007072163 | 6/2007 |
| WO | 2007117401 | 10/2007 |
| WO | 2008008359 | 1/2008 |
| WO | 2008031556 | 3/2008 |
| WO | WO 2008031556 A2 * | 3/2008 |
| WO | 2008060766 | 5/2008 |
| WO | 2008100565 | 8/2008 |
| WO | 2009038673 | 3/2009 |

OTHER PUBLICATIONS

Ash et al., "Receptors mediating some actions of histamine," Pharmac. Chemother (1966) 27(2):427-439.
Bell et al., "Involvement of histamine H4 and H1 receptors in scratching induced by histamine receptor agonists in Balb C mice.," Br. J. Pharmcol. (2004) 142(2):374-380.
Blom et al., "Preparative LC-MS purification: improved compound-specific method optimization," J. Combi Chem., (2004) 6(6):874-83.
Blom, "Two-pump at-column-dilution configuration for preparative liquid chromatography-mass spectrometry," J. Combi. Chem. (2002) 4(4):295-301.
Blom et al., "Optimizing Preparative LC/MS Configurations and Methods for Parallel Synthesis Purification,"J. Combi. Chem. (2003) 5(5):670-683.
Breunig et al., "Histamine excites neurones in the human submucous plexus through activation of H1, H2, H3 and H4 receptors," J. Physiol., (2007) 583(Pt.2):731-742.
Buckland et al., "Histamine induces cytoskeletal changes in human eosinophils via the H(4) receptor," Br. J. Pharmacol. (2003) 140(6):1117-1127.
Coruzzi et al., "Antiinflammatory and antinociceptive effects of the selective histamine H4-receptor antagonists JNJ7777120 and VUF6002 in a rat model of carrageenan-induced acute inflammation," Eur. J. Pharmacol. (2007) 563 (-13):240-244.
Dunford et al., "Histamine H4 receptor antagonists are superior to traditional antihistamines in the attenuation of experimental pruritus," J. Allergy Clin. Immunol. (2007) 119(1):176-183.
Dunford et al., "The histamine H4 receptor mediates allergic airway inflammation by regulating the activation of CD4+ T cells" J. Immunol., (2006) 176(11):7062-7070.
Gutzmer et al., "Histamine H4 receptor stimulation suppresses IL-12p70 production and mediates chemotaxis in human monocyte-derived dendritic cells," J. Immunol., (2005 )174(9):5224-5232.
Hofstra et al., "Histamine H4 receptor mediates chemotaxis and calcium mobilization of mast cells," J. Pharmacol. Exp. Ther.(2003) 305(3):1212-1221.
Black et al., "Definition and antagonism of histamine H 2 -receptors," Nature, (1972) 236(5347):385-390.
Arrang et al., "Auto-inhibition of brain histamine release mediated by a novel class (H3) of histamine receptor," Nature (1983) 302(5911):832-837.
Chazot, Eur. Histamine Res. Soc.-37th Ann. Meeting (2008).

(Continued)

*Primary Examiner* — Kahsay T Habte
(74) *Attorney, Agent, or Firm* — Pepper Hamilton LLP

(57) ABSTRACT

The present invention relates to substituted heterocyclic compounds of Formula I:

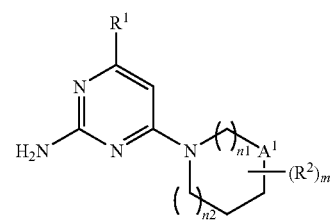

or pharmaceutically acceptable salts or N-oxides or quaternary ammonium salts thereof wherein constituent members are provided herewith, as well as their compositions and methods of use, which are histamine H4 receptor inhibitors/antagonists useful in the treatment of histamine H4 receptor-associated conditions or diseases or disorders including, for example, inflammatory diseases or disorders, pruritus, and pain.

5 Claims, No Drawings

OTHER PUBLICATIONS

Cogé et al., "Structure and expression of the human histamine H4-receptor gene," Biochem. Biophy. Res. Commun. (2001) 284(2):301-309.

Hirasawa et al., "Modification of the picryl chloride-induced allergic dermatitis model in mouse ear lobes by 12-O-tetradecanoylphorbol 13-acetate, and analysis of the role of histamine in the modified model," Int. Arch. Allergy Immunol. (2009) 148(4):279-288.

Ling et al., "Histamine H4 receptor mediates eosinophil chemotaxis with cell shape change and adhesion molecule upregulation," Br. J. Pharmcol. (2004) 142(1):161-171.

Liu et al., "Cloning and pharmacological characterization of a fourth histamine receptor (H(4)) expressed in bone marrow," Mol. Pharmacol (2001) 59(3):420-426, 2001.

Oda et al., "Molecular cloning and characterization of a novel type of histamine receptor preferentially expressed in leukocytes," J. Biol. Chem. (2001) 275(47):36781-36786.

O'Reilly et al., "Identification of a histamine H4 receptor on human eosinophils—role in eosinophil chemotaxis," J. Recept. Signal Transduct. (2002)22(1-4):431-448.

Morse et al., "Cloning and characterization of a novel human histamine receptor," Pharmacol. Exp. Ther. (2001) 296 (3):1058-1066, 2001.

Nguyen et al., "Discovery of a novel member of the histamine receptor family," Mol. Pharmacol. (2001) 59(3):427-433.

Parsons et al., "Histamine and its receptors," Br. J. Pharm. (2006) 147(Suppl 1):S127-S135.

Takeshita et al., "Critical role of histamine H4 receptor in leukotriene B4 production and mast cell-dependent neutrophil recruitment induced by zymosan in vivo," J. Pharmacol. Exp.Ther. (2003) 307(3):1072-1078.

Thurmond et al., "The role of histamine H1 and H4 receptors in allergic inflammation: the search for new antihistamines," Nature Review Drug Discovery (2008) 7(1):41-53.

Thurmond et al., "A potent and selective histamine H4 receptor antagonist with anti-inflammatory properties," J. Pharmacol. Exp. Ther. (2004) 309(1):404-413.

Varga et al., "Inhibitory effects of histamine H4 receptor antagonists on experimental colitis in the rat," Eur. J. Pharmacol. (2005) 522(1-3):130-138.

Zhu et al., "Cloning, expression, and pharmacological characterization of a novel human histamine receptor," Mol. Pharmcol. (2001) 59(3):434-441, 2001.

Altenbach et al., "Structure-activity studies on a series of a 2-aminopyrimidine-containing histamine H4 receptor ligands," Journal of Medicinal Chemistry (2008) 51(20):6571-6580.

Hawthorne et al., "Amine Reactivity Changes in Imide Formation from Heterocyclic Bases," High Performance Polymers (1999) 11(3):315-329.

International Search Report dated Apr. 6, 2010 cited in International Application No. PCT/US2009/068969.

Office Action dated Jul. 30, 2012 received in copending U.S. Appl. No. 12/727,490.

Bissyris et al., "2-amino-4-pyrrolidinothieno[2,3-d]pyrimidine-6-carboxylic acid as an N-terminal surrogate in amino acid and peptide analogues," Synthesis (2005) 18:3159-3166.

Berge et al., "Pharmaceutical Salts," (1977) Journal of Pharmaceutical Science 66:1-19.

T.W. Greene and P.G.M. Wuts, Protective Groups in Organic Synthesis, 3rd Ed., Wiley & Sons, Inc., New York (1999).

Remington's Pharmaceutical Sciences, 17th Ed,, Mack Publishing Company, Easton, PA 1985, p. 1418.

Wolfe et al., "Simple, efficient catalyst system for the palladium-catalyzed amination of aryl chlorides, bromides, and inflates," J Org Chem (2000) 65(4):1158-1174.

* cited by examiner

SUBSTITUTED HETEROCYCLIC COMPOUNDS

This application claims benefit of priority to U.S. provisional patent application Ser. No. 61/139,896 filed on Dec. 22, 2008, which is hereby incorporated by reference in its entirety.

FIELD OF THE INVENTION

The present invention relates to substituted heterocyclic compounds, and compositions thereof as well as methods of use the same for treatment of histamine H4 receptor associated conditions or diseases or disorders such as inflammatory disorders, pruritus, and pain.

BACKGROUND OF THE INVENTION

Histamine is a biogenic amine that exerts its physiological and pathological functions through four G-protein coupled receptors, histamine receptors H1, H2, H3, and H4 (Parsons and Ganellin, Br. J. Pharm., 147:S127-S135, 2006). The roles of the first three receptors in mediating histamine functions have been well characterized: histamine mediates acute allergic responses via histamine H1 receptor (A. S. F. Ash and H. O. Schild, Br. J. Pharmac. Chemother., 27:427-439, 1966), gastric acid secretion via histamine H2 receptors (J. W. Black et al., Nature, 236:385-390, 1972), and controls neurotransmitter release in the central nervous system via histamine H3 receptor (J. M. Arrang et al., Nature, 302:832-837, 1983). Drugs based on histamine H1 or H2 receptors have achieved "block-bluster" status on the market and several therapeutic indications based on histamine H3 receptor inhibition are in different stages of clinical development for various neural disorders. Importantly, histamine has many additional functions in humans that cannot be explained by signaling pathways involving only histamine H1, H2 and/or H3 receptors. For examples, histamine is known to be involved in asthma and in the pruritus associated with atopic dermatitis and chronic idiopathic urticaria, but current anti-H1 and anti-H2 compounds (antagonists of H1 and/or H2 receptor), which are not active against H4 receptor (Thurmond et al., Nature Review Drug Discovery, 7:41-53, 2008), are ineffective in treating these conditions. With the human genome having been almost completely explored, histamine H4 receptor is the last and most likely the only histamine receptor left to account for these remaining functions of histamine.

Histamine has a relatively high affinity for histamine H4 receptor (Kd=10 nM), which was cloned based on sequence homology to histamine H3 receptor (Oda et al., J. Biol. Chem., 275:36781-36786, 2001; Liu et al., Mol. Pharmacol., 59:420-426, 2001; Morse et al., J. Pharmacol. Exp. Ther., 296:1058-1066, 2001; Nguyen et al., Mol. Pharmacol., 59:427-433, 2001; Zhu et al., Mol. Pharmcol., 59:434-441, 2001; O'Reilly et al., J. Recept. Signal Transduct., 22:431-448, 2002). Histamine H4 receptors are predominantly expressed in the cells of hematopoietic origins (Parsons and Ganellin, Br. J. Pharm., 147:5127-5135, 2006). Possible expression of H4 receptors was also reported in selective tissues within both rodent and human central nerve systems (P. Chazot, Eur. Histamine Res. Soc.-37th Ann. Meeting, 2008; Coge et al., Biochem. Biophy. Res. Commun., 284:301-309, 2001) as well as submucous plexus (Breunig et al., J. Physiol., 583:731-742, 2007). In vitro studies indicated that histamine H4 receptor mediates histamine-induced migration of dendritic cells, mast cells and eosinophils (Hofstra et al., J. Pharmacol. Exp. Ther., 305:1212-1221, 2003; Buckland et al., Br. J. Pharmacol., 140:1117-1127, 2003; Ling et al., Br. J. Pharmcol., 142:161-171, 2004; Gutzmer et al., J. Immunol., 174:5224-5232, 2005). In addition, through histamine H4 receptor, histamine can synergize with other chemotactic agents to enhance migration of eosinophils (O'Reilly et al., supra; Buckland et al., supra; Ling et al., supra). These in vitro data clearly point to a role for histamine H4 receptor in inflammation, immune and possibly neurologic responses.

The predicted functions of histamine H4 receptor based on in vitro studies have been borne out in animal models. Using both H4 knockout animals as well as small molecule inhibitors (antagonists), histamine H4 receptor has been shown to mediate mast cell migration in the trachea of mice after histamine inhalation (Thurmond et al., J. Pharmacol. Exp. Ther., 309:404-413, 204). Histamine H4 receptor has also been shown to play a critical role in a number of different acute and chronic inflammation models, including carrageenan-induced edema (Coruzzi et al., Eur. J. Pharmacol., 563:240-244, 2007), zymosan-induced pleurisy and peritonitis (Thurmond et al., J. Pharmacol. Exp. Ther., 309:404-413, 2004; Takeshita et al., J. Pharmacol. Exp. Ther., 307:1072-1078, 2003), trinitriobenzene sulphonic acid-induced colitis (Varga et al., Eur. J. Pharmacol., 522:130-138, 2005), picryl chloride-induced and 12-o-tetradecannoylphorbol 13-acetate-modified atopic dermatitis (Hirasawa et al., Int. Arch. Allergy Immunol., 148:279-288, 2009), and allergic lung inflammation (Dunford et al., J. Immunol., 176:7062-7070, 2006). Consistent with its expression in the nervous system, histamine H4 receptor was demonstrated to mediate histamine or antigen-specific IgE-induced acute itch responses (Bell et al., Br. J. Pharmcol., 142:374-380; Dunford et al., J. Allergy Clin. Immunol., 119:176-183, 2007) and inhibition of histamine H4 receptor had antinociceptive effects in various pain models (Coruzzi et al., supra; Altenbach et al., WO2008/060766 A2).

Taken together, histamine appears to mediate many immune, inflammatory, and/or neurologic responses through histamine H4 receptor. Accordingly, histamine H4 receptor is an attractive therapeutic target for inflammatory disorders, pruritus, and pain, including allergic rhinitis, asthma, rheumatoid arthritis, atopic dermatitis, idiopathic chronic urticaria, inflammatory pain, neuropathic pain, and osteoarthritic pain Thus, new or improved agents that modulate (such as inhibiting/antagonizing) histamine H4 receptor are continually needed for developing new and more effective pharmaceuticals to treat histamine H4 receptor-associated conditions or diseases or disorders, such as inflammatory disorders, pruritus, and pain, including allergic rhinitis, asthma, rheumatoid arthritis, atopic dermatitis, idiopathic chronic urticaria, inflammatory pain, neuropathic pain, and osteoarthrtic pain, to name a few. The compounds, compositions and methods described herein are directed toward these needs and other ends.

SUMMARY OF THE INVENTION

The present invention provides, inter alia, compounds of Formula I, II, IIa, IIb, IIc, or III:

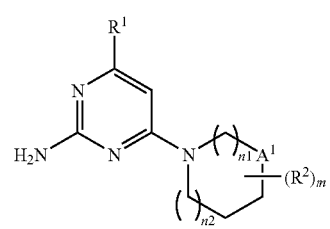

I

-continued

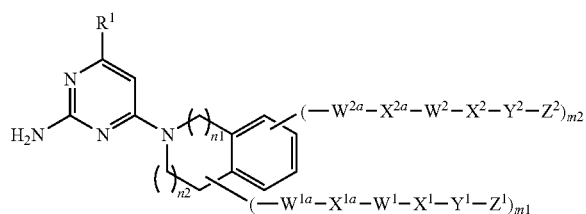

II

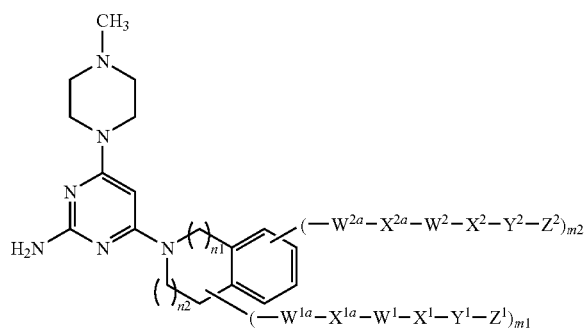

IIa

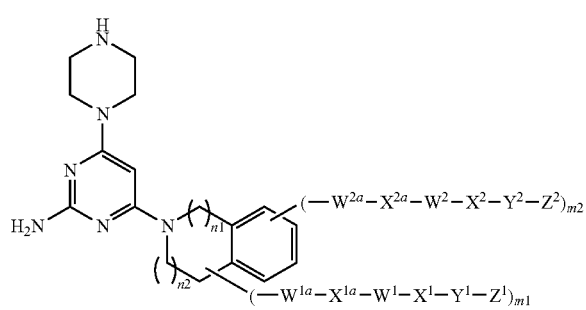

IIb

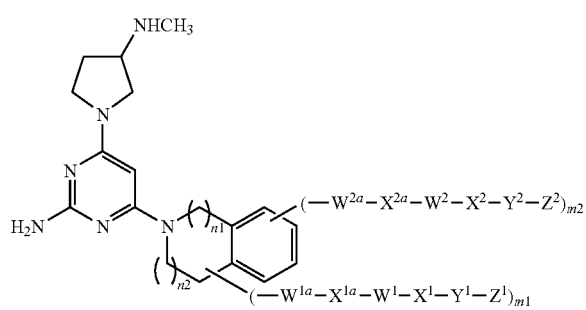

IIc

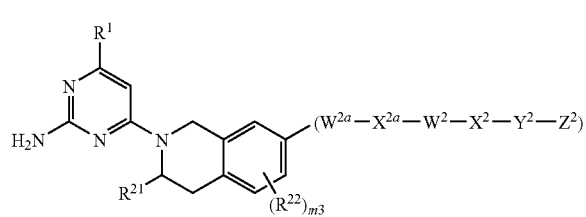

III

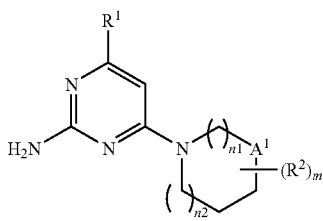

or pharmaceutically acceptable salts thereof or N-oxides thereof or quaternary ammonium salts thereof, wherein constituent members are provided below.

The present invention further provides pharmaceutical compositions comprising a compound of Formula I, II, IIa, IIb, IIc, or III, or pharmaceutically acceptable salt thereof, and at least one pharmaceutically acceptable carrier.

The present invention further provides methods of modulating an activity of histamine H4 receptor, comprising contacting the histamine H4 receptor with a compound of Formula I, II, IIa, IIb, IIc, or III, or pharmaceutically acceptable salt of the same.

The present invention further provides methods of inhibiting/antagonizing an activity of histamine H4 receptor with a compound of Formula I, II, IIa, IIb, IIc, or III, or pharmaceutically acceptable salt of the same.

The present invention further provides methods of treating one or more of the various histamine H4 receptor-associated conditions, diseases, and disorders named herein by administering to a patient a therapeutically effective amount of a compound of Formula I, II, IIa, IIb, IIc, or III, or pharmaceutically acceptable salt of the same.

The present invention further provides compounds of Formula I, II, IIa, IIb, IIc, or III, or pharmaceutically acceptable salts thereof, for use in therapy.

The present invention further provides use of the compounds of Formula I, II, IIa, IIb, IIc, or III, or pharmaceutically acceptable salts thereof, for the manufacture/preparation of a medicament for use in therapy.

DETAILED DESCRIPTION

The present invention provides, inter alia, compounds of Formula I:

I or pharmaceutically acceptable salts thereof or N-oxide thereofs or quaternary ammonium salts thereof, wherein:

$A^1$ is $CH_2$, $CHR^2$, $C(R^2)_2$, NH, $NR^2$, O, or S;

$R^1$ is $NR^3R^4$, wherein $R^3$ and $R^4$ together with the N atom to which they are attached form a 4-10 membered heterocycloalkyl group wherein each of the ring-forming atoms of the 4-10 membered heterocycloalkyl group is independently selected from C, N, O, and S, and wherein the 4-10 membered heterocycloalkyl group is substituted with 0, 1, 2, 3, 4, 5, 6, 7, or 8 $R^5$;

each $R^2$ is independently —$W^{1a}$—$X^{1a}$—$W^1$—$X^1$—$Y^1$—$Z^1$;

or any two adjacent $R^2$ together with the two atoms to which they are attached form a fused 3-14 membered cycloalkyl group, a fused 3-14 membered heterocycloalkyl group, a fused aryl group, or a fused heteroaryl group, each substituted with 0, 1, 2, 3, 4, or 5 —$W^{2a}$—$X^{2a}$—$W^2$—$X^2$—$Y^2$—$Z^2$ or any two $R^2$ together with the same carbon atom to which they are attached form a carbonyl group (i.e. C=O);

provided that two adjacent $R^2$ together with the two atoms to which they are attached form a fused 3-14 membered cycloalkyl group, a fused 3-14 membered heterocycloalkyl group, a fused aryl group, or a fused heteroaryl group, each substituted with 0, 1, 2, 3, 4, or 5 —$W^{2a}$—$X^{2a}$—$W^2$—$X^2$—$Y^2$—$Z^2$ wherein —$W^{1a}$—$X^{1a}$—$W^1$—$X^1$—$Y^1$—$Z^1$ is other than H;

wherein —$W^{2a}$—$X^{2a}$—$W^2$—$X^2$—$Y^2$—$Z^2$ is other than H;

each $R^5$ is independently selected from halo, CN, $C_{1-6}$ alkyl, $C_{1-6}$ haloalkyl, OH, $C_{1-6}$ alkoxy, $C_{1-6}$ haloalkoxy, $NH_2$, $NH(C_{1-4}$ alkyl), and $N(C_{1-4}$ alkyl$)_2$, wherein each of the $C_{1-6}$ alkyl and $C_{1-6}$ haloalkyl is substituted with 0, 1, 2, or 3 substituents each independently selected from OH, CN, $NH_2$, $NH(C_{1-4}$ alkyl), and $N(C_{1-4}$ alkyl$)_2$;

$W^{1a}$, $W^{2a}$, $W^1$, and $W^2$ are each, independently, selected from absent, $C_{1-6}$ alkylenyl, $C_{2-6}$ alkenylenyl, $C_{2-6}$ alkynylenyl, $(CR^{11a}R^{11b})_{p1}O(CR^{11a}R^{11b})_{p2}$, $(CR^{11a}R^{11b})_{p1}S(CR^{11a}R^{11b})_{p2}$, $(CR^{11a}R^{11b})_{p1}NR^e(CR^{11a}R^{11b})_{p2}$, $(CR^{11a}R^{11b})_{p1}C(O)(CR^{11a}R^{11b})_{p2}$, $(CR^{11a}R^{11b})_{p1}C(S)(CR^{11a}R^{11b})_{p2}$, $(CR^{11a}R^{11b})_{p1}C(O)O(CR^{11a}R^{11b})_{p2}$, $(CR^{11a}R^{11b})_{p1}C(O)NR^e(CR^{11a}R^{11b})_{p2}$, $(CR^{11a}R^{11b})_{p1}C(S)NR^e(CR^{11a}R^{11b})_{p2}$, $(CR^{11a}R^{11b})_{p1}S(O)(CR^{11a}R^{11b})_{p2}$, $(CR^{11a}R^{11b})_{p1}S(O)_2(CR^{11a}R^{11b})_{p2}$, $(CR^{11a}R^{11b})_{p1}S(O)NR^c(CR^{11a}R^{11b})_{p2}$, $(CR^{11a}R^{11b})_{p1}S(O)_2NR^c(CR^{11a}R^{11b})_{p2}$, $(CR^{11a}R^{11b})_{p1}NR^cC(O)NR^f(CR^{11a}R^{11b})_{p2}$, $(CR^{11a}R^{11b})_{p1}NR^cC(S)NR^f(CR^{11a}R^{11b})_{p2}$, $(CR^{11a}R^{11b})_{p1}NR^cS(O)_2NR^f(CR^{11a}R^{11b})_{p2}$, $(CR^{11a}R^{11b})_{p1}C(=NR^g)NR^c(CR^{11a}R^{11b})_{p2}$, $(CR^{11a}R^{11b})_{p1}NR^cC(=NR^g)NR^f(CR^{11a}R^{11b})_{p2}$, $O(CR^{11a}R^{11b})_{q1}C(O)$, $S(CR^{11a}R^{11b})_{q1}C(O)$, $NR^c(CR^{11a}R^{11b})_{q1}C(O)$, $C(O)(CR^{11a}R^{11b})_{q1}C(O)$, $NR^e(CR^{11a}R^{11b})_{q1}NR^f$, $O(CR^{11a}R^{11b})_{q1}NR^f$, and $O(CR^{11a}R^{11b})_{q1}O$, wherein each of the $C_{1-6}$alkylenyl, $C_{2-6}$ alkenylenyl and $C_{2-6}$ alkynylenyl is substituted with 0, 1, 2, 3, 4, 5, 6, 7, or 8 substituents each independently selected from halo, CN, $NO_2$, $OR^a$, $SR^a$, $C(O)R^b$, $C(O)NR^cR^d$, $C(O)OR^a$, $OC(O)R^b$, $OC(O)NR^cR^d$, $NR^cR^d$, $NR^cC(O)R^b$, $NR^c(O)NR^cR^d$, $NR^cC(O)OR^a$, $C(=NR^g)NR^cR^d$, $NR^cC(=NR^g)NR^cR^d$, $NR^cS(O)_2NR^cR^d$, $S(O)R^b$, $S(O)NR^cR^d$, $S(O)_2R^b$, $NR^cS(O)_2R^b$, $S(O)_2NR^cR^d$, $P(R^f)_2$, $P(OR^e)_2$, $P(O)R^eR^f$, and $P(O)OR^eOR^f$;

$X^{1a}$, $X^{2a}$, $X^1$, and $X^2$ are each, independently, selected from absent, $C_{1-6}$alkylenyl, $C_{2-6}$ alkenylenyl, $C_{2-6}$ alkynylenyl, aryl, cycloalkyl, heteroaryl, heterocycloalkyl, arylalkyl, heteroarylalkyl, cycloalkylalkyl, and heterocycloalkylalkyl, wherein each of said $C_{1-6}$alkylenyl, $C_{2-6}$ alkenylenyl, $C_{2-6}$ alkynylenyl, aryl, cycloalkyl, heteroaryl, heterocycloalkyl, arylalkyl, heteroarylalkyl, cycloalkylalkyl, and heterocycloalkylalkyl is substituted with 0, 1, 2, 3, 4, 5, 6, 7, or 8 substituents each independently selected from $R^{XX}$, halo, CN, $NO_2$, $OR^a$, $SR^a$, $SF_5$, $C(O)R^b$, $C(O)NR^cR^d$, $C(O)OR^a$, $OC(O)R^b$, $OC(O)NR^cR^d$, $NR^cR^d$, $NR^cC(O)R^b$, $NR^c(O)NR^cR^d$, $NR^cC(O)OR^a$, $C(=NR^g)NR^cR^d$, $NR^cC(=NR^g)NR^cR^d$, $NR^cS(O)_2NR^cR^d$, $S(O)R^b$, $S(O)NR^cR^d$, $S(O)_2R^b$, $NR^cS(O)_2R^b$, $S(O)_2NR^cR^d$, $P(R^f)_2$, $P(OR^e)_2$, $P(O)R^eR^f$, and $P(O)OR^eOR^f$;

$Y^1$ and $Y^2$ are each, independently, selected from absent, $C_{1-6}$alkylenyl, $C_{2-6}$ alkenylenyl, $C_{2-6}$ alkynylenyl, $(CR^{12a}R^{12b})_{p3}O(CR^{12a}R^{12b})_{p4}$, $(CR^{12a}R^{12b})_{p3}S(CR^{12a}R^{12b})_{p4}$, $(CR^{12a}R^{12b})_{p3}NR^e(CR^{12a}R^{12b})_{p4}$, $(CR^{12a}R^{12b})_{p3}C(O)(CR^{12a}R^{12b})_{p4}$, $(CR^{12a}R^{12b})_{p3}C(S)(CR^{12a}R^{12b})_{p4}$, $(CR^{12a}R^{12b})_{p3}C(O)O(CR^{12a}R^{12b})_{p4}$, $(CR^{12a}R^{12b})_{p3}C(O)NR^e(CR^{12a}R^{12b})_{p4}$, $(CR^{12a}R^{12b})_{p3}C(S)NR^e(CR^{12a}R^{12b})_{p4}$, $(CR^{12a}R^{12b})_{p3}S(O)(CR^{12a}R^{12b})_{p4}$, $(CR^{12a}R^{12b})_{p3}S(O)_2(CR^{12a}R^{12b})_{p4}$, $(CR^{12a}R^{12b})_{p3}S(O)NR^c(CR^{12a}R^{12b})_{p4}$, $(CR^{12a}R^{12b})_{p3}S(O)_2NR^c(CR^{12a}R^{12b})_{p4}$, $(CR^{12a}R^{12b})_{p3}NR^cC(S)NR^f(CR^{12a}R^{12b})_{p4}$, $(CR^{12a}R^{12b})_{p3}NR^cS(O)NR^f(CR^{12a}R^{12b})_{p4}$, $(CR^{12a}R^{12b})_{p3}C(=NR^g)NR^c(CR^{12a}R^{12b})_{p4}$, $(CR^{12a}R^{12b})_3NR^cC(=NR^gNR^f(CR^{12a}R^{12b})_{p4}$, $O(CR^{12a}R^{12b})_{q2}C(O)$, $S(CR^{12a}R^{12b})_{q2}C(O)$, $NR^e(CR^{12a}R^{12b})_{q2}C(O)$, $NR^e(CR^{12a}R^{12b})_{q2}NR^f$, $O(CR^{12a}R^{12b})_{q2}NR^f$, and $O(CR^{12a}R^{12b})_{q2}O$, wherein each of the $C_{1-6}$ alkylenyl, $C_{2-6}$ alkenylenyl, and $C_{2-6}$ alkynylenyl is substituted with 0, 1, 2, 3, 4, 5, 6, 7, or 8 substituents independently selected from $C_{1-6}$ alkyl, $C_{1-6}$ haloalkyl, $C_{2-6}$ alkenyl, $C_{2-6}$ alkynyl, halo, CN, $NO_2$, $OR^a$, $SR^a$, $SF_5$, $C(O)R^b$, $C(O)NR^cR^d$, $C(O)OR^a$, $OC(O)R^b$, $OC(O)NR^cR^d$, $NR^cR^d$, $NR^cC(O)R^b$, $NR^cC(O)NR^cR^d$, $NR^cC(O)OR^a$, $C(=NR^g)NR^cR^d$, $NR^cC(=NR^g)NR^cR^d$, $NR^cS(O)_2NR^cR^d$, $S(O)R^b$, $S(O)NR^cR^d$, $S(O)_2R^b$, $NR^cS(O)_2R^b$, $S(O)_2NR^cR^d$, $P(R^f)_2$, $P(OR^e)_2$, $P(O)R^eR^f$, and $P(O)OR^eOR^f$;

$Z^1$ and $Z^2$ are each, independently, selected from H, halo, CN, $NO_2$, OH, $C_{1-6}$alkoxy, $C_{1-6}$ haloalkoxy, $C_{2-8}$ alkoxyalkoxy, amino, $C_{1-6}$ alkylamino, $C_{2-8}$dialkylamino, $C_{1-6}$ alkyl, $C_{1-6}$ haloalkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl, and heterocycloalkylalkyl, wherein each of the $C_{1-6}$ alkyl, $C_{1-6}$haloalkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl, and heterocycloalkylalkyl is substituted with 0, 1, 2, 3, 4, 5, 6, 7, or 8 substituents each independently selected from $R^{ZZ}$, halo, CN, $NO_2$, $OR^a$, $SR^a$, $SF_5$, $C(O)R^b$, $C(O)NR^cR^d$, $C(O)OR^a$, $OC(O)R^b$, $OC(O)NR^cR^d$, $NR^cR^d$, $NR^cC(O)R^d$, $NR^cC(O)OR^a$, $NR^cS(O)_2R^b$, $NR^cS(O)_2NR^cR^d$, $S(O)R^b$, $S(O)NR^cR^d$, $S(O)_2R^b$, $S(O)_2NR^cR^d$, $P(R^f)_2$, $P(OR^e)_2$, $P(O)R^eR^f$, and $P(O)OR^eOR^f$;

$R^{11a}$, $R^{11b}$, $R^{12a}$, and $R^{12b}$ are each, independently, selected from H, halo, $C_{1-6}$ alkyl, $C_{2-6}$ alkenyl, $C_{2-6}$ alkynyl, $C_{1-6}$ haloalkyl, cycloalkyl, heterocycloalkyl, aryl, heteroaryl, arylalkyl, heteroarylalkyl, cycloalkylalkyl, heterocycloalkylalkyl, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $NR^{c1}R^{d1}$, $NR^{c1}C(O)R^{b1}$, $NR^{c1}C(O)NR^{c1}R^{d1}$, $NR^{c1}C(O)OR^{a1}$, $C(=NR^{g1})NR^{c1}R^{d1}$, $NR^{c1}C(=NR^{g1})NR^{c1}R^{d1}$, $NR^{c1}S(O)_2NR^{c1}R^{d1}$, $S(O)R^{b1}$, $S(O)R^{b1}$, $S(O)NR^{c1}R^{d1}$, $S(O)_2^{b1}$, $NR^{c1}S(O)_2R^{b1}$, $S(O)_2NR^{c1}R^{d1}$, $P(R^{f1})_2$, $P(OR^{e1})R^{e1}R^{f1}$, and $P(O)OR^{e1}OR^{f1}$, wherein each of said $C_{1-6}$ alkyl, $C_{2-6}$ alkenyl, $C_{2-6}$ alkynyl, $C_{1-6}$ haloalkyl, cycloalkyl, heterocycloalkyl, aryl, heteroaryl, arylalkyl, heteroarylalkyl, cycloalkylalkyl, and heterocycloalkylalkyl is substituted with 0, 1, 2, 3, 4, or 5 substituents each independently selected from halo, $C_{1-6}$ alkyl, $C_{2-6}$ alkenyl, $C_{2-6}$ alkynyl, $C_{1-6}$ haloalkyl, cycloalkyl, heterocycloalkyl, aryl, heteroaryl, arylalkyl, heteroarylalkyl, cycloalkylalkyl, heterocycloalkylalkyl, CN, $NO_2$, $OR^{a1}$, $SR^{a1}$, $SF_5$, $C(O)R^{b1}$, $C(O)NR^{c1}R^{d1}$, $C(O)OR^{a1}$, $OC(O)R^{b1}$, $OC(O)NR^{c1}R^{d1}$, $NR^{c1}R^{d1}$, $NR^{c1}C(O)R^{b1}$, $NR^{c1}C(O)NR^{c1}R^{d1}$, $NR^{c1}C(O)OR^{a1}$, $C(=NR^g)NR^{c1}R^{d1}$, $NR^{c1}C(=NR^g)NR^{c1}R^{d1}$, $NR^{c1}S(O)_2NR^{c1}R^{d1}$, $S(O)R^{b1}$, $S(O)NR^{c1}R^{d1}$, $S(O)_2R^{b1}$, $NR^{c1}S(O)_2R^{b1}$, $S(O)_2NR^{c1}R^{d1}$, $P(R^{f1})_2$, $P(OR^{e1})_2$, $P(O)R^{e1}R^{f1}$, and $P(O)OR^{e1}OR^{a}$;

each $R^{XX}$ is independently selected from $C_{1-6}$ alkyl, $C_{1-6}$ haloalkyl, arylalkyl, heteroarylalkyl, cycloalkylalkyl, heterocycloalkylalkyl, $C_{2-6}$ alkenyl, $C_{2-6}$ alkynyl, aryl, cycloalkyl, heteroaryl, and heterocycloalkyl, each substituted with 0, 1, 2, 3, 4, or 5 substituents each independently selected from $C_{1-6}$ alkyl, $C_{1-6}$ haloalkyl, arylalkyl, heteroarylalkyl, cycloalkylalkyl, heterocycloalkylalkyl, $C_{2-6}$ alkenyl, $C_{2-6}$ alkynyl, aryl, cycloalkyl, heteroaryl, heterocycloalkyl, halo, CN, $NO_2$, $OR^{a2}$, $SR^{a2}$, $SF_5$, $C(O)R^{b2}$, $C(O)NR^{c2}R^{d2}$, $C(O)OR^{a2}$, $OC(O)R^{b2}$, $OC(O)NR^{c2}R^{d2}$, $NR^{c2}R^{d2}$, $NR^{c2}C(O)R^{b2}$, $NR^{c2}C(O)NR^{c2}R^{d2}$, $NR^{c2}C(O)OR^{a2}$, $C(=NR^{g2})NR^{c2}R^{d2}$, $NR^{c2}C(=NR^{g2})NR^{c2}R^{d2}$, $NR^{c2}S(O)_2NR^{c2}R^{d2}$, $S(O)R^{b2}$, $S(O)NR^{c2}R^{d2}$, $S(O)_2R^{b2}$, $NR^{c2}S(O)_2R^{b2}$, $S(O)_2NR^{c2}R^{d2}$, $P(OR^{c2})_2$, $P(OR^{c2})_2$, $P(O)R^{c2}R^{f2}$, and $P(O)OR^{c2}OR^{f2}$;

each $R^{zz}$ is independently selected from $C_{1-6}$ alkyl, $C_{1-6}$ haloalkyl, arylalkyl, heteroarylalkyl, cycloalkylalkyl, heterocycloalkylalkyl, $C_{2-6}$ alkenyl, $C_{2-6}$ alkynyl, aryl, cycloalkyl, heteroaryl, and heterocycloalkyl, each substituted with 0, 1, 2, 3, 4, or 5 substituents each independently selected from $C_{1-6}$ alkyl, $C_{1-6}$ haloalkyl, arylalkyl, heteroarylalkyl, cycloalkylalkyl, heterocycloalkylalkyl, $C_{2-6}$ alkenyl, $C_{2-6}$ alkynyl, aryl, cycloalkyl, heteroaryl, heterocycloalkyl, halo, CN, $NO_2$, $OR^{a3}$, $SR^{a3}$, $SF_5$, $C(O)R^{b3}$, $C(O)NR^{c3}R^{d3}$, $C(O)OR^{a3}$, $OC(O)R^{b3}$, $OC(O)NR^{c3}R^{d3}$, $NR^{c3}R^{d3}$, $NR^{c3}C(O)R^{b3}$, $NR^{c3}C(O)NR^{c3}R^{d3}$, $NR^{c3}C(O)OR^{a3}$, $C(=NR^{g3})NR^{c3}R^{d3}$, $NR^{c3}C(=NR^{g2})NR^{c3}R^{d3}$, $NR^{c3}S(O)_2NR^{c3}R^{d3}$, $NR^{c3}S(O)_2NR^{c3}R^{d3}$, $S(O)NR^{c3}R^{d3}$, $S(O)_2R^{b3}$, $NR^{c3}S(O)_2R^{b3}$, $S(O)_2NR^{c3}R^{d3}$, $P(R^{f3})_2$, $P(OR^{e3})_2$, $P(O)R^{e3}R^{f3}$, and $P(O)OR^{e3}OR^{f3}$;

$R^a$, $R^{a1}$, $R^{a2}$, and $R^{a3}$ are each, independently, selected from H, $C_{1-6}$ alkyl, $C_{1-6}$ haloalkyl, arylalkyl, heteroarylalkyl, cycloalkylalkyl, heterocycloalkylalkyl, $C_{2-6}$ alkenyl, $C_{2-6}$ alkynyl, aryl, cycloalkyl, heteroaryl and heterocycloalkyl, wherein each of the $C_{1-6}$ alkyl, $C_{1-6}$ haloalkyl, arylalkyl, heteroarylalkyl, cycloalkylalkyl, heterocycloalkylalkyl, $C_{2-6}$ alkenyl, $C_{2-6}$ alkynyl, aryl, cycloalkyl, heteroaryl and heterocycloalkyl is substituted with 0, 1, 2, 3, 4, or 5 substituents each independently selected from OH, CN, amino, $C_{1-6}$ alkylamino, $C_{2-8}$ dialkylamino, halo, $C_{1-6}$ alkyl, $C_{1-6}$ haloalkyl, $C_{1-6}$ hydroxylalkyl, $C_{1-6}$ cyanoalkyl, $C_{1-6}$ alkoxy, $C_{1-6}$ haloalkoxy, $C_{2-8}$ alkoxyalkoxy, aryl, arylalkyl, heteroaryl, heteroarylalkyl, cycloalkyl, and heterocycloalkyl;

$R^b$, $R^{b1}$, $R^{b2}$, and $R^{b3}$ are each, independently, selected from H, $C_{1-6}$ alkyl, $C_{1-6}$ haloalkyl, arylalkyl, heteroarylalkyl, cycloalkylalkyl, heterocycloalkylalkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl and heterocycloalkylalkyl, wherein each of the $C_{1-6}$ alkyl, $C_{1-6}$ haloalkyl, arylalkyl, heteroarylalkyl, cycloalkylalkyl, heterocycloalkylalkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl and heterocycloalkylalkyl is substituted with 0, 1, 2, 3, 4, or 5 substituents each independently selected from OH, amino, $C_{1-6}$ alkylamino, $C_{2-8}$ dialkylamino, halo, $C_{1-6}$ alkyl, $C_{1-6}$ haloalkyl, $C_{1-6}$ hydroxylalkyl, $C_{1-6}$ cyanoalkyl, $C_{1-6}$ alkoxy, $C_{1-6}$ haloalkoxy, $C_{2-8}$ alkoxyalkoxy, aryl, arylalkyl, heteroaryl, heteroarylalkyl, cycloalkyl, and heterocycloalkyl; $R^c$ and $R^d$ are independently selected from H, $C_{1-10}$ alkyl, $C_{1-6}$ haloalkyl, arylalkyl, heteroarylalkyl, cycloalkylalkyl, heterocycloalkylalkyl, $C_{2-6}$ alkenyl, $C_{2-6}$ alkynyl, aryl, heteroaryl, cycloalkyl, heterocycloalkyl, arylalkyl, heteroarylalkyl, cycloalkylalkyl and heterocycloalkylalkyl, wherein each of the $C_{1-10}$ alkyl, $C_{1-6}$ haloalkyl, arylalkyl, heteroarylalkyl, cycloalkylalkyl, heterocycloalkylalkyl, $C_{2-6}$ alkenyl, $C_{2-6}$ alkynyl, aryl, heteroaryl, cycloalkyl, heterocycloalkyl, arylalkyl, heteroarylalkyl, cycloalkylalkyl and heterocycloalkylalkyl is substituted with 0, 1, 2, 3, 4, or 5 substituents each independently selected from OH, amino, $C_{1-6}$ alkylamino, $C_{2-8}$ dialkylamino, halo, $C_{1-6}$ alkyl, $C_{1-6}$ haloalkyl, $C_{1-6}$ hydroxylalkyl, $C_{1-6}$ cyanoalkyl, $C_{1-6}$ alkoxy, $C_{1-6}$ haloalkoxy, $C_{2-8}$ alkoxyalkoxy, aryl, arylalkyl, heteroaryl, heteroarylalkyl, cycloalkyl, and heterocycloalkyl;

or $R^c$ and $R^d$ together with the N atom to which they are attached form a 4-, 5-, 6- or 7-membered heterocycloalkyl group that is substituted with 0, 1, 2, 3, 4, or 5 substituents each independently selected from OH, amino, $C_{1-6}$ alkylamino, $C_{2-8}$ dialkylamino, halo, $C_{1-6}$ alkyl, $C_{1-6}$ haloalkyl, $C_{1-6}$ hydroxylalkyl, $C_{1-6}$ cyanoalkyl, $C_{1-6}$ alkoxy, $C_{1-6}$ haloalkoxy, $C_{2-8}$ alkoxyalkoxy, aryl, arylalkyl, heteroaryl, heteroarylalkyl, cycloalkyl, and heterocycloalkyl;

$R^{c1}$ and $R^{d1}$ are independently selected from H, $C_{1-10}$ alkyl, $C_{1-6}$ haloalkyl, arylalkyl, heteroarylalkyl, cycloalkylalkyl, heterocycloalkylalkyl, $C_{2-6}$ alkenyl, $C_{2-6}$ alkynyl, aryl, heteroaryl, cycloalkyl, heterocycloalkyl, arylalkyl, heteroarylalkyl, cycloalkylalkyl and heterocycloalkylalkyl, wherein each of the $C_{1-10}$ alkyl, $C_{1-6}$ haloalkyl, arylalkyl, heteroarylalkyl, cycloalkylalkyl, heterocycloalkylalkyl, $C_{2-6}$ alkenyl, $C_{2-6}$ alkynyl, aryl, heteroaryl, cycloalkyl, heterocycloalkyl, arylalkyl, heteroarylalkyl, cycloalkylalkyl and heterocycloalkylalkyl is substituted with 0, 1, 2, 3, 4, or 5 substituents each independently selected from OH, amino, $C_{1-6}$ alkylamino, $C_{2-8}$ dialkylamino, halo, $C_{1-6}$ alkyl, $C_{1-6}$ haloalkyl, $C_{1-6}$ hydroxylalkyl, $C_{1-6}$ cyanoalkyl, $C_{1-6}$ alkoxy, $C_{1-6}$ haloalkoxy, $C_{2-8}$ alkoxyalkoxy, aryl, arylalkyl, heteroaryl, heteroarylalkyl, cycloalkyl, and heterocycloalkyl;

or $R^{c1}$ and $R^{d1}$ together with the N atom to which they are attached form a 4-, 5-, 6- or 7-membered heterocycloalkyl group that is substituted with 0, 1, 2, 3, 4, or 5 substituents each independently selected from OH, amino, $C_{1-6}$ alkylamino, $C_{2-8}$ dialkylamino, halo, $C_{1-6}$ alkyl, $C_{1-6}$ haloalkyl, $C_{1-6}$ hydroxylalkyl, $C_{1-6}$ cyanoalkyl, $C_{1-6}$ alkoxy, $C_{1-6}$ haloalkoxy, $C_{2-8}$ alkoxyalkoxy, aryl, arylalkyl, heteroaryl, heteroarylalkyl, cycloalkyl, and heterocycloalkyl;

$R^{c2}$ and $R^{d2}$ are independently selected from H, $C_{1-10}$ alkyl, $C_{1-6}$ haloalkyl, arylalkyl, heteroarylalkyl, cycloalkylalkyl, heterocycloalkylalkyl, $C_{2-6}$ alkenyl, $C_{2-6}$ alkynyl, aryl, heteroaryl, cycloalkyl, heterocycloalkyl, arylalkyl, heteroarylalkyl, cycloalkylalkyl and heterocycloalkylalkyl, wherein each of the $C_{1-10}$ alkyl, $C_{1-6}$ haloalkyl, arylalkyl, heteroarylalkyl, cycloalkylalkyl, heterocycloalkylalkyl, $C_{2-6}$ alkenyl, $C_{2-6}$ alkynyl, aryl, heteroaryl, cycloalkyl, heterocycloalkyl, arylalkyl, heteroarylalkyl, cycloalkylalkyl and heterocycloalkylalkyl is substituted with 0, 1, 2, 3, 4, or 5 substituents each independently selected from OH, amino, $C_{1-6}$ alkylamino, $C_{2-8}$ dialkylamino, halo, $C_{1-6}$ alkyl, $C_{1-6}$ haloalkyl, $C_{1-6}$ hydroxylalkyl, $C_{1-6}$ cyanoalkyl, $C_{1-6}$ alkoxy, $C_{1-6}$ haloalkoxy, $C_{2-8}$ alkoxyalkoxy, aryl, arylalkyl, heteroaryl, heteroarylalkyl, cycloalkyl, and heterocycloalkyl;

or $R^{c2}$ and $R^{d2}$ together with the N atom to which they are attached form a 4-, 5-, 6- or 7-membered heterocycloalkyl group that is substituted with 0, 1, 2, 3, 4, or 5 substituents each independently selected from OH, amino, $C_{1-6}$ alkylamino, $C_{2-8}$ dialkylamino, halo, $C_{1-6}$ alkyl, $C_{1-6}$ haloalkyl, $C_{1-6}$ hydroxylalkyl, $C_{1-6}$ cyanoalkyl, $C_{1-6}$ alkoxy, $C_{1-6}$ haloalkoxy, $C_{2-8}$ alkoxyalkoxy, aryl, arylalkyl, heteroaryl, heteroarylalkyl, cycloalkyl, and heterocycloalkyl;

$R^{c3}$ and $R^{d3}$ are independently selected from H, $C_{1-10}$ alkyl, $C_{1-6}$ haloalkyl, arylalkyl, heteroarylalkyl, cycloalkylalkyl, heterocycloalkylalkyl, $C_{2-6}$ alkenyl, $C_{2-6}$ alkynyl, aryl, heteroaryl, cycloalkyl, heterocycloalkyl, arylalkyl, heteroarylalkyl, cycloalkylalkyl and heterocycloalkylalkyl, wherein each of the $C_{1-10}$ alkyl, $C_{1-6}$ haloalkyl, arylalkyl, heteroarylalkyl, cycloalkylalkyl, heterocycloalkylalkyl, $C_{2-6}$ alkenyl, $C_{2-6}$ alkynyl, aryl, heteroaryl, cycloalkyl, heterocycloalkyl, arylalkyl, heteroarylalkyl, cycloalkylalkyl and heterocycloalkylalkyl is substituted with 0, 1, 2, 3, 4, or 5 substituents each independently selected from OH, amino, $C_{1-6}$ alkylamino, $C_{2-8}$ dialkylamino, halo, $C_{1-6}$ alkyl, $C_{1-6}$ haloalkyl, $C_{1-6}$ hydroxylalkyl, $C_{1-6}$ cyanoalkyl, $C_{1-6}$ alkoxy, $C_{1-6}$ haloalkoxy, $C_{2-8}$ alkoxyalkoxy, aryl, arylalkyl, heteroaryl, heteroarylalkyl, cycloalkyl, and heterocycloalkyl;

or $R^{c3}$ and $R^{d3}$ together with the N atom to which they are attached form a 4-, 5-, 6- or 7-membered heterocycloalkyl group that is substituted with 0, 1, 2, 3, 4, or 5 substituents each independently selected from OH, amino, $C_{1-6}$ alkylamino, $C_{2-8}$ dialkylamino, halo, $C_{1-6}$ alkyl, $C_{1-6}$ haloalkyl, $C_{1-6}$ hydroxylalkyl, $C_{1-6}$ cyanoalkyl, $C_{1-6}$ alkoxy, $C_{1-6}$ haloalkoxy, $C_{2-8}$ alkoxyalkoxy, aryl, arylalkyl, heteroaryl, heteroarylalkyl, cycloalkyl, and heterocycloalkyl;

$R^e$, $R^{e1}$, $R^{e2}$, $R^{e3}$, $R^f$, $R^{f1}$, $R^{f2}$, and $R^{f3}$ are each, independently, selected from H, $C_{1-10}$ alkyl, $C_{1-6}$ haloalkyl, arylalkyl, heteroarylalkyl, cycloalkylalkyl, heterocycloalkylalkyl, $C_{2-6}$ alkenyl, $C_{2-6}$ alkynyl, aryl, heteroaryl, cycloalkyl, heterocycloalkyl, arylalkyl, heteroarylalkyl, cycloalkylalkyl and heterocycloalkylalkyl, wherein each of the $C_{1-10}$ alkyl, $C_{1-6}$ haloalkyl, arylalkyl, heteroarylalkyl, cycloalkylalkyl, heterocycloalkylalkyl, $C_{2-6}$ alkenyl, $C_{2-6}$ alkynyl, aryl, heteroaryl, cycloalkyl, heterocycloalkyl, arylalkyl, heteroarylalkyl, cycloalkylalkyl and heterocycloalkylalkyl is substituted with 0, 1, 2, 3, 4, or 5 substituents each independently selected from OH, amino, $C_{1-6}$ alkylamino, $C_{2-8}$ dialkylamino, halo, $C_{1-6}$ alkyl, $C_{1-6}$ haloalkyl, $C_{1-6}$ hydroxylalkyl, $C_{1-6}$ cyanoalkyl, $C_{1-6}$ alkoxy, $C_{1-6}$ haloalkoxy, $C_{2-8}$ alkoxyalkoxy, aryl, arylalkyl, heteroaryl, heteroarylalkyl, cycloalkyl, and heterocycloalkyl;

$R^g$, $R^{g1}$, $R^{g2}$, and $R^{g3}$ are each, independently, selected from H, CN, and $NO_2$;

each p1 is, independently, 0, 1, or 2;
each p2 is, independently, 0, 1, or 2;
each p3 is, independently, 0, 1, or 2;
each p4 is, independently, 0, 1, or 2;
each q1 is, independently, 1 or 2;
each q2 is, independently, 1 or 2;
n1 is 0, 1, 2, or 3;
n2 is 0, 1, 2, or 3; and
m is 2, 3, 4, 5, or 6.

In some embodiments, the moiety (QR2):

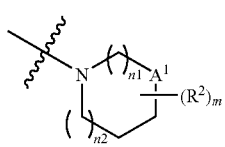

of Formula I is other than a moiety having the structure of

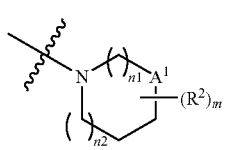

wherein m10, m11, and n20 are each, independently, 0 or 1; $R^{150}$ is $C_{1-4}$ alkyl; and $R^{151}$ is halo.

In some embodiments, when two adjacent $R^2$ together with the two carbon atoms to which they are attached form a fused optionally substituted aryl group, then the fused optionally substituted aryl group is other than a fused benzo group optionally substituted with a halo group.

In some embodiments, when the moiety (QR2):

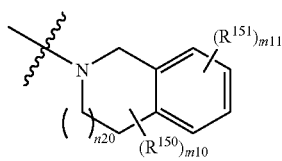

of Formula I is a moiety having the structure of

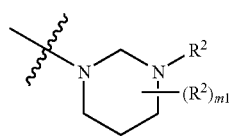

wherein m1 is 1, 2, 3, 4, or 5, and the $R^2$ attached to the N atom and one of its adjacent $R^2$ groups together with the two atoms to which they are attached form a fused 3-14 membered heterocycloalkyl group, then the fused 3-14 membered heterocycloalkyl group is substituted with at least one —$W^{2a}$—$X^{2a}$—$W^2$—$X^2$—$Y^2$—$Z^2$.

In some embodiments, $R^1$ is other than a moiety having the structure of

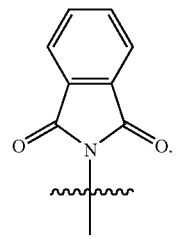 [SMILES: *N1C(=O)c2ccccc2C1=O]

In some embodiments, $R^1$ is other than a moiety having the structure of

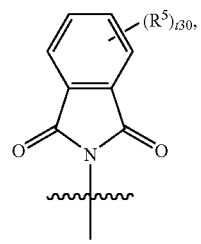

wherein t30 is 0, 1, 2, or 3.

In some embodiments, at least two adjacent $R^2$ together with the two atoms to which they are attached form a fused 3-14 membered cycloalkyl group, a fused 3-14 membered heterocycloalkyl group, a fused aryl group, or a fused heteroaryl group, wherein the fused ring group is substituted with at least one —$W^{2a}$—$X^{2a}$—$W^2$—$X^2$—$Y^2$—$Z^2$ that is other than $C_{1-4}$ alkyl or halo.

In some embodiments, the ring formed by $R^3$ and $R^4$ together with the N atom to which they are attached is a 4-10 membered heterocycloalkyl group substituted with 0, 1, 2, 3, 4, or 5 $R^5$, and wherein each of the ring-forming atoms of the 4-10 membered heterocycloalkyl group is C, O, or N. In some further embodiments, the 4-10 membered heterocycloalkyl group is mono- or bi-cyclic. In other further embodiments, the 4-10 membered heterocycloalkyl group is saturated [i.e., it does not have any unsaturated ring bond (i.e. no double or triple bond as a ring bond for the 4-10 membered heterocycloalkyl group)].

In some embodiments, $R^3$ and $R^4$ together with the N atom to which they are attached form a 4-9 membered heterocycloalkyl group wherein each of the ring-forming atoms of the 4-9 membered heterocycloalkyl group is independently selected from C, N, and O, and wherein the 4-9 membered heterocycloalkyl group is substituted with 0, 1, 2, 3, 4, or 5 $R^5$. In some further embodiments, the 4-9 membered heterocycloalkyl group is substituted with 0, 1, or 2 $R^5$. In yet further embodiments, the 4-9 membered heterocycloalkyl group is substituted with 0 or 1 $R^5$.

In some embodiments, the ring formed by $R^3$ and $R^4$ together with the N atom to which they are attached is a 5-7 membered heterocycloalkyl group substituted with 0, 1, 2, 3, 4, or 5 $R^5$, and wherein each of the ring-forming atoms of the 5-7 membered heterocycloalkyl group is C or N.

In some embodiments, the ring formed by $R^3$ and $R^4$ together with the N atom to which they are attached is a pyrrolidine ring, a piperidine ring, or a piperazine ring, each substituted with 0, 1, 2, 3, 4, or 5 $R^5$.

In some embodiments, the ring formed by $R^3$ and $R^4$ together with the N atom to which they are attached is substituted with 0, 1, 2, or 3 $R^5$; and each $R^5$ is independently selected from $C_{1-6}$ alkyl, $C_{1-6}$ haloalkyl, $NH_2$, $NH(C_{1-4}$ alkyl), and $N(C_{1-4}$ alkyl$)_2$, wherein each of the $C_{1-6}$ alkyl and $C_{1-6}$ haloalkyl is substituted with 0 or 1 substituent selected from $NH_2$, $NH(C_{1-4}$ alkyl), and $N(C_{1-4}$ alkyl$)_2$. In some embodiments, the ring formed by $R^3$ and $R^4$ together with the N atom to which they are attached is selected from:

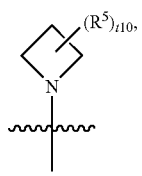
(Q1)

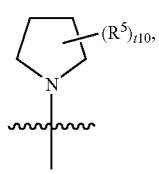
(Q2)

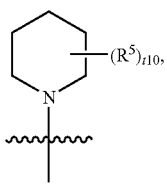
(Q3)

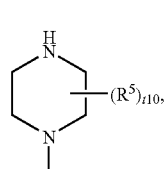
(Q4)

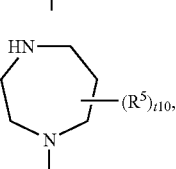
(Q5)

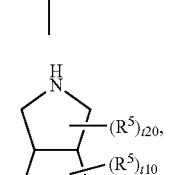
(Q6)

-continued

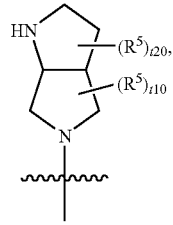
(Q7)

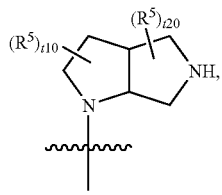
(Q8)

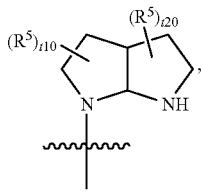
(Q9)

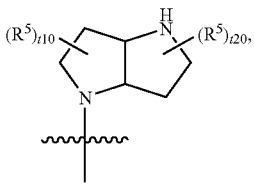
(Q10)

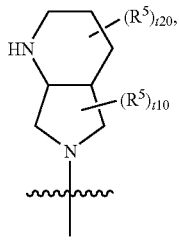
(Q11)

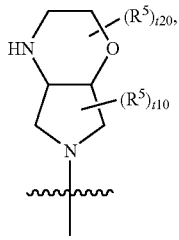
(Q12)

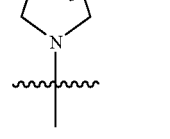
(Q13)

(Q14)
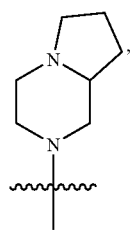

(Q15)
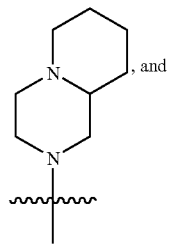, and (Q16)
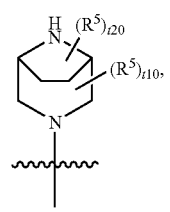

wherein t10 and t20 are each, independently, 0, 1, or 2. In some further embodiments, each $R^5$ is independently selected from $C_{1-6}$ alkyl, $NH_2$, $NH(C_{1-4}$ alkyl), and $N(C_{1-4}$ alkyl$)_2$, wherein the $C_{1-6}$ alkyl is substituted with 0 or 1 substituent selected from $NH_2$, $NH(C_{1-4}$ alkyl), and $N(C_{1-4}$ alkyl$)_2$. In yet further embodiments, each $R^5$ is independently selected from methyl and $NH(CH_3)$.

In some embodiments, each $R^5$ is independently selected from $C_{1-6}$ alkyl, $NH_2$, $NH(C_{1-4}$ alkyl), and $N(C_{1-4}$ alkyl$)_2$, wherein the $C_{1-6}$ alkyl is substituted with 0 or 1 substituent selected from $NH_2$, $NH(C_{1-4}$ alkyl), and $N(C_{1-4}$ alkyl$)_2$.

In some embodiments, each $R^5$ is independently selected from $C_{1-6}$ alkyl and $NH(C_{1-4}$ alkyl), wherein the $C_{1-6}$ alkyl is substituted with 0 or 1 $NH(C_{1-4}$ alkyl). In some embodiments, each $R^6$ is independently selected from methyl and $NH(CH_3)$.

In some embodiments, $R^1$ is selected from (A), (B), (C), (Q14), (Q17), (Q18), (Q19), (Q20), and (Q21):

(A)
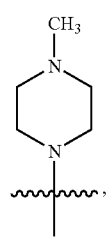

(B)
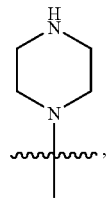

(C)
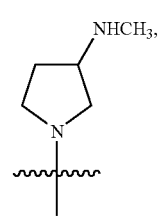

(Q14)
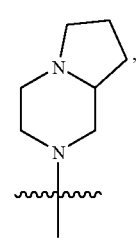

(Q17)
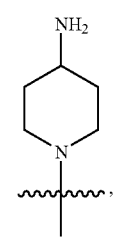

(Q18)
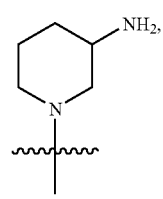

(Q19)
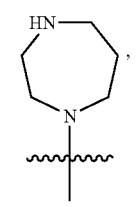

(Q20)
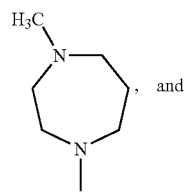, and

-continued

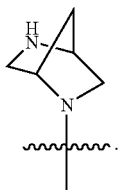

(Q21)

In some embodiments, $R^1$ is selected from (A), (B), and (C):

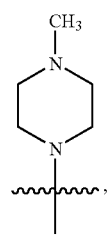

(A)

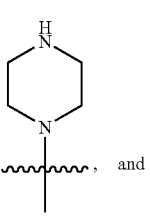

(B) and

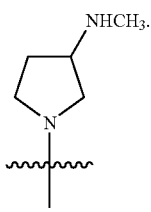

(C)

In some embodiments, $R^1$ is (A):

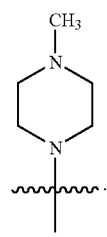

(A)

In some embodiments, two adjacent $R^2$ together with the two atoms (i.e. the two ring-forming atoms) to which they are attached form a fused aryl group or a fused heteroaryl group, each substituted with 0, 1, 2, 3, 4, or 5 —$W^{2a}$—$X^{2a}$—$W^2$—$X^2$—$Y^2$—$Z^2$.

In some embodiments, two adjacent $R^2$ together with the two atoms (i.e. the two ring-forming atoms) to which they are attached form a fused aryl group substituted with 0, 1, 2, 3, 4, or 5 —$W^{2a}$—$X^{2a}$—$W^2$—$X^2$—$Y^2$—$Z^2$.

In some embodiments, two adjacent $R^2$ together with the two atoms to which they are attached form a fused heteroaryl group substituted with 0, 1, 2, 3, 4, or 5 —$W^{2a}$—$X^{2a}$—$W^2$—$X^2$—$Y^2$—$Z^2$.

In some embodiments, two adjacent $R^2$ together with the two carbon atoms to which they are attached form a fused aryl group substituted with 0, 1, 2, 3, 4, or 5 —$W^{2a}$—$X^{2a}$—$W^2$—$X^2$—$Y^2$—$Z^2$.

In some embodiments, two adjacent $R^2$ together with the two carbon atoms (i.e. the two ring-forming carbon atoms) to which they are attached form a fused benzo group substituted with 0, 1, 2, 3, 4, or 5 —$W^{2a}$—$X^{2a}$—$W^2$—$X^2$—$Y^2$—$Z^2$.

In some embodiments, two adjacent $R^2$ together with the two carbon atoms to which they are attached form a fused heteroaryl group substituted with 0, 1, 2, 3, 4, or 5 —$W^{2a}$—$X^{2a}$—$W^2$—$X^2$—$Y^2$—$Z^2$.

In some embodiments, two adjacent $R^2$ together with the two atoms to which they are attached form a fused cycloalkyl group substituted with 0, 1, 2, 3, 4, or 5 —$W^{2a}$—$X^{2a}$—$W^2$—$X^2$—$Y^2$—$Z^2$.

In some embodiments, two adjacent $R^2$ together with the two atoms to which they are attached form a fused heterocycloalkyl group substituted with 0, 1, 2, 3, 4, or 5 —$W^{2a}$—$X^{2a}$—$W^2$—$X^2$—$Y^2$—$Z^2$.

In some embodiments, $A^1$ is $CH_2$, $CHR^2$, $C(R^2)_2$, or N.

In some embodiments, $A^1$ is $CH_2$, $CHR^2$, or $C(R^2)_2$.

In some embodiments, $A^1$ is N, O, or S.

In some embodiments, $A^1$ is N.

In some embodiments, $A^1$ is O or S.

In some embodiments, $A^1$ is O.

In some embodiments, $A^1$ is S.

In some embodiments, at least one substituent —$W^{2a}$—$X^{2a}$—$W^2$—$X^2$—$Y^2$—$Z^2$ is a —$W^{2a}$—$X^{2a}$—$W^2$—$X^2$—$Y^2$—$Z^2$ wherein $W^{2a}$ is selected from absent, O, S, and $NR^e$; and $X^{2a}$ is aryl, cycloalkyl, heteroaryl, or heterocycloalkyl, each substituted with 0, 1, 2, 3, 4, 5, 6, 7, or 8 substituents each independently selected from $R^{XX}$, halo, CN, $NO_2$, $OR^a$, $SR^a$, $C(O)R^b$, $C(O)NR^cR^d$, $C(O)OR^a$, $OC(O)R^b$, $OC(O)NR^cR^d$, $NR^cR^d$, $NR^cC(O)R^b$, $NR^cC(O)NR^cR^d$, $NR^cC(O)OR^a$, $C(=NR^g)NR^cR^d$, $NR^cC(=NR^g)NR^cR^d$, $NR^cS(O)_2NR^cR^d$, $S(O)R^b$, $S(O)NR^cR^d$, $S(O)_2R^b$, $NR^cS(O)_2R^b$, and $S(O)_2NR^cR^d$. In some further embodiments, —$W^2$—$X^2$—$Y^2$—$Z^2$ is other than H.

In some embodiments, at least one substituent —$W^{2a}$—$X^{2a}$—$W^2$—$X^2$—$Y^2$—$Z^2$ is a —$W^{2a}$—$X^{2a}$—$W^2$—$X^2$—$Y^2$—$Z^2$ wherein $W^{2a}$ is absent, O, S, or $NR^e$; and $X^{2a}$ is aryl or heteroaryl, each substituted with 0, 1, 2, 3, 4, or 5 substituents each independently selected from $R^{XX}$, halo, CN, $NO_2$, $OR^a$, $SR^a$, $C(O)R^b$, $C(O)NR^c R^d$, $C(O)OR^a$, $OC(O)R^b$, $OC(O)NR^cR^d$, $NR^cR^d$, $NR^cC(O)R^b$, $NR^cC(O)NR^cR^d$, $NR^cC(O)OR^a$, $C(=NR^g)NR^cR^d$, $NR^c(=NR^g)NR^cR^d$, $NR^cS(O)_2NR^cR^d$, $S(O)R^b$, $S(O)NR^cR^d$, $S(O)_2R^b$, $NR^cS(O)_2R^b$, and $S(O)_2NR^cR^d$. In some further embodiments, —$W^2$—$X^2$—$Y^2$—$Z^2$ is other than H.

In some embodiments, at least one substituent —$W^{2a}$—$X^{2a}$—$W^2$—$X^2$—$Y^2$—$Z^2$ is a —$W^{2a}$—$X^{2a}$—$W^2$—$X^2$—$Y^2$—$Z^2$ wherein $W^{2a}$ is absent, O, S, or NH; and $X^{2a}$ is aryl or heteroaryl, each substituted with 0, 1, 2, 3, 4, or 5 substituents each independently selected from $R^{XX}$, halo, CN, $NO_2$, $OR^a$, $SR^a$, $C(O)R^b$, $C(O)NR^c R^d$, $C(O)OR^a$, $OC(O)R^b$, $OC(O)NR^cR^d$, $NR^cR^d$, $NR^cC(O)R^b$, $NR^cC(O)NR^cR^d$, $NR^cC(O)OR^a$, $C(=NR^g)NR^cR^d$, $NR^cC(=NR^g)NR^cR^d$, $NR^cS(O)_2NR^cR^d$, $S(O)R^b$, $S(O)NR^cR^d$, $S(O)_2R^b$, $NR^cS(O)_2R^b$, and $S(O)_2NR^cR^d$. In some further embodiments, —$W^2$—$X^2$—$Y^2$—$Z^2$ is other than H.

In some embodiments, at least one substituent —$W^{2a}$—$X^{2a}$—$W^2$—$X^2$—$Y^2$—$Z^2$ is a —$W^{2a}$—$X^{2a}$—$W^2$—$X^2$—

$Y^2$—$Z^2$ wherein $W^{2a}$ is absent; and $X^{2a}$ is aryl or heteroaryl, each substituted with 0, 1, 2, 3, 4, or 5 substituents each independently selected from $R^{xx}$, halo, CN, $NO_2$, $OR^a$, $SR^a$, $C(O)R^b$, $C(O)NR^cR^d$, $C(O)OR^a$, $OC(O)R^b$, $OC(O)NR^cR^d$, $NR^cR^d$, $NR^cC(O)R^b$, $NR^cC(O)NR^cR^d$, $NR^cC(O)OR^a$, $C(=NR^g)NR^cR^d$, $NR^cC(=NR^g)NR^cR^d$, $NR^cS(O)_2NR^cR^d$, $S(O)R^b$, $S(O)NR^cR^d$, $S(O)_2R^b$, $NR^cS(O)_2R^b$, and $S(O)_2NR^cR^d$. In some further embodiments, —$W^2$—$X^2$—$Y^2$—$Z^2$ is other than H.

In some embodiments, at least one substituent —$W^{2a}$—$X^{2a}$—$W^2$—$X^2$—$Y^2$—$Z^2$ is a —$W^{2a}$—$X^{2a}$—$W^2$—$X^2$—$Y^2$—$Z^2$ wherein $W^{2a}$ is O; and $X^{2a}$ is aryl or heteroaryl, each substituted with 0, 1, 2, 3, 4, or 5 substituents each independently selected from $R^{xx}$, halo, CN, $NO_2$, $OR^a$, $SR^a$, $C(O)R^b$, $C(O)NR^cR^d$, $C(O)OR^a$, $OC(O)R^b$, $OC(O)NR^cR^d$, $NR^cR^d$, $NR^cC(O)R^b$, $NR^cC(O)NR^cR^d$, $NR^cC(O)OR^a$, $C(=NR^g)NR^cR^d$, $NR^cC(=NR^g)NR^cR^d$, $NR^cS(O)_2NR^cR^d$, $S(O)R^b$, $S(O)NR^cR^d$, $S(O)_2R^b$, $NR^cS(O)_2R^b$, and $S(O)_2NR^cR^d$. In some further embodiments, —$W^2$—$X^2$—$Y^2$—$Z^2$ is other than H.

In some embodiments, at least one substituent —$W^{2a}$—$X^{2a}$—$W^2$—$X^2$—$Y^2$—$Z^2$ is a —$W^{2a}$—$X^{2a}$—$W^2$—$X^2$—$Y^2$—$Z^2$ wherein $W^{2a}$ is $NR^e$; and $X^{2a}$ is aryl or heteroaryl, each substituted with 0, 1, 2, 3, 4, or 5 substituents each independently selected from $R^{xx}$, halo, CN, $NO_2$, $OR^a$, $SR^a$, $C(O)R^b$, $C(O)NR^cR^d$, $C(O)OR^a$, $OC(O)R^b$, $OC(O)NR^cR^d$, $NR^cR^d$, $NR^cC(O)R^b$, $NR^cC(O)NR^cR^d$, $NR^cC(O)OR^a$, $C(=NR^g)NR^cR^d$, $NR^cC(=NR^g)NR^cR^d$, $NR^cS(O)_2NR^cR^d$, $S(O)R^b$, $S(O)NR^cR^d$, $S(O)_2R^b$, $NR^cS(O)_2R^b$, and $S(O)_2NR^cR^d$. In some further embodiments, —$W^2$—$X^2$—$Y^2$—$Z^2$ is other than H.

In some embodiments, at least one substituent —$W^{2a}$—$X^{2a}$—$W^2$—$X^2$—$Y^2$—$Z^2$ is a —$W^{2a}$—$X^{2a}$—$W^2$—$X^2$—$Y^2$—$Z^2$ wherein $W^{2a}$ is absent; O, S, or $NR^e$; and $X^{2a}$ is aryl or heteroaryl, each substituted with 0, 1, 2, 3, 4, or 5 substituents each independently selected from $R^{xx}$, halo, CN, $NO_2$, $OR^a$, $SR^a$, $C(O)R^b$, $C(O)NR^cR^d$, $C(O)OR^a$, $OC(O)R^b$, $OC(O)NR^cR^d$, $NR^cR^d$, $NR^cC(O)R^b$, $NR^cC(O)NR^cR^d$, $NR^cC(O)OR^a$, $C(=NR^g)NR^cR^d$, $NR^cC(=NR^g)NR^cR^d$, $NR^cS(O)_2NR^cR^d$, $S(O)R^b$, $S(O)NR^cR^d$, $S(O)_2R^b$, $NR^cS(O)_2R^b$, and $S(O)_2NR^cR^d$. In some further embodiments, —$W^2$—$X^2$—$Y^2$—$Z^2$ is other than H.

In some embodiments, at least one substituent —$W^{2a}$—$X^{2a}$—$W^2$—$X^2$—$Y^2$—$Z^2$ is a —$W^{2a}$—$X^{2a}$—$W^2$—$X^2$—$Y^2$—$Z^2$ wherein $W^2a$ is absent or selected from O, NH, $N(C_{1-6}$ alkyl), $C(O)$, $C(O)NH$, $C(O)N(C_{1-6}$ alkyl), and $OC(O)NH$; $X^{2a}$ is alkyl, arylalkyl, aryl, cycloalkyl, heteroaryl, or heterocycloalkyl, each substituted with 0, 1, 2, 3, 4, or 5 substituents each independently selected from $C_{1-6}$ alkyl, $C_{1-6}$haloalkyl, $C_{1-6}$alkoxy, $C_{1-6}$ haloalkoxy, amino, $C_{1-6}$ alkylamino, $C_{2-8}$ dialkylamino, halo, CN, and OH; $W^2$— is absent or selected from $C_{1-6}$ alkylenyl, —$C(O)$—, —$C(O)O$—, —$C(O)NH$—, —$C(O)N(C_{1-6}$ alkyl)-, $X^2$ is absent or selected from $C_{1-6}$ alkyl, aryl, cycloalkyl, heteroaryl, heterocycloalkyl, cycloalkylalkyl, and heterocycloalkylalkyl, each substituted with 0, 1, 2, 3, 4, or 5 substituents each independently selected from $C_{1-6}$ alkyl, $C_{1-6}$haloalkyl, $C_{1-6}$ alkoxy, $C_{1-6}$ haloalkoxy, amino, $C_{1-6}$ alkylamino, $C_{2-8}$ dialkylamino, halo, CN, and OH; $Y^2$— is absent or selected from $C_{1-6}$alkylenyl, O, $C(O)$, $C(O)O$, $C(O)NH$, $C(O)N(C_{1-6}$ alkyl), and $S(O)_2$; and $Z^2$ is selected from H, halo, CN, OH, $C_{1-6}$ alkoxy, $C_{1-6}$haloalkoxy, amino, $C_{1-6}$ alkylamino, $C_{2-8}$ dialkylamino, $C_{1-6}$ alkyl, aryl, cycloalkyl, heteroaryl, heterocycloalkyl, arylalkyl, heteroarylalkyl, cycloalkylalkyl, and heterocycloalkylalkyl, wherein each of the $C_{1-6}$ alkyl, aryl, cycloalkyl, heteroaryl, heterocycloalkyl, arylalkyl, heteroarylalkyl, cycloalkylalkyl, and heterocycloalkylalkyl is substituted with 0, 1, 2, or 3 substituents each independently selected from halo, CN, OH, $C_{1-6}$alkoxy, $C_{1-6}$ haloalkoxy, $C_{1-6}$ alkyl, $C_{1-6}$ haloalkyl,amino, $C_{1-6}$ alkylamino, $C_{2-8}$dialkylamino, $C(O)NH_2$, $C(O)NH(C_{1-6}$ alkyl), and $C(O)N(C_{1-6}$ alkyl)$_2$;

In some embodiments, at least one substituent —$W^{2a}$—$X^{2a}$—$W^2$—$X^2$—$Y^2$—$Z^2$ is a —$W^{2a}$—$X^{2a}$—$W^2$—$X^2$—$Y^2$—$Z^2$ wherein $W^{2a}$ is selected from O, NH, $N(C_{1-6}$ alkyl), $C(O)$, $C(O)NH$, $C(O)N(C_{1-6}$ alkyl), and $OC(O)NH$; $X^{2a}$ is alkyl, arylalkyl, aryl, cycloalkyl, heteroaryl, or heterocycloalkyl, each substituted with 0, 1, 2, 3, 4, or 5 substituents each independently selected from $C_{1-6}$ alkyl, $C_{1-6}$haloalkyl, $C_{1-6}$alkoxy, $C_{1-6}$haloalkoxy, amino, $C_{1-6}$ alkylamino, $C_{2-8}$ dialkylamino, halo, CN, and OH; $W^2$— is absent or selected from $C_{1-6}$ alkylenyl, —$C(O)$—, —$C(O)O$—, —$C(O)NH$—, —$C(O)N(C_{1-6}$ alkyl)-, $X^2$ is absent or selected from $C_{1-6}$ alkyl, aryl, cycloalkyl, heteroaryl, heterocycloalkyl, cycloalkylalkyl, and heterocycloalkylalkyl, each substituted with 0, 1, 2, 3, 4, or 5 substituents each independently selected from $C_{1-6}$ alkyl, $C_{1-6}$haloalkyl, $C_{1-6}$alkoxy, $C_{1-6}$ haloalkoxy, amino, $C_{1-6}$ alkylamino, $C_{2-8}$ dialkylamino, halo, CN, and OH; $Y^2$— is absent or selected from $C_{1-6}$ alkylenyl, O, $C(O)$, $C(O)O$, $C(O)NH$, $C(O)N(C_{1-6}$ alkyl), and $S(O)_2$; and $Z^2$ is selected from H, halo, CN, OH, $C_{1-6}$alkoxy, $C_{1-6}$haloalkoxy, amino, $C_{1-6}$alkylamino, $C_{2-8}$dialkylamino, $C_{1-6}$ alkyl, aryl, cycloalkyl, heteroaryl, heterocycloalkyl, arylalkyl, heteroarylalkyl, cycloalkylalkyl, and heterocycloalkylalkyl, wherein each of the $C_{1-6}$ alkyl, aryl, cycloalkyl, heteroaryl, heterocycloalkyl, arylalkyl, heteroarylalkyl, cycloalkylalkyl, and heterocycloalkylalkyl is substituted with 0, 1, 2, or 3 substituents each independently selected from halo, CN, OH, $C_{1-6}$alkoxy, $C_{1-6}$ haloalkoxy, $C_{1-6}$ alkyl, $C_{1-6}$ haloalkyl,amino, $C_{1-6}$ alkylamino, $C_{2-8}$dialkylamino, $C(O)NH_2$, $C(O)NH(C_{1-6}$ alkyl), and $C(O)N(C_{1-6}$ alkyl)$_2$.

In some embodiments, at least one substituent —$W^{2a}$—$X^{2a}$—$W^2$—$X^2$—$Y^2$—$Z^2$ is a —$W^{2a}$—$X^{2a}$—$W^2$—$X^2$—$Y^2$—$Z^2$ wherein $W^{2a}$ is selected from O, NH, $N(C_{1-6}$ alkyl), $C(O)$, $C(O)NH$, $C(O)N(C_{1-6}$ alkyl), and $OC(O)NH$; $X^{2a}$ is heteroaryl or heterocycloalkyl, each substituted with 0, 1, 2, 3, 4, or 5 substituents each independently selected from $C_{1-6}$ alkyl, $C_{1-6}$haloalkyl, $C_{1-6}$ alkoxy, $C_{1-6}$haloalkoxy, amino, $C_{1-6}$ alkylamino, $C_{2-8}$ dialkylamino, halo, CN, and OH; $W^2$— is absent or selected from $C_{1-6}$ alkylenyl, —C(O)—, —C(O)O—, —C(O)NH—, —C(O)N($C_{1-6}$ alkyl)-, $X^2$ is absent or selected from $C_{1-6}$ alkyl, aryl, cycloalkyl, heteroaryl, heterocycloalkyl, cycloalkylalkyl, and heterocycloalkylalkyl, each substituted with 0, 1, 2, 3, 4, or 5 substituents each independently selected from $C_{1-6}$ alkyl, $C_{1-6}$haloalkyl, $C_{1-6}$alkoxy, $C_{1-6}$ haloalkoxy, amino, $C_{1-6}$ alkylamino, $C_{2-8}$ dialkylamino, halo, CN, and OH; $Y^2$— is absent or selected from $C_{1-6}$ alkylenyl, O, C(O), C(O)O, C(O)NH, C(O)N($C_{1-6}$ alkyl), and S(O)$_2$; and $Z^2$ is selected from H, halo, CN, OH, $C_{1-6}$ alkoxy, $C_{1-6}$haloalkoxy, amino, $C_{1-6}$ alkylamino, $C_{2-8}$dialkylamino, $C_{1-6}$ alkyl, aryl, cycloalkyl, heteroaryl, heterocycloalkyl, arylalkyl, heteroarylalkyl, cycloalkylalkyl, and heterocycloalkylalkyl, wherein each of the $C_{1-6}$ alkyl, aryl, cycloalkyl, heteroaryl, heterocycloalkyl, arylalkyl, heteroarylalkyl, cycloalkylalkyl, and heterocycloalkylalkyl is substituted with 0, 1, 2, or 3 substituents each independently selected from halo, CN, OH, $C_{1-6}$ alkoxy, $C_{1-6}$ haloalkoxy, $C_{1-6}$ alkyl, $C_{1-6}$ haloalkyl,amino, $C_{1-6}$ alkylamino, $C_{2-8}$dialkylamino, C(O)NH$_2$, C(O)NH($C_{1-6}$ alkyl), and C(O)N($C_{1-6}$ alkyl)$_2$.

In some embodiments, at least one substituent —$W^{2a}$—$X^{2a}$—$W^2$—$X^2$—$Y^2$—$Z^2$ is a —$W^{2a}$—$X^{2a}$—$W^2$—$X^2$—$Y^2$—$Z^2$ wherein $W^{2a}$ is selected from O, NH, C(O), C(O)NH, C(O)N($C_{1-6}$ alkyl), and OC(O)NH; $X^{2a}$ is heteroaryl or heterocycloalkyl, each substituted with 0, 1, 2, 3, 4, or 5 substituents each independently selected from $C_{1-6}$ alkyl, $C_{1-6}$haloalkyl, $C_{1-6}$ alkoxy, $C_{1-6}$ haloalkoxy, amino, $C_{1-6}$ alkylamino, $C_{2-8}$ dialkylamino, halo, CN, and OH; $W^2$— is absent or selected from $C_{1-6}$ alkylenyl, —C(O)—, —C(O)O—, —C(O)NH—, —C(O)N($C_{1-6}$alkyl)-, $X^2$ is absent or selected from $C_{1-6}$ alkyl, aryl, cycloalkyl, heteroaryl, heterocycloalkyl, cycloalkylalkyl, and heterocycloalkylalkyl, each substituted with 0, 1, 2, 3, 4, or 5 substituents each independently selected from $C_{1-6}$ alkyl, $C_{1-6}$haloalkyl, $C_{1-6}$ alkoxy, $C_{1-6}$haloalkoxy, amino, $C_{1-6}$ alkylamino, $C_{2-8}$ dialkylamino, halo, CN, and OH; $Y^2$— is absent or selected from $C_{1-6}$ alkylenyl, C(O), C(O)O, C(O)NH, C(O)N($C_{1-6}$ alkyl), and S(O)$_2$; $Z^2$ is selected from H, halo, CN, OH, $C_{1-6}$ alkoxy, $C_{1-6}$ haloalkoxy, amino, $C_{1-6}$ alkylamino, $C_{2-8}$ dialkylamino, $C_{1-6}$ alkyl, aryl, cycloalkyl, heteroaryl, heterocycloalkyl, arylalkyl, heteroarylalkyl, cycloalkylalkyl, and heterocycloalkylalkyl, wherein each of the $C_{1-6}$ alkyl, aryl, cycloalkyl, heteroaryl, heterocycloalkyl, arylalkyl, heteroarylalkyl, cycloalkylalkyl, and heterocycloalkylalkyl is substituted with 0, 1, 2, or 3 substituents each independently selected from halo, CN, OH, $C_{1-6}$ alkoxy, $C_{1-6}$haloalkoxy, $C_{1-6}$ alkyl, $C_{1-6}$haloalkyl,amino, $C_{1-6}$ alkylamino, $C_{2-8}$ dialkylamino, C(O)NH$_2$, C(O)NH($C_{1-6}$ alkyl), and C(O)N($C_{1-6}$alkyl)$_2$.

In some embodiments, at least one substituent —$W^{2a}$—$X^{2a}$—$W^2$—$X^2$—$Y^2$—$Z^2$ is a —$W^{2a}$—$X^{2a}$—$W^2$—$X^2$—$Y^2$—$Z^2$ wherein $W^{2a}$ is absent; $X^{2a}$ is heteroaryl or heterocycloalkyl, each substituted with 0, 1, 2, or 3 substituents each independently selected from $C_{1-6}$ alkyl, halo, CN, and OH; $W^2$— is absent or selected from $C_{1-6}$ alkylenyl, C(O)NH, and C(O)N($C_{1-6}$ alkyl); $X^2$ is absent or selected from $C_{1-6}$ alkyl, cycloalkyl, heteroaryl, heterocycloalkyl, cycloalkylalkyl, and heterocycloalkylalkyl, each substituted with 0, 1, 2, 3, 4, or 5 substituents each independently selected from $C_{1-6}$ alkyl, $C_{1-6}$haloalkyl, $C_{1-6}$ alkoxy, $C_{1-6}$ haloalkoxy, amino, $C_{1-6}$ alkylamino, $C_{2-8}$ dialkylamino, halo, CN, and OH; $Y^2$— is absent or selected from $C_{1-6}$ alkylenyl, O, C(O), C(O)O, C(O)NH, C(O)N($C_{1-6}$ alkyl), and S(O)$_2$; $Z^2$ is selected from H, halo, CN, OH, $C_{1-6}$ alkoxy, $C_{1-6}$haloalkoxy, amino, $C_{1-6}$ alkylamino, $C_{2-8}$ dialkylamino, $C_{1-6}$ alkyl, aryl, cycloalkyl, heteroaryl, heterocycloalkyl, arylalkyl, heteroarylalkyl, cycloalkylalkyl, and heterocycloalkylalkyl, wherein each of the $C_{1-6}$ alkyl, aryl, cycloalkyl, heteroaryl, heterocycloalkyl, arylalkyl, heteroarylalkyl, cycloalkylalkyl, and heterocycloalkylalkyl is substituted with 0, 1, 2, or 3 substituents each independently selected from halo, CN, OH, $C_{1-6}$ alkoxy, $C_{1-6}$haloalkoxy, $C_{1-6}$ alkyl, $C_{1-6}$haloalkyl,amino, $C_{1-6}$ alkylamino, $C_{2-8}$ dialkylamino, C(O)NH$_2$, C(O)NH($C_{1-6}$ alkyl), and C(O)N($C_{1-6}$alkyl)$_2$. In some further embodiments, $X^{2a}$ is heteroaryl substituted with 0, 1, 2, or 3 substituents each independently selected from $C_{1-6}$ alkyl, halo, CN, and OH. In yet further embodiments, $X^{2a}$ is selected from pyridinyl, pyrazolyl, pyrrolyl, pyrimidinyl, and 1,3-thiazolyl, each substituted with 0, 1, 2, or 3 substituents each independently selected from $C_{1-6}$ alkyl, halo, CN, and OH.

In some embodiments, at least one substituent —$W^{2a}$—$X^{2a}$—$W^2$—$X^2$—$Y^2$—$Z^2$ is a $W^{2a}$—$X^{2a}$—$W^2$—$X^2$—$Y^2$—$Z^2$ wherein $W^{2a}$ is absent or selected from O, NH, N($C_{1-6}$ alkyl), C(O), C(O)NH, C(O)N($C_{1-6}$ alkyl), and OC(O)NH; $X^{2a}$ is aryl substituted with 0, 1, 2, 3, 4, or 5 substituents each independently selected from $C_{1-6}$ alkyl, $C_{1-6}$haloalkyl, $C_{1-6}$ alkoxy, $C_{1-6}$haloalkoxy, amino, $C_{1-6}$ alkylamino, $C_{2-8}$ dialkylamino, halo, CN, and OH; $W^2$— is absent or selected from $C_{1-6}$ alkylenyl, —C(O)—, —C(O)O—, —C(O)NH—, —C(O)N($C_{1-6}$ alkyl)—, $X^2$ is absent or selected from $C_{1-6}$ alkyl, aryl, cycloalkyl, heteroaryl, heterocycloalkyl, cycloalkylalkyl, and heterocycloalkylalkyl, each substituted with 0, 1, 2, 3, 4, or 5 substituents each independently selected from $C_{1-6}$ alkyl, $C_{1-6}$ haloalkyl, $C_{1-6}$ alkoxy, $C_{1-6}$haloalkoxy, amino, $C_{1-6}$ alkylamino, $C_{2-8}$ dialkylamino, halo, CN, and OH; $Y^2$— is absent or selected from $C_{1-6}$ alkylenyl, O, C(O), C(O)O, C(O)NH, C(O)N($C_{1-6}$ alkyl), and S(O)$_2$; $Z^2$ is selected from H, halo, CN, OH, $C_{1-6}$ alkoxy, $C_{1-6}$ haloalkoxy, amino, $C_{1-6}$ alkylamino, $C_{2-8}$ dialkylamino, $C_{1-6}$ alkyl, aryl, cycloalkyl, heteroaryl, heterocycloalkyl, arylalkyl, heteroarylalkyl, cycloalkylalkyl, and heterocycloalkylalkyl, wherein each of the $C_{1-6}$ alkyl, aryl, cycloalkyl, heteroaryl, heterocycloalkyl, arylalkyl, heteroarylalkyl, cycloalkylalkyl, and heterocycloalkylalkyl is substituted with 0, 1, 2, or 3 substituents each independently selected from halo, CN, OH, $C_{1-6}$alkoxy, In some embodiments, at least one substituent —$W^{2a}$—$X^{2a}$—$W^2$—$X^2$—$Y^2$—$Z^2$ is a —$W^{2a}$—$X^{2a}$—$W^2$—$X^2$—$Y^2$—$Z^2$ wherein $W^{2a}$ is absent; $X^{2a}$ is aryl substituted with 0, 1, 2, 3, 4, or 5 substituents each independently selected from $C_{1-6}$ alkyl, $C_{1-6}$haloalkyl, $C_{1-6}$ alkoxy, $C_{1-6}$ haloalkoxy, amino, $C_{1-6}$ alkylamino, $C_{2-8}$ dialkylamino, halo, CN, and OH; $W^2$— is absent or selected from $C_{1-6}$ alkylenyl, —C(O)—, —C(O)O—, —C(O)NH—, —C(O)N($C_{1-6}$ alkyl)—, $X^2$ is absent or selected from $C_{1-6}$ alkyl, aryl, cycloalkyl, heteroaryl, heterocycloalkyl, cycloalkylalkyl, and heterocycloalkylalkyl, each substituted with 0, 1, 2, 3, 4, or 5 substituents each independently selected from $C_{1-6}$ alkyl, $C_{1-6}$haloalkyl, $C_{1-6}$ alkoxy, $C_{1-6}$haloalkoxy, amino, $C_{1-6}$ alkylamino, $C_{2-8}$ dialkylamino, halo, CN, and OH; $Y^2$— is absent or selected from $C_{1-6}$ alkylenyl, O, C(O), C(O)O, C(O)NH, C(O)N($C_{1-6}$ alkyl), and S(O)$_2$; $Z^2$ is selected from H, halo, CN, OH, $C_{1-6}$ alkoxy, $C_{1-6}$ haloalkoxy, amino, $C_{1-6}$ alkylamino, $C_{2-8}$dialkylamino, $C_{1-6}$ alkyl, aryl, cycloalkyl, heteroaryl, heterocycloalkyl, arylalkyl, heteroarylalkyl, cycloalkylalkyl, and heterocycloalkylalkyl, wherein each of the $C_{1-6}$ alkyl, aryl, cycloalkyl, heteroaryl, heterocycloalkyl, arylalkyl, heteroarylalkyl, cycloalkylalkyl, and heterocycloalkylalkyl is substituted with 0, 1, 2, or 3 substituents each independently selected from halo, CN, OH, $C_{1-6}$alkoxy, $C_{1-6}$haloalkoxy, $C_{1-6}$ alkyl, $C_{1-6}$haloalkyl,amino, $C_{1-6}$ alkylamino, $C_{2-8}$ dialkylamino, $C(O)NH_2$, $C(O)NH(C_{1-6}$ alkyl), and $C(O)N(C_{1-6}$alkyl$)_2$.

In some embodiments, at least one substituent —$W^{2a}$—$X^{2a}$—$W^2$—$X^2$—$Y^2$—$Z^2$ is a —$W^{2a}$—$X^{2a}$—$W^2$—$X^2$—$Y^2$—$Z^2$ wherein $W^{2a}$ is selected from O, NH, N($C_{1-6}$ alkyl), C(O), C(O)NH, C(O)N($C_{1-6}$ alkyl), and OC(O)NH; $X^{2a}$ is aryl substituted with 0, 1, 2, 3, 4, or 5 substituents each independently selected from $C_{1-6}$ alkyl, $C_{1-6}$ haloalkyl, $C_{1-6}$ alkoxy, $C_{1-6}$ haloalkoxy, amino, $C_{1-6}$ alkylamino, $C_{2-8}$dialkylamino, halo, CN, and OH; $W^2$— is absent or selected from $C_{1-6}$ alkylenyl, —C(O)—, —C(O)O—, —C(O)NH—, —C(O)N($C_{1-6}$alkyl)—, $X^2$ is absent or selected from $C_{1-6}$ alkyl, aryl, cycloalkyl, heteroaryl, heterocycloalkyl, cycloalkylalkyl, and heterocycloalkylalkyl, each substituted with 0, 1, 2, 3, 4, or 5 substituents each independently selected from $C_{1-6}$ alkyl, $C_{1-6}$ haloalkyl, $C_{1-6}$ alkoxy, $C_{1-6}$ haloalkoxy, amino, $C_{1-6}$ alkylamino, $C_{2-8}$ dialkylamino, halo, CN, and OH; $Y^2$— is absent or selected from $C_{1-6}$ alkylenyl, O, C(O), C(O)O, C(O)NH, C(O)N($C_{1-6}$ alkyl), and S(O)$_2$; $Z^2$ is selected from H, halo, CN, OH, $C_{1-6}$ alkoxy, $C_{1-6}$ haloalkoxy, amino, $C_{1-6}$ alkylamino, $C_{2-8}$ dialkylamino, $C_{1-6}$ alkyl, aryl, cycloalkyl, heteroaryl, heterocycloalkyl, arylalkyl, heteroarylalkyl, cycloalkylalkyl, and heterocycloalkylalkyl, wherein each of the $C_{1-6}$ alkyl, aryl, cycloalkyl, heteroaryl, heterocycloalkyl, arylalkyl, heteroarylalkyl, cycloalkylalkyl, and heterocycloalkylalkyl is substituted with 0, 1, 2, or 3 substituents each independently selected from halo, CN, OH, $C_{1-6}$ alkoxy, $C_{1-6}$haloalkoxy, $C_{1-6}$ alkyl, $C_{1-6}$haloalkyl,amino, $C_{1-6}$ alkylamino, $C_{2-8}$ dialkylamino, $C(O)NH_2$, C(O)NH($C_{1-6}$ alkyl), and $C(O)N(C_{1-6}$alkyl$)_2$.

In some embodiments, at least one substituent —$W^{2a}$—$X^{2a}$—$W^2$—$X^2$—$Y^2$—$Z^2$ is a —$W^{2a}$—$X^{2a}$—$W^2$—$X^2$—$Y^2$—$Z^2$ wherein $W^{2a}$ is absent; $X^{2a}$ is heteroaryl or heterocycloalkyl, each substituted with 0, 1, 2, or 3 substituents each independently selected from $C_{1-6}$ alkyl, halo, CN, and OH; $W^2$— is absent or selected from $C_{1-6}$ alkylenyl, C(O)NH, and C(O)N($C_{1-6}$ alkyl); $X^2$ is absent or selected from $C_{1-6}$ alkyl, cycloalkyl, heteroaryl, heterocycloalkyl, cycloalkylalkyl, and heterocycloalkylalkyl, each substituted with 0, 1, 2, 3, 4, or 5 substituents each independently selected from $C_{1-6}$ alkyl, $C_{1-6}$ haloalkyl, $C_{1-6}$ alkoxy, $C_{1-6}$ haloalkoxy, amino, $C_{1-6}$ alkylamino, $C_{2-8}$ dialkylamino, halo, CN, and OH; $Y^2$— is absent or selected from $C_{1-6}$ alkylenyl, O, C(O), C(O)O, C(O)NH, C(O)N($C_{1-6}$ alkyl), and S(O)$_2$; and $Z^2$ is selected from H, halo, CN, OH, $C_{1-6}$ alkoxy, $C_{1-6}$haloalkoxy, amino, $C_{1-6}$ alkylamino, $C_{2-8}$dialkylamino, $C_{1-6}$ alkyl, aryl, cycloalkyl, heteroaryl, heterocycloalkyl, arylalkyl, heteroarylalkyl, cycloalkylalkyl, and heterocycloalkylalkyl, wherein each of the $C_{1-6}$ alkyl, aryl, cycloalkyl, heteroaryl, heterocycloalkyl, arylalkyl, heteroarylalkyl, cycloalkylalkyl, and heterocycloalkylalkyl is substituted with 0, 1, 2, or 3 substituents each independently selected from halo, CN, OH, $C_{1-6}$ alkoxy, $C_{1-6}$ haloalkoxy, $C_{1-6}$ alkyl, $C_{1-6}$ haloalkyl,amino, $C_{1-6}$ alkylamino, $C_{2-8}$dialkylamino, $C(O)NH_2$, C(O)NH($C_{1-6}$ alkyl), and $C(O)N(C_{1-6}$ alkyl$)_2$ In some embodiments, at least one substituent —$W^{2a}$—$X^{2a}$—$W^2$—$X^2$—$Y^2$—$Z^2$ is a —$W^{2a}$—$X^{2a}$—$W^2$—$X^2$—$Y^2$—$Z^2$ wherein $W^{2a}$ is absent; $X^{2a}$ is heteroaryl (for example a 5-membered heteroaryl, 6-membered heteroaryl, a 9-membered heteroaryl, or a 10-membered heteroaryl) substituted with 0, 1, 2, or 3 substituents each independently selected from $C_{1-6}$ alkyl, halo, CN, and OH; $W^2$— is absent or selected from $C_{1-6}$ alkylenyl, C(O)NH, and C(O)N($C_{1-6}$ alkyl); $X^2$ is absent or selected from $C_{1-6}$ alkyl, cycloalkyl, heteroaryl, heterocycloalkyl, cycloalkylalkyl, and heterocycloalkylalkyl, each substituted with 0, 1, 2, 3, 4, or 5 substituents each independently selected from $C_{1-6}$ alkyl, $C_{1-6}$haloalkyl, $C_{1-6}$ alkoxy, $C_{1-6}$ haloalkoxy, amino, $C_{1-6}$ alkylamino, $C_{2-8}$ dialkylamino, halo, CN, and OH; $Y^2$— is absent or selected from $C_{1-6}$ alkylenyl, O, C(O), C(O)O, C(O)NH, C(O)N($C_{1-6}$ alkyl), and S(O)$_2$; and $Z^2$ is selected from H, halo, CN, OH, $C_{1-6}$ alkoxy, $C_{1-6}$haloalkoxy, amino, $C_{1-6}$ alkylamino, $C_{2-8}$dialkylamino, $C_{1-6}$ alkyl, aryl, cycloalkyl, heteroaryl, heterocycloalkyl, arylalkyl, heteroarylalkyl, cycloalkylalkyl, and heterocycloalkylalkyl, wherein each of the $C_{1-6}$ alkyl, aryl, cycloalkyl, heteroaryl, heterocycloalkyl, arylalkyl, heteroarylalkyl, cycloalkylalkyl, and heterocycloalkylalkyl is substituted with 0, 1, 2, or 3 substituents each independently selected from halo, CN, OH, $C_{1-6}$ alkoxy, $C_{1-6}$ haloalkoxy, $C_{1-6}$ alkyl, $C_{1-6}$ haloalkyl, amino, $C_{1-6}$ alkylamino, $C_{2-8}$ dialkylamino, $C(O)NH_2$, C(O)NH($C_{1-6}$ alkyl), and $C(O)N(C_{1-6}$alkyl$)_2$.

In some embodiments, at least one substituent —$W^{2a}$—$X^{2a}$—$W^2$—$X^2$—$Y^2$—$Z^2$ is a —$W^{2a}$—$X^{2a}$—$W^2$—$X^2$—$Y^2$—$Z^2$ wherein $W^{2a}$ is absent; $X^{2a}$ is selected from pyridinyl, pyrazolyl, pyrrolyl, pyrimidinyl, 1,3-thiazolyl, and 3H-imidazo[4,5-b]pyridinyl, each substituted with 0, 1, 2, or 3 substituents each independently selected from $C_{1-6}$ alkyl, halo, CN, and OH; $W^2$— is absent or selected from $C_{1-6}$ alkylenyl, C(O)NH, and C(O)N($C_{1-6}$ alkyl); $X^2$ is absent or selected from $C_{1-6}$ alkyl, cycloalkyl, heteroaryl, heterocycloalkyl, cycloalkylalkyl, and heterocycloalkylalkyl, each substituted with 0, 1, 2, 3, 4, or 5 substituents each independently selected from $C_{1-6}$ alkyl, $C_{1-6}$haloalkyl, $C_{1-6}$ alkoxy, $C_{1-6}$ haloalkoxy, amino, $C_{1-6}$ alkylamino, $C_{2-8}$ dialkylamino, halo, CN, and OH; $Y^2$— is absent or selected from $C_{1-6}$ alkylenyl, O, C(O), C(O)O, C(O)NH, C(O)N($C_{1-6}$ alkyl), and S(O)$_2$; and $Z^2$ is selected from H, halo, CN, OH, $C_{1-6}$ alkoxy, $C_{1-6}$ haloalkoxy, amino, $C_{1-6}$ alkylamino, $C_{2-8}$ dialkylamino, $C_{1-6}$ alkyl, aryl, cycloalkyl, heteroaryl, heterocycloalkyl, arylalkyl, heteroarylalkyl, cycloalkylalkyl, and heterocycloalkylalkyl, wherein each of the $C_{1-6}$ alkyl, aryl, cycloalkyl, heteroaryl, heterocycloalkyl, arylalkyl, heteroarylalkyl, cycloalkylalkyl, and heterocycloalkylalkyl is substituted with 0, 1, 2, or 3 substituents each independently selected from halo, CN, OH, $C_{1-6}$ alkoxy, $C_{1-6}$haloalkoxy, $C_{1-6}$ alkyl, $C_{1-6}$ haloalkyl, amino, $C_{1-6}$ alkylamino, $C_{2-8}$ dialkylamino, $C(O)NH_2$, C(O)NH($C_{1-6}$ alkyl), and $C(O)N(C_{1-6}$alkyl$)_2$.

In some embodiments, at least one substituent —$W^{2a}$—$X^{2a}$—$W^2$—$X^2$—$Y^2$—$Z^2$ is a —$W^{2a}$—$X^{2a}$—$W^2$—$X^2$—$Y^2$—$Z^2$ wherein $W^{2a}$ is absent, C(O), or C(O)NH; $X^{2a}$ is heterocycloalkyl substituted with 0, 1, 2, or 3 substituents each independently selected from $C_{1-6}$ alkyl, halo, CN, and OH; $W^2$— is absent or selected from $C_{1-6}$ alkylenyl, C(O)NH, and C(O)N($C_{1-6}$ alkyl); $X^2$ is absent or selected from $C_{1-6}$ alkyl, cycloalkyl, heteroaryl, heterocycloalkyl, cycloalkylalkyl, and heterocycloalkylalkyl, each substituted with 0, 1, 2, 3, 4, or 5 substituents each independently selected from $C_{1-6}$ alkyl, $C_{1-6}$haloalkyl, $C_{1-6}$ alkoxy, $C_{1-6}$ haloalkoxy, amino, $C_{1-6}$ alkylamino, $C_{2-8}$ dialkylamino, halo, CN, and OH; $Y^2$— is absent or selected from $C_{1-6}$ alkylenyl, O, C(O), C(O)O, C(O)NH, C(O)N($C_{1-6}$ alkyl), and S(O)$_2$; and $Z^2$ is selected from H, halo, CN, OH, $C_{1-6}$ alkoxy, $C_{1-6}$haloalkoxy, amino, $C_{1-6}$ alkylamino, $C_{2-8}$dialkylamino, $C_{1-6}$ alkyl, aryl, cycloalkyl, heteroaryl, heterocycloalkyl, arylalkyl, heteroarylalkyl, cycloalkylalkyl, and heterocycloalkylalkyl, wherein each of the $C_{1-6}$ alkyl, aryl, cycloalkyl, heteroaryl, heterocycloalkyl, arylalkyl, heteroarylalkyl, cycloalkylalkyl, and heterocycloalkylalkyl is substituted with 0, 1, 2, or 3 substituents each independently selected from halo, CN, OH, $C_{1-6}$ alkoxy, $C_{1-6}$ haloalkoxy, $C_{1-6}$ alkyl, $C_{1-6}$ haloalkyl, amino, $C_{1-6}$ alkylamino, $C_{2-8}$dialkylamino, $C(O)NH_2$, C(O)NH($C_{1-6}$ alkyl), and $C(O)N(C_{1-6}$ alkyl$)_2$.

In some embodiments, at least one substituent —$W^{2a}$—$X^{2a}$—$W^2$—$X^2$—$Y^2$—$Z^2$ is a —$W^{2a}$—$X^{2a}$—$W^2$—$X^2$—$Y^2$—$Z^2$ wherein $W^{2a}$ is absent; $X^{2a}$ is heterocycloalkyl substituted with 0, 1, 2, or 3 substituents each independently selected from $C_{1-6}$ alkyl, halo, CN, and OH; $W^2$— is absent or selected from $C_{1-6}$ alkylenyl, C(O)NH, and C(O)N($C_{1-6}$ alkyl); $X^2$ is absent or selected from $C_{1-6}$ alkyl, cycloalkyl, heteroaryl, heterocycloalkyl, cycloalkylalkyl, and heterocycloalkylalkyl, each substituted with 0, 1, 2, 3, 4, or 5 substituents each independently selected from $C_{1-6}$ alkyl, $C_{1-6}$haloalkyl, $C_{1-6}$ alkoxy, $C_{1-6}$haloalkoxy, amino, $C_{1-6}$ alkylamino, $C_{2-8}$ dialkylamino, halo, CN, and OH; $Y^2$— is absent or selected from $C_{1-6}$ alkylenyl, O, C(O), C(O)O, C(O)NH, C(O)N($C_{1-6}$ alkyl), and S(O)$_2$; and $Z^2$ is selected from H, halo, CN, OH, $C_{1-6}$ alkoxy, $C_{1-6}$ haloalkoxy, amino, $C_{1-6}$ alkylamino, $C_{2-8}$dialkylamino, $C_{1-6}$ alkyl, aryl, cycloalkyl, heteroaryl, heterocycloalkyl, arylalkyl, heteroarylalkyl, cycloalkylalkyl, and heterocycloalkylalkyl, wherein each of the $C_{1-6}$ alkyl, aryl, cycloalkyl, heteroaryl, heterocycloalkyl, arylalkyl, heteroarylalkyl, cycloalkylalkyl, and heterocycloalkylalkyl is substituted with 0, 1, 2, or 3 substituents each independently selected from halo, CN, OH, $C_{1-6}$ alkoxy, $C_{1-6}$haloalkoxy, $C_{1-6}$ alkyl, $C_{1-6}$ haloalkyl,amino, $C_{1-6}$ alkylamino, $C_{2-8}$ dialkylamino, C(O)NH$_2$, C(O)NH($C_{1-6}$ alkyl), and C(O)N($C_{1-6}$alkyl)$_2$.

In some embodiments, at least one substituent —$W^{2a}$—$X^{2a}$—$W^2$—$X^2$—$Y^2$—$Z^2$ is a —$W^{2a}$—$X^{2a}$—$W^2$—$X^2$—$Y^2$—$Z^2$ wherein $W^{2a}$ is absent, C(O), C(O)NH; $X^{2a}$ is selected from piperidinyl, piperazinyl, 1,2,3,6-tetrahydropyridinyl, 2-oxo-piperazinyl, 2(1H)-oxo-pyridinyl, 1-oxo-isoindolinyl, isoindolinyl, pyrrolidinyl, and 2H-3(4H)-oxo-benzo[b][1,4]oxazinyl, each substituted with 0, 1, 2, or 3 substituents each independently selected from $C_{1-6}$ alkyl, halo, CN, and OH; $W^2$— is absent or selected from $C_{1-6}$ alkylenyl, C(O)NH, and C(O)N($C_{1-6}$ alkyl); $X^2$ is absent or selected from $C_{1-6}$ alkyl, cycloalkyl, heteroaryl, heterocycloalkyl, cycloalkylalkyl, and heterocycloalkylalkyl, each substituted with 0, 1, 2, 3, 4, or 5 substituents each independently selected from $C_{1-6}$ alkyl, $C_{1-6}$haloalkyl, $C_{1-6}$ alkoxy, $C_{1-6}$haloalkoxy, amino, $C_{1-6}$ alkylamino, $C_{2-8}$ dialkylamino, halo, CN, and OH; $Y^2$— is absent or selected from $C_{1-6}$ alkylenyl, O, C(O), C(O)O, C(O)NH, C(O)N($C_{1-6}$ alkyl), and S(O)$_2$; and $Z^2$ is selected from H, halo, CN, OH, $C_{1-6}$ alkoxy, $C_{1-6}$ haloalkoxy, amino, $C_{1-6}$ alkylamino, $C_{2-8}$ dialkylamino, $C_{1-6}$ alkyl, aryl, cycloalkyl, heteroaryl, heterocycloalkyl, arylalkyl, heteroarylalkyl, cycloalkylalkyl, and heterocycloalkylalkyl, wherein each of the $C_{1-6}$ alkyl, aryl, cycloalkyl, heteroaryl, heterocycloalkyl, arylalkyl, heteroarylalkyl, cycloalkylalkyl, and heterocycloalkylalkyl is substituted with 0, 1, 2, or 3 substituents each independently selected from halo, CN, OH, $C_{1-6}$ alkoxy, $C_{1-6}$haloalkoxy, $C_{1-6}$ alkyl, $C_{1-6}$haloalkyl,amino, $C_{1-6}$ alkylamino, $C_{2-8}$ dialkylamino, C(O)NH$_2$, C(O)NH($C_{1-6}$ alkyl), and C(O)N($C_{1-6}$alkyl)$_2$.

In some embodiments, at least one substituent —$W^{2a}$—$X^{2a}$—$W^2$—$X^2$—$Y^2$—$Z^2$ is a —$W^{2a}$—$X^{2a}$—$W^2$—$X^2$—$Y^2$—$Z^2$ wherein $W^{2a}$ is absent; $X^{2a}$ is selected from piperidinyl, piperazinyl, 1,2,3,6-tetrahydropyridinyl, 2-oxo-piperazinyl, 2(1H)-oxo-pyridinyl, 1-oxo-isoindolinyl, isoindolinyl, pyrrolidinyl, and 2H-3(4H)-oxo-benzo[b][1,4]oxazinyl, each substituted with 0, 1, 2, or 3 substituents each independently selected from $C_{1-6}$ alkyl, halo, CN, and OH; $W^2$— is absent or selected from $C_{1-6}$ alkylenyl, C(O)NH, and C(O)N($C_{1-6}$ alkyl); $X^2$ is absent or selected from $C_{1-6}$ alkyl, cycloalkyl, heteroaryl, heterocycloalkyl, cycloalkylalkyl, and heterocycloalkylalkyl, each substituted with 0, 1, 2, 3, 4, or 5 substituents each independently selected from $C_{1-6}$ alkyl, $C_{1-6}$haloalkyl, $C_{1-6}$ alkoxy, $C_{1-6}$ haloalkoxy, amino, $C_{1-6}$ alkylamino, $C_{2-8}$ dialkylamino, halo, CN, and OH; $Y^2$— is absent or selected from $C_{1-6}$ alkylenyl, O, C(O), C(O)O, C(O)NH, C(O)N($C_{1-6}$ alkyl), and S(O)$_2$; and $Z^2$ is selected from H, halo, CN, OH, $C_{1-6}$ alkoxy, $C_{1-6}$ haloalkoxy, amino, $C_{1-6}$ alkylamino, $C_{2-8}$ dialkylamino, $C_{1-6}$ alkyl, aryl, cycloalkyl, heteroaryl, heterocycloalkyl, arylalkyl, heteroarylalkyl, cycloalkylalkyl, and heterocycloalkylalkyl, wherein each of the $C_{1-6}$ alkyl, aryl, cycloalkyl, heteroaryl, heterocycloalkyl, arylalkyl, heteroarylalkyl, cycloalkylalkyl, and heterocycloalkylalkyl is substituted with 0, 1, 2, or 3 substituents each independently selected from halo, CN, OH, $C_{1-6}$ alkoxy, $C_{1-6}$haloalkoxy, $C_{1-6}$ alkyl, $C_{1-6}$haloalkyl,amino, $C_{1-6}$ alkylamino, $C_{2-8}$ dialkylamino, C(O)NH$_2$, C(O)NH($C_{1-6}$ alkyl), and C(O)N($C_{1-6}$alkyl)$_2$.

In some embodiments, at least one substituent —$W^{2a}$—$X^{2a}$—$W^2$—$X^2$—$Y^2$—$Z^2$ is a —$W^{2a}$—$X^{2a}$—$W^2$—$X^2$—$Y^2$—$Z^2$ wherein $W^{2a}$ is absent; $X^{2a}$ is heterocycloalkyl substituted with 0, 1, 2, or 3 substituents each independently selected from $C_{1-6}$ alkyl, halo, CN, and OH; $W^2$— is absent or selected from $C_{1-6}$ alkylenyl, C(O)NH, and C(O)N($C_{1-6}$ alkyl); $X^2$ is absent or selected from $C_{1-6}$ alkyl, cycloalkyl, heteroaryl, heterocycloalkyl, cycloalkylalkyl, and heterocycloalkylalkyl, each substituted with 0, 1, 2, 3, 4, or 5 substituents each independently selected from $C_{1-6}$ alkyl, $C_{1-6}$haloalkyl, $C_{1-6}$ alkoxy, $C_{1-6}$haloalkoxy, amino, $C_{1-6}$ alkylamino, $C_{2-8}$ dialkylamino, halo, CN, and OH; $Y^2$— is absent or selected from $C_{1-6}$ alkylenyl, C(O), C(O)O, C(O)NH, C(O)N ($C_{1-6}$ alkyl), and S(O)$_2$; and $Z^2$ is selected from H, halo, CN, OH, $C_{1-6}$ alkoxy, $C_{1-6}$ haloalkoxy, amino, $C_{1-6}$ alkylamino, $C_{2-8}$dialkylamino, $C_{1-6}$ alkyl, aryl, cycloalkyl, heteroaryl, heterocycloalkyl, arylalkyl, heteroarylalkyl, cycloalkylalkyl, and heterocycloalkylalkyl, wherein each of the $C_{1-6}$ alkyl, aryl, cycloalkyl, heteroaryl, heterocycloalkyl, arylalkyl, heteroarylalkyl, cycloalkylalkyl, and heterocycloalkylalkyl is substituted with 0, 1, 2, or 3 substituents each independently selected from halo, CN, OH, $C_{1-6}$ alkoxy, $C_{1-6}$haloalkoxy, $C_{1-6}$ alkyl, $C_{1-6}$haloalkyl,amino, $C_{1-6}$ alkylamino, $C_{2-8}$ dialkylamino, C(O)NH$_2$, C(O)NH($C_{1-6}$ alkyl), and C(O)N ($C_{1-6}$alkyl)$_2$ In some embodiments, at least one substituent —$W^{2a}$—$X^{2a}$—$W^2$—$X^2$—$Y^2$—$Z^2$ is a —$W^{2a}$—$X^{2a}$—$W^2$—$X^2$—$Y^2$—$Z^2$ wherein $W^{2a}$ is absent; $X^{2a}$ is $X^{2a}$ is selected from piperidinyl, piperazinyl, 1,2,3,6-tetrahydropyridinyl, 2-oxo-piperazinyl, 2(1H)-oxo-pyridinyl, 1-oxo-isoindolinyl, and 2H-3(4H)-oxo-benzo[b][1,4]oxazinyl, OH; $W^2$— is absent or selected from $C_{1-6}$ alkylenyl, C(O)NH, and C(O)N($C_{1-6}$ alkyl); $X^2$ is absent or selected from $C_{1-6}$ alkyl, cycloalkyl, heteroaryl, heterocycloalkyl, cycloalkylalkyl, and heterocycloalkylalkyl, each substituted with 0, 1, 2, 3, 4, or 5 substituents each independently selected from $C_{1-6}$ alkyl, $C_{1-6}$ haloalkyl, $C_{1-6}$ alkoxy, $C_{1-6}$ haloalkoxy, amino, $C_{1-6}$ alkylamino, $C_{2-8}$ dialkylamino, halo, CN, and OH; $Y^2$— is absent or selected from $C_{1-6}$ alkylenyl, O, C(O), C(O)O, C(O)NH, C(O)N($C_{1-6}$ alkyl), and S(O)$_2$; and $Z^2$ is selected from H, halo, CN, OH, $C_{1-6}$ alkoxy, $C_{1-6}$ haloalkoxy, amino, $C_{1-6}$ alkylamino, $C_{2-8}$ dialkylamino, $C_{1-6}$ alkyl, aryl, cycloalkyl, heteroaryl, heterocycloalkyl, arylalkyl, heteroarylalkyl, cycloalkylalkyl, and heterocycloalkylalkyl, wherein each of the $C_{1-6}$ alkyl, aryl, cycloalkyl, heteroaryl, heterocycloalkyl, arylalkyl, heteroarylalkyl, cycloalkylalkyl, and heterocycloalkylalkyl is substituted with 0, 1, 2, or 3 substituents each independently selected from halo, CN, OH, $C_{1-6}$ alkoxy, $C_{1-6}$haloalkoxy, $C_{1-6}$ alkyl, $C_{1-6}$haloalkyl,amino, $C_{1-6}$ alkylamino, $C_{2-8}$ dialkylamino, C(O)NH$_2$, C(O)NH($C_{1-6}$ alkyl), and C(O)N($C_{1-6}$alkyl)$_2$.

In some embodiments, at least one substituent —$W^{2a}$—$X^{2a}$—$W^2$—$X^2$—$Y^2$—$Z^2$ is a —$W^{2a}$—$X^{2a}$—$W^2$—$X^2$—

$Y^2$—$Z^2$ wherein $W^2$— is absent; $X^2$ is absent; $Y^2$— is absent or selected from $C_{1-6}$ alkylenyl, C(O), C(O)O, C(O)NH, C(O)N($C_{1-6}$ alkyl), and S(O)$_2$; and $Z^2$ is selected from H, halo, CN, OH, $C_{1-6}$ alkoxy, $C_{1-6}$ haloalkoxy, amino, $C_{1-6}$ alkylamino, $C_{2-8}$ dialkylamino, $C_{1-6}$ alkyl, aryl, cycloalkyl, heteroaryl, heterocycloalkyl, arylalkyl, heteroarylalkyl, cycloalkylalkyl, and heterocycloalkylalkyl, wherein each of the $C_{1-6}$ alkyl, aryl, cycloalkyl, heteroaryl, heterocycloalkyl, arylalkyl, heteroarylalkyl, cycloalkylalkyl, and heterocycloalkylalkyl is substituted with 0, 1, 2, or 3 substituents each independently selected from halo, CN, OH, $C_{1-6}$ alkoxy, $C_{1-6}$ haloalkoxy, $C_{1-6}$ alkyl, $C_{1-6}$haloalkyl,amino, $C_{1-6}$ alkylamino, $C_{1-8}$ dialkylamino, C(O)NH$_2$, C(O)NH($C_{1-6}$ alkyl), and C(O)N($C_{1-6}$alkyl)$_2$.

In some embodiments, at least one substituent —$W^{2a}$—$X^{2a}$—$W^2$—$X^2$—$Y^2$—$Z^2$ is a —$W^{2a}$—$X^{2a}$—$W^2$—$X^2$—$Y^2$—$Z^2$ wherein $W^2$— is absent; $X^2$ is absent; $Y^2$— is absent or selected from $C_{1-6}$ alkylenyl, C(O), C(O)O, C(O)NH, C(O)N($C_{1-6}$ alkyl), and S(O)$_2$; and $Z^2$ is selected from H, halo, CN, OH, $C_{1-6}$ alkoxy, $C_{1-6}$ haloalkoxy, amino, $C_{1-6}$ alkylamino, $C_{2-8}$ dialkylamino, $C_{1-6}$ alkyl, aryl, cycloalkyl, heteroaryl, heterocycloalkyl, arylalkyl, heteroarylalkyl, cycloalkylalkyl, and heterocycloalkylalkyl, wherein each of the $C_{1-6}$ alkyl, aryl, cycloalkyl, heteroaryl, heterocycloalkyl, arylalkyl, heteroarylalkyl, cycloalkylalkyl, and heterocycloalkylalkyl is substituted with 0, 1, 2, or 3 substituents each independently selected from halo, CN, OH, $C_{1-6}$ alkoxy, $C_{1-6}$haloalkoxy, $C_{1-6}$ alkyl, $C_{1-6}$haloalkyl,amino, $C_{1-6}$ alkylamino, $C_{2-8}$ dialkylamino, C(O)NH$_2$, C(O)NH($C_{1-6}$ alkyl), and C(O)N($C_{1-6}$alkyl)$_2$. In some further embodiments, at least one substituent —$W^{2a}$—$X^{2a}$—$W^2$—$X^2$—$Y^2$—$Z^2$ is a —$W^{2a}$—$X^{2a}$—$W^2$—$X^2$—$Y^2$—$Z^2$ wherein $X^{2a}$ is heterocycloalkyl substituted with 0, 1, 2, or 3 substituents each independently selected from $C_{1-6}$ alkyl, halo, CN, and OH. In yet further embodiments, at least one substituent —$W^{2a}$—$X^{2a}$—$W^2$—$X^2$—$Y^2$—$Z^2$ is a —$W^{2a}$—$X^{2a}$—$W^2$—$X^2$—$Y^2$—$Z^2$ wherein $X^{2a}$ is selected from piperidinyl, piperazinyl, 1,2,3,6-tetrahydropyridinyl, 2-oxo-piperazinyl, 2(1H)-oxo-pyridinyl, 1-oxo-isoindolinyl, and 2H-3(4H)-oxo-benzo[b][1,4]oxazinyl, each substituted with 0, 1, 2, or 3 substituents each independently selected from $C_{1-6}$ alkyl, halo, CN, and OH.

In some embodiments, at least one substituent —$W^{2a}$—$X^{2a}$—$W^2$—$X^2$—$Y^2$—$Z^2$ is a —$W^{2a}$—$X^{2a}$—$W^2$—$X^2$—$Y^2$—$Z^2$ wherein $W^2$— is absent; $X^2$ is absent; $Y^2$— is absent or selected from $C_{1-6}$ alkylenyl, C(O), C(O)O, C(O)NH, C(O)N($C_{1-6}$ alkyl), and S(O)$_2$; and $Z^2$ is selected from H, halo, CN, OH, $C_{1-6}$ alkoxy, $C_{1-6}$ haloalkoxy, amino, $C_{1-6}$ alkylamino, $C_{2-8}$ dialkylamino, $C_{1-6}$ alkyl, aryl, cycloalkyl, heteroaryl, heterocycloalkyl, arylalkyl, heteroarylalkyl, cycloalkylalkyl, and heterocycloalkylalkyl, wherein each of the $C_{1-6}$ alkyl, aryl, cycloalkyl, heteroaryl, heterocycloalkyl, arylalkyl, heteroarylalkyl, cycloalkylalkyl, and heterocycloalkylalkyl is substituted with 0, 1, 2, or 3 substituents each independently selected from halo, CN, OH, $C_{1-6}$ alkoxy, $C_{1-6}$haloalkoxy, $C_{1-6}$ alkyl, $C_{1-6}$haloalkyl,amino, $C_{1-6}$ alkylamino, $C_{2-8}$ dialkylamino, C(O)NH$_2$, C(O)NH($C_{1-6}$ alkyl), and C(O)N($C_{1-6}$alkyl)$_2$.

In some embodiments, $Z^2$ is selected from H, halo, CN, OH, $C_{1-6}$ alkoxy, $C_{1-6}$ haloalkoxy, amino, $C_{1-6}$ alkylamino, $C_{2-8}$ dialkylamino, $C_{1-6}$ alkyl, aryl (e.g. phenyl), cycloalkyl (e.g. cyclopropyl, cyclopentyl, or cyclohexyl), heteroaryl [e.g. pyridinyl (such as pyridin-2-yl, pyridin-3-yl, or pyridin-4-yl) or furanyl], heterocycloalkyl (e.g. azetidinyl, pyrrolidinyl, piperidinyl, piperazinyl, tetrahydrofuranyl, tetrahydro-2H-pyranyl, or S,S-di-oxo-tetrahydrothienyl), arylalkyl (e.g. benzyl), heteroarylalkyl (e.g. pyridin-2-ylmethyl or pyridin-3-ylmethyl), cycloalkylalkyl (e.g. cylcopropylmethyl, cyclobutylmethyl or cyclopentylmethyl), and heterocycloalkylalkyl (e.g. morpholinoethyl or tetrahydrofuran-2-ylmethyl), wherein each of the $C_{1-6}$ alkyl, aryl, cycloalkyl, heteroaryl, heterocycloalkyl, arylalkyl, heteroarylalkyl, cycloalkylalkyl, and heterocycloalkylalkyl is substituted with 0, 1, 2, or 3 substituents each independently selected from halo, CN, OH, $C_{1-6}$ alkoxy, $C_{1-6}$haloalkoxy, $C_{1-6}$ alkyl, $C_{1-6}$haloalkyl,amino, $C_{1-6}$ alkylamino, $C_{2-8}$ dialkylamino, C(O)NH$_2$, C(O)NH($C_{1-6}$ alkyl), and C(O)N($C_{1-6}$alkyl)$_2$.

In some embodiments, at least one substituent —$W^{2a}$—$X^{2a}$—$W^2$—$X^2$—$Y^2$—$Z^2$ is halo, $C_{1-6}$ alkyl, $C_{1-6}$ haloalkyl. In some further embodiments, at least one substituent —$W^{2a}$—$X^{2a}$—$W^2$—$X^2$—$Y^2$—$Z^2$ is halo, $C_{1-3}$ alkyl, $C_{1-3}$ haloalkyl. In yet further embodiments, at least one substituent —$W^{2a}$—$X^{2a}$—$W^2$—$X^2$—$Y^2$—$Z^2$ is halo (e.g. F, Cl, or Br), $C_1$ alkyl (i.e. methyl), $C_1$ haloalkyl (e.g. trifluoromethyl). In still further embodiments, at least one substituent —$W^{2a}$—$X^{2a}$—$W^2$—$X^2$—$Y^2$—$Z^2$ is halo (e.g. F).

In some embodiments, m is 2, 3, 4 or 5. In some embodiments, m is 2, 3, or 4. In some embodiments, m is 2 or 3. In some embodiments, m is 3 or 4.

In some embodiments, n1 is 0, 1, or 2. In some embodiments, n1 is 0 or 1. In some embodiments, n1 is 1 or 2. In some embodiments, n1 is 1.

In some embodiments, n2 is 0, 1, or 2. In some embodiments, n2 is 0 or 1. In some embodiments, n2 is 1 or 2.

In some embodiments, n1 is 1 and n2 is 1 or 2.

In some embodiments, the compound of Formula I is a compound of Formula II, IIa, IIb,

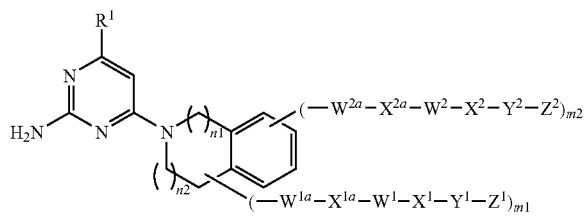

II

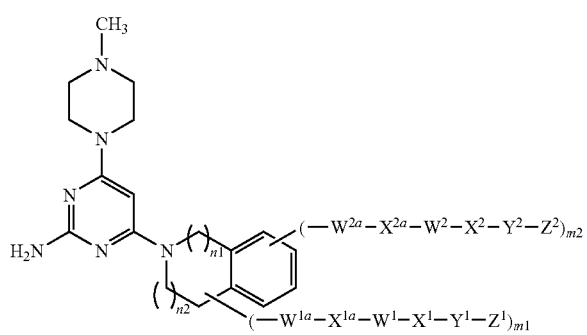

IIa

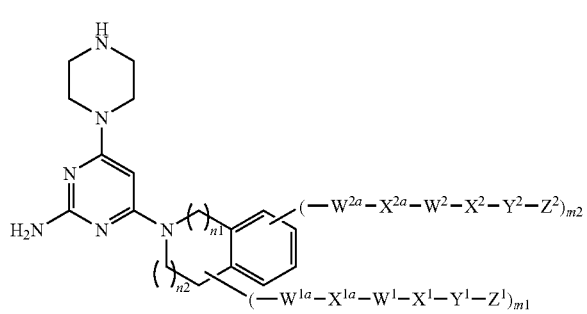

IIb

-continued

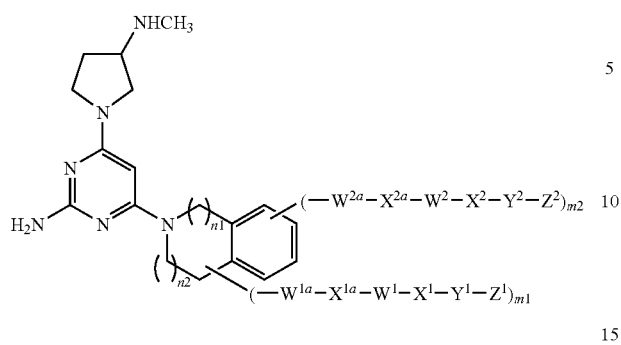
IIc wherein:
m1 is 0, 1, 2, 3, or 4;
m2 is 1, 2, 3, or 4;
n1 is 0 or 1; and
n2 is 0 or 1.

In some embodiments, the compound of Formula I is a compound of Formula II.

In some embodiments, the compound of Formula I is a compound of Formula IIa.

In some embodiments, the compound of Formula I is a compound of Formula IIb.

In some embodiments, the compound of Formula I is a compound of Formula IIc.

In some embodiments of compounds of Formula I, II, IIa, IIb, or IIc, n1 is 1. In some embodiments of compounds of Formula I, II, IIa, IIb, or IIc, n1 is 2.

In some embodiments of compounds of Formula I, II, IIa, IIb, or IIc, n2 is 0. In some other embodiments, n2 is 1. In some other embodiments, n2 is 2.

In some embodiments of compounds of Formula I, II, IIa, IIb, or IIc, n1 is 1 or 2; and n2 is 0, 1, or 2. In some embodiments, n1 is 1; and n2 is 1 or 2.

In some embodiments of compound of Formula II, IIa, IIb, or IIc, each —$W^{1a}$—$X^{1a}$—$W^1$—$X^1$—$Y^1$—$Z^1$ is independently selected from $C_{1-6}$ alkyl subsituted with 0, 1, 2, or 3 substituents each independently selected from OH and halo. In some further embodiments, each —$W^{1a}$—$X^{1a}$,$W^1$—$X^1$—$Y^1$—$Z^1$ is independently selected from methyl subsituted with 0, 1, 2, or 3 substituents each independently selected from OH and halo.

In some embodiments, the compound of Formula I is a compound of Formula III:

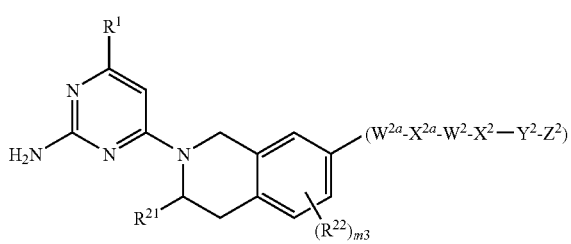
III wherein:
$R^1$ is selected from (A), (B), (C), (Q14), (Q17), (Q18), (Q19), (Q20), and (Q21):

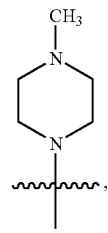
(A)

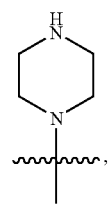
(B)

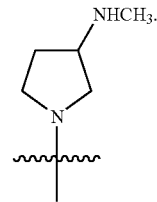
(C)

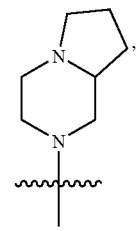
(Q14)

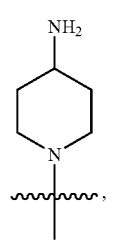
(Q17)

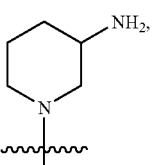
(Q18)

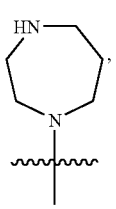
(Q19)

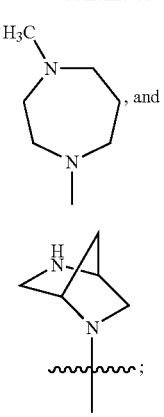

(Q20)

(Q21)

$R^{21}$ is H, CN, $C_{1-6}$ alkyl, $C_{1-6}$ haloalkyl, $C_{1-6}$ hydroxylalkyl, $C_{1-6}$cyanoalkyl, $C_{1-6}$ alkoxy, or $C_{1-6}$ haloalkoxy, wherein the $C_{1-6}$ alkyl is substituted with 0, 1, 2, or 3 substituents each independently selected from CN, OH, and halo;

$R^{22}$ is halo, CN, $C_{1-6}$ alkyl, $C_{1-6}$haloalkyl, or $C_{1-6}$cyanoalkyl;

$W^{2a}$ is absent or selected from O, NH, N($C_{1-6}$ alkyl), C(O), C(O)NH, C(O)N($C_{1-6}$ alkyl), and OC(O)NH;

$X^{2a}$ is alkyl, arylalkyl, aryl, cycloalkyl, heteroaryl, or heterocycloalkyl, each substituted with 0, 1, 2, 3, 4, or 5 substituents each independently selected from $C_{1-6}$ alkyl, $C_{1-6}$ haloalkyl, $C_{1-6}$alkoxy, $C_{1-6}$ haloalkoxy, amino, $C_{1-6}$ alkylamino, $C_{2-8}$ dialkylamino, halo, CN, and OH;

$W^2$— is absent or selected from $C_{1-6}$ alkylenyl, —C(O)—, —C(O)O—, —C(O)NH—, —C(O)N($C_{1-6}$alkyl)—, $X^2$ is absent or selected from $C_{1-6}$ alkyl, aryl, cycloalkyl, heteroaryl, heterocycloalkyl, cycloalkylalkyl, and heterocycloalkylalkyl;

$Y^2$— is absent or selected from $C_{1-6}$ alkylenyl, O, C(O), C(O)O, C(O)NH, C(O)N($C_{1-6}$ alkyl), and S(O)$_2$;

$Z^2$ is selected from H, halo, CN, OH, $C_{1-6}$alkoxy, $C_{1-6}$ haloalkoxy, amino, $C_{1-6}$ alkylamino, $C_{2-8}$ dialkylamino, $C_{1-6}$ alkyl, aryl, cycloalkyl, heteroaryl, heterocycloalkyl, arylalkyl, heteroarylalkyl, cycloalkylalkyl, and heterocycloalkylalkyl, wherein each of the $C_{1-6}$ alkyl, aryl, cycloalkyl, heteroaryl, heterocycloalkyl, arylalkyl, heteroarylalkyl, cycloalkylalkyl, and heterocycloalkylalkyl is substituted with 0, 1, 2, or 3 substituents each independently selected from halo, CN, OH, $C_{1-6}$alkoxy, $C_{1-6}$haloalkoxy, $C_{1-6}$ alkyl, $C_{1-6}$ haloalkyl,amino, $C_{1-6}$ alkylamino, $C_{2-8}$ dialkylamino, C(O)NH$_2$, C(O)NH($C_{1-6}$ alkyl), and C(O)N($C_{1-6}$alkyl)$_2$; and m3 is 0 or 1.

In some embodiments of the compound of Formula III or pharmaceutically acceptable salt or N-oxide or quaternary ammonium salt thereof, $R^{21}$ is H or $C_{1-6}$ alkyl, wherein the $C_{1-6}$ alkyl is substituted with 0, 1, 2, or 3 substituents each independently selected from OH and halo. In some further embodiments, $R^{21}$ is H or $C_{1-3}$ alkyl, wherein the $C_{1-3}$ alkyl is substituted with 0, 1, 2, or 3 substituents each independently selected from OH and halo. In some yet further embodiments, $R^{21}$ is H or methyl, wherein the methyl is substituted with 0, 1, 2, or 3 substituents each independently selected from OH and halo.

In some embodiments of the compound of Formula III or pharmaceutically acceptable salt or N-oxide or quaternary ammonium salt thereof, $R^{22}$ is halo, CN, $C_{1-3}$ alkyl, $C_{1-3}$ haloalkyl, or $C_{1-3}$ cyanoalkyl. In some further embodiments, $R^{22}$ is halo, CN, $C_{1-3}$ alkyl, or $C_{1-3}$ haloalkyl. In some yet further embodiments, $R^{22}$ is methyl, halo, or trihalomethyl. In some still further embodiments, $R^{22}$ is halo (e.g. F or Cl).

In some embodiments of the compound of Formula III or pharmaceutically acceptable salt or N-oxide or quaternary ammonium salt thereof, $R^{21}$ is H or methyl, wherein the methyl is substituted with 0, 1, 2, or 3 substituents each independently selected from OH and halo; and $R^{22}$ is methyl, halo, or trihalomethyl.

In some embodiments of the compound of Formula III or pharmaceutically acceptable salt or N-oxide or quaternary ammonium salt thereof:

$R^1$ is (A):

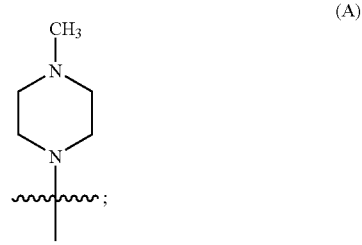 [SMILES: *N1CCN(C)CC1 ; "."]

(A)

$R^{21}$ is H, methyl, or hydroxylmethyl;
$R^{22}$ is halo (e.g. F, Cl or Br);
$W^{2a}$ is selected from O, NH, N($C_{1-6}$ alkyl), C(O), C(O)NH, C(O)N($C_{1-6}$ alkyl), and OC(O)NH;

$X^{2a}$ is alkyl, arylalkyl, aryl, cycloalkyl, heteroaryl, or heterocycloalkyl, each substituted with 0, 1, 2, 3, 4, or 5 substituents each independently selected from $C_{1-6}$ alkyl, $C_{1-6}$ haloalkyl, $C_{1-6}$ alkoxy, $C_{1-6}$ haloalkoxy, amino, $C_{1-6}$ alkylamino, $C_{2-8}$ dialkylamino, halo, CN, and OH;

$W^2$— is absent or selected from $C_{1-6}$ alkylenyl, —C(O)—, —C(O)O—, —C(O)NH—, —C(O)N($C_{1-6}$ alkyl)—, $X^2$ is absent or selected from $C_{1-6}$ alkyl, aryl, cycloalkyl, heteroaryl, heterocycloalkyl, cycloalkylalkyl, and heterocycloalkylalkyl, each substituted with 0, 1, 2, 3, 4, or 5 substituents each independently selected from $C_{1-6}$ alkyl, $C_{1-6}$ haloalkyl, $C_{1-6}$alkoxy, $C_{1-6}$ haloalkoxy, amino, $C_{1-6}$ alkylamino, $C_{2-8}$ dialkylamino, halo, CN, and OH;

$Y^2$— is absent or selected from $C_{1-6}$ alkylenyl, O, C(O), C(O)O, C(O)NH, C(O)N($C_{1-6}$ alkyl), and S(O)$_2$;

$Z^2$ is selected from H, halo, CN, OH, $C_{1-6}$alkoxy, $C_{1-6}$ haloalkoxy, amino, $C_{1-6}$ alkylamino, $C_{2-8}$ dialkylamino, $C_{1-6}$ alkyl, aryl, cycloalkyl, heteroaryl, heterocycloalkyl, arylalkyl, heteroarylalkyl, cycloalkylalkyl, and heterocycloalkylalkyl, wherein each of the $C_{1-6}$ alkyl, aryl, cycloalkyl, heteroaryl, heterocycloalkyl, arylalkyl, heteroarylalkyl, cycloalkylalkyl, and heterocycloalkylalkyl is substituted with 0, 1, 2, or 3 substituents each independently selected from halo, CN, OH, $C_{1-6}$alkoxy, $C_{1-6}$haloalkoxy, $C_{1-6}$ alkyl, $C_{1-6}$ haloalkyl,amino, $C_{1-6}$ alkylamino, $C_{2-8}$ dialkylamino, C(O)NH$_2$, C(O)NH($C_{1-6}$ alkyl), and C(O)N($C_{1-6}$alkyl)$_2$; and m3 is 0 or 1.

In some embodiments of the compound of Formula III or pharmaceutically acceptable salt or N-oxide or quaternary ammonium salt thereof:

$R^1$ is (A):

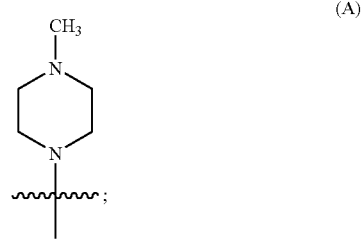 [SMILES: *N1CCN(C)CC1 ; ";"]

(A)

$R^{21}$ is H, methyl, or hydroxylmethyl;
$R^{22}$ is halo (e.g. F, Cl, or Br);
$W^{2a}$ is absent;

$X^{2a}$ is heteroaryl or heterocycloalkyl, each substituted with 0, 1, 2, or 3 substituents each independently selected from $C_{1-6}$ alkyl, halo, CN, and OH;

$W^2$— is absent or selected from $C_{1-6}$alkylenyl, C(O)NH, and C(O)N($C_{1-6}$ alkyl);

$X^2$ is absent or selected from $C_{1-6}$ alkyl, cycloalkyl, heteroaryl, heterocycloalkyl, cycloalkylalkyl, and heterocycloalkylalkyl, each substituted with 0, 1, 2, 3, 4, or 5 substituents each independently selected from $C_{1-6}$ alkyl, $C_{1-6}$ haloalkyl, $C_{1-6}$ alkoxy, $C_{1-6}$ haloalkoxy, amino, $C_{1-6}$ alkylamino, $C_{2-8}$ dialkylamino, halo, CN, and OH;

$Y^2$— is absent or selected from $C_{1-6}$ alkylenyl, O, C(O), C(O)O, C(O)NH, C(O)N($C_{1-6}$ alkyl), and S(O)$_2$;

$Z^2$ is selected from H, halo, CN, OH, $C_{1-6}$alkoxy, $C_{1-6}$haloalkoxy, amino, $C_{1-6}$ alkylamino, $C_{2-8}$ dialkylamino, $C_{1-6}$ alkyl, aryl, cycloalkyl, heteroaryl, heterocycloalkyl, arylalkyl, heteroarylalkyl, cycloalkylalkyl, and heterocycloalkylalkyl, wherein each of the $C_{1-6}$ alkyl, aryl, cycloalkyl, heteroaryl, heterocycloalkyl, arylalkyl, heteroarylalkyl, cycloalkylalkyl, and heterocycloalkylalkyl is substituted with 0, 1, 2, or 3 substituents each independently selected from halo, CN, OH, $C_{1-6}$alkoxy, $C_{1-6}$haloalkoxy, $C_{1-6}$ alkyl, $C_{1-6}$haloalkyl, amino, $C_{1-6}$ alkylamino, $C_{2-8}$ dialkylamino, C(O)NH$_2$, C(O)NH($C_{1-6}$ alkyl), and C(O)N($C_{1-6}$alkyl)$_2$; and m3 is 0 or 1.

In some embodiments of the compound of Formula III or pharmaceutically acceptable salt or N-oxide or quaternary ammonium salt thereof, $X^{2a}$ is heteroaryl substituted with 0, 1, 2, or 3 substituents each independently selected from $C_{1-6}$ alkyl, halo, CN, and OH. In some further embodiments, $X^{2a}$ is selected from pyridinyl, pyrazolyl, pyrrolyl, pyrimidinyl, 1,3-thiazolyl, and 3H-imidazo[4,5-b]pyridinyl, each substituted with 0, 1, 2, or 3 substituents each independently selected from $C_{1-6}$ alkyl, halo, CN, and OH.

In some embodiments of the compound of Formula III or pharmaceutically acceptable salt or N-oxide or quaternary ammonium salt thereof:

$W^2$— is absent;

$X^2$ is absent;

$Y^2$— is absent or selected from $C_{1-6}$ alkylenyl, C(O), C(O)O, C(O)NH, C(O)N($C_{1-6}$ alkyl), and S(O)$_2$; and $Z^2$ is selected from H, halo, CN, OH, $C_{1-6}$alkoxy, $C_{1-6}$haloalkoxy, amino, $C_{1-6}$ alkylamino, $C_{2-8}$ dialkylamino, $C_{1-6}$ alkyl, aryl, cycloalkyl, heteroaryl, heterocycloalkyl, arylalkyl, heteroarylalkyl, cycloalkylalkyl, and heterocycloalkylalkyl, wherein each of the $C_{1-6}$ alkyl, aryl, cycloalkyl, heteroaryl, heterocycloalkyl, arylalkyl, heteroarylalkyl, cycloalkylalkyl, and heterocycloalkylalkyl is substituted with 0, 1, 2, or 3 substituents each independently selected from halo, CN, OH, $C_{1-6}$alkoxy, $C_{1-6}$haloalkoxy, $C_{1-6}$ alkyl, $C_{1-6}$haloalkyl, amino, $C_{1-6}$ alkylamino, $C_{2-8}$ dialkylamino, C(O)NH$_2$, C(O)NH($C_{1-6}$ alkyl), and C(O)N($C_{1-6}$alkyl)$_2$.

In some embodiments of the compound of Formula III or pharmaceutically acceptable salt or N-oxide or quaternary ammonium salt thereof, $X^{2a}$ is heterocycloalkyl substituted with 0, 1, 2, or 3 substituents each independently selected from $C_{1-6}$ alkyl, halo, CN, and OH. In some further embodiments, $X^{2a}$ is selected from piperidinyl, piperazinyl, 1,2,3,6-tetrahydropyridinyl, 2-oxo-piperazinyl, 2(1H)-oxo-pyridinyl, 1-oxo-isoindolinyl, and 2H-3(4H)-oxo-benzo[b][1,4]oxazinyl, each substituted with 0, 1, 2, or 3 substituents each independently selected from $C_{1-6}$ alkyl, halo, CN, and OH.

In some embodiments of the compound of Formula III or pharmaceutically acceptable salt or N-oxide or quaternary ammonium salt thereof:

$W^2$— is absent;

$X^2$ is absent;

$Y^2$— is absent or selected from $C_{1-6}$ alkylenyl, C(O), C(O)O, C(O)NH, C(O)N($C_{1-6}$alkyl), and S(O)$_2$; and $Z^2$ is selected from H, halo, CN, OH, $C_{1-6}$alkoxy, $C_{1-6}$haloalkoxy, amino, $C_{1-6}$ alkylamino, $C_{2-8}$ dialkylamino, $C_{1-6}$ alkyl, aryl (e.g. phenyl), cycloalkyl (e.g. cyclopropyl, cyclopentyl, or cyclohexyl), heteroaryl [e.g. pyridinyl (such as pyridin-2-yl, pyridin-3-yl, or pyridin-4-yl) or furanyl], heterocycloalkyl (e.g. azetidinyl, pyrrolidinyl, piperidinyl, piperazinyl, tetrahydrofuranyl, tetrahydro-2H-pyranyl, or S,S-di-oxo-tetrahydrothienyl), arylalkyl (e.g. benzyl), heteroarylalkyl (e.g. pyridin-2-ylmethyl or pyridin-3-ylmethyl), cycloalkylalkyl (e.g. cylcopropylmethyl, cyclobutylmethyl or cyclopentylmethyl), and heterocycloalkylalkyl (e.g. morpholinoethyl or tetrahydrofuran-2-ylmethyl), wherein each of the $C_{1-6}$ alkyl, aryl, cycloalkyl, heteroaryl, heterocycloalkyl, arylalkyl, heteroarylalkyl, cycloalkylalkyl, and heterocycloalkylalkyl is substituted with 0, 1, 2, or 3 substituents each independently selected from halo, CN, OH, $C_{1-6}$ alkoxy, $C_{1-6}$haloalkoxy, $C_{1-6}$ alkyl, $C_{1-6}$haloalkyl, amino, $C_{1-6}$ alkylamino, $C_{2-8}$ dialkylamino, C(O)NH$_2$, C(O)NH ($C_{1-6}$ alkyl), and C(O)N($C_{1-6}$alkyl)$_2$.

At various places in the present specification, substituents of compounds of the invention are disclosed in groups or in ranges. It is specifically intended that the invention include each and every individual subcombination of the members of such groups and ranges. For example, the term "$C_{1-6}$ alkyl" is specifically intended to individually disclose methyl, ethyl, $C_3$ alkyl, $C_4$ alkyl, $C_5$ alkyl, and $C_6$ alkyl.

For compounds of the invention in which a variable appears more than once, each variable can be a different moiety selected from the Markush group defining the variable. For example, each of $R^5$, —$W^{1a}$—$X^{1a}$—$W^1$—$X^1$—$Y^1$—$Z^1$ and —$W^{2a}$—$X^{2a}$—$W^2$—$X^2$—$Y^2$—$Z^2$ can be a different moiety selected from the Markush group defining the variable. For another example, where a structure is described having two R groups that are simultaneously present on the same compound; the two R groups can represent different moieties selected from the Markush group defined for R. In another example, when an optionally multiple substituent is designated in the form:

then it is understood that substituent R can occur s number of times on the ring, and R can be a different moiety at each occurrence. Further, in the above example, should the variable T' be defined to include hydrogens, such as when $T^1$ is said to be CH$_2$, NH, etc., any floating substituent such as R in the above example, can replace a hydrogen of the $T^1$ variable as well as a hydrogen in any other non-variable component of the ring.

As used herein, the term "adjacent" in describing the relative positions of two substitution groups on a same ring structure refers to two substitution groups that are respectively attached to two ring-forming atoms of the same ring, wherein the two-ring forming atoms are directly connected through a chemical bond. For example, in the following structure:

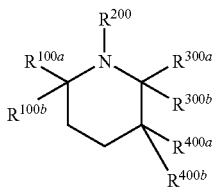

$R^{100a}$ and $R^{200}$ are two adjacent groups. For another example, each of $R^{200}$, $R^{400a}$, and $R^{400b}$ is an adjacent group of $R^{300a}$. For yet another example, each of $R^{200}$, $R^{400a}$, and $R^{400b}$ is an adjacent group of $R^{300b}$.

It is further appreciated that certain features of the invention, which are, for clarity, described in the context of separate embodiments, can also be provided in combination in a single embodiment. Conversely, various features of the invention which are, for brevity, described in the context of a single embodiment, can also be provided separately or in any suitable subcombination.

The term "n-membered" where n is an integer typically describes the number of ring-forming atoms in a moiety where the number of ring-forming atoms is n. For example, pyridine is an example of a 6-membered heteroaryl ring and thiophene is an example of a 5-membered heteroaryl group.

As used herein, the term "alkyl" is meant to refer to a saturated hydrocarbon group which is straight-chained or branched. Example alkyl groups include, but are not limited to, methyl (Me), ethyl (Et), propyl (e.g., n-propyl and isopropyl), butyl (e.g., n-butyl, isobutyl, t-butyl), pentyl (e.g., n-pentyl, isopentyl, neopentyl), and the like. An alkyl group can contain from 1 to about 20, from 2 to about 20, from 1 to about 10, from 1 to about 8, from 1 to about 6, from 1 to about 4, or from 1 to about 3 carbon atoms. The term "alkylene" refers to a divalent alkyl linking group. An example of alkylene is methylene ($CH_2$).

As used herein, "alkenyl" refers to an alkyl group having one or more double carbon-carbon bonds. Example alkenyl groups include, but are not limited to, ethenyl, propenyl, cyclohexenyl, and the like. The term "alkenylenyl" refers to a divalent linking alkenyl group.

As used herein, "alkynyl" refers to an alkyl group having one or more triple carbon-carbon bonds. Example alkynyl groups include, but are not limited to, ethynyl, propynyl, and the like. The term "alkynylenyl" refers to a divalent linking alkynyl group.

As used herein, "haloalkyl" refers to an alkyl group having one or more halogen substituents. Example haloalkyl groups include, but are not limited to, $CF_3$, $C_2F_5$, $CHF_2$, $CCl_3$, $CHCl_2$, $C_2Cl_5$, $CH_2CF_3$, and the like. As used herein, "trihalomethyl" refers to a methyl group having three halogen substituents. Example trihalomethyl groups include, but are not limited to, $CF_3$, $CClF_2$, $CCl_2F$, $CCl_3$, and the like.

As used herein, "aryl" refers to monocyclic or polycyclic (e.g., having 2, 3 or 4 fused rings) aromatic hydrocarbons such as, for example, phenyl, naphthyl, anthracenyl, phenanthrenyl, indanyl, indenyl, and the like. In some embodiments, aryl groups have from 6 to about 20 carbon atoms. In some embodiments, aryl groups have from 6 to about 10 carbon atoms.

As used herein, "cycloalkyl" refers to non-aromatic cyclic hydrocarbons including cyclized alkyl, alkenyl, and alkynyl groups that contain up to 20 ring-forming carbon atoms. Cycloalkyl groups can include mono- or polycyclic ring systems such as fused ring systems, bridged ring systems, and spiro ring systems. In some embodiments, examples of polycyclic ring systems include 2, 3, or 4 fused rings. A cycloalkyl group can contain from 3 to about 15, from 3 to about 10, from 3 to about 8, from 3 to about 6, from 4 to about 6, from 3 to about 5, or from 5 to about 6 ring-forming carbon atoms. Ring-forming carbon atoms of a cycloalkyl group can be optionally substituted by oxo or sulfido. Example cycloalkyl groups include, but are not limited to, cyclopropyl, cyclobutyl, cyclopentyl, cyclohexyl, cycloheptyl, cyclopentenyl, cyclohexenyl, cyclohexadienyl, cycloheptatrienyl, norbornyl, norpinyl, norcarnyl, adamantyl, and the like. Also included in the definition of cycloalkyl are moieties that have one or more aromatic rings fused (i.e., having a bond in common with) to the cycloalkyl ring, for example, benzo or thienyl derivatives of pentane, pentene, hexane, and the like (e.g., 2,3-dihydro-1H-inden-1-yl, or 1H-inden-2(3H)-one-1-yl).

As used herein, "heteroaryl" groups refer to an aromatic heterocycle having up to 20 ring-forming atoms and having at least one heteroatom ring member (ring-forming atom) such as sulfur, oxygen, or nitrogen. In some embodiments, the heteroaryl group has at least one or more heteroatom ring-forming atoms each independently selected from sulfur, oxygen, and nitrogen. Heteroaryl groups include monocyclic and polycyclic (e.g., having 2, 3 or 4 fused rings) systems. Examples of heteroaryl groups include without limitation, pyridyl, pyrimidinyl, pyrazinyl, pyridazinyl, triazinyl, furyl, quinolyl, isoquinolyl, thienyl, imidazolyl, thiazolyl, indolyl, pyrryl, oxazolyl, benzofuryl, benzothienyl, benzthiazolyl, isoxazolyl, pyrazolyl, triazolyl, tetrazolyl, indazolyl, 1,2,4-thiadiazolyl, isothiazolyl, benzothienyl, purinyl, carbazolyl, benzimidazolyl, indolinyl, and the like. In some embodiments, the heteroaryl group has from 1 to about 20 carbon atoms, and in further embodiments from about 1 to about 5, from about 1 to about 4, from about 1 to about 3, from about 1 to about 2, carbon atoms as ring-forming atoms. In some embodiments, the heteroaryl group contains 3 to about 14, 3 to about 7, or 5 to 6 ring-forming atoms. In some embodiments, the heteroaryl group has 1 to about 4, 1 to about 3, or 1 to 2 heteroatoms.

As used herein, "heterocycloalkyl" refers to non-aromatic heterocycles having up to 20 ring-forming atoms including cyclized alkyl, alkenyl, and alkynyl groups where one or more of the ring-forming carbon atoms is replaced by a heteroatom such as an O, N, or S atom. Hetercycloalkyl groups can be mono or polycyclic (e.g., fused, bridged, or spiro systems). Example "heterocycloalkyl" groups include morpholino, thiomorpholino, piperazinyl, tetrahydrofuranyl, tetrahydrothienyl, 2,3-dihydrobenzofuryl, 1,2,3,6-tetrahydropyridinyl, 1,3-benzodioxole, benzo-1,4-dioxane, piperidinyl, pyrrolidinyl, piperazinyl, isoxazolidinyl, isothiazolidinyl, pyrazolidinyl, oxazolidinyl, thiazolidinyl, imidazolidinyl, pyrrolidin-2-one-3-yl, and the like. Ring-forming carbon atoms and heteroatoms of a heterocycloalkyl group can be optionally substituted by oxo or sulfido. For example, a ring-forming S atom can be substituted by 1 or 2 oxo [i.e., form a $S(O)$ or $S(O)_2$]. For another example, a ring-forming C atom can be substituted by oxo (i.e., form carbonyl). Accordingly, example "heterocycloalkyl" groups also include S,S-dioxo-tetrahydrothienyl, 2-oxo-piperazinyl, 2(1H)-oxo-pyridinyl (i.e. 2-oxo-1,2-dihydropyridinyl), 1-oxo-isoindolinyl, and 2H-3(4H)-oxo-benzo[b][1,4]oxazinyl, where the oxo groups are considered to be part of the heterocycloalkyl group.— Also included in the definition of heterocycloalkyl are moieties that have one or more aromatic rings fused (i.e., having a bond in common with) to the nonaromatic heterocyclic ring, for example pyridinyl, thiophenyl, phthalimidyl, naphthalimidyl, and benzo derivatives of heterocycles such as indolene, isoindolene, isoindolin-1-one-3-yl, 4,5,6,7-tetrahydrothieno[2,3-c]pyridine-5-yl, 5,6-dihydrothieno[2,3-c]pyridin-7(4H)-one-5-yl, and 3,4-dihydroisoquinolin-1(2H)-one-3yl groups. Ring-forming carbon atoms and heteroatoms of the heterocycloalkyl group can be optionally substituted by oxo or sulfido. In some embodiments, the heterocycloalkyl group has from 1 to about 20 carbon atoms, and in further embodiments from about 3 to about 20 carbon atoms. In some embodiments, the heterocycloalkyl group contains 3 to about 14, 3 to about 7, or 5 to 6 ring-forming atoms. In some embodiments, the heterocycloalkyl group has 1 to about 4, 1 to about 3, or 1 to 2 heteroatoms. In some embodiments, the heterocycloalkyl group contains 0 to 3 double bonds. In some embodiments, the heterocycloalkyl group contains 0 to 2 triple bonds.

As used herein, "halo" or "halogen" includes fluoro, chloro, bromo, and iodo.

As used herein, "alkoxy" refers to an —O-alkyl group. Example alkoxy groups include methoxy, ethoxy, propoxy (e.g., n-propoxy and isopropoxy), t-butoxy, and the like.

As used herein, "haloalkoxy" refers to an —O-haloalkyl group. An example haloalkoxy group is $OCF_3$.

As used herein, "cyanoalkyl" refers to an alkyl group substituted by a cyano group (CN). One example of cyanoalkyl is —$CH_2$—CN.

As used herein, "alkoxyalkoxy" refers to an alkoxy group substituted by an alkoxy group. One example of alkoxyalkoxy is —$OCH_2CH_2$—$OCH_3$.

As used herein, "arylalkyl" refers to a $C_{1-6}$ alkyl substituted by aryl and "cycloalkylalkyl" refers to $C_{1-6}$ alkyl substituted by cycloalkyl.

As used herein, "heteroarylalkyl" refers to a $C_{1-6}$ alkyl group substituted by a heteroaryl group, and "heterocycloalkylalkyl" refers to a $C_{1-6}$ alkyl substituted by heterocycloalkyl.

As used herein, "amino" refers to $NH_2$.

As used herein, "alkylamino" refers to an amino group substituted by an alkyl group.

As used herein, "dialkylamino" refers to an amino group substituted by two alkyl groups.

As used herein, "hydroxylalkyl" or "hydroxylalkyl" refers to an alkyl group substituted by a hydroxyl group. An example is —$CH_2OH$ (i.e. hydroxylmethyl) or —$CH_2CH_2OH$.

As used here, C(O) refers to C(=O).
As used here, C(S) refers to C(=S).
As used here, S(O) refers to S(=O).
As used here, $S(O)_2$ refers to $S(=O)_2$.

As used herein, the term "optionally substituted" means that substitution is optional and therefore includes both unsubstituted and substituted atoms and moieties. A "substituted" atom or moiety indicates that any hydrogen on the designated atom or moiety can be replaced with a selection from the indicated substituent group, provided that the normal valency of the designated atom or moiety is not exceeded, and that the substitution results in a stable compound. For example, if a methyl group (i.e., $CH_3$) is optionally substituted, then 3 hydrogen atoms on the carbon atom can be replaced with substituent groups.

The compounds described herein can be asymmetric (e.g., having one or more stereocenters). All stereoisomers, such as enantiomers and diastereomers, are intended unless otherwise indicated. Compounds of the present invention that contain asymmetrically substituted carbon atoms can be isolated in optically active or racemic forms. Methods on how to prepare optically active forms from optically active starting materials are known in the art, such as by resolution of racemic mixtures or by stereoselective synthesis. Many geometric isomers of olefins, C=N double bonds, and the like can also be present in the compounds described herein, and all such stable isomers are contemplated in the present invention. Cis and trans geometric isomers of the compounds of the present invention are described and may be isolated as a mixture of isomers or as separated isomeric forms. Where a compound capable of stereoisomerism or geometric isomerism is designated in its structure or name without reference to specific R/S or cis/trans configurations, it is intended that all such isomers are contemplated.

Resolution of racemic mixtures of compounds can be carried out by any of numerous methods known in the art. An example method includes fractional recrystallizaion using a chiral resolving acid which is an optically active, salt-forming organic acid. Suitable resolving agents for fractional recrystallization methods are, for example, optically active acids, such as the D and L forms of tartaric acid, diacetyltartaric acid, dibenzoyltartaric acid, mandelic acid, malic acid, lactic acid or the various optically active camphorsulfonic acids such as β-camphorsulfonic acid. Other resolving agents suitable for fractional crystallization methods include stereoisomerically pure forms of α-methylbenzylamine (e.g., S and R forms, or diastereomerically pure forms), 2-phenylglycinol, norephedrine, ephedrine, N-methylephedrine, cyclohexylethylamine, 1,2-diaminocyclohexane, and the like.

Resolution of racemic mixtures can also be carried out by elution on a column packed with an optically active resolving agent (e.g., dinitrobenzoylphenylglycine). Suitable elution solvent composition can be determined by one skilled in the art.

In some embodiments, two enantiomers of a compound of the present invention (such as Example 49A and Example 49B in the Example 49 hereinbelow) are separated. Those skilled in the art would readily recognize that one of the two enantiomers of the compound has the R configuration and the other has the S configuration. Those skilled in the art can determine the absolute stereochemistry by suitable method such as single crystal X-ray analysis.

Compounds of the invention also include tautomeric forms. Tautomeric forms result from the swapping of a single bond with an adjacent double bond together with the concomitant migration of a proton. Tautomeric forms include prototropic tautomers which are isomeric protonation states having the same empirical formula and total charge. Example prototropic tautomers include ketone—enol pairs, amide—imidic acid pairs, lactam—lactim pairs, amide—imidic acid pairs, enamine—imine pairs, and annular forms where a proton can occupy two or more positions of a heterocyclic system, for example, 1H- and 3H-imidazole, 1H-, 2H- and 4H-1,2,4-triazole, 1H- and 2H-isoindole, and 1H- and 2H-pyrazole. Tautomeric forms can be in equilibrium or sterically locked into one form by appropriate substitution.

Compounds of the invention further include hydrates and solvates, as well as anhydrous and non-solvated forms.

The term, "compound," as used herein is meant to include all stereoisomers, geometric iosomers, tautomers, and isotopes of the structures depicted.

All compounds and pharmaceutically acceptable salts thereof, can be prepared or present together with other substances such as water and solvents (e.g. hydrates and solvates) or can be isolated.

Compounds of the invention can also include all isotopes of atoms occurring in the intermediates or final compounds. Isotopes include those atoms having the same atomic number but different mass numbers. For example, isotopes of hydrogen include tritium and deuterium.

In some embodiments, the compounds of the invention, or salts thereof, are substantially isolated. By "substantially isolated" is meant that the compound is at least partially or substantially separated from the environment in which is formed or detected. Partial separation can include, for example, a composition enriched in the compound of the invention. Substantial separation can include compositions containing at least about 50%, at least about 60%, at least about 70%, at least about 80%, at least about 90%, at least about 95%, at least about 97%, or at least about 99% by weight of the compound of the invention, or salt thereof. Methods for isolating compounds and their salts are routine in the art.

Compounds of the invention are intended to include compounds with stable structures. As used herein, "stable compound" and "stable structure" are meant to indicate a compound that is sufficiently robust to survive isolation to a useful degree of purity from a reaction mixture, and formulation into an efficacious therapeutic agent.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The expressions, "ambient temperature" and "room temperature," as used herein, are understood in the art, and refer generally to a temperature, e.g. a reaction temperature, that is about the temperature of the room in which the reaction is carried out, for example, a temperature from about 20° C. to about 30° C.

The present invention also includes pharmaceutically acceptable salts of the compounds described herein. As used herein, "pharmaceutically acceptable salts" refers to derivatives of the disclosed compounds wherein the parent compound is modified by converting an existing acid or base moiety to its salt form. Examples of pharmaceutically acceptable salts include, but are not limited to, mineral or organic acid salts of basic residues such as amines; alkali or organic salts of acidic residues such as carboxylic acids; and the like. The pharmaceutically acceptable salts of the present invention include the conventional non-toxic salts of the parent compound formed, for example, from non-toxic inorganic or organic acids. The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile (ACN) are preferred. Lists of suitable salts are found in *Remington's Pharmaceutical Sciences,* 17th ed., Mack Publishing Company, Easton, Pa., 1985, p. 1418 and *Journal of Pharmaceutical Science,* 66, 2 (1977), each of which is incorporated herein by reference in its entirety.

The present invention also includes quaternary ammonium salts of the compounds described herein, where the compounds have one or more tertiary amine moieties. As used herein, "quaternary ammonium salts" refers to derivatives of the disclosed compounds with one or more tertiary amine moieties wherein at least one of the tertiary amine moieties in the parent compound is modified by converting the tertiary amine moiety to a quaternary ammonium cation via alkylation (and the cations are balanced by anions such as Cl$^-$, $CH_3COO^-$, or $CF_3COO^-$), for example methylation or ethylation.

The present invention also includes N-oxides of the compounds described herein. An N-oxide of a compound can be formed where the nitrogen atom of a tertiary amine moiety (including nitrogen-containing aromatic moiety) of the parent compound is oxidized to form the N-oxide.

Synthesis

Compounds of the invention, including salts thereof and N-oxides thereof and quaternary ammonium salts thereof, can be prepared using known organic synthesis techniques and can be synthesized according to any of numerous possible synthetic routes.

The reactions for preparing compounds of the invention can be carried out in suitable solvents which can be readily selected by one of skill in the art of organic synthesis. Suitable solvents can be substantially non-reactive with the starting materials (reactants), the intermediates, or products at the temperatures at which the reactions are carried out, e.g., temperatures which can range from the solvent's freezing temperature to the solvent's boiling temperature. A given reaction can be carried out in one solvent or a mixture of more than one solvent. Depending on the particular reaction step, suitable solvents for a particular reaction step can be selected by the skilled artisan.

Preparation of compounds of the invention can involve the protection and deprotection of various chemical groups. The need for protection and deprotection, and the selection of appropriate protecting groups, can be readily determined by one skilled in the art. The chemistry of protecting groups can be found, for example, in T. W. Greene and P. G. M. Wuts, *Protective Groups in Organic Synthesis,* 3$^{rd}$ Ed., Wiley & Sons, Inc., New York (1999), which is incorporated herein by reference in its entirety.

Reactions can be monitored according to any suitable method known in the art. For example, product formation can be monitored by spectroscopic means, such as nuclear magnetic resonance spectroscopy (e.g., $^1$H or $^{13}$C), infrared spectroscopy, spectrophotometry (e.g., UV-visible), mass spectrometry, or by chromatographic methods such as high performance liquid chromatography (HPLC) or thin layer chromatography (TLC).

The compounds of invention can be prepared, for example, according to the reaction pathways, synthetic procedures, and techniques described below.

A series of amino-pyrimidine derivatives 1-6 can be prepared by methods outlined in Scheme 1. Pyrimidine 1-1 [wherein $Lg^1$ and $Lg^2$ are each, independently, a leaving group such as triflate group (—OTf) or halo (e.g. Cl or Br)] for example commercial available 4,6-dichloropyrimidin-2-amine can be reacted with amine $HNR^3R^4$ to afford compound 1-2 under suitable conditions [for example, in the presence of an organic base e.g. a tertiary amine such as triethylamine (TEA), diisopropylethylamine (DIPEA), N-methylmorpholine (NMM)]. Compound 1-2 can be reacted with a substituted tetrahydroisoquinoline 1-3 [wherein $Lg^3$ is a leaving group such as triflate group (—OTf) or halo (e.g. Cl or Br)] to afford compound 1-4. Compound 1-4 can be reacted with an aryl/heteroaryl boronic acid or its derivative 1-5 [wherein ring $Q^{100}$ is an optionally substituted aryl or heteroaryl group, for example substituted with 0, 1, or 2 substituents such as halo, $C_{1-6}$ alkyl, $C_{1-6}$ haloalkyl, or —$W^2$—$X^2$—$Y^2$—$Z^2$; and $R^{61}$ and $R^{62}$ are each, independently, H or $C_{1-6}$ alkyl; or $B(OR^{61})(OR^{62})$ together form a 4-9 membered heterocycloalkyl optionally substituted with one or more $C_{1-6}$ alkyl] under Suzuki-Miyaura reaction condition/ Suzuki coupling conditions to give pyridine compound 1-6. [For reviews of the Suzuki-Miyaura reaction, see e.g. Miyaura, N; Suzuki, A. Chem. Rev., 1995, 95:2457-2483].

Scheme 1

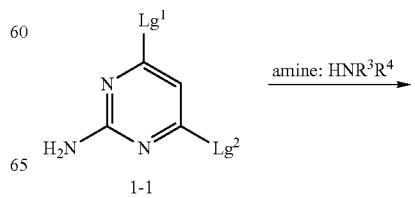

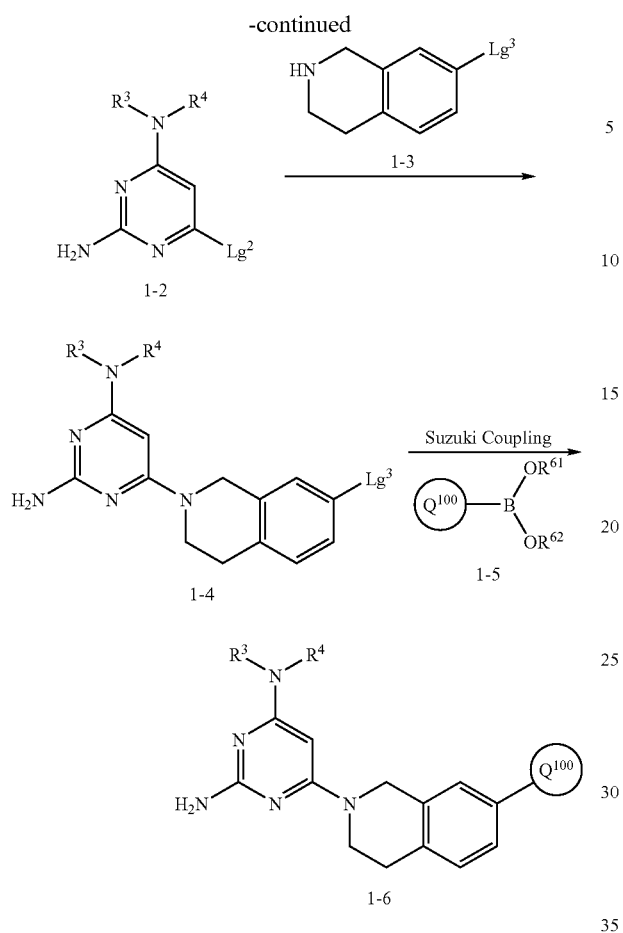

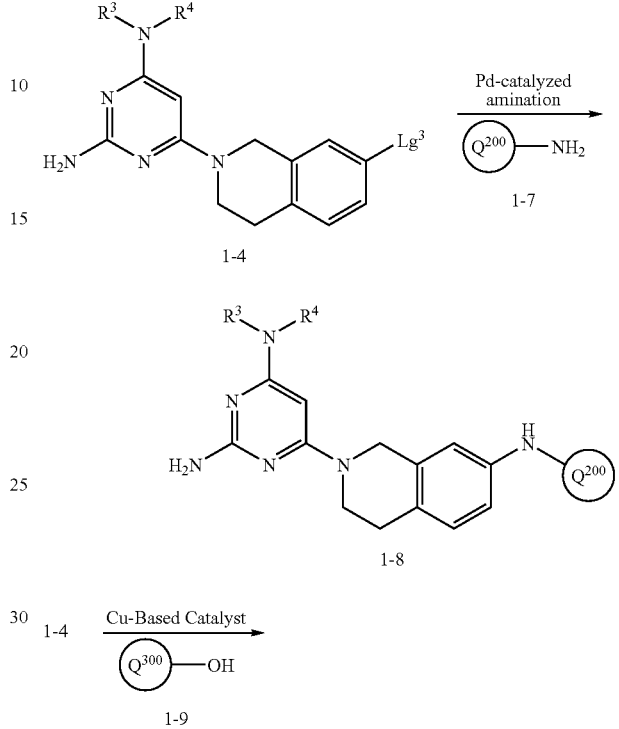

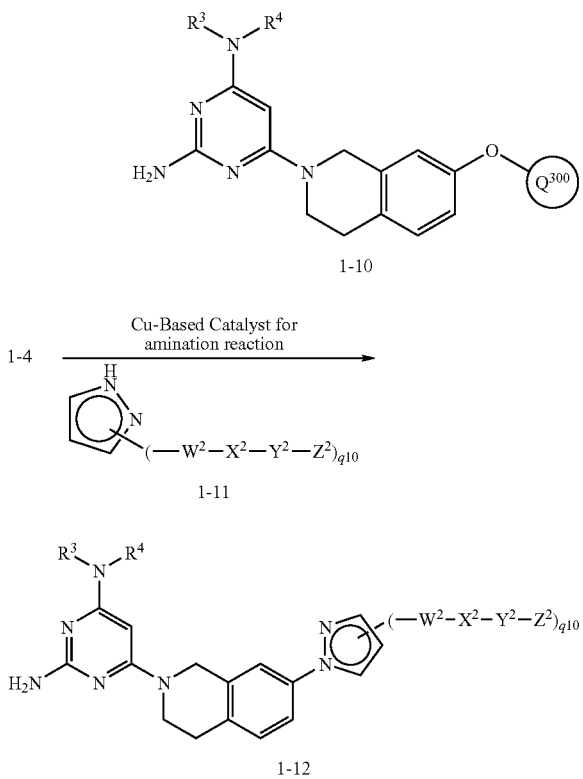

As shown in Scheme 1-a, compound 1-4 [wherein $Lg^3$ is a leaving group such as triflate group (—OTf) or halo (e.g. Cl or Br)] can undergo further chemical transformations under appropriate conditions. For example, compound 1-4 can undergo palladium catalyzed amination with an amine compound such as amine 1-7 [wherein ring $Q^{200}$ is an optionally substituted aryl or heteroaryl group, for example, substituted with 0, 1, or 2 substituents such as halo, $C_{1-6}$ alkyl, $C_{1-6}$ haloalkyl, or —$W^2$—$X^2$—$Y^2$—$Z^2$] to form compound 1-8. [See e.g. J. P. Wolfe, et. al.; "Simple, Efficient Catalyst System for the Palladium-Catalyzed Amination of Aryl Chlorides, Bromides, and Triflates"; J. Org. Chem., 2000, 65 (4), pp 1158-1174.] For another example, compound 1-4 can undergo Copper-catalyzed etherification (for example in the presence of CuI) with an alcohol compound such as alcohol 1-9 [wherein ring $Q^{300}$ is an optionally substituted aryl or heteroaryl group, for example substituted with 0, 1, or 2 substituents such as halo, $C_{1-6}$ alkyl, $C_{1-6}$ haloalkyl, or —$W^2$—$X^2$—$Y^2$—$Z^2$.] to form compound 1-10. [See e.g. T. Schareina, et. al, "Bio-inspired copper catalysts for the formation of diaryl ethers," Tetrahedron Letters, Volume 49, Issue 11, 10 Mar. 2008, Pages 1851-1855; see also M. Beller, Org. Process Res. & Dev., 2008, 12, 537; and R. A. Altman, "An Improved Cu-Based Catalyst System for the Reactions of Alcohols with Aryl Halides," J. Org. Chem., 2008, 73 (1), pp 284-286]. For yet another example, compound 1-4 can undergo Copper-catalyzed amination (for example in the presence of CuI) with an amine compound such as amine 1-11 to form compound 1-12. [See e.g., J. C. Antilla, et. al., "Copper-diamine-catalyzed N-arylation of pyrroles, pyrazoles, indazoles, imidazoles, and triazoles", J. Org. Chem., 2004, 69, 5578-87; see also Z. Lu, "Copper-catalyzed aryl amination in aqueous media with 2-dimethylaminoethanol ligand," Tetrahedron Letters, Volume 46, Issue 17, Pages 2997-3001]

A series of aminopyrimidine derivative 2-3 can be prepared by the methods outlined in Scheme 2. Suzuki coupling of pyrimidine amine 2-1 with a suitable pyridinyl boronic acid or ester 2-2 wherein the pyridinyl ring is substituted with COOH [wherein $R^{61}$ and $R^{62}$ are each, independently, H or $C_{1-6}$ alkyl; or $B(OR^{61})(OR^{62})$ together form a 4-9 membered heterocycloalkyl optionally substituted with one or more $C_{1-6}$ alkyl] affords carboxylic acid 2-3. Acid 2-3 can be transformed to amide 2-4 by reacting the acid with an amine of $HNR^e(-X^2-Y^2-Z^2)$ under suitable conditions such as in the presence of a suitable coupling reagent for amide bond formation and in the presence of a suitable base such as a tertiary amine [e.g., TEA, DIPEA, pyridine, and/or dimethylaminopyridine (DMAP)]. Some non-limiting examples of suitable coupling reagents include 1-hydroxybenzotriazole (HOBt), N,N'-dicyclohexylcarbodiimide (DCC), benzotriazol-1-yloxytris(dimethyl-amino)phosphonium hexafluorophosphate (BOP), benzotriazol-1-yloxytri(pyrrolidino)phosphonium hexafluorophosphate (PyBOP), O-(7-azabenzotriazol-1-yl)-1,1,3,3-tetramethyluronium hexafluorophosphate (HATU), and O-(benzotriazol-1-yl)-1,1,3,3-tetramethyluronium hexafluorophosphate (HBTU).

A series of aminopyrimidine derivative 3-8 can be prepared by the methods outlined in Scheme 3. Reductive amination of the appropriate ketone 3-1 (where R can be, for example, optionally substituted alkyl such as methyl, ethyl, or hydroxylmethyl) with ammonia in alcohol such as ethanol can give the corresponding amine derivative 3-2 which can be transformed to a carbamate such as 3-3 by reaction with suitable chloroformate such as $CH_3OCOCl$. Cyclization of the carbamate 3-3 to 3,4-dihydroisoquinoline derivative 3-4 can be achieved by reaction with paraformaldehyde [i.e. $(CH_2O)_n$] in the presence of an acid such sulfuric acid. Removal of the methoxy carbonyl group of compound 3-4 can yield the corresponding 3,4-dihydroisoquinoline 3-5 which can be conveniently converted to the amino aminopyrimidine derivative 3-8 by reaction with di-chloroaminopyrimidine 3-6 follow reaction with appropriate amine.

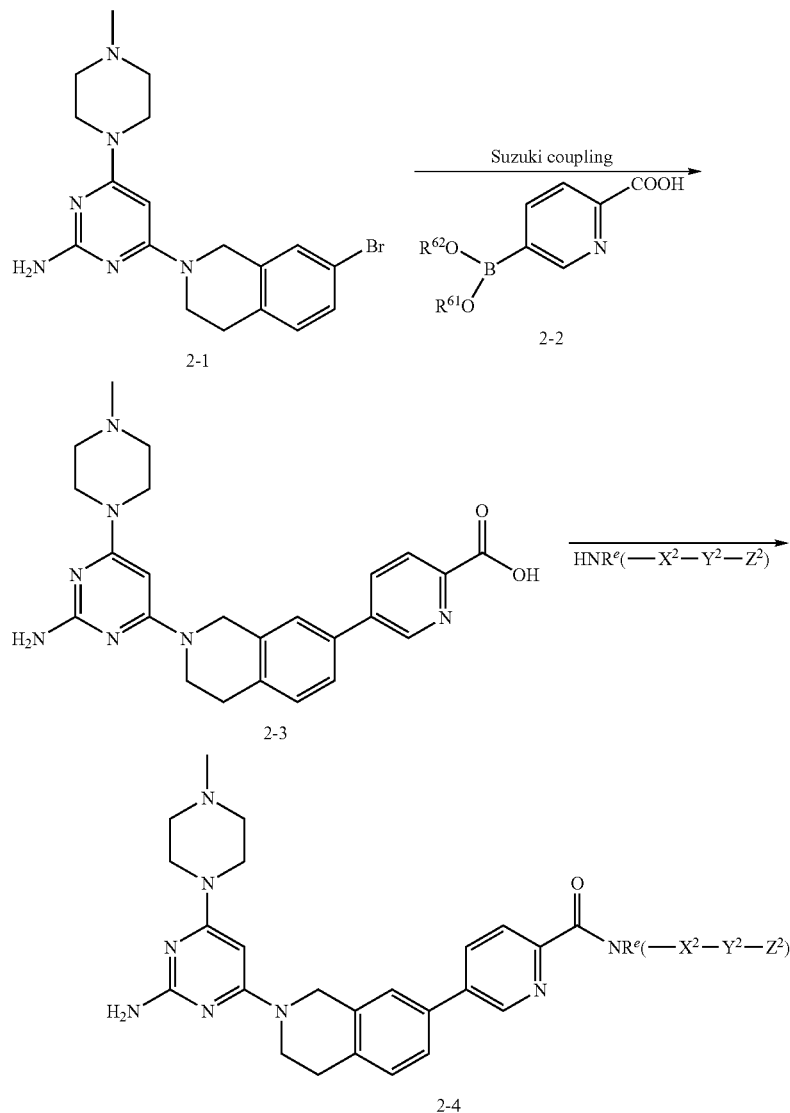

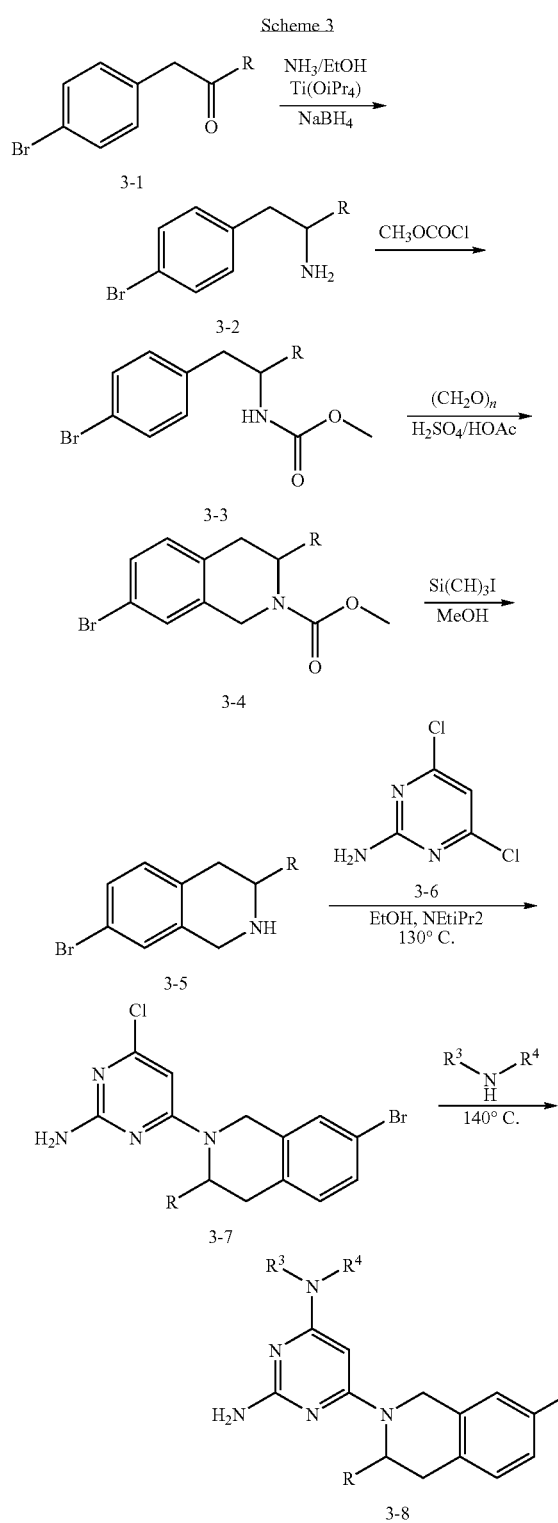

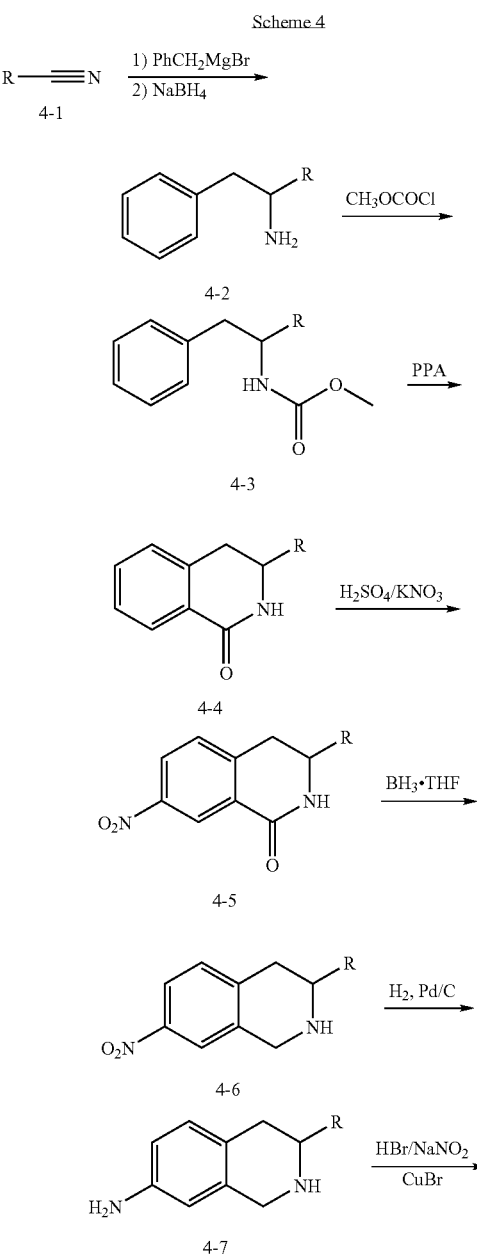

which can be treated with a suitable haloformate such as methyl chloroformate to afford carbamate 4-3. Cyclization of the carbamate 4-3 to lactam 4-4 can be achieved by treatment with polyphosphoric acid (PPA). Nitration of the lactam 4-4 using sulfuric acid and potassium nitrate can produce a nitro substituted lactam 4-5. Reduction of the carbonyl group in 4-5 with a borane reagent (such as $BH_3$-THF) can yield the corresponding 3,4-dihydroisoquinoline 4-6 which can be further reduced to aniline 4-7 by hydrogenation in the presence of a catalyst such as palladium on carbon or $PtO_2$. Sandmeyer bromination reaction (See e.g. Bigelow, L. A., Org. Synth. 1932, 1, 130-132) of the aniline 4-7 can afford the 3,4-dihydroisoquinoline 4-8 which can be conveniently converted to the amino aminopyrimidine derivative 4-11 by reaction with di-chloroaminopyrimidine 4-9 followed by reaction with an appropriate amine $HNR^3R^4$ as previous described.

Alternatively, a series of 3,4-dihydroisoquinoline derivative 4-11 can be prepared by the methods outlined in Scheme 4. Reaction of a nitrile derivative 4-1 (where R can be, for example, optionally substituted alkyl such as methyl, ethyl, or hydroxylmethyl) with a Grignard reagent such as benzyl magnesium bromide followed by reduction with a reducing reagent such as $NaBH_4$ to yield the amine derivative 4-2,

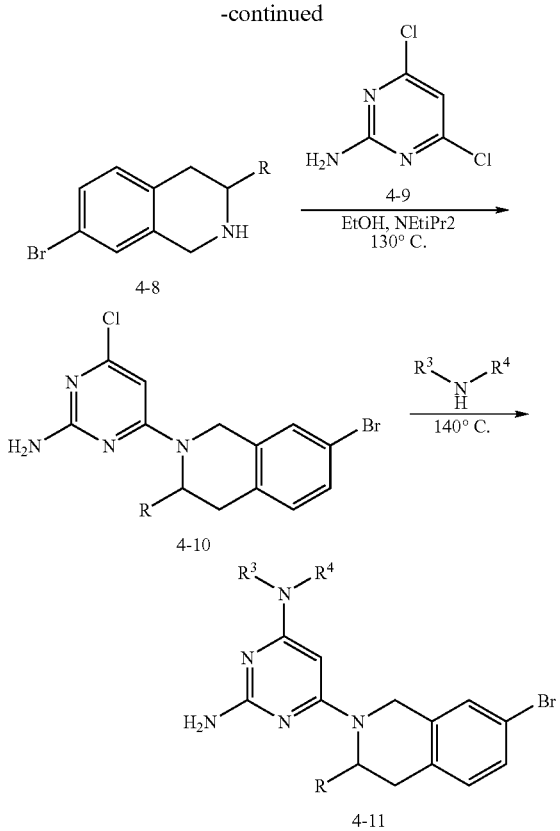

Additional starting materials and intermediates useful for making the compounds of the present invention can be obtained from chemical vendors such as Sigma-Aldrich or can be made according to methods described in the chemical art. For example, introducing pentafluorosulfanyl (SF$_5$) group to aromatic rings can be achieved according to the methods disclosed in U.S. Pat. No. 6,919,484 and/or the references cited therein.

Those skilled in the art can recognize that in all of the schemes described herein, if there are functional (reactive) groups present on a substituent group such as $R^1$, $R^2$, etc., further modification can be made if appropriate and/or desired. For example, a CN group can be hydrolyzed to afford an amide group; a carboxylic acid can be converted to an amide; a carboxylic acid can be converted to an ester, which in turn can be reduced to an alcohol, which in turn can be further modified. For another example, an OH group can be converted into a better leaving group such as mesylate, which in turn is suitable for nucleophilic substitution, such as by CN. For another example, an —S— can be oxidized to —S(O)— and/or —S(O)$_2$—. For yet another example, unsaturated bond such as C═C or C≡C can be reduced to saturated bond by hydrogenation. In some embodiments, a primary amine or a secondary amine moiety (present on a substituent group such as $R^1$, $R^2$, etc.) can be converted to amide, sulfonamide, urea, or thiourea moiety by reacting it with an appropriate reagent such as an acid chloride, a sulfonyl chloride, an isocyanate, or a thioisocyanate compound. In some embodiments, a primary amine, a secondary amine, or a tertiary amine moiety (such as those present on a substituent group such as $R^1$, $R^2$, $R^3$, etc.) can be alkylated to form a quaternary ammonium salt. One skilled in the art will recognize further such modifications. Thus, a compound of Formula I (such as compound 1-6 of Scheme 1) having a substituent which contains a functional group can be converted to another compound of Formula I having a different substituent group.

As used herein, the term "reacting" refers to the bringing together of designated chemical reactants such that a chemical transformation takes place generating a compound different from any initially introduced into the system. Reacting can take place in the presence or absence of solvent.

Methods

Compounds of the invention (including pharmaceutically acceptable salts thereof or N-oxides thereof or quaternary ammonium salts thereof) and/or compositions thereof, can modulate activity of histamine H4 receptor. The term "modulate" is meant to refer to an ability to increase or decrease activity of a histamine H4 receptor. Accordingly, compounds of the invention can be used in methods of modulating a histamine H4 receptor by contacting the histamine H4 receptor with any one or more of the compounds (or pharmaceutically acceptable salts thereof or N-oxides thereof or quaternary ammonium salts thereof) or compositions described herein. In some embodiments, compounds of the present invention can act as inhibitors (or antagonists) of histamine H4 receptor. In further embodiments, the compounds of the invention can be used to modulate activity of a histamine H4 receptor in an individual in need of modulation of the receptor by administering a modulating amount of a compound of the invention.

In some embodiments, one or more of the compounds of the invention can be used in treating a condition or disease or disorder in a patient, wherein the condition or disease or disorder is associated with histamine H4 receptor (for example, associated with expression of histamine H4 receptor or mediated by activity of histamine H4 receptor). In some embodiments, the condition or disease or disorder associated with expression of histamine H4 receptor or mediated by activity of histamine H4 receptor is selected from an inflammatory disease or disorder, pruritus/pruritis, and pain. In some embodiments, the condition or disease or disorder associated with expression of histamine H4 receptor or mediated by activity of histamine H4 receptor is selected from rhinitis, asthma, rheumatoid arthritis, atopic dermatitis, idiopathic chronic urticaria, inflammatory pain, and neuropathic pain.

In some embodiments, examples of the condition or disease or disorder histamine H4 receptor include inflammatory disorders (inflammation), allergic disorders (allergy), dermatological disorders, rheumatoid arthritis, asthma, pruritis, autoimmune diseases, lymphatic disorders, and immunodeficiency disorders. See e.g. WO 2008008359 and WO 2008100565. In some embodiments, examples condition or disease or disorder associated with histamine H4 receptor include allergy, asthma, chronic obstructed pulmonary disease (COPD), atherosclerosis, rheumatoid arthritis, multiple sclerosis, inflammatory bowel diseases, colitis, Crohn's disease, ulcerative colitis, psoriasis, pruritis, itchy skin, atopic dermatitis, urticaria, hives, ocular inflammation, conjunctivitis, dry eye, nasal polyps, allergic rhinitis, nasal itch, scleroderma, autoimmune thyroid diseases, immune-mediated diabetes mellitus, lupus, Myasthenia gravis, autoimmune neuropathies, Guillain-Barre, autoimmune uveitis, autoimmune hemolytic anemia, pernicious anemia, autoimmune thrombocytopenia, temporal arteritis, anti-phospholipid syndrome, vasculitides, Wegener's granulomatosis, Behcet's disease, dermatitis herpetiformis, pemphigus vulgaris, vitiligio, primary biliary cirrhosis, autoimmune hepatitis, autoimmune oophoritis, autoimmune orchitis, autoimmune disease of the adrenal gland, polymyositis, dermatomyositis, spondyloarthropathies, ankylosing spondylitis, and Sjogren's syndrome. See WO 2008008359.

In some embodiments, examples condition or disease or disorder associated with histamine H4 receptor include allergy, rheumatoid arthritis, asthma, autoimmune diseases, and pruritis. See WO 2008100565. In some embodiments, examples condition or disease or disorder associated with histamine H4 receptor include inflammatory diseases, respiratory diseases (e.g. adult respiratory distress syndrome, acute respiratory distress syndrome, bronchitis, chronic bronchitis, chronic obstructive pulmonary disease, cystic fibrosis, asthma, emphysema, rhinitis, chronic sinusitis), allergy; allergy-induced airway responses, allergic rhinitis, viral rhinitis, non-allergic rhinitis, perennial and seasonal rhinitis, nasal congestion, allergic congestion, female and male sexual dysfunction, skin diseases such as dermatitis and psoriasis, cardiac dysfunctions such as myocardial ischaemia and arrythmia, diseases of the gastrointestinal tract such as inflammatory bowel disease, Crohn's disease and colitis ulcerosa, cancer, rheumatoid arthritis, hypotension, pain and overactive bladder conditions. See WO2007072163. Additional examples of condition or disease or disorder associated with histamine H4 receptor can be found, for example, in WO 2007117401 and WO 2005014579.

In some embodiments, one or more of the compounds of the invention can be used in combination with one or more other histamine H1, H2, H3, and/or H4 receptor inhibitors/antagonists (in particular one or more other histamine H4 receptor inhibitors/antagonists).

In some embodiments, one or more H4 receptor inhibitors/antagonists of the invention can be used in combination with one or more other therapeutics used in the treatment of histamine H4 receptor-mediated/associated conditions/diseases/disorders, and may improve the treatment response as compared to the response to the other therapeutics alone, without exacerbation of its toxic effects. Examples of the other therapeutical agents suitable for combination include, for example, H4 receptor inhibitors/anatgonists such as N-Cyclohexyl-4-(1H-imidazol-4-yl)piperidine-1-carbothioamide (Thioperamide), 5-chloro-2-[(4-methylpiperazin-1-yl)carbonyl]-1H-indole (JNJ-7777120), and 5-Chloro-2-[4-methylpiperazin-1-yl)carbonyl]-1H-benzimidazole (VUF-6002 or JNJ 10191584). Additive or synergistic effects are desirable outcomes of combining an H4 receptor inhibitors/antagonists of the present invention with one or more additional agent. The additional agents can be combined with the present compounds in a single or continuous dosage form, or the agents can be administered simultaneously or sequentially as separate dosage forms. In some embodiments, one or more additional agents can be administered to a patient in combination with at least one H4 receptor inhibitor/antagonist described herein where the additional agents are administered intermittently as opposed to continuously.

Pharmaceutical Formulations and Dosage Forms

When employed as pharmaceuticals, the compounds of the invention can be administered in the form of pharmaceutical compositions. These compositions can be prepared in a manner well known in the pharmaceutical art, and can be administered by a variety of routes, depending upon whether local or systemic treatment is desired and upon the area to be treated. Administration may be topical (including transdermal, epidermal, ophthalmic and to mucous membranes including intranasal, vaginal and rectal delivery), pulmonary (e.g., by inhalation or insufflation of powders or aerosols, including by nebulizer; intratracheal or intranasal), oral or parenteral. Parenteral administration includes intravenous, intraarterial, subcutaneous, intraperitoneal intramuscular or injection or infusion; or intracranial, e.g., intrathecal or intraventricular, administration. Parenteral administration can be in the form of a single bolus dose, or may be, for example, by a continuous perfusion pump. Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable. Coated condoms, gloves and the like may also be useful.

This invention also includes pharmaceutical compositions which contain, as the active ingredient, one or more of the compounds of the invention above in combination with one or more pharmaceutically acceptable carriers (excipients). In making the compositions of the invention, the active ingredient is typically mixed with an excipient, diluted by an excipient or enclosed within such a carrier in the form of, for example, a capsule, sachet, paper, or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, suppositories, sterile injectable solutions, and sterile packaged powders.

In preparing a formulation, the active compound can be milled to provide the appropriate particle size prior to combining with the other ingredients. If the active compound is substantially insoluble, it can be milled to a particle size of less than 200 mesh. If the active compound is substantially water soluble, the particle size can be adjusted by milling to provide a substantially uniform distribution in the formulation, e.g. about 40 mesh.

The compounds of the invention may be milled using known milling procedures such as wet milling to obtain a particle size appropriate for tablet formation and for other formulation types. Finely divided (nano particulate) preparations of the compounds of the invention can be prepared by processes known in the art, for example see International Patent Application No. WO 2002/000196.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents. The compositions of the invention can be formulated so as to provide quick, sustained or delayed release of the active ingredient after administration to the patient by employing procedures known in the art.

The compositions can be formulated in a unit dosage form, each dosage containing from about 5 to about 1000 mg (1 g), more usually about 100 to about 500 mg, of the active ingredient. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient.

The active compound can be effective over a wide dosage range and can be generally administered in a pharmaceutically effective amount. For example, the dosage of the active compounds of the invention as employed for the treatment of a patient in need thereof (such as an adult human) may range from 0.1 to 3000 mg per day, depending on the route and frequency of administration. Such a dosage corresponds to 0.001 to 50 mg/kg per day. In some embodiments, the dosage of the active compounds of the invention as employed for the treatment of a patient in need thereof (such as an adult human) may range from 1 to 2000 mg per day, from 1 to 1000 mg per day, from 10 to 1000 mg per day, or from 10 to 500 mg per day. It will be understood, however, that the amount of the compound actually administered will usually be determined by a physician, according to the relevant circumstances, including the condition to be treated, the chosen route of administration, the actual compound administered, the age, weight, and response of the individual patient, the severity of the patient's symptoms, and the like.

For preparing solid compositions such as tablets, the principal active ingredient can be mixed with a pharmaceutical excipient to form a solid pre-formulation composition containing a homogeneous mixture of a compound of the present invention. When referring to these pre-formulation compositions as homogeneous, the active ingredient is typically dispersed evenly throughout the composition so that the composition can be readily subdivided into equally effective unit dosage forms such as tablets, pills and capsules. This solid pre-formulation is then subdivided into unit dosage forms of the type described above containing from, for example, about 0.1 to about 1000 mg of the active ingredient of the present invention.

The tablets or pills of the present invention can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

The liquid forms in which the compounds and compositions of the present invention can be incorporated for administration orally or by injection include aqueous solutions, suitably flavored syrups, aqueous or oil suspensions, and flavored emulsions with edible oils such as cottonseed oil, sesame oil, coconut oil, or peanut oil, as well as elixirs and similar pharmaceutical vehicles.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. In some embodiments, the compositions are administered by the oral or nasal respiratory route for local or systemic effect. Compositions in can be nebulized by use of inert gases. Nebulized solutions may be breathed directly from the nebulizing device or the nebulizing device can be attached to a face masks tent, or intermittent positive pressure breathing machine. Solution, suspension, or powder compositions can be administered orally or nasally from devices which deliver the formulation in an appropriate manner.

The amount of compound or composition administered to a patient will vary depending upon what is being administered, the purpose of the administration, such as prophylaxis or therapy, the state of the patient, the manner of administration, and the like. In therapeutic applications, compositions can be administered to a patient already suffering from a disease in an amount sufficient to cure or at least partially arrest the symptoms of the disease and its complications. Effective doses will depend on the disease condition being treated as well as by the judgment of the attending clinician depending upon factors such as the severity of the disease, the age, weight and general condition of the patient, and the like.

The compositions administered to a patient can be in the form of pharmaceutical compositions described above. These compositions can be sterilized by conventional sterilization techniques, or may be sterile filtered. Aqueous solutions can be packaged for use as is, or lyophilized, the lyophilized preparation being combined with a sterile aqueous carrier prior to administration. The pH of the compound preparations typically will be between 3 and 11, more preferably from 5 to 9 and most preferably from 7 to 8. It will be understood that use of certain of the foregoing excipients, carriers, or stabilizers will result in the formation of pharmaceutical salts.

The therapeutic dosage of the compounds of the present invention can vary according to, for example, the particular use for which the treatment is made, the manner of administration of the compound, the health and condition of the patient, and the judgment of the prescribing physician. The proportion or concentration of a compound of the invention in a pharmaceutical composition can vary depending upon a number of factors including dosage, chemical characteristics (e.g., hydrophobicity), and the route of administration. For example, the compounds of the invention can be provided in an aqueous physiological buffer solution containing about 0.1 to about 10% w/v of the compound for parenteral administration. Some typical dose ranges are from about 1 µg/kg to about 1 µg/kg of body weight per day. In some embodiments, the dose range is from about 0.01 mg/kg to about 100 mg/kg of body weight per day. The dosage is likely to depend on such variables as the type and extent of progression of the disease or disorder, the overall health status of the particular patient, the relative biological efficacy of the compound selected, formulation of the excipient, and its route of administration. Effective doses can be extrapolated from dose-response curves derived from in vitro or animal model test systems.

The compositions of the invention can further include one or more additional pharmaceutical agents such as a chemotherapeutic, steroid, anti-inflammatory compound, or immunosuppressant, examples of which are listed hereinabove.

Labeled Compounds and Assay Methods

Another aspect of the present invention relates to labeled compounds of the invention (radio-labeled, fluorescent-labeled, etc.) that would be useful not only in radio-imaging but also in assays, both in vitro and in vivo, for localizing and quantitating the enzyme in tissue samples, including human, and for identifying ligands by inhibition binding of a labeled compound. Accordingly, the present invention includes enzyme assays that contain such labeled compounds.

The present invention further includes isotopically-labeled compounds of the invention. An "isotopically" or "radio-labeled" compound is a compound of the invention where one or more atoms are replaced or substituted by an atom having an atomic mass or mass number different from the atomic mass or mass number typically found in nature (i.e., naturally occurring). Suitable radionuclides that may be incorporated in compounds of the present invention include but are not limited to $^{2}H$ (also written as D for deuterium), $^{3}H$ (also written as T for tritium), $^{11}C$, $^{13}C$, $^{14}C$, $^{13}N$, $^{15}N$, $^{15}O$, $^{17}O$, $^{18}O$, $^{18}F$, $^{35}S$, $^{36}Cl$, $^{82}Br$, $^{75}Br$, $^{76}Br$, $^{77}Br$, $^{123}I$, $^{124}I$, $^{125}I$ and $^{131}I$. The radionuclide that is incorporated in the radio-labeled compounds will depend on the specific application of that radio-labeled compound. For example, for in vitro receptor labeling and competition assays, compounds that incorporate $^{3}H$, $^{14}C$, $^{82}Br$, $^{125}I$, $^{131}I$, $^{35}S$ or will generally be most useful. For radio-imaging applications $^{11}C$, $^{18}F$, $^{125}I$, $^{123}I$, $^{124}I$, $^{131}I$, $^{75}Br$, $^{76}Br$ or $^{77}Br$ will generally be most useful.

It is understood that a "radio-labeled compound" is a compound that has incorporated at least one radionuclide. In some embodiments the radionuclide is selected from $^{3}H$, $^{14}C$, $^{125}I$, $^{35}S$ and $^{82}Br$.

In some embodiments, the labeled compounds of the present invention contain a fluorescent label.

Synthetic methods for incorporating radio-isotopes and fluorescent labels into organic compounds are well known in the art.

A labeled compound of the invention (radio-labeled, fluorescent-labeled, etc.) can be used in a screening assay to identify/evaluate compounds. For example, a newly synthesized or identified compound (i.e., test compound) which is labeled can be evaluated for its ability to bind a histamine H4 receptor by monitoring its concentration variation when contacting with the histamine H4 receptor, through tracking the labeling. For another example, a test compound (labeled) can be evaluated for its ability to reduce binding of another compound which is known to bind to histamine H4 receptor (i.e., standard compound). Accordingly, the ability of a test compound to compete with the standard compound for binding to the histamine H4 receptor directly correlates to its binding affinity. Conversely, in some other screening assays, the standard compound is labeled and test compounds are unlabeled. Accordingly, the concentration of the labeled standard compound is monitored in order to evaluate the competition between the standard compound and the test compound, and the relative binding affinity of the test compound is thus ascertained.

Kits

The present invention also includes pharmaceutical kits useful, for example, in the treatment or prevention of histamine H4 receptor-mediated conditions/diseases/disorders such as inflammatory disorders, pruritus, and pain (including rhinitis, asthma, rheumatoid arthritis, atopic dermatitis, idiopathic chronic urticaria, inflammatory pain, and other diseases referred to herein), which include one or more containers containing a pharmaceutical composition comprising a therapeutically effective amount of a compound of the invention. Such kits can further include, if desired, one or more of various conventional pharmaceutical kit components, for example, containers with one or more pharmaceutically acceptable carriers, additional containers, etc., as will be readily apparent to those skilled in the art. Instructions, either as inserts or as labels, indicating quantities of the components to be administered, guidelines for administration, and/or guidelines for mixing the components, can also be included in the kit.

The invention will be described in greater detail by way of specific examples. The following examples are offered for illustrative purposes, and are not intended to limit the invention in any manner. Those of skill in the art will readily recognize a variety of non-critical parameters which can be changed or modified to yield essentially the same results. In some instances where the compounds of the examples were isolated by preparative HPLC in the presence of trifluoroacetic acid (TFA) or other acid, the compound may have been obtained as the corresponding salt. Certain compounds of the Examples were found to be inhibitors/antagonists of histamine H4 receptor according to one or more of the assays provided herein. In some embodiments, the $IC_{50}$ value for the compound of invention with respect to histamine H4 receptor is less than about 100, 80, 50, 20, 10, 8, 5, 2, or 1 μM. In some embodiments, the $IC_{50}$ value for the compound of invention with respect to histamine H4 receptor is less than about 1000, 800, 500, 200, 100, 80, 50, 20, or 10 nM. Certain compounds described in Tables A1 and in the Example section were tested for inhibitory activity of histamine H4 receptor targets according to assays such as those described herein or those known in the art [e.g., histamine H4 binding assays described in WO 2008100565]. For instance, Examples 1-9 were found to have $IC_{50}$ values less than 1000 nM, 800 nM, 500 nM, 200 nM, or 100 nM for histamine H4 receptor.

EXAMPLES

Experimental procedures for compounds of the invention are provided below. Open Access Prep LC-MS Purification of some of the compounds prepared were performed on Waters mass directed fractionation systems. The basic equipment setup, protocols, and control software for the operation of these systems have been described in detail in literature. See e.g. "Two-Pump At Column Dilution Configuration for Preparative LC-MS", K. Blom, *J. Combi. Chem.*, 4, 295 (2002); "Optimizing Preparative LC-MS Configurations and Methods for Parallel Synthesis Purification", K. Blom, R. Sparks, J. Doughty, G. Everlof, T. Hague, A. Combs, *J. Combi. Chem.*, 5, 670 (2003); and "Preparative LC-MS Purification: Improved Compound Specific Method Optimization", K. Blom, B. Glass, R. Sparks, A. Combs, *J. Combi. Chem.*, 6, 874-883 (2004). The compounds separated were typically subjected to analytical liquid chromatography mass spectrometry (LCMS) for purity under the following conditions: Instrument; Agilent 1100 series, LC/MSD, Column: Waters Sunfire™ $C_{18}$ 5 Tm, 2.1×5.0 mm, Buffers: mobile phase A: 0.025% TFA in water and mobile phase B: 0.025% TFA in acetonitrile; gradient 2% to 80% of B in 3 minutes with flow rate 1.5 mL/minute.

Some of the compounds prepared were also separated on a preparative scale by reverse-phase high performance liquid chromatography (RP-HPLC) with MS detector or flash chromatography (silica gel) as indicated in the Examples. Typical preparative reverse-phase high performance liquid chromatography (RP-HPLC) column conditions are as follows:

pH=2 purifications: Waters Sunfire™ $C_{18}$ 5 Tm, 19×100 mm column, eluting with mobile phase A: 0.1% TFA (trifluoroacetic acid) in water and mobile phase B: 0.1% TFA in acetonitrile; the flow rate was 30 mL/minute, the separating gradient was optimized for each compound using the Compound Specific Method Optimization protocol as described in the literature [see "Preparative LCMS Purification: Improved Compound Specific Method Optimization", K. Blom, B. Glass, R. Sparks, A. Combs, *J. Comb. Chem.*, 6, 874-883 (2004)]. Typically, the flow rate used with the with 30×100 mm column was 60 mL/minute.

pH=10 purifications: Waters XBridge $C_{18}$ 5 Tm, 19×100 mm column, eluting with mobile phase A: 0.15% $NH_4OH$ in water and mobile phase B: 0.15% $NH_4OH$ in acetonitrile; the flow rate was 30 mL/minute, the separating gradient was optimized for each compound using the Compound Specific Method Optimization protocol as described in the literature [See "Preparative LCMS Purification: Improved Compound Specific Method Optimization", K. Blom, B. Glass, R. Sparks, A. Combs, *J. Comb. Chem.*, 6, 874-883 (2004)]. Typically, the flow rate used with 30×100 mm column was 60 mL/minute.

Example 1

4-(7-Bromo-3,4-dihydroisoquinolin-2(1H)-yl)-6-(4-methylpiperazin-1-yl)pyrimidin-2-amine

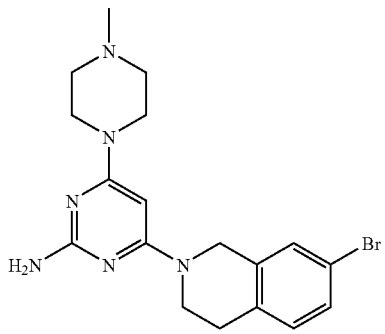 [SMILES: CN1CCN(c2cc(N3CCc4ccc(Br)cc4C3)nc(N)n2)CC1]

Step 1: 4-chloro-6-(4-methylpiperazin-1-yl)pyrimidin-2-amine

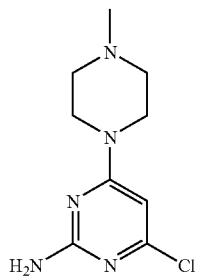

A mixture of 2-Amino-4,6-dichloropyrimidine (1.0 g, 6.1 mmol, Alfa Aesar, Cat. No. A11330), 1-methyl piperazine (0.74 mL, 6.7 mmol, Aldrich, Cat. No. 130001), and N,N-diisopropylethylamine (1.3 mL, 7.3 mmol) in isopropyl alcohol (5 mL) was heated at 110° C. for 2 hours. The reaction mixture was cooled to room temperature (r.t.). The precipitate formed was filtered and then washed by a small amount of isopropanol. The precipitate collected was dried under vacuum to afford this compound and used in the next step without further purification. LCMS(M+H)$^+$: m/z=228.1.

Step 2: 4-(7-bromo-3,4-dihydroisoquinolin-2(1H)-yl)-6-(4-methylpiperazin-1-yl)pyrimidin-2-amine

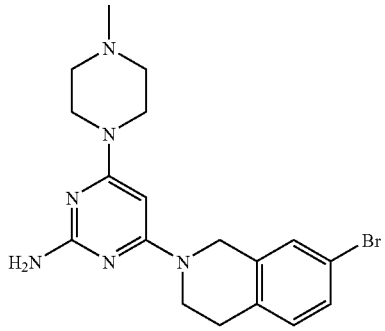 [SMILES: CN1CCN(c2cc(N3CCc4ccc(Br)cc4C3)nc(N)n2)CC1]

A mixture of 4-chloro-6-(4-methylpiperazin-1-yl)pyrimidin-2-amine (500.0 mg, 2.196 mmol), 7-bromo-1,2,3,4-tetrahydroisoquinoline (512.3 mg, 2.416 mmol, Alfa Aesar, Cat. No. B25712) and 4-methylmorpholine (289.7 µL, 2.635 mmol) in N-methylpyrrolidinone (10 mL) was heated at 180° C. overnight. The reaction mixture was cooled to r.t., poured into water, extracted with AcOEt, washed with brine, dried with MgSO$_4$, filtered, and concentrated. The residue was purified by flash chromatograph on a silica gel column using 10% MeOH in CH$_2$Cl$_2$ (include 1% NH$_3$) as eluent to afford the desired compound 695 mg (yield 78.5%). LCMS (M+H)$^+$: m/z=403.2.

Example 2

5-{2-[2-Amino-6-(4-methylpiperazin-1-yl)pyrimidin-4-yl]-1,2,3,4-tetrahydroisoquinolin-7-yl}-N-methylpyridine-2-carboxamide

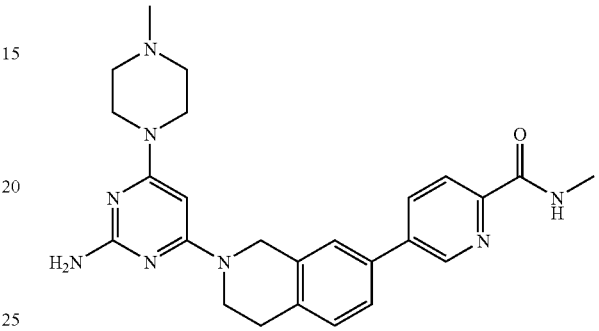

A mixture of 4-(7-bromo-3,4-dihydroisoquinolin-2(1H)-yl)-6-(4-methylpiperazin-1-yl)pyrimidin-2-amine (15 mg, 0.037 mmol, Example 1), N-methyl-5-(4,4,5,5-tetramethyl-1,3,2-dioxaborolan-2-yl)pyridine-2-carboxamide (15 mg, 0.056 mmol, Frontier, Cat. No. M10074), [1,1'-Bis(diphenylphosphino)ferrocene]dichloropalladium(II), complex with dichloromethane (1:1) (1.8 mg, 0.0022 mmol, Aldrich Cat. No. 379670), and potassium phosphate (24 mg, 0.11 mmol) in 1,4-dioxane (1 mL) and water (0.2 mL) was heated at 120° C. for 2 hours. The reaction mixture was cooled to r.t., and then concentrated. The residue was dissolved in MeOH, and purified by RP-HPLC (pH=10) to afford the desired compound. LCMS (M+H)$^±$: m/z=459.4.

Example 3

N-(5-{2-[2-Amino-6-(4-methylpiperazin-1-yl)pyrimidin-4-yl]-1,2,3,4-tetrahydroisoquinolin-7-yl}pyridin-2-yl)acetamide

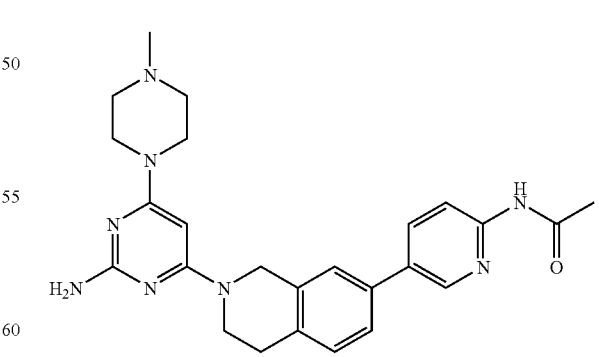

A mixture of 4-(7-bromo-3,4-dihydroisoquinolin-2(1H)-yl)-6-(4-methylpiperazin-1-yl)pyrimidin-2-amine (15 mg, 0.037 mmol, Example 1), N4-[4-(4,4,5,5-tetramethyl-1,3,2-dioxaborolan-2-yl)pyridin-2-yl]acetamide (15 mg, 0.056 mmol, Aldrich, Cat. No. 683892), tetrakis(triphenylphosphine)palladium(0) (2.6 mg, 0.0022 mmol, Aldrich, Cat. No. 216666), and potassium phosphate (24 mg, 0.11 mmol) in 1,4-dioxane (1 mL) and water (0.2 mL) was heated at 120° C. for 2 hours. The reaction mixture was cooled to r.t. and then concentrated. The residue was dissolved in MeOH and purified by RP-HPLC (pH=10) to afford the desired compound. LCMS (M+H)+: m/z=459.4.

Example 4

4-(4-Methylpiperazin-1-yl)-6-[7-(1-methyl-1H-pyrazol-4-yl)-3,4-dihydroisoquinolin-2(1H)-yl]pyrimidin-2-amine

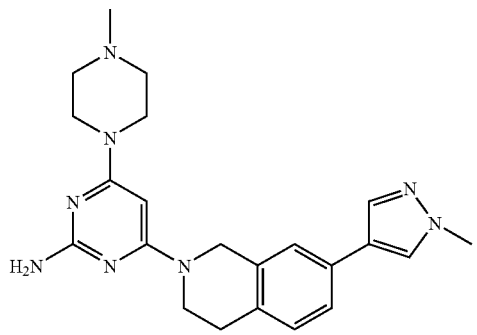 [SMILES: CN1CCN(c2cc(N3CCc4ccc(-c5cnn(C)c5)cc4C3)nc(N)n2)CC1]

This compound was prepared by using procedures analogous to those described for the synthesis of Example 2 starting from 4-(7-bromo-3,4-dihydroisoquinolin-2(1H)-yl)-6-(4-methylpiperazin-1-yl)pyrimidin-2-amine and 1-methyl-4-(4,4,5,5-tetramethyl-1,3,2-dioxaborolan-2-yl)-1H-pyrazole (Aldrich, Cat. No. 595214). LCMS (M+H)+: m/z=405.4.

Example 5

4-(4-Methylpiperazin-1-yl)-6-[7-[2-(4-methylpiperazin-1-yl)pyridin-4-yl]-3,4-dihydroisoquinolin-2(1H)-yl]pyrimidin-2-amine

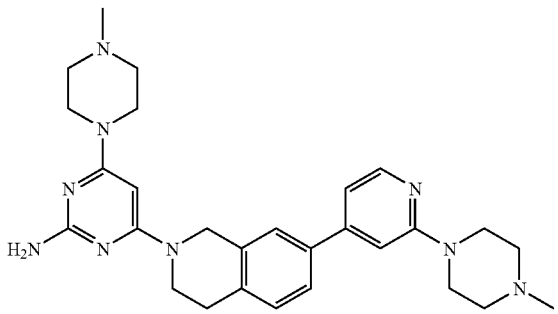 [SMILES: CN1CCN(c2cc(-c3ccc4c(c3)CN(c3cc(N5CCN(C)CC5)nc(N)n3)CC4)ccn2)CC1]

This compound was prepared by using procedures analogous to those described for the synthesis of Example 2 starting from 4-(7-bromo-3,4-dihydroisoquinolin-2(1H)-yl)-6-(4-methylpiperazin-1-yl)pyrimidin-2-amine and 1-methyl-4-[4(4,4,5,5-tetramethyl-1,3,2-dioxaborolan-2-yl)pyridin-2-yl]piperazine (Oadwood, Cat. No. 021854). LCMS (M+H)+: m/z=500.5.

Example 6

4-[7-(6-Chloro-5-fluoropyridin-3-yl)-3,4-dihydroisoquinolin-2(1H)-yl]-6-(4-methylpiperazin-1-yl)pyrimidin-2-amine

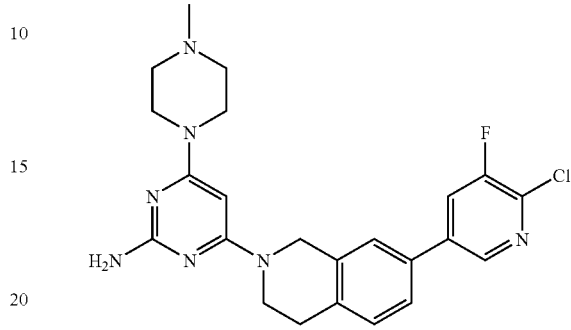

This compound was prepared by using procedures analogous to those described for the synthesis of Example 2 starting from 4-(7-bromo-3,4-dihydroisoquinolin-2(1H)-yl)-6-(4-methylpiperazin-1-yl)pyrimidin-2-amine and 6-chloro-5-fluoropyridin-3-yl)boronic acid (Asymchem., Cat. No. 110496).
LCMS (M+H)+: m/z=454.3.

Example 7

5-{2-[2-Amino-6-(4-methylpiperazin-1-yl)pyrimidin-4-yl]-1,2,3,4-tetrahydroisoquinolin-7-yl}-3-fluoropyridine-2-carbonitrile

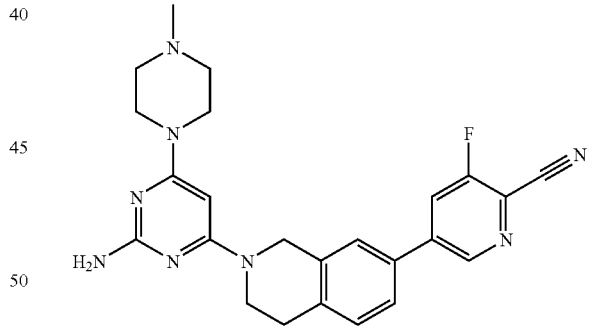

4-[7-(6-chloro-5-fluoropyridin-3-yl)-3,4-dihydroisoquinolin-2(1H)-yl]-6-(4-methylpiperazin-1-yl)pyrimidin-2-amine (186 mg, 0.410 mmol, Example 6), Zinc cyanide (57 mg, 0.48 mmol), N,N,N',N'-tetramethylethylenediamine (86 µL, 0.57 mmol), tris(dibenzylideneacetone)dipalladium(0) (16 mg, 0.018 mmol, Alfa Aesar Cat. No. 12760) and (9,9-dimethyl-9H-xanthene-4,5-diyl)bis(diphenylphosphine) (30 mg, 0.053 mmol) (Aldrich, Cat. No. 526460) were added successively to N-Methylpyrrolidinone (5 mL) in a microwave tube. The tube was sealed and degassed with nitrogen and heated at 160° C. overnight. The reaction mixture was cooled to r.t. and filtered. The filtration was diluted with MeOH and purified by RP-HPLC (pH=10) to afford the desired compound. LCMS (M+H)+: m/z=445.3.

Example 8 tert-Butyl 4-(5-{2-[2-amino-6-(4-methylpiperazin-1-yl)pyrimidin-4-yl]-1,2,3,4-tetrahydroisoquinolin-7-yl}-pyrimidin-2-yl)piperazine-1-carboxylate

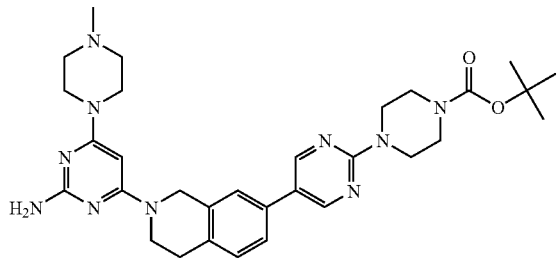 [SMILES: CN1CCN(c2cc(N3CCc4ccc(-c5cnc(N6CCN(C(=O)OC(C)(C)C)CC6)nc5)cc4C3)nc(N)n2)CC1]

This compound was prepared by using procedures analogous to those described for the synthesis of Example 2 starting from 4-(7-bromo-3,4-dihydroisoquinolin-2(1H)-yl)-6-(4-methylpiperazin-1-yl)pyrimidin-2-amine and tert-butyl 4-[5-(4,4,5,5-tetramethyl-1,3,2-dioxaborolan-2-yl)pyrimidin-2-yl]piperazine-1-carboxylate, (Frontier., Cat. P1821). LCMS (M+H)+: m/z=587.5.

Example 9

4-(4-Methylpiperazin-1-yl)-6-[7-(2-piperazin-1-ylpyrimidin-5-yl)-3,4-dihydroisoquinolin-2(1H)-yl]pyrimidin-2-amine

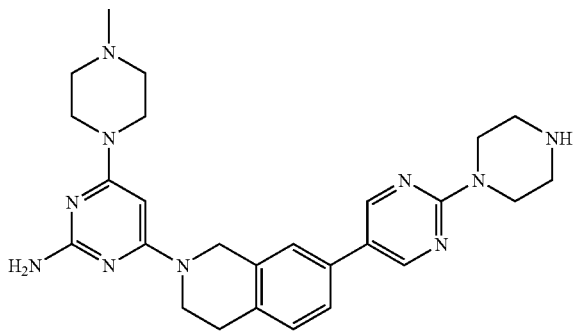 [SMILES: CN1CCN(c2cc(N3CCc4ccc(-c5cnc(N6CCNCC6)nc5)cc4C3)nc(N)n2)CC1]

A mixture of tert-butyl 4-(5-{2-[2-amino-6-(4-methylpiperazin-1-yl)pyrimidin-4-yl]-1,2,3,4-tetrahydroisoquinolin-7-yl}pyrimidin-2-yl)piperazine-1-carboxylate (10 mg, 0.02 mmol, Example 8) and a solution of hydrogen chloride in 1,4-dioxane (0.01704 mL, 0.06817 mmol, 4 M) with a few drops of water was stirred at r.t. for 2 hours. The solution was concentrated. The residue was dissolved in MeOH and purified by RP-HPLC (pH=10) to afford the desired compound. LCMS (M+H)+: m/z=487.4.

Example 10

4-[7-{1-[(6-Ethoxypyridin-3-yl)methyl]-1H-pyrazol-4-yl}-3,4-dihydroisoquinolin-2(1H)-yl]-6-(4-methylpiperazin-1-yl)pyrimidin-2-amine

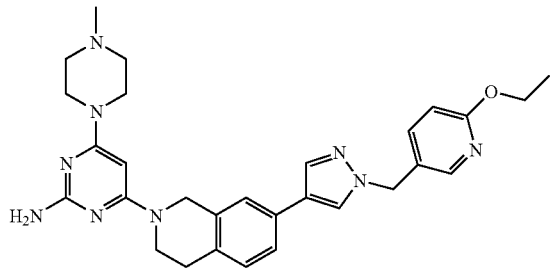 [SMILES: CCOc1ccc(Cn2cc(-c3ccc4c(c3)CN(c3cc(N5CCN(C)CC5)nc(N)n3)CC4)cn2)cn1]

Step 1: (6-ethoxypyridin-3-yl)methanol

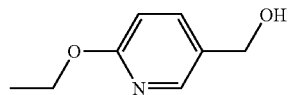

A mixture of (6-chloropyridin-3-yl)methanol (1.4 g, 0.010 mol, Aldrich, Cat. 536016) and sodium ethoxide (3.0 g, 0.044 mol) in ethanol (30 mL) was stirred at 95° C. for 36 hours. The reaction mixture was cooled to r.t., diluted with ethyl acetate, washed with water and brine successively, dried with MgSO4, and concentrated to afford the desired compound. The crude product was directly used in the next step without further purification. LCMS (M+H)+: m/z=154.3.

Step 2: 5-(chloromethyl)-2-ethoxypyridine

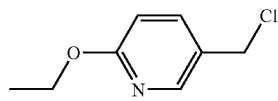

(6-Ethoxypyridin-3-yl)methanol (1.0 g, 6.5 mmol) was dissolved in methylene chloride (20 mL), and triethylamine (1.8 mL, 13 mmol) was added. The reaction mixture was cooled in an ice bath and methanesulfonyl chloride (0.67 mL, 8.6 mmol, Aldrich, Cat. 471259) was slowly added. The reaction mixture was stirred for 2 hours and then the reaction mixture was partitioned between ethyl acetate and water. The organic layer was washed with brine, dried with MgSO4, and concentrated. The residue was purified by flash chromatograph on a silica gel column using 20% Ethyl acetate in hexane as eluent to afford the desired compound. LCMS (M+H)+: m/z=172.2.

Step 3: 2-ethoxy-5-{[4-(4,4,5,5-tetramethyl-1,3,2-dioxaborolan-2-yl)-1H-pyrazol-1-yl]methyl}pyridine

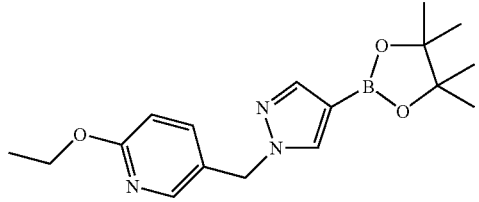 [SMILES: CCOc1ccc(Cn2cc(B3OC(C)(C)C(C)(C)O3)cn2)cn1]

To a mixture of 4-(4,4,5,5-tetramethyl-1,3,2-dioxaborolan-2-yl)-1H-pyrazole (0.58 g, 3.0 mmol, Aldrich, Cat. 525057) in tert-butyl alcohol (5.0 mL) was added a solution of potassium tert-butoxide in tert-butyl alcohol (5.0 mL, 5.0 mmol, 1.00 M, Aldrich Cat. 331341). The reaction mixture was stirred at r.t. for 10 minutes followed by an addition of 5-(chloromethyl)-2-ethoxypyridine (0.54062 g, 3.15 mmol). The reaction mixture was stirred at 65° C. overnight. The reaction mixture was cooled to r.t., quenched with aqueous ammonium chloride, and extracted with EtOAc. The combined organic layers were washed with water and brine successively, dried with MgSO4, and concentrated. The residue was purified by flash chromatograph on a silica gel column using 20% ethyl acetate in methylene chloride as eluent to afford the desired compound. LCMS (M+H)+: m/z=330.4.

Step 4: 4-[7-{1-[(6-ethoxypyridin-3-yl)methyl]-1H-pyrazol-4-yl}-3,4-dihydroisoquinolin-2(1H)-yl]-6-(4-methylpiperazin-1-yl)pyrimidin-2-amine

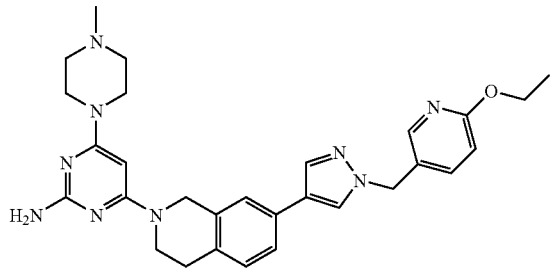 [SMILES: CCOc1ccc(Cn2cc(-c3ccc4c(c3)CN(c3cc(N5CCN(C)CC5)nc(N)n3)CC4)cn2)cn1]

This compound was prepared by using procedures analogous to those described for the synthesis of Example 2 starting from 4-(7-bromo-3,4-dihydroisoquinolin-2(1H)-yl)-6-(4-methylpiperazin-1-yl)pyrimidin-2-amine and 2-ethoxy-5-{[4-(4,4,5,5-tetramethyl-1,3,2-dioxaborolan-2-yl)-1H-pyrazol-1-yl]methyl}pyridine. LCMS(M+H)$^+$: m/z=526.4

Example 11

[1-(4-{2-[2-Amino-6-(4-methylpiperazin-1-yl)pyrimidin-4-yl]-1,2,3,4-tetrahydroisoquinolin-7-yl}-1H-pyrazol-1-yl)cyclopentyl]acetonitrile

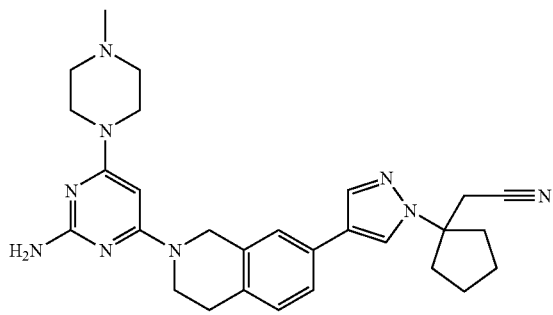 [SMILES: CN1CCN(c2cc(N3CCc4ccc(-c5cnn(C6(CC#N)CCCC6)c5)cc4C3)nc(N)n2)CC1]

Step 1: cyclopentylideneacetonitrile

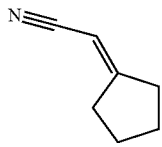

To a solution of potassium tert-butoxide in tetrahydrofuran (12 mL, 0.012 mol, 1.0 M, Aldrich Cat. No. 328650) was added a solution of diethyl cyanomethylphosphonate (2.1 g, 0.012 mol, Aldrich Cat. No. D91705) in tetrahydrofuran (2.0 mL) at 0° C. The mixture was stirred at this temperature for 5 minutes then at r.t. for one hour. Then the mixture was cooled to 0° C. followed by a slow addition of a solution of cyclopentanone (1.0 g, 0.012 mol, Aldrich, Cat. W391018) in tetrahydrofuran (1.0 mL). After completion of the addition, the ice-water bath was removed and the reaction mixture was stirred at r.t. for 2 hours. The reaction mixture was quenched with water and extracted with ethyl acetate. The organic extract was washed with NaHCO$_3$ aqueous solution, water, and brine successively; and then dried with Na$_2$SO$_4$. After filtration, the filtrate was concentrated to yield 1.5 g of crude product which was used in the next step without further purification.

Step 2: {1-[4-(4,4,5,5-tetramethyl-1,3,2-dioxaborolan-2-yl)-1H-pyrazol-1-yl]cyclopentyl}acetonitrile

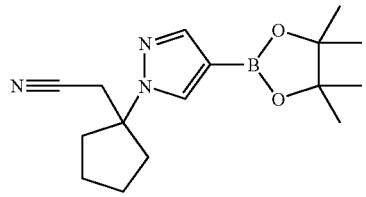 [SMILES: CC1(C)OB(c2cnn(C3(CC#N)CCCC3)c2)OC1(C)C]

A mixture of cyclopentylideneacetonitrile (0.65 g, 0.0061 mol), 4-(4,4,5,5-tetramethyl-1,3,2-dioxaborolan-2-yl)-1H-pyrazole (0.60 g, 0.0031 mol, Aldrich, Cat. 525057), and 1,8-diazabicyclo[5.4.0]undec-7-ene (47 mg, 0.00031 mol, Aldrich, Cat. No. 139009) in acetonitrile (7 mL) was stirred at 60° C. overnight. After cooling to r.t., the reaction mixture was concentrated. The crude residue was purified by flash column chromatography on a silica gel column using 40% ethyl acetate in hexane as eluent to afford the desired compound (161 mg, 17.29%). LCMS (M+H)$^+$: m/z=302.4.

Step 3: [1-(4-{2-[2-amino-6-(4-methylpiperazin-1-yl)pyrimidin-4-yl]-1,2,3,4-tetrahydroisoquinolin-7-yl}-1H-pyrazol-1-yl)cyclopentyl]acetonitrile

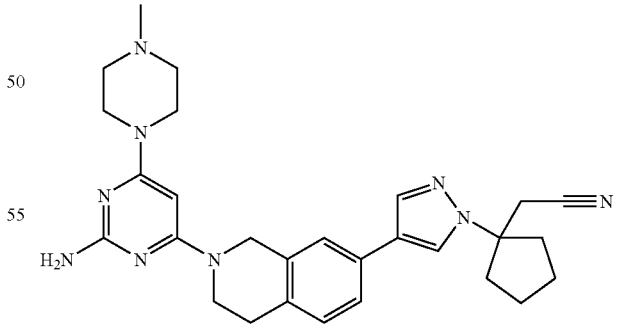

This compound was prepared by using procedures analogous to those described for the synthesis of Example 2 starting from 4-(7-bromo-3,4-dihydroisoquinolin-2(1H)-yl)-6-(4-methylpiperazin-1-yl)pyrimidin-2-amine and {1-[4-(4,4,5,5-tetramethyl-1,3,2-dioxaborolan-2-yl)-1H-pyrazol-1-yl]cyclopentyl}acetonitrile. LCMS(M+H)$^+$: m/z=498.5

Example 12 tert-Butyl 4-(4-{2-[2-amino-6-(4-methylpiperazin-1-yl)pyrimidin-4-yl]-1,2,3,4-tetrahydroisoquinolin-7-yl}-1H-pyrazol-1-yl)piperidine-1-carboxylate

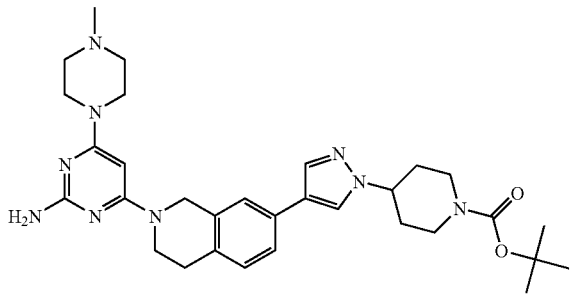 [SMILES: CN1CCN(c2cc(N3CCc4ccc(-c5cnn(C6CCN(C(=O)OC(C)(C)C)CC6)c5)cc4C3)nc(N)n2)CC1]

Step 1: tert-butyl 4-[(methylsulfonyl)oxy]piperidine-1-carboxylate

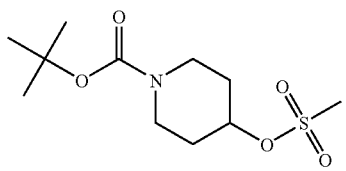 [SMILES: CC(C)(C)OC(=O)N1CCC(OS(C)(=O)=O)CC1]

To a solution of tert-butyl 4-hydroxypiperidine-1-carboxylate (5.03 g, 0.0250 mol, Aldrich Cat. No. 495484) in methylene chloride (50 mL) were added methanesulfonyl chloride (2.03 mL, 0.0262 mol, Aldrich, Cat. No. 471259) and triethylamine (3.66 mL, 0.0262 mol) at 0° C. The solution was stirred at r.t. overnight, then diluted with AcOEt, and washed with NaHCO₃ aqueous solution and brine successively. The organic layer was dried with MgSO₄ and then concentrated to afford the desired product which was directly used in next step. LCMS (M+Na)⁺: m/z=302.3.

Step 2: tert-butyl 4-[4-(4,4,5,5-tetramethyl-1,3,2-dioxaborolan-2-yl)-1H-pyrazol-1-yl]piperidine-1-carboxylate

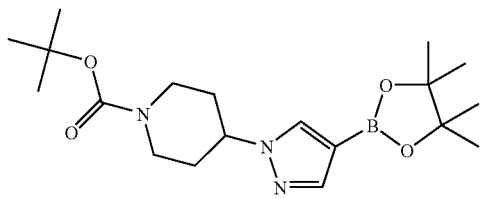 [SMILES: CC(C)(C)OC(=O)N1CCC(n2cc(B3OC(C)(C)C(C)(C)O3)cn2)CC1]

To a solution of 4-(4,4,5,5-tetramethyl-1,3,2-dioxaborolan-2-yl)-1H-pyrazole (4.12 g, 21.2 mmol, Aldrich, Cat. 525057) in N,N-dimethylformamide (20 mL) was added sodium hydride (1.78 g, 44.5 mmol) at 0° C. The resulting solution was stirred at r.t. for one hour, and then tert-butyl 4-[methylsulfonyl)oxy]piperidine-1-carboxylate (6.3 g, 22 mmol) in DMF (2 mL) was added. The reaction mixture was heated at 90° C. overnight. Then the reaction mixture was cooled to r.t., quenched with water, and extracted with AcOEt. The organic layer was washed with NaHCO₃ aqueous solution and brine successively, dried with MgSO₄, and concentrated. The residue was purified by flash column chromatography on a silica gel column using 30% ethyl acetate in hexane as eluent to afford the desired compound (2.30 g, 28.74%). LCMS (M+H)⁺: m/z=378.4.

Step 3: tert-butyl 4-(4-{2-[2-amino-6-(4-methylpiperazin-1-yl)pyrimidin-4-yl]-1,2,3,4-tetrahydroisoquinolin-7-yl}-1H-pyrazol-1-yl)piperidine-1-carboxylate

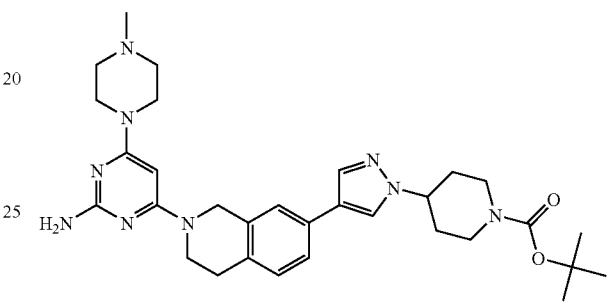

This compound was prepared by using procedures analogous to those described for the synthesis of Example 2 starting from 4-(7-bromo-3,4-dihydroisoquinolin-2(1H)-yl)-6-(4-methylpiperazin-1-yl)pyrimidin-2-amine and tert-butyl 4-[4-(4,4,5,5-tetramethyl-1,3,2-dioxaborolan-2-yl)-1H-pyrazol-1-yl]piperidine-1-carboxylate. LCMS (M+H)⁺: m/z=574.5.

Example 13

4-(4-Methylpiperazin-1-yl)-6-[7-(1-piperidin-4-yl-1H-pyrazol-4-yl)-3,4-dihydroisoquinolin-2(1H)-yl]pyrimidin-2-amine

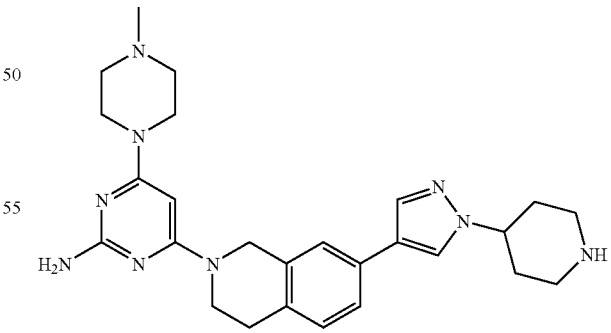

This compound was prepared by using procedures analogous to those described for the synthesis of Example 9 starting from tert-butyl 4-(4-{2-[2-amino-6-(4-methylpiperazin-1-yl)pyrimidin-4-yl]-1,2,3,4-tetrahydroisoquinolin-7-yl}-1H-pyrazol-1-yl)piperidine-1-carboxylate, LCMS(M+H)⁺: m/z=474.4

Example 14

4-[7-(4-Chloro-1H-pyrazol-1-yl)-3,4-dihydroisoquinolin-2(1H)-yl]-6-(4-methylpiperazin-1-yl)pyrimidin-2-amine

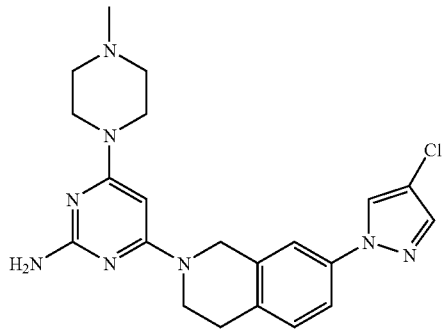 [SMILES: CN1CCN(c2cc(N3CCc4ccc(-n5cc(Cl)cn5)cc4C3)nc(N)n2)CC1]

To a solution of 4-(7-bromo-3,4-dihydroisoquinolin-2 (1H)-yl)-6-(4-methylpiperazin-1-yl)pyrimidin-2-amine (20 mg, 0.05 mmol, Example 1), 4-chloro-1H-pyrazole (6.1 mg, 0.060 mmol, Astatech, Cat. No. 64527) in 1,4-dioxane (1 mL), potassium carbonate (14 mg, 0.10 mmol), (1S,2S)-N, N'-dimethylcyclohexane-1,2-diamine (1.4 mg, 0.0099 mmol, Aldrich, Cat. No. 633089), and Copper(I) iodide (0.94 mg, 0.0050 mmol, Aldrich, Cat. No. 215554) were added. The mixture was degassed with nitrogen and heated at 120° C. overnight. The reaction mixture was concentrated. The residue was dissolved in MeOH, and purified by RP-HPLC (pH=10) to afford the desired compound. LCMS(M+H)$^+$: m/z=425.3.

Example 15

{(3S)-2-[2-Amino-6-(4-methylpiperazin-1-yl)pyrimidin-4-yl]-1,2,3,4-tetrahydroisoquinolin-3-yl}methanol

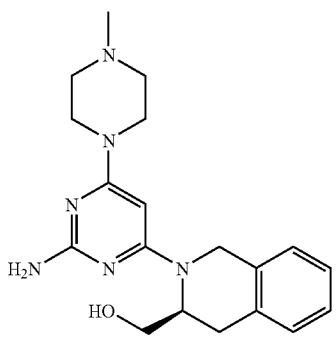 [SMILES: CN1CCN(c2cc(N3Cc4ccccc4C[C@H]3CO)nc(N)n2)CC1]

A mixture of 4-chloro-6-(4-methylpiperazin-1-yl)pyrimidin-2-amine (20 mg, 87.8 mmol), (3 S)-1,2,3,4-tetrahydroisoquinolin-3-ylmethanol (21.5 mg, 132 mmol, Aldrich, Cat. 494186) and triethylamine (0.5 mL, 4 mmol) in N-methylpyrrolidinone (1 mL) was heated at 120° C. overnight. The reaction mixture was diluted in MeOH, and purified by RP-HPLC (pH=10) to afford the desired compound. LCMS (M+H)$^+$: m/z=355.3.

Example 16

2-[2-Amino-6-(4-methylpiperazin-1-yl)pyrimidin-4-yl]-N-(6-methylpyridin-2-yl)-1,2,3,4-tetrahydroisoquinolin-7-amine

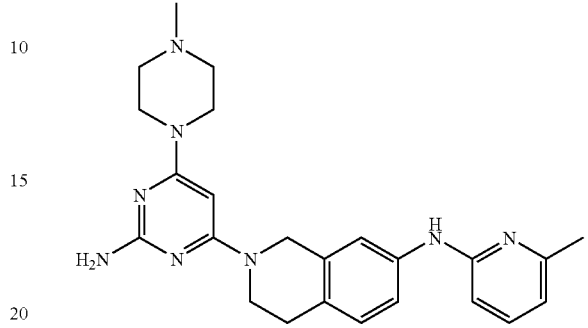

A mixture of 4-(7-bromo-3,4-dihydroisoquinolin-2(1H)-yl)-6-(4-methylpiperazin-1-yl)pyrimidin-2-amine (20.0 mg, 0.0496 mmol), 6-methyl-2-pyridinamine, (8.04 mg, 0.0744 mmol, Aldrich, Cat. No. A75706), a solution of potassium tert-butoxide in tetrahydrofuran (0.0992 mL, 0.0992 mmol, 1.00 M, Aldrich Cat. 328650), palladium acetate (0.445 mg, 0.00198 mmol, Aldrich, Cat. No. 379875), and 2-[dicyclohexylphosphino]biphenyl (0.869 mg, 0.00248 mmol, Aldrich, Cat. No. 638099) in 1,4-dioxane (1 mL) was degassed with nitrogen and then heated at 120° C. for 16 hours. The reaction mixture was cooled to r.t. and concentrated. Then the reaction mixture was dissolved in MeOH and purified by RP-HPLC (pH=10) to afford the desired compound. LCMS (M+H)$^+$: m/z=431.4.

Example 17

4-[7-(2-Chlorophenoxy)-3,4-dihydroisoquinolin-2 (1H)-yl]-6-(4-methylpiperazin-1-yl)pyrimidin-2-amine

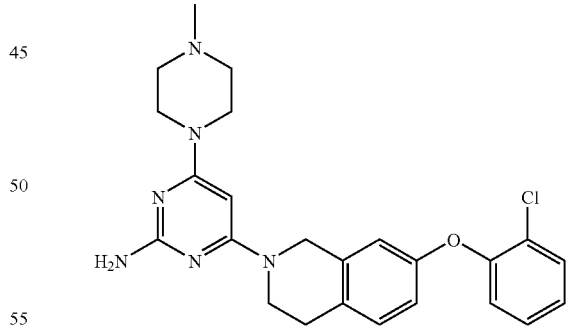

A mixture of 4-(7-bromo-3,4-dihydroisoquinolin-2(1H)-yl)-6-(4-methylpiperazin-1-yl)pyrimidin-2-amine (20.0 mg, 0.0496 mmol), 2-chlorophenol (0.00765 g, 0.0595 mmol, Aldrich, Cat. No. 185779), 1-methylimidazole (2.04 mg, 0.0248 mmol, Aldrich, Cat. No. M50834), Cuprous monochloride (0.245 mg, 0.00248 mmol, Aldrich, Cat. No. 229628), and potassium carbonate (13.7 mg, 0.0992 mmol) in 1,4-dioxane (0.8 mL) was heated at 140° C. overnight. The reaction mixture was cooled to r.t. and concentrated. Then the reaction mixture was dissolved in MeOH and filtered, the filtration was purified by RP-HPLC (pH=10) to afford the desired compound. LCMS(M+H)$^+$: m/z=451.3.

Example 18

5-{2-[2-Amino-6-(4-methylpiperazin-1-yl)pyrimidin-4-yl]-1,2,3,4-tetrahydroisoquinolin-7-yl}-N-(pyridin-2-ylmethyl)pyridine-2-carboxamide

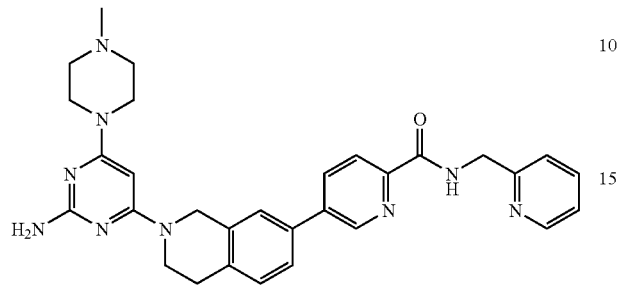

Step 1: 5-{2-[2-amino-6-(4-methylpiperazin-1-yl)pyrimidin-4-yl]-1,2,3,4-tetrahydroisoquinolin-7-yl}pyridine-2-carboxylic acid

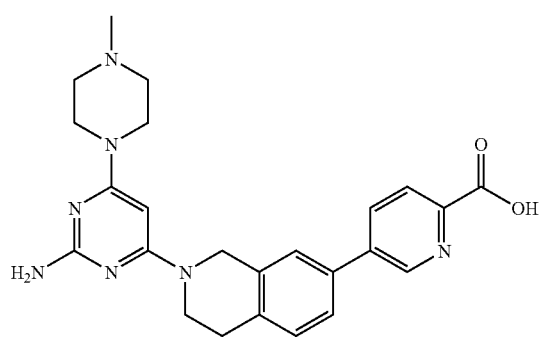 [SMILES: CN1CCN(c2cc(N3CCc4ccc(-c5ccc(C(=O)O)nc5)cc4C3)nc(N)n2)CC1]

This compound was prepared by using procedures analogous to those described for the synthesis of Example 2, starting from 4-(7-bromo-3,4-dihydroisoquinolin-2(1H)-yl)-6-(4-methylpiperazin-1-yl)pyrimidin-2-amine (Example 1) and methyl 5-(4,4,5,5-tetramethyl-1,3,2-dioxaborolan-2-yl)pyridine-2-carboxylate (Frontier Cat. No. M2012). LCMS (M+H)$^+$: m/z=446.3.

Step 2: 5-{2-[2-amino-6-(4-methylpiperazin-1-yl)pyrimidin-4-yl]-1,2,3,4-tetrahydroisoquinolin-7-yl}-N-(pyridin-2-ylmethyl)pyridine-2-carboxamide

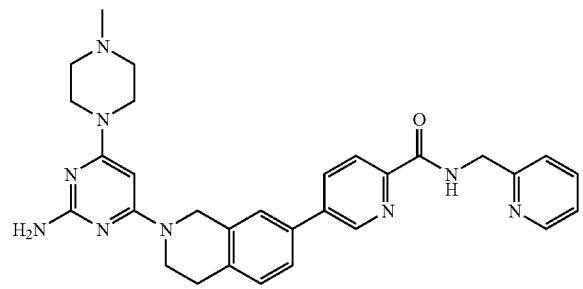 [SMILES: CN1CCN(c2cc(N3CCc4ccc(-c5ccc(C(=O)NCc6ccccn6)nc5)cc4C3)nc(N)n2)CC1]

To a mixture of 5-{2-[2-amino-6-(4-methylpiperazin-1-yl)pyrimidin-4-yl]-1,2,3,4-tetrahydroisoquinolin-7-yl}pyridine-2-carboxylic acid (15 mg, 0.034 mmol) and 2-pyridinemethanamine (7.3 mg, 0.067 mmol, Aldrich, Cat. No. A65204) in N,N-dimethylformamide (1 mL) were added (benzotriazol-1-yloxy)tripyrrolidinophosphonium hexafluorophosphate (21 mg, 0.040 mmol, NovaBiochem, Cat. 01-62-0016) and N,N-diisopropylethylamine (18 μL, 0.10 mmol). The resulting mixture was stirred at r.t. for two hours. Then the reaction solution was diluted in MeOH and purified by RP-HPLC (pH=10 system) to afford the desired compound. LCMS(M+H)$^+$: m/z=536.4.

Example 19

5-{2-[2-Amino-6-(4-methylpiperazin-1-yl)pyrimidin-4-yl]-1,2,3,4-tetrahydroisoquinolin-7-yl}-N-(2-hydroxy-2-methylpropyl)pyridine-2-carboxamide

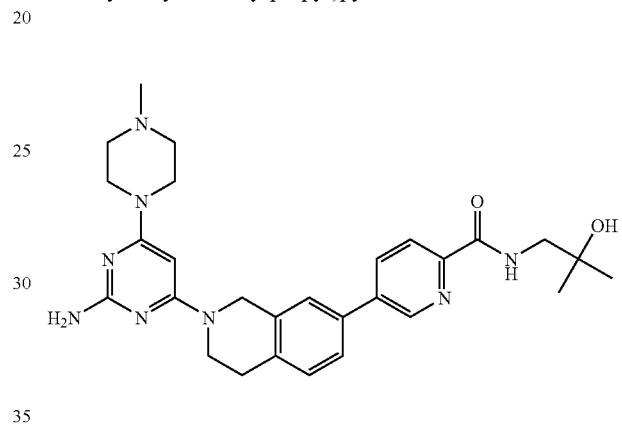

This compound was prepared by using procedures analogous to those described for the synthesis of Example 18 starting from 5-{2-[2-amino-6-(4-methylpiperazin-1-yl)pyrimidin-4-yl]-1,2,3,4-tetrahydroisoquinolin-7-yl}pyridine-2-carboxylic acid and 1-amino-2-methyl-2-propanol (Tyger, Cat. No. A57123). LCMS (M+H)$^+$: m/z=517.4.

Example 20

5-{2-[2-Amino-6-(4-methylpiperazin-1-yl)pyrimidin-4-yl]-1,2,3,4-tetrahydroisoquinolin-7-yl}-N-(trans-4-hydroxycyclohexyl)pyridine-2-carboxamide

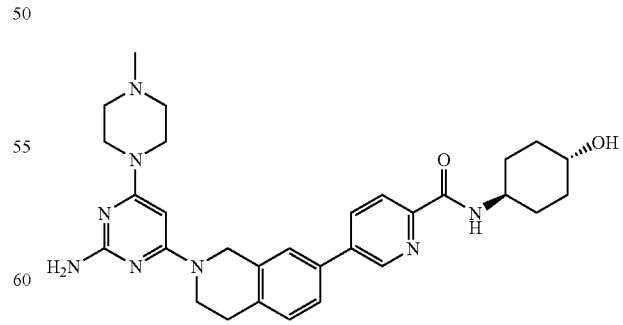

This compound was prepared by using procedures analogous to those described for the synthesis of Example 18 starting from 5-{2-[2-amino-6-(4-methylpiperazin-1-yl)pyrimidin-4-yl]-1,2,3,4-tetrahydroisoquinolin-7-yl}pyridine- 2-carboxylic acid and trans-4-aminocyclohexanol (Acros Organics, Cat. 34668). LCMS (M+H)+: m/z=543.4.

Example 21

1-[2-Amino-6-(4-methylpiperazin-1-yl)pyrimidin-4-yl]-1,2,3,4-tetrahydroquinolin-7-ol

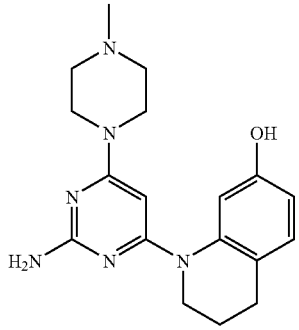 [SMILES: CN1CCN(c2cc(N3CCCc4ccc(O)cc43)nc(N)n2)CC1]

Step 1: 7{[tert-butyl(dimethyl)silyl]oxy}quinoline

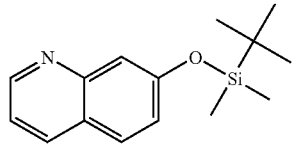 [SMILES: CC(C)(C)[Si](C)(C)Oc1ccc2cccnc2c1]

At room temperature to a solution of quinolin-7-ol (Matrix Scientific, Cat. No. 007603; 0.6 g, 4 mmol) in N,N-Dimethylformamide (10 mL, 100 mmol) was added 1H-imidazole (0.670 g, 9.84 mmol), followed by tert-butyldimethylsilyl chloride (0.934 g, 6.20 mmol) with stirring. The mixture was stirred at room temperature overnight, then quenched with sat'd NaHCO₃ solution, and extracted with methylene chloride (3×). The combined extracts were washed with water and brine successively, and then dried over Na₂SO₄. After filtration, the filtrate was concentrated and purified with flash column using 15% ethyl acetate in hexane as eluent to yield 0.88 g of the product. LCMS (M+H)+: m/z=260.3.

Step 2: 7-{[tert-butyl(dimethyl)silyl]oxy}-1,2,3,4-tetrahydroquinoline

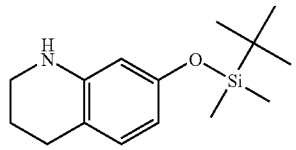 [SMILES: CC(C)(C)[Si](C)(C)Oc1ccc2c(c1)NCCC2]

7-{[tert-Butyl(dimethyl)silyl]oxy}quinoline (0.40 g, 1.5 mmol) in methanol (10 mL, 200 mmol) with 40 mg of 10% Pd on carbon was loaded in a bottle of a Parr Shaker hydrogenator, and shaken for 1 hour under hydrogen atmosphere (50 psi). LC/MS showed that only less than 20% of the reduced product was formed. The reaction mixture continued to be shaken under the same condition for an additional 4 hours. Then LC/MS showed that starting materials were consumed. After filtration, the filtrate was concentrated to yield the desired product. LCMS (M+H)+: m/z=264.3.

Step 3: 1-[2-amino-6-(4-methylpiperazin-1-yl)pyrimidin-4-yl]-1,2,3,4-tetrahydroquinolin-7-ol

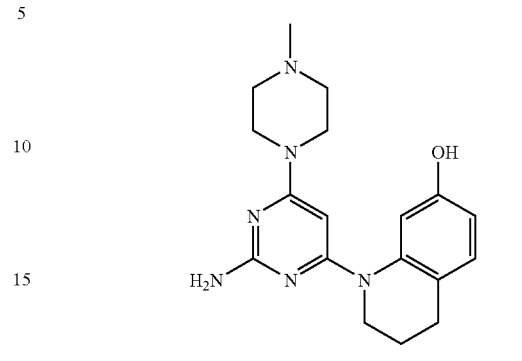

A mixture of 4-chloro-6-(4-methylpiperazin-1-yl)pyrimidin-2-amine (200 mg, 0.9 mmol), 7-{[tert-butyl(dimethyl)silyl]oxy}-1,2,3,4-tetrahydroquinoline (0.28 g, 1.0 mmol), a solution of potassium tert-butoxide in tetrahydrofuran (1.8 mL, 1.8 mmol, 1.00 M), palladium acetate (7.9 mg, 0.035 mmol), and 2-[dicyclohexylphosphino]biphenyl (Aldrich: cat. #: 638099; 15 mg, 0.044 mmol) in 1,4-dioxane (3 mL, 40 mmol) was degassed with nitrogen gas for 3 min. Then the reaction vial was sealed and heated at 120° C. overnight. After cooling, the solid was filtered off. The filtrate was concentrated and purified with flash column (eluted with methanol/methylene chloride: 0/100 at 2 minutes to 10/90 at 22 minutes). Two fractions were obtained: fraction one was 4-[7-{[tert-butyl(dimethyl)silyl]oxy}-3,4-dihydroquinolin-1(2H)-yl]-6-(4-methylpiperazin-1-yl)pyrimidin-2-amine (45 mg); and fraction two was 1-[2-amino-6-(4-methylpiperazin-1-yl)pyrimidin-4-yl]-1,2,3,4-tetrahydroquinolin-7-ol (61 mg). LCMS (M+H)+: m/z=341.3. Then fraction one was dissolved in 1% HCl-ethanol solution (3 mL) at room temperature over 2 days to remove the protecting group and to provide additional products.

Experiment 22

4-({2-[2-Amino-6-(4-methylpiperazin-1-yl)pyrimidin-4-yl]-1,2,3,4-tetrahydroisoquinolin-7-yl}oxy)-2-chlorobenzonitrile

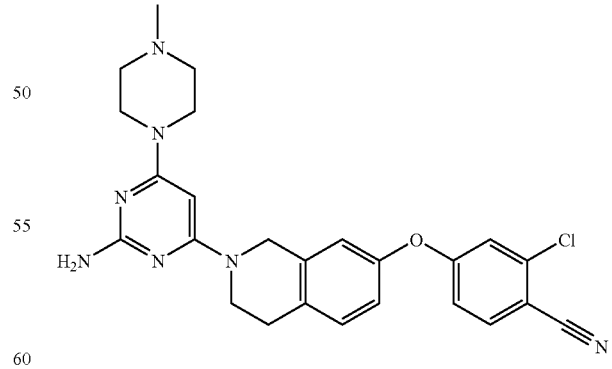

This compound was prepared by using procedures analogous to those described for the synthesis of Example 17 starting from 4-(7-bromo-3,4-dihydroisoquinolin-2(1H)-yl)-6-(4-methylpiperazin-1-yl)pyrimidin-2-amine and 2-chloro-4-hydroxybenzonitrile (Aldrich, Cat. No. 346071). LCMS (M+H)+: m/z=476.3.

Experiment 23

2-[2-Amino-6-(4-methylpiperazin-1-yl)pyrimidin-4-yl]-1,4-dihydroisoquinolin-3(2H)-one

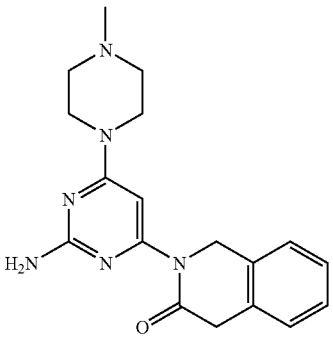 [SMILES: CN1CCN(c2cc(N3Cc4ccccc4CC3=O)nc(N)n2)CC1]

To a solution of 4-chloro-6-(4-methylpiperazin-1-yl)pyrimidin-2-amine (20 mg, 0.09 mmol, Example 1) and 1,4-dihydroisoquinolin-3(2H)-one (16 mg, 0.10 mmol, Tyger, Cat. No. D30080) in 1,4-dioxane (1 mL) was added (9,9-dimethyl-9H-xanthene-4,5-diyl)bis(diphenylphosphine) (20 mg, 0.04 mmol, Aldrich, Cat. No. 526460), palladium acetate (4 mg, 0.02 mmol, Aldrich, Cat. No. 205869) and cesium carbonate (60 mg, 0.2 mmol, Aldrich, Cat. No. 202126). The mixture was degassed with nitrogen and heated at 100° C. 20 h. The reaction mixture was concentrated under reduced pressure. The residue was dissolved in MeOH, and purified by RP-HPLC (pH=10 system) to afford the desired compound. LCMS(M+H)$^+$: m/z=339.4

Example 24

4-(4-Methylpiperazin-1-yl)-6-[7-[(3-phenylpyrrolidin-1-yl)carbonyl]-3,4-dihydroisoquinolin-2(1H)-yl]pyrimidin-2-amine

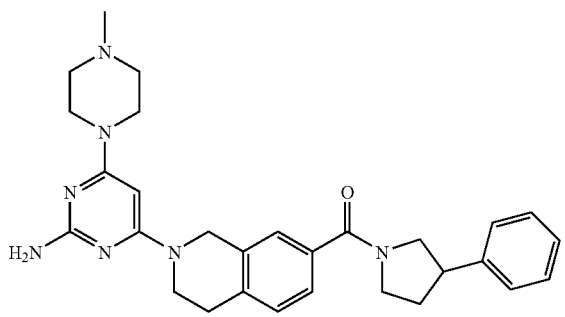 [SMILES: CN1CCN(c2cc(N3CCc4ccc(C(=O)N5CCC(c6ccccc6)C5)cc4C3)nc(N)n2)CC1]

Step 1: 2-[2-amino-6-(4-methylpiperazin-1-yl)pyrimidin-4-yl]-1,2,3,4-tetrahydroisoquinoline-7-carbonitrile

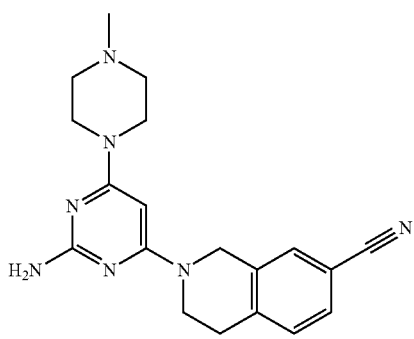 [SMILES: CN1CCN(c2cc(N3CCc4ccc(C#N)cc4C3)nc(N)n2)CC1]

This compound was prepared by using procedures analogous to those described for the synthesis of Example 1 starting from 4-chloro-6-(4-methylpiperazin-1-yl)pyrimidin-2-amine and 1,2,3,4-tetrahydroisoquinoline-7-carbonitrile (Asta Tech, Cat. No. 48330). LCMS (M+H)$^+$: m/z=350.2.

Step 2: 2-[2-amino-6-(4-methylpiperazin-1-yl)pyrimidin-4-yl]-1,2,3,4-tetrahydroisoquinoline-7-carboxylic acid

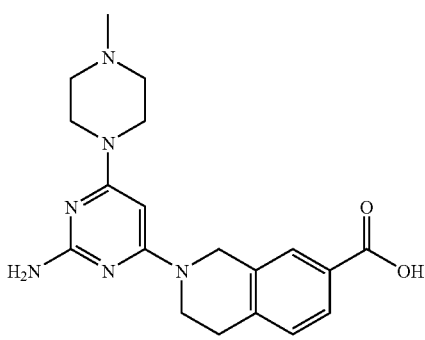 [SMILES: CN1CCN(c2cc(N3CCc4ccc(C(=O)O)cc4C3)nc(N)n2)CC1]

The mixture of 2-[2-amino-6-(4-methylpiperazin-1-yl)pyrimidin-4-yl]-1,2,3,4-tetrahydroisoquinoline-7-carbonitrile (1 g, 2.86 mmol) and sodium hydroxide (801 mg, 20.0 mmol) in water (30 ml) was heated at 100° C. for 2 days. The reaction mixture was cooled to r.t., and acidified carefully to neutral with 6N HCl aqueous solution. The precipitate was filtered and washed with a little water, dried under vacuum to afford the desired compound (1 g, 94.8%). LCMS(M+H)$^+$: m/z=369.1.

Step 3: 4-(4-methylpiperazin-1-yl)-6-[7-[(3-phenylpyrrolidin-1-yl)carbonyl]-3,4-dihydroisoquinolin-2(1H)-yl]pyrimidin-2-amine

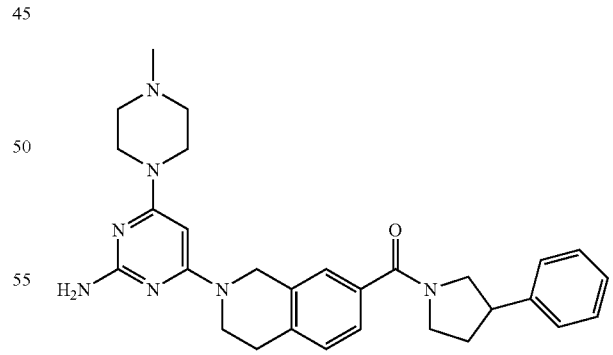

This compound was prepared by using procedures analogous to those described for the synthesis of Example 18 starting from 2-[2-amino-6-(4-methylpiperazin-1-yl)pyrimidin-4-yl]-1,2,3,4-tetrahydroisoquinoline-7-carboxylic acid and 3-Phenyl-pyrrolidine (Matrix Scientific, Cat. No. 018619).

LCMS (M+H)$^+$: m/z=498.2.

Example 25

2-[2-Amino-6-(4-methylpiperazin-1-yl)pyrimidin-4-yl]-N-(3-fluorobenzyl)-N-methyl-1,2,3,4-tetrahydroisoquinoline-7-carboxamide

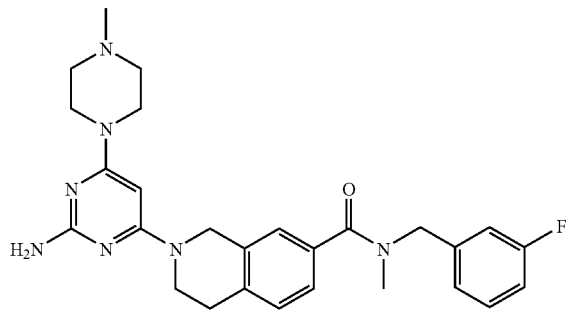 [SMILES: CN1CCN(c2cc(N3CCc4ccc(C(=O)N(C)Cc5cccc(F)c5)cc4C3)nc(N)n2)CC1]

This compound was prepared by using procedures analogous to those described for the synthesis of Example 18 starting from 2-[2-amino-6-(4-methylpiperazin-1-yl)pyrimidin-4-yl]-1,2,3,4-tetrahydroisoquinoline-7-carboxylic acid and (3-fluorobenzyl)methylamine (Aldrich Cat. No. 631108).

LCMS (M+H)$^+$: m/z=490.2.

Example 26

4-[7-(1,3-Dihydro-2H-isoindol-2-ylcarbonyl)-3,4-dihydroisoquinolin-2(1H)-yl]-6-(4-methylpiperazin-1-yl)pyrimidin-2-amine

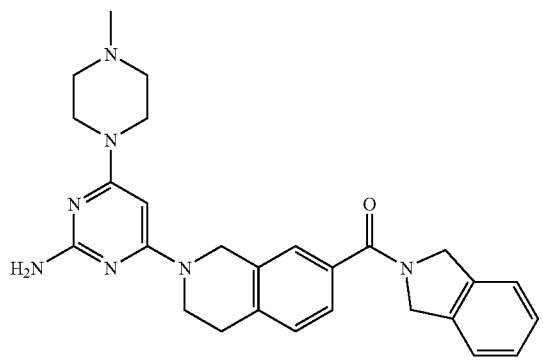 [SMILES: CN1CCN(c2cc(N3CCc4ccc(C(=O)N5Cc6ccccc6C5)cc4C3)nc(N)n2)CC1]

This compound was prepared by using procedures analogous to those described for the synthesis of Example 18 starting from 2-[2-amino-6-(4-methylpiperazin-1-yl)pyrimidin-4-yl]-1,2,3,4-tetrahydroisoquinoline-7-carboxylic acid and isoindoline (Aldrich Cat. No. 515574). LCMS (M+H)$^+$: m/z=470.2.

Example 27

2-[2-Amino-6-(4-methylpiperazin-1-yl)pyrimidin-4-yl]-N,N-dimethyl-1,2,3,4-tetrahydroisoquinoline-7-carboxamide

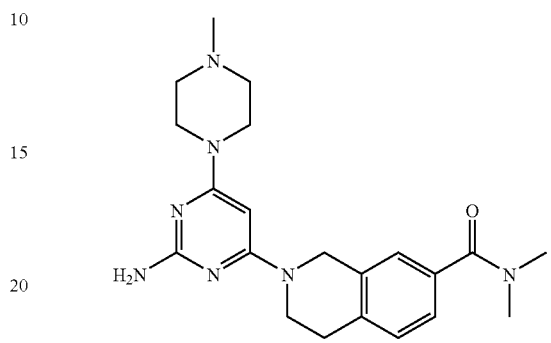

This compound was prepared by using procedures analogous to those described for the synthesis of Example 18 starting from 2-[2-amino-6-(4-methylpiperazin-1-yl)pyrimidin-4-yl]-1,2,3,4-tetrahydroisoquinoline-7-carboxylic acid and dimethylamine hydrochloride (Aldrich Cat. No. 391956).

LCMS (M+H)$^+$: m/z=396.2.

Example 28

2-[2-Amino-6-(4-methylpiperazin-1-yl)pyrimidin-4-yl]-N-cyclopentyl-1,2,3,4-tetrahydroisoquinoline-7-carboxamide

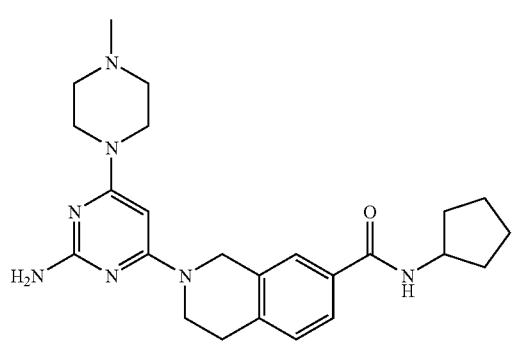 [SMILES: CN1CCN(c2cc(N3CCc4ccc(C(=O)NC5CCCC5)cc4C3)nc(N)n2)CC1]

This compound was prepared by using procedures analogous to those described for the synthesis of Example 18 starting from 2-[2-amino-6-(4-methylpiperazin-1-yl)pyrimidin-4-yl]-1,2,3,4-tetrahydroisoquinoline-7-carboxylic acid and cyclopentylamine (Aldrich Cat. No. C115002). LCMS (M+H)$^+$: m/z=436.3.

Example 29

4-(4-Methylpiperazin-1-yl)-6-[7-(pyrrolidin-1-ylcarbonyl)-3,4-dihydroisoquinolin-2(1H)-yl]pyrimidin-2-amine

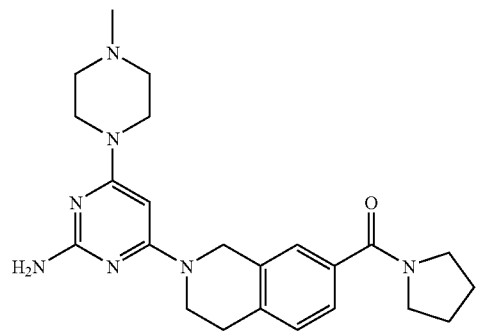 [SMILES: CN1CCN(c2cc(N3CCc4ccc(C(=O)N5CCCC5)cc4C3)nc(N)n2)CC1]

This compound was prepared by using procedures analogous to those described for the synthesis of Example 18 starting from 2-[2-amino-6-(4-methylpiperazin-1-yl)pyrimidin-4-yl]-1,2,3,4-tetrahydroisoquinoline-7-carboxylic acid and pyrrolidine (Aldrich Cat. No. P73803). LCMS (M+H)$^+$: m/z=422.2.

Example 30

Ethyl 4-{2-[2-amino-6-(4-methylpiperazin-1-yl)pyrimidin-4-yl]-1,2,3,4-tetrahydroisoquinolin-7-yl}piperazine-1-carboxylate

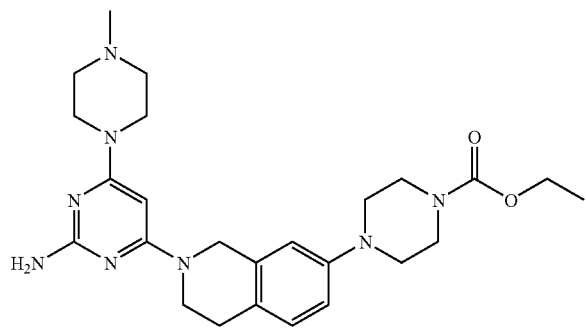 [SMILES: CCOC(=O)N1CCN(c2ccc3c(c2)CN(c2cc(N4CCN(C)CC4)nc(N)n2)CC3)CC1]

A mixture of 4-(7-bromo-3,4-dihydroisoquinolin-2(1H)-yl)-6-(4-methylpiperazin-1-yl)pyrimidin-2-amine (20 mg, 0.05 mmol), ethyl 1-piperazinecarboxylic acid ester (0.012 g, 0.074 mmol, Aldrich, Cat. No. E45600), sodium tert-butoxide (11 mg, 0.12 mmol, Aldrich, Cat. No. 359270), palladium acetate (0.33 mg, 0.0015 mmol, Aldrich, Cat. No. 379875), and 2-(di-t-butylphosphino)biphenyl (0.44 mg, 0.0015 mmol, Aldrich, Cat. No. 638439) in 1,4-dioxane (1 mL) was degassed with nitrogen and then refluxed for 1 h, The reaction mixture was cooled to r.t., and concentrated under reduced pressure. The residue was dissolved in MeOH and purified by RP-HPLC (pH=10 system) to afford the desired compound. LCMS(M+H)$^+$: m/z=481.2.

Example 31

4-[7-(4-Acetylpiperazin-1-yl)-3,4-dihydroisoquinolin-2(1H)-yl]-6-(4-methylpiperazin-1-yl)pyrimidin-2-amine

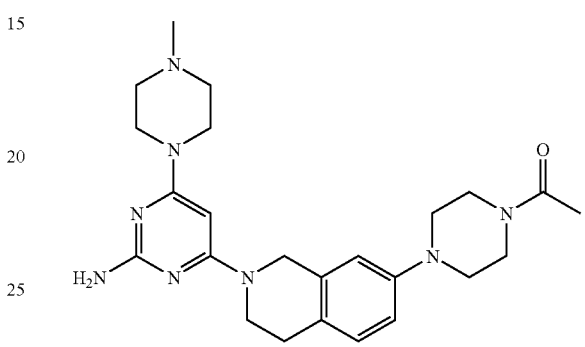

This compound was prepared by using procedures analogous to those described for the synthesis of Example 30 starting from 4-(7-bromo-3,4-dihydroisoquinolin-2(1H)-yl)-6-(4-methylpiperazin-1-yl)pyrimidin-2-amine and 1-acetylpiperazine (Aldrich Cat. No. 359513). LCMS (M+H)$^+$: m/z=451.2.

Example 32

4-{7-[4-(2-Furoyl)piperazin-1-yl]-3,4-dihydroisoquinolin-2(1H)-yl}-6-(4-methylpiperazin-1-yl)pyrimidin-2-amine

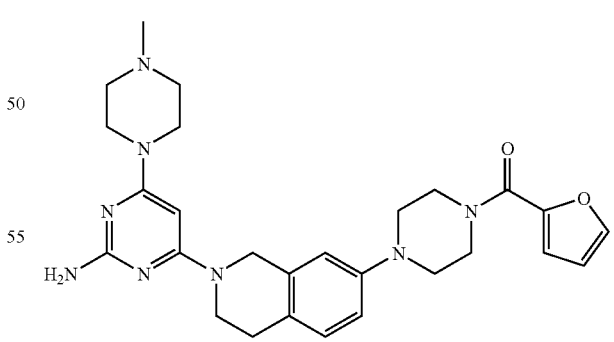

This compound was prepared by using procedures analogous to those described for the synthesis of Example 30 starting from 4-(7-bromo-3,4-dihydroisoquinolin-2(1H)-yl)-6-(4-methylpiperazin-1-yl)pyrimidin-2-amine and 1-(2-furoyl)piperazine (Acros Organics, Cat. No. 23505). LCMS (M+H)$^+$: m/z=503.2.

Example 33

4-{2-[2-Amino-6-(4-methylpiperazin-1-yl)pyrimidin-4-yl]-1,2,3,4-tetrahydroisoquinolin-7-yl}-N-(4-chlorophenyl)piperazine-1-carboxamide

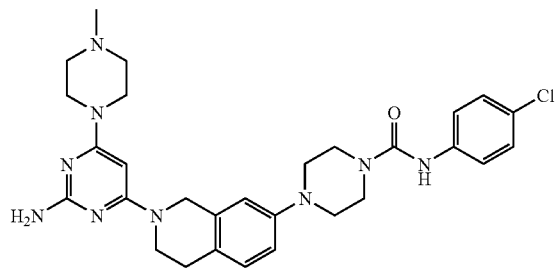 [SMILES: CN1CCN(c2cc(N3CCc4ccc(N5CCN(C(=O)Nc6ccc(Cl)cc6)CC5)cc4C3)nc(N)n2)CC1]

Step 1: tert-butyl 4-{2-[2-amino-6-(4-methylpiperazin-1-yl)pyrimidin-4-yl]-1,2,3,4-tetrahydroisoquinolin-7-yl}piperazine-1-carboxylate

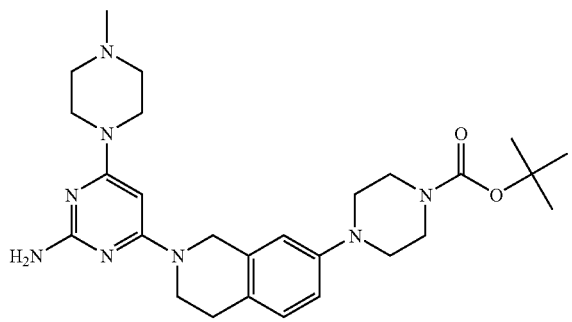 [SMILES: CN1CCN(c2cc(N3CCc4ccc(N5CCN(C(=O)OC(C)(C)C)CC5)cc4C3)nc(N)n2)CC1]

This compound was prepared by using procedures analogous to those described for the synthesis of Example 30 starting from 4-(7-bromo-3,4-dihydroisoquinolin-2(1H)-yl)-6-(4-methylpiperazin-1-yl)pyrimidin-2-amine and 1-Boc-piperazine (Aldrich, Cat. No. 343536). LCMS (M+H)+: m/z=509.3.

Step 2: 4-{2-[2-amino-6-(4-methylpiperazin-1-yl)pyrimidin-4-yl]-1,2,3,4-tetrahydroisoquinolin-7-yl}-N-(4-chlorophenyl)piperazine-1-carboxamide

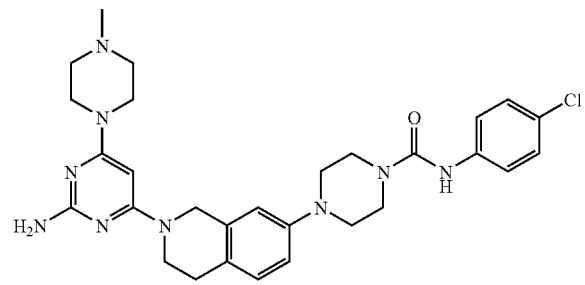 [SMILES: CN1CCN(c2cc(N3CCc4ccc(N5CCN(C(=O)Nc6ccc(Cl)cc6)CC5)cc4C3)nc(N)n2)CC1]

tert-Butyl 4-{2-[2-amino-6-(4-methylpiperazin-1-yl)pyrimidin-4-yl]-1,2,3,4-tetrahydroisoquinolin-7-yl}piperazine-1-carboxylate (16 mg, 0.031 mmol) was treated with 4M HCl in dioxane (0.5 mL) at r.t. for 1 h. The reaction mixture was concentrated to dryness. 1-Chloro-4-isocyanatobenzene (5.0 uL, 0.041 mmol, Aldrich, Cat. No. 152277) was added to a mixture of above residue and triethylamine (22 uL, 0.16 mmol) in acetonitrile (1.0 mL). After stirring at r.t. for 2 h., the reaction mixture was diluted with MeOH and purified by RP-HPLC (pH=10 system) to afford the desired compound. LCMS(M+H)+: m/z=562.3.

Example 34

Ethyl {2-[2-amino-6-(4-methylpiperazin-1-yl)pyrimidin-4-yl]-1,2,3,4-tetrahydroisoquinolin-7-yl}carbamate

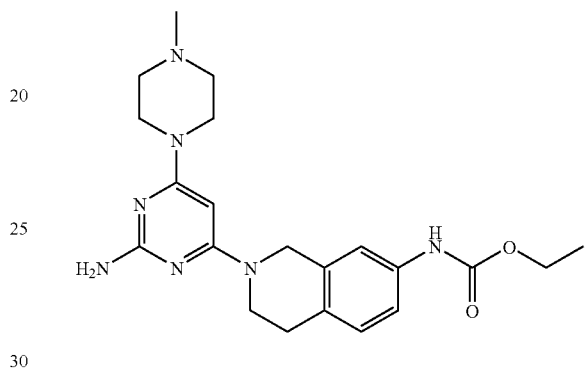

A mixture of 4-(7-bromo-3,4-dihydroisoquinolin-2(1H)-yl)-6-(4-methylpiperazin-1-yl)pyrimidin-2-amine (22.4 mg, 0.0556 mmol), (9,9-dimethyl-9H-xanthene-4,5-diyl)bis(diphenylphosphine) (12.9 mg, 0.0222 mmol, Aldrich, Cat. No. 526460), palladium acetate (2.50 mg, 0.0111 mmol, Aldrich, Cat. No. 379875), cesium carbonate (36.2 mg, 0.111 mmol) and urethane (7.43 mg, 0.0834 mmol, Aldrich, Cat. No. 418331) in 1,4-dioxane (1 mL) was degassed with nitrogen and then heated at 120° C. for 20 h. The reaction mixture was cooled to r.t. and concentrated under reduced pressure. The residue was dissolved in MeOH and purified by RP-HPLC (pH=10) to afford the desired compound. LCMS (M+H)+: m/z=412.2.

Example 35

N-{2-[2-Amino-6-(4-methylpiperazin-1-yl)pyrimidin-4-yl]-1,2,3,4-tetrahydroisoquinolin-7-yl}piperidine-1-carboxamide

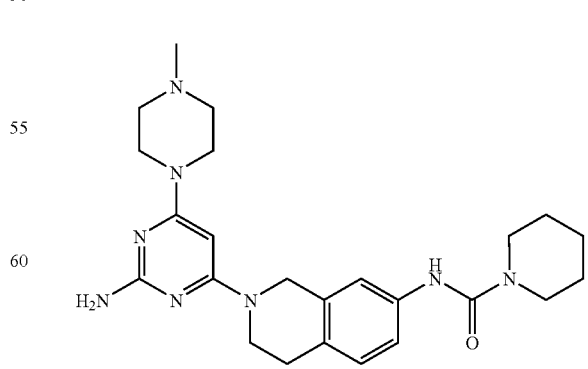

This compound was prepared by using procedures analogous to those described for the synthesis of Example 34 starting from 4-(7-bromo-3,4-dihydroisoquinolin-2(1H)-yl)-6-(4-methylpiperazin-1-yl)pyrimidin-2-amine and 1-piperidinecarboxamide (Aldrich Cat. No. 344753). LCMS (M+H)+: m/z=451.2.

Example 36

1-{2-[2-Amino-6-(4-methylpiperazin-1-yl)pyrimidin-4-yl]-1,2,3,4-tetrahydroisoquinolin-7-yl}piperidine-4-carbonitrile

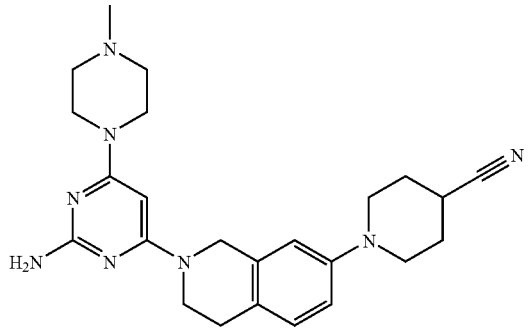 [SMILES: CN1CCN(c2cc(N3CCc4ccc(N5CCC(C#N)CC5)cc4C3)nc(N)n2)CC1]

A mixture of 4-(7-bromo-3,4-dihydroisoquinolin-2(1H)-yl)-6-(4-methylpiperazin-1-yl)pyrimidin-2-amine (40 mg, 0.1 mmol), piperidine-4-carbonitrile (22 mg, 0.20 mmol, Oakwood, Cat. No. 024547), sodium tert-butoxide (23 mg, 0.24 mmol), 2-(2'-di-tert-butylphosphine)biphenyl palladium(II) acetate (2.8 mg, 0.0060 mmol, Aldrich, Cat. No. 655414) in 1,4-dioxane (1 mL) was degassed with nitrogen and then heated at 120° C. overnight. The reaction mixture was cooled to r.t. and concentrated under reduced pressure. The residue was dissolved in MeOH and purified by RP-HPLC (pH=10) to afford the desired compound. LCMS (M+H)+: m/z=433.3.

Example 37

1-{2-[2-Amino-6-(4-methylpiperazin-1-yl)pyrimidin-4-yl]-1,2,3,4-tetrahydroisoquinolin-7-yl}-4-phenylpiperidin-4-ol

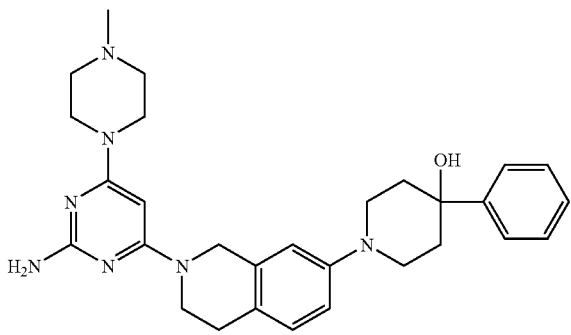 [SMILES: CN1CCN(c2cc(N3CCc4ccc(N5CCC(O)(c6ccccc6)CC5)cc4C3)nc(N)n2)CC1]

This compound was prepared by using procedures analogous to those described for the synthesis of Example 36 starting from 4-(7-bromo-3,4-dihydroisoquinolin-2(1H)-yl)-6-(4-methylpiperazin-1-yl)pyrimidin-2-amine and 4-hydroxy-4-phenylpiperidine (Aldrich Cat. No. H52201). LCMS (M+H)+: m/z=500.3.

Example 38

4-(4-Methylpiperazin-1-yl)-6-[7-(4-pyridin-4-ylpiperidin-1-yl)-3,4-dihydroisoquinolin-2(1H)-yl]pyrimidin-2-amine

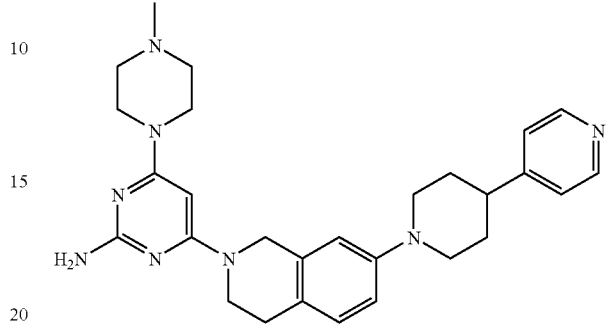

This compound was prepared by using procedures analogous to those described for the synthesis of Example 36 starting from 4-(7-bromo-3,4-dihydroisoquinolin-2(1H)-yl)-6-(4-methylpiperazin-1-yl)pyrimidin-2-amine and 4-(pyridinyl)piperidine (Matrix Scientific, Cat. No. 018549). LCMS (M+H)+: m/z=485.3.

Example 39

4-(1-{2-[2-Amino-6-(4-methylpiperazin-1-yl)pyrimidin-4-yl]-1,2,3,4-tetrahydroisoquinolin-7-yl}piperidin-4-yl)-N-methylbenzamide

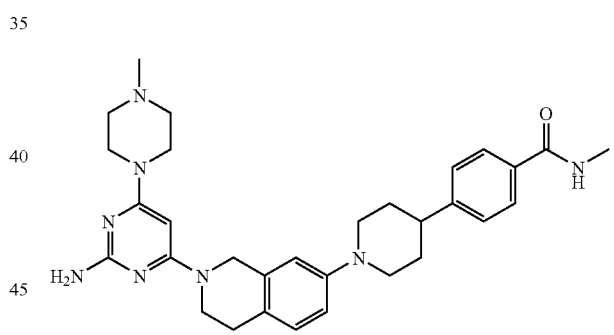

Step 1: 4-(1-{2-[2-amino-6-(4-methylpiperazin-1-yl)pyrimidin-4-yl]-1,2,3,4-tetrahydroisoquinolin-7-yl}piperidin-4-yl)benzoic acid

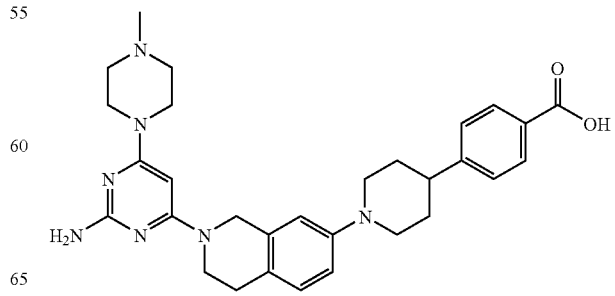

This compound was prepared by using procedures analogous to those described for the synthesis of Example 36 starting from 4-(7-bromo-3,4-dihydroisoquinolin-2(1H)-yl)-6-(4-methylpiperazin-1-yl)pyrimidin-2-amine and methyl 4-(piperidin-4-yl)benzoate hydrochloride (APAC Pharm. LLC, Cat. No. 875920). LCMS (M+H)+: m/z=528.3.

Step 2: 4-(1-{2-[2-amino-6-(4-methylpiperazin-1-yl)pyrimidin-4-yl]-1,2,3,4-tetrahydroisoquinolin-7-yl}piperidin-4-yl)-N-methylbenzamide

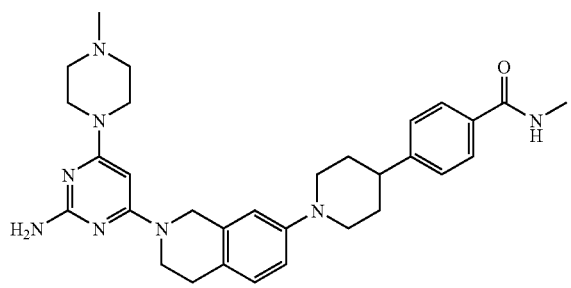 [SMILES: CNC(=O)c1ccc(C2CCN(c3ccc4c(c3)CN(c3cc(N5CCN(C)CC5)nc(N)n3)CC4)CC2)cc1]

This compound was prepared by using procedures analogous to those described for the synthesis of Example 18 starting from 4-(1-{2-[2-amino-6-(4-methylpiperazin-1-yl)pyrimidin-4-yl]-1,2,3,4-tetrahydroisoquinolin-7-yl}piperidin-4-yl)benzoic acid and methylamine in THF (2.0 M). LCMS (M+H)+: m/z=541.3.

Example 40

4-(1-{2-[2-Amino-6-(4-methylpiperazin-1-yl)pyrimidin-4-yl]-1,2,3,4-tetrahydroisoquinolin-7-yl}piperidin-4-yl)benzamide

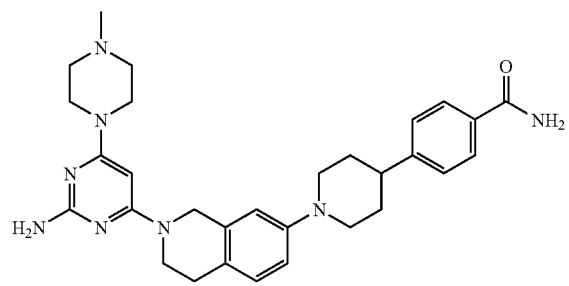 [SMILES: CN1CCN(c2cc(N3CCc4ccc(N5CCC(c6ccc(C(N)=O)cc6)CC5)cc4C3)nc(N)n2)CC1]

This compound was prepared by using procedures analogous to those described for the synthesis of Example 18 starting from 4-(1-{2-[2-amino-6-(4-methylpiperazin-1-yl)pyrimidin-4-yl]-1,2,3,4-tetrahydroisoquinolin-7-yl}piperidin-4-yl)benzoic acid and ammonia solution in water. LCMS (M+H)+: m/z=527.3.

Example 41

4-(1-{2-[2-Amino-6-(4-methylpiperazin-1-yl)pyrimidin-4-yl]-1,2,3,4-tetrahydroisoquinolin-7-yl}piperidin-4-yl)-1-methylpyridin-2(1H)-one

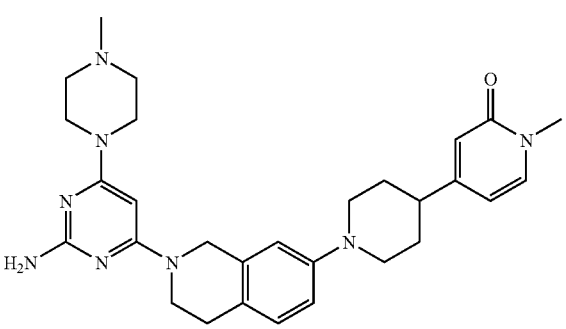 [SMILES: CN1CCN(c2cc(N3CCc4ccc(N5CCC(c6ccn(C)c(=O)c6)CC5)cc4C3)nc(N)n2)CC1]

Step 1: 4-iodo-1-methylpyridin-2(1H)-one

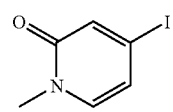

To a solution of 4-iodopyridin-2-ol (450 mg, 2.0 mmol, Maybridge, Cat. No. MO07919) in N,N-dimethylformamide (7 mL) was added sodium hydride (120 mg, 3.0 mmol, 60% dispersion in mineral oil) at 0° C., the solution was stirred 5 min., then methyl iodide (250 uL, 4.1 mmol) was added. The reaction mixture was stirred at r.t. for 2 h., and then poured into aqueous NaHCO₃ solution, extracted with AcOEt. The organic layer was washed by water and brine, dried over MgSO₄, filtered, and concentrated to afford the desired compound which was directly used in the next step reaction without further purification. LCMS (M+H)+: m/z=235.9.

Step 2: tert-butyl 1'-methyl-2'-oxo-1',2',3,6-tetrahydro-4,4'-bipyridine-1(2H)-carboxylate

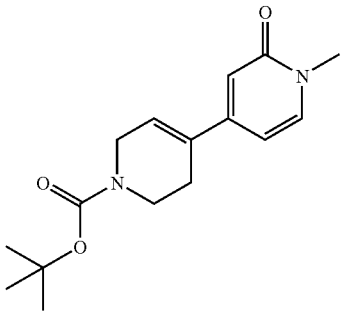 [SMILES: Cn1ccc(C2=CCN(C(=O)OC(C)(C)C)CC2)cc1=O]

This compound was prepared by using procedures analogous to those described for the synthesis of Example 2 starting from 4-iodo-1-methylpyridin-2(1H)-one and tert-butyl 4-(4,4,5,5-tetramethyl-1,3,2-dioxaborolan-2-yl)-3,6-dihydropyridine-1(2H)-carboxylate (Frontier, Cat. No. P1164). LCMS (M+H)+: m/z=291.1.

Step 3: 1-methyl-4-(1,2,3,6-tetrahydropyridin-4-yl)pyridin-2(1H)-one hydrochloride

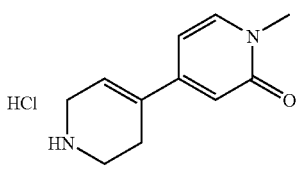

A solution of tert-Butyl 1'-methyl-2'-oxo-1',2',3,6-tetrahydro-4,4'-bipyridine-1(2H)-carboxylate (100 mg, 0.3 mmol) in AcOEt (2 mL) was treated with 4 M of hydrogen chloride in 1,4-dioxane (0.1722 mL, 0.6888 mmol). The mixture was stirred at r.t. 2 h., and concentrated under reduced pressure to afford the desired compound as HCl salt which was directly used in the next step reaction without further purification. LCMS (M+H)$^+$: m/z=191.1.

Step 4: 4-(1-{2-[2-amino-6-(4-methylpiperazin-1-yl)pyrimidin-4-yl]-1,2,3,4-tetrahydroisoquinolin-7-yl}piperidin-4-yl)-1-methylpyridin-2(1H)-one

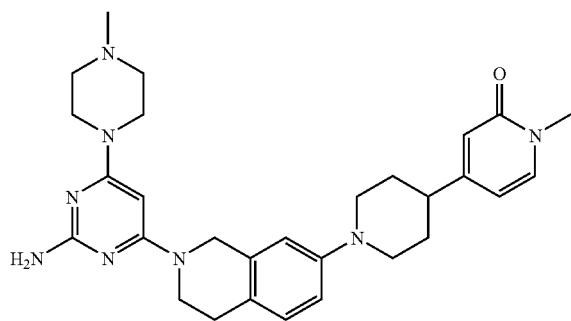 [SMILES: CN1CCN(c2cc(N3CCc4ccc(N5CCC(c6ccn(C)c(=O)c6)CC5)cc4C3)nc(N)n2)CC1]

This compound was prepared by using procedures analogous to those described for the synthesis of Example 36 starting from 4-(7-bromo-3,4-dihydroisoquinolin-2(1H)-yl)-6-(4-methylpiperazin-1-yl)pyrimidin-2-amine and 1-methyl-4-(1,2,3,6-tetrahydropyridin-4-yl)pyridin-2(1H)-one hydrochloride. LCMS (M+H)$^+$: m/z=515.3.

Example 42

5-(1-{2-[2-Amino-6-(4-methylpiperazin-1-yl)pyrimidin-4-yl]-1,2,3,4-tetrahydroisoquinolin-7-yl}piperidin-4-yl)-1-methylpyridin-2(1H)-one

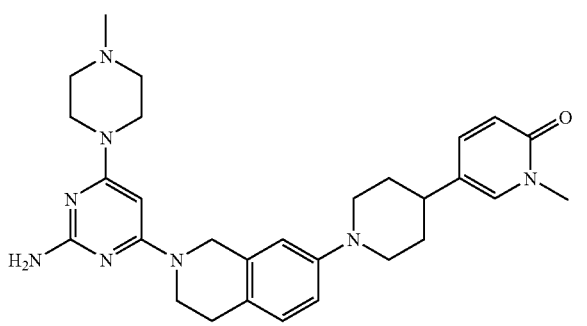 [SMILES: CN1CCN(c2cc(N3CCc4ccc(N5CCC(c6ccc(=O)n(C)c6)CC5)cc4C3)nc(N)n2)CC1]

This compound was prepared by using procedures analogous to those described for the synthesis of Example 41 from 5-bromo-2-hydroxypyridine (Aldrich, Cat. No. 528226) and 4-(7-bromo-3,4-dihydroisoquinolin-2(1H)-yl)-6-(4-methylpiperazin-1-yl)pyrimidin-2-amine. LCMS (M+H)$^+$: m/z=515.3.

Example 43

4-{2-[2-Amino-6-(4-methylpiperazin-1-yl)pyrimidin-4-yl]-1,2,3,4-tetrahydroisoquinolin-7-yl}-1-methylpyridin-2(1H)-one

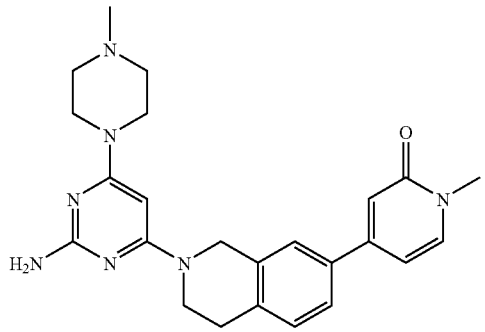 [SMILES: CN1CCN(c2cc(N3CCc4ccc(-c5ccn(C)c(=O)c5)cc4C3)nc(N)n2)CC1]

Step 1: 1-methyl-4-(4,4,5,5-tetramethyl-1,3,2-dioxaborolan-2-yl)pyridin-2(1H)-one

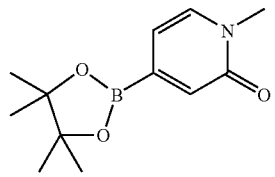 [SMILES: Cn1ccc(B2OC(C)(C)C(C)(C)O2)cc1=O]

A mixture of 4-iodo-1-methylpyridin-2(1H)-one (170 mg, 0.72 mmol), 4,4,5,5,4',4',5',5'-octamethyl-[2,2']bi[[1,3,2]dioxaborolanyl] (239 mg, 0.940 mmol, Aldrich, Cat. No. 473294), [1,1'-bis(diphenylphosphino)ferrocene]dichloropalladium(II), complex with dichloromethane (1:1) (17.7 mg, 0.0217 mmol, Aldrich, Cat. No. 379270), 1,1'-bis(diphenylphosphino)ferrocene (12.0 mg, 0.0217 mmol, Aldrich, Cat. No. 177261) and potassium acetate (213 mg, 2.17 mmol, Aldrich, Cat. No. 255785) in 1,4-dioxane (10 mL) was degassed with nitrogen and heated at 120° C. 5 h. The reaction mixture was cooled to r.t., and then filtered, and washed with AcOEt. The filtrate was concentrated under reduced pressure to afford the desired compound which was directly used in the next step reaction without further purification. LCMS (M+H)$^+$: m/z=236.1.

Step 2: 4-{2-[2-amino-6-(4-methylpiperazin-1-yl)pyrimidin-4-yl]-1,2,3,4-tetrahydroisoquinolin-7-yl}-1-methylpyridin-2(1H)-one

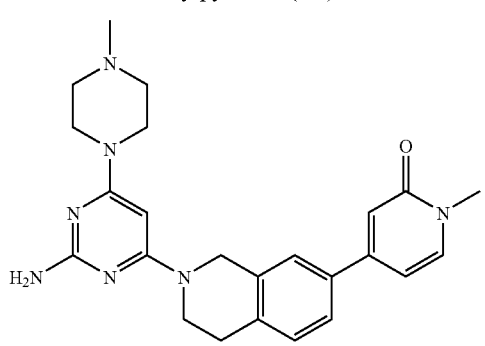

This compound was prepared by using procedures analogous to those described for the synthesis of Example 2 starting from 4-(7-bromo-3,4-dihydroisoquinolin-2(1H)-yl)-6-(4-methylpiperazin-1-yl)pyrimidin-2-amine and 1-methyl-4-(4,4,5,5-tetramethyl-1,3,2-dioxaborolan-2-yl)pyridin-2(1H)-one. LCMS (M+H)$^+$: m/z=432.2.

Example 44

6-(4-{2-[2-Amino-6-(4-methylpiperazin-1-yl)pyrimidin-4-yl]-1,2,3,4-tetrahydroisoquinolin-7-yl}-3-oxopiperazin-1-yl)-N-methylnicotinamide

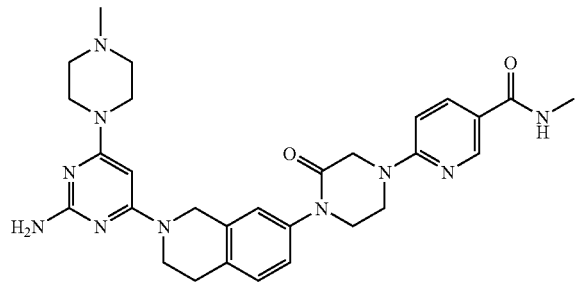 [SMILES: CNC(=O)c1ccc(N2CCN(c3ccc4c(c3)CN(c3cc(N5CCN(C)CC5)nc(N)n3)CC4)C(=O)C2)nc1]

Step 1: tert-butyl 4-{2-[2-amino-6-(4-methylpiperazin-1-yl)pyrimidin-4-yl]-1,2,3,4-tetrahydroisoquinolin-7-yl}-3-oxopiperazine-1-carboxylate

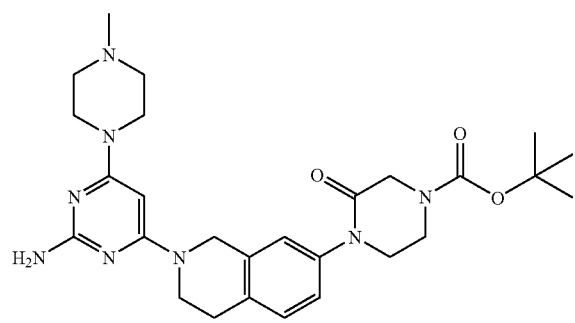 [SMILES: CN1CCN(c2cc(N3CCc4ccc(N5CCN(C(=O)OC(C)(C)C)CC5=O)cc4C3)nc(N)n2)CC1]

This compound was prepared by using procedures analogous to those described for the synthesis of Example 14 starting from 4-(7-bromo-3,4-dihydroisoquinolin-2(1H)-yl)-6-(4-methylpiperazin-1-yl)pyrimidin-2-amine and tert-butyl 3-oxopiperazine-1-carboxylate (Aldrich, Cat. No. 641057). LCMS (M+H)$^+$: m/z=523.2.

Step 2: 1-{2-[2-amino-6-(4-methylpiperazin-1-yl)pyrimidin-4-yl]-1,2,3,4-tetrahydroisoquinolin-7-yl}piperazin-2-one hydrochloride

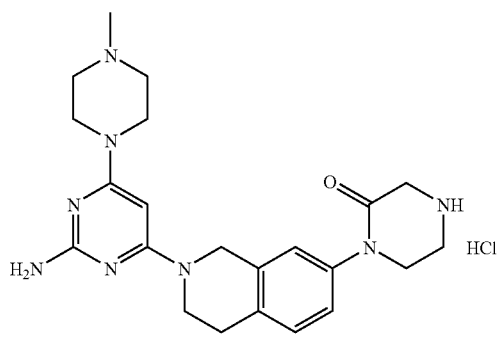 [SMILES: CN1CCN(c2cc(N3CCc4ccc(N5CCNCC5=O)cc4C3)nc(N)n2)CC1 ; Cl]

This compound was prepared by using procedures analogous to those described for the synthesis of Example 41(Step 3) starting from tert-butyl 4-{2-[2-amino-6-(4-methylpiperazin-1-yl)pyrimidin-4-yl]-1,2,3,4-tetrahydroisoquinolin-7-yl}-3-oxopiperazine-1-carboxylate. LCMS (M+H)$^+$: m/z=423.2.

Step 3: ethyl 6-(4-{2-[2-amino-6-(4-methylpiperazin-1-yl)pyrimidin-4-yl]-1,2,3,4-tetrahydroisoquinolin-7-yl}-3-oxopiperazin-1-yl)nicotinate

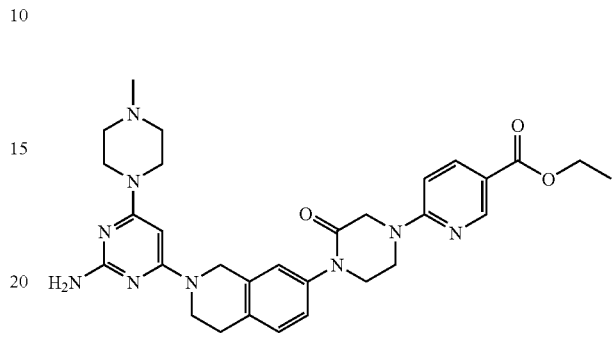

This compound was prepared by using procedures analogous to those described for the synthesis of Example 1, Step 2 starting from 1-{2-[2-amino-6-(4-methylpiperazin-1-yl)pyrimidin-4-yl]-1,2,3,4-tetrahydroisoquinolin-7-yl}piperazin-2-one hydrochloride and ethyl 6-chloronicotinate (Aldrich, Cat. No. 531197). LCMS (M+H)$^+$: m/z=572.3.

Step 4: 6-(4-{2-[2-amino-6-(4-methylpiperazin-1-yl)pyrimidin-4-yl]-1,2,3,4-tetrahydroisoquinolin-7-yl}-3-oxopiperazin-1-yl)-N-methylnicotinamide

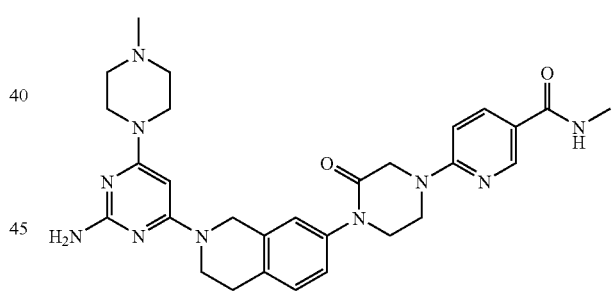

The mixture of ethyl 6-(4-{2-[2-amino-6-(4-methylpiperazin-1-yl)pyrimidin-4-yl]-1,2,3,4-tetrahydroisoquinolin-7-yl}-3-oxopiperazin-1-yl)nicotinate (60 mg, 0.1 mmol) and lithium hydroxide monohydrate (18 mg, 0.42 mmol) in tetrahydrofuran (1 mL) with drops of water was stirred at r.t. overnight. The reaction mixture was acidified to acid condition using 4M HCl in dioxane solution, and then concentrated to dryness.

To a solution of above residue in N,N-dimethylformamide (1 mL) were added methylamine hydrochloride (14 mg, 0.21 mmol), (benzotriazol-1-yloxy)tripyrrolidino phosphonium hexafluorophosphate (66 mg, 0.12 mmol, NovaBiochem, Cat. No. 01-62-0016) and N,N-diisopropylethylamine (55 uL, 0.31 mmol). The solution was stirred at r.t. for 1 h. The reaction solution was diluted with MeOH and purified by RP-HPLC (pH=10 system) to afford the desired compound. LCMS (M+H)$^+$: m/z=557.3.

Example 45

5-{2-[2-Amino-6-(4-methylpiperazin-1-yl)pyrimidin-4-yl]-1,2,3,4-tetrahydroisoquinolin-7-yl}-N,3-dimethylpyridine-2-carboxamide

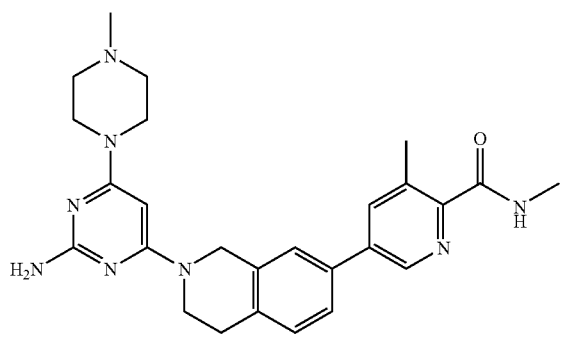 [SMILES: CNC(=O)c1ncc(-c2ccc3c(c2)CN(c2cc(N4CCN(C)CC4)nc(N)n2)CC3)cc1C]

Step 1: 5-{2-[2-amino-6-(4-methylpiperazin-1-yl)pyrimidin-4-yl]-1,2,3,4-tetrahydroisoquinolin-7-yl}-3-methylpyridine-2-carbonitrile

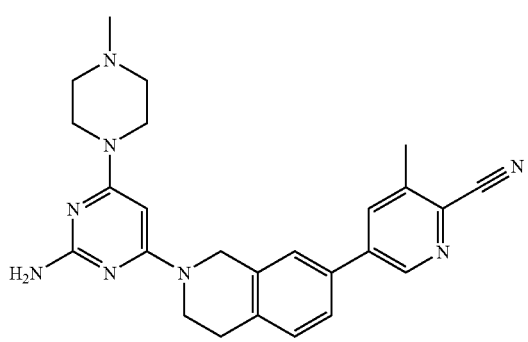 [SMILES: Cc1cc(-c2ccc3c(c2)CN(c2cc(N4CCN(C)CC4)nc(N)n2)CC3)cnc1C#N]

This compound was prepared by using procedures analogous to those described for the synthesis of Example 2 starting from 4-(7-bromo-3-methyl-3,4-dihydroisoquinolin-2(1H)-yl)-6-(4-methylpiperazin-1-yl)pyrimidin-2-amine and (6-cyano-5-methylpyridin-3-yl)boronic acid (Combi-Blocks, Cat. No. PN-5814). LCMS (M+H)$^+$: m/z=441.1.

Step 2: 5-{2-[2-amino-6-(4-methylpiperazin-1-yl)pyrimidin-4-yl]-1,2,3,4-tetrahydroisoquinolin-7-yl}-3-methylpyridine-2-carboxylic acid

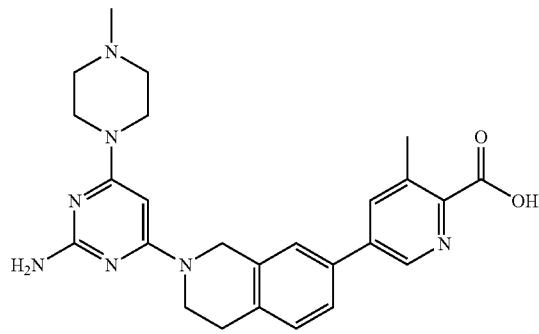 [SMILES: Cc1cc(-c2ccc3c(c2)CN(c2cc(N4CCN(C)CC4)nc(N)n2)CC3)cnc1C(=O)O]

This compound was prepared by using procedures analogous to those described for the synthesis of Example 24, Step 2 starting from 5-{2-[2-amino-6-(4-methylpiperazin-1-yl)pyrimidin-4-yl]-1,2,3,4-tetrahydroisoquinolin-7-yl}-3-methylpyridine-2-carbonitrile and sodium hydroxide. LCMS (M+H)$^+$: m/z=460.2.

Step 3: 5-{2-[2-amino-6-(4-methylpiperazin-1-yl)pyrimidin-4-yl]-1,2,3,4-tetrahydroisoquinolin-7-yl}-N,3-dimethylpyridine-2-carboxamide This compound was prepared by using procedures analogous to those described for the synthesis of Example 18 starting from 5-{2-[2-amino-6-(4-methylpiperazin-1-yl)pyrimidin-4-yl]-1,2,3,4-tetrahydroisoquinolin-7-yl}-3-methylpyridine-2-carboxylic acid and methylamine hydrochloride. LCMS (M+H)$^+$: m/z=473.2.

Example 46

5-{2-[2-Amino-6-(4-methylpiperazin-1-yl)pyrimidin-4-yl]-1,2,3,4-tetrahydroisoquinolin-7-yl}-N,N,3-trimethylpyridine-2-carboxamide

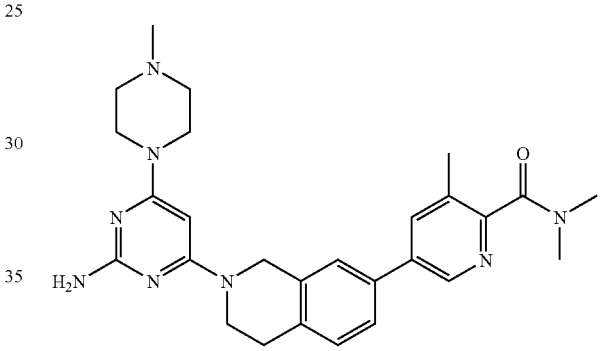

This compound was prepared by using procedures analogous to those described for the synthesis of Example 18 starting from 5-{2-[2-amino-6-(4-methylpiperazin-1-yl)pyrimidin-4-yl]-1,2,3,4-tetrahydroisoquinolin-7-yl}-3-methylpyridine-2-carboxylic acid and dimethylamine hydrochloride. LCMS (M+H)$^+$: m/z=487.3.

Example 47

2-{2-[2-Amino-6-(4-methylpiperazin-1-yl)pyrimidin-4-yl]-1,2,3,4-tetrahydroisoquinolin-7-yl}-N-methyl-1,3-thiazole-4-carboxamide

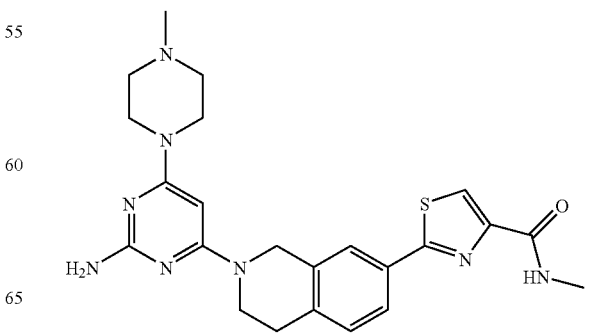

Step 1: tert-butyl 7-bromo-3,4-dihydroisoquinoline-2(1H)-carboxylate

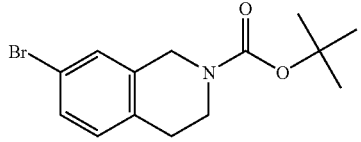 [SMILES: CC(C)(C)OC(=O)N1CCc2ccc(Br)cc2C1]

Di-tert-butyldicarbonate (0.34 g, 1.6 mmol) was added to a mixture of 7-bromo-1,2,3,4-tetrahydroisoquinoline (0.30 g, 1.4 mmol) and triethylamine (0.29 g, 2.8 mmol) in tetrahydrofuran (4.0 mL). The mixture was stirred at r.t. for 1 h. The reaction was quenched with aqueous NaHCO$_3$ solution, and then extracted with AcOEt (3×20 mL). The combined organic layers were washed with water and brine, dried with MgSO$_4$, filtered, and concentrated under reduced pressure to afford the desired compound. LCMS(M+Na)$^+$: m/z=334.2.

Step 2: tert-butyl 7-(4,4,5,5-tetramethyl-1,3,2-dioxaborolan-2-yl)-3,4-dihydroisoquinoline-2(1H)-carboxylate

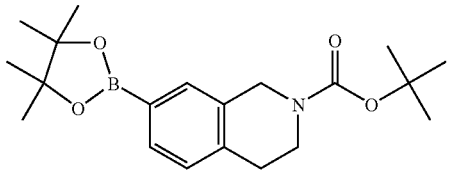 [SMILES: CC(C)(C)OC(=O)N1CCc2ccc(B3OC(C)(C)C(C)(C)O3)cc2C1]

This compound was prepared by using procedures analogous to those described for the synthesis of Example 43, Step 1 starting from tert-butyl 7-bromo-3,4-dihydroisoquinoline-2(1H)-carboxylate. LCMS (M+Na)$^+$: m/z=382.3.

Step 3: tert-butyl 7-[4-(ethoxycarbonyl)-1,3-thiazol-2-yl]-3,4-dihydroisoquinoline-2(1H)-carboxylate

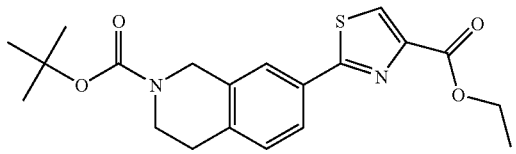 [SMILES: CCOC(=O)c1csc(-c2ccc3c(c2)CN(C(=O)OC(C)(C)C)CC3)n1]

This compound was prepared by using procedures analogous to those described for the synthesis of Example 2 starting from tert-butyl 7-(4,4,5,5-tetramethyl-1,3,2-dioxaborolan-2-yl)-3,4-dihydroisoquinoline-2(1H)-carboxylate and ethyl 2-bromo-1,3-thiazole-4-carboxylate (Combi-Blocks, Cat. No. HI-1116). LCMS (M+H)$^+$: m/z=389.0.

Step 4: ethyl 2-{2-[2-amino-6-(4-methylpiperazin-1-yl)pyrimidin-4-yl]-1,2,3,4-tetrahydro isoquinolin-7-yl}-1,3-thiazole-4-carboxylate

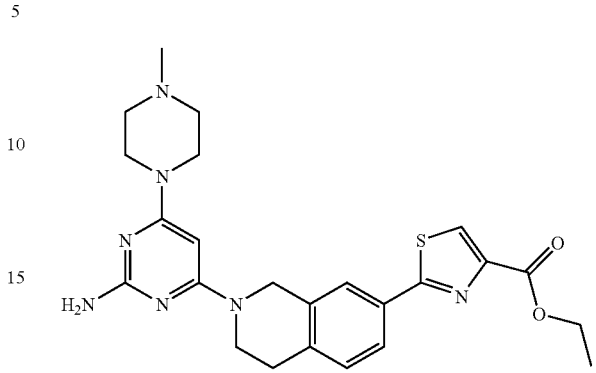

To a solution of tert-butyl 7-[4-(ethoxycarbonyl)-1,3-thiazol-2-yl]-3,4-dihydroisoquinoline-2(1H)-carboxylate (80 mg, 0.2 mmol) in AcOEt (1 mL) was added 4 M of hydrogen chloride in 1,4-dioxane (0.1030 mL, 0.4118 mmol). The mixture was stirred at r.t. for 2 h., and then concentrated to dryness.

The above residue and 4-chloro-6-(4-methylpiperazin-1-yl)pyrimidin-2-amine (51.6 mg, 0.226 mmol) and 4-methylmorpholine (0.5794 mL, 5.270 mmol) in N-methylpyrrolidinone (2 mL) was heated at 180° C. overnight. The reaction mixture was cooled to r.t., and then poured into water, extracted with AcOEt. The organic layer was washed with NaHCO$_3$ aqueous solution and brine, dried with MgSO$_4$, filtered, and concentrated. The residue was purified by prep-HPLC (pH=10) to afford the desired compound. LCMS (M+H)$^+$: m/z=480.1.

Step 5: 2-{2-[2-amino-6-(4-methylpiperazin-1-yl)pyrimidin-4-yl]-1,2,3,4-tetrahydroisoquinolin-7-yl}-N,N-dimethyl-1,3-thiazole-4-carboxamide This compound was prepared by using procedures analogous to those described for the synthesis of Example 44, Step 4 starting from ethyl 2-{2-[2-amino-6-(4-methylpiperazin-1-yl)pyrimidin-4-yl]-1,2,3,4-tetrahydro isoquinolin-7-yl}-1,3-thiazole-4-carboxylate and methylamine in THF solution (2.0 M). LCMS (M+H)$^+$: m/z=465.2.

Example 48

4-(4-Methylpiperazin-1-yl)-6-[7-[4-(pyrrolidin-1-ylcarbonyl)-1,3-thiazol-2-yl]-3,4-dihydroisoquinolin-2(1H)-yl]pyrimidin-2-amine

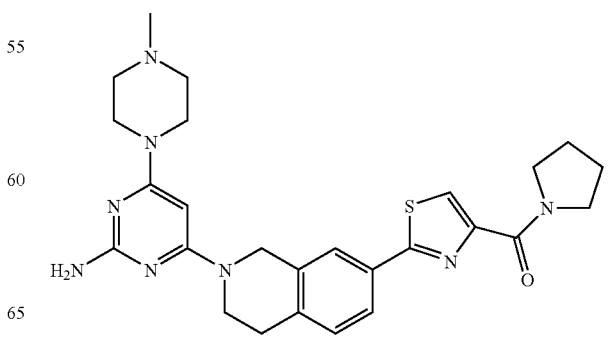

This compound was prepared by using procedures analogous to those described for the synthesis of Example 47 starting from ethyl 2-{2-[2-amino-6-(4-methylpiperazin-1-yl)pyrimidin-4-yl]-1,2,3,4-tetrahydro isoquinolin-7-yl}-1,3-thiazole-4-carboxylate and pyrrolidine. LCMS (M+H)⁺: m/z=505.2.

Example 49

5-{2-[2-Amino-6-(4-methylpiperazin-1-yl)pyrimidin-4-yl]-3-methyl-1,2,3,4-tetrahydroisoquinolin-7-yl}-N-methylpyridine-2-carboxamide

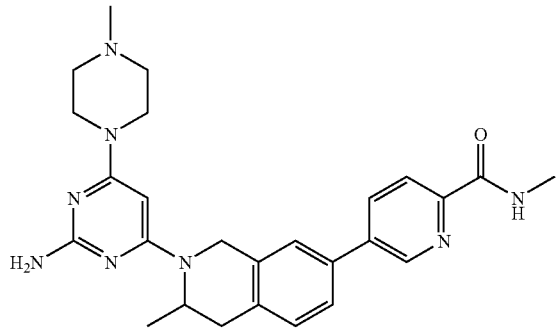 [SMILES: CNC(=O)c1ccc(-c2ccc3c(c2)CN(c2cc(N4CCN(C)CC4)nc(N)n2)C(C)C3)cn1]

Step 1: 1-(4-bromophenyl)propan-2-amine

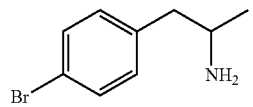

To a mixture of 2.0 M of ammonia in ethanol (117 mL, 235 mmol, Aldrich, Cat. No. 392685) and titanium tetraisopropoxide (27.7 mL, 93.9 mmol, Aldrich, Cat. No. 377996) was added 1-(4-bromophenyl)acetone (10.0 g, 46.9 mmol, Alfa Aesar, Cat. No. A19028). The reaction mixture was stirred at r.t. under nitrogen overnight. Sodium tetrahydroborate (2.66 g, 70.4 mmol) was added. The mixture was stirred at r.t. for additional 3 h. The reaction mixture was quenched with 2M ammonia in water, and filtered. The solid was washed with AcOEt. The filtrate was concentrated to remove most ethanol, and then was washed with AcOEt twice. The combined organic layers were extracted with 1N HCl aqueous solution (twice). The aqueous HCl solutions were combined, and adjusted with ammonia aqueous solution to pH=10. The result solution was extracted with CH₂Cl₂. The organic layer was dried with MgSO₄, filtered, and concentrated to afford the desired compound which was directly used in the next step reaction without further purification. LCMS (M+H)⁺: m/z=214.2.

Step 2: methyl [2-(4-bromophenyl)-1-methylethyl]carbamate

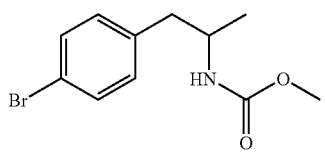

To a solution of 1-(4-bromophenyl)propan-2-amine (0.5 g, 2 mmol) in methylene chloride (5 mL) was added pyridine (380 uL, 4.7 mmol) and methyl chloroformate (270 uL, 3.5 mmol, Aldrich, Cat. No. M35304). The reaction mixture was stirred at r.t. overnight, and concentrated under reduced pressure. The residue was dissolved in EtOAc, and washed with NaHCO₃ aqueous solution, 1N HCl aqueous solution and brine. The organic layer was dried with MgSO4, filtered, and concentrated under reduced pressure. The residue was purified by flash chromatograph on a silica gel column using 25% Ethyl acetate in hexane to afford the desired compound. LCMS (M+H)⁺: m/z=272.2.

Step 3: methyl 7-bromo-3-methyl-3,4-dihydroisoquinoline-2(1H)-carboxylate

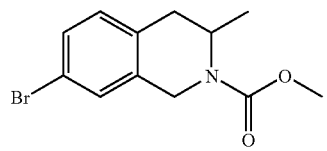 [SMILES: COC(=O)N1Cc2cc(Br)ccc2CC1C]

To a mixture of methyl [2-(4-bromophenyl)-1-methylethyl]carbamate (465 mg, 1.71 mmol) and paraformaldehyde (82.1 mg, 2.73 mmol) was added a mixture of concentrated sulfuric acid (2.5 mL, 47 mmol) and glacial acetic acid (3.75 mL, 66.0 mmol). The resulting mixture was stirred at r.t. overnight. The reaction mixture was poured into ice-water, and extracted with CH₂Cl₂. The organic layer was washed with water, saturated NaCO₃ aqueous solution and brine, dried with MgSO₄. After filtration, the filtrate was concentrated to afford the desired compound (490 mg, 100%) which was directly used in the next step reaction without further purification. LCMS (M+H)⁺: m/z=284.2.

Step 4: 7-bromo-3-methyl-1,2,3,4-tetrahydroisoquinoline

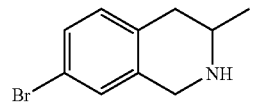

Iodotrimethylsilane (0.982 mL, 0.00690 mol, Aldrich, Cat. No. 195529) was added to a solution of methyl 7-bromo-3-methyl-3,4-dihydroisoquinoline-2(1H)-carboxylate (490 mg, 0.0017 mol) in methylene chloride (10 mL) and the reaction was stirred at 50° C. for 2 h. The reaction was cooled to r.t. and anhydrous methanol (2 mL) was added. The reaction mixture was stirred for additional 5 min, and the volatiles were removed under reduced pressure. The residue was treated with diethyl ether and filtered. The solid was washed with ether, dried under vacuum to provide the desired compound which was directly used in the next step reaction without further purification. LCMS (M+H)⁺: m/z=226.2.

Step 5: 4-(7-bromo-3-methyl-3,4-dihydroisoquinolin-2(1H)-yl)-6-chloropyrimidin-2-amine

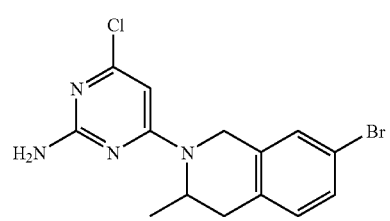 [SMILES: CC1Cc2ccc(Br)cc2CN1c1cc(Cl)nc(N)n1]

This compound was prepared by using procedures analogous to those described for the synthesis of Example 1 starting from 7-bromo-3-methyl-1,2,3,4-tetrahydroisoquinoline and 2-Amino-4,6-dichloropyrimidine (Alfa Aesar, Cat. No. A11330). LCMS (M+H)+: m/z=353.0.

Step 6: 4-(7-bromo-3-methyl-3,4-dihydroisoquinolin-2(1H)-yl)-6-(4-methylpiperazin-1-yl)pyrimidin-2-amine

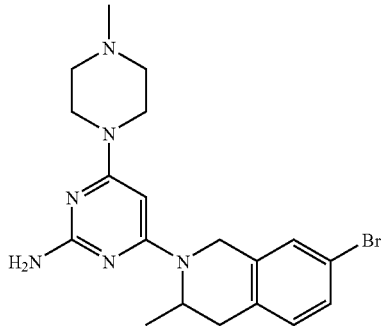 [SMILES: CC1Cc2ccc(Br)cc2CN1c1cc(N2CCN(C)CC2)nc(N)n1]

A mixture of 4-(7-bromo-3-methyl-3,4-dihydroisoquinolin-2(1H)-yl)-6-chloropyrimidin-2-amine (2.3 g, 6.5 mmol) and 1-methyl piperazine (3.61 mL, 32.6 mmol) in tert-butyl alcohol (10 mL) and was heated at 120° C. for 20 h. The reaction mixture was cooled to r.t., poured into water, extracted with AcOEt, washed with sat'd NaHCO₃ aqueous solution and brine, dried with MgSO₄. After filtration, the filtrate was concentrated under reduced pressure. The residue was purified by flash chromatography on a silica gel column using 10% methanol in methylene chloride to afford the desired compound. LCMS (M+H)+: m/z=417.1.

Step 7: Enantiomer 1 and Enantiomer 2: 4-(7-bromo-3-methyl-3,4-dihydroisoquinolin-2(1H)-yl)-6-(4-methylpiperazin-1-yl)pyrimidin-2-amine

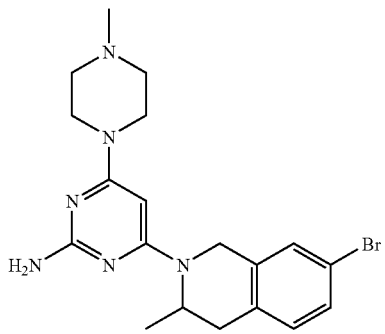 [SMILES: CC1Cc2ccc(Br)cc2CN1c1cc(N2CCN(C)CC2)nc(N)n1]

Compound 4-(7-bromo-3-methyl-3,4-dihydroisoquinolin-2(1H)-yl)-6-(4-methylpiperazin-1-yl)pyrimidin-2-amine was separated into enantiomer 1 and enantiomer 2 by chiral column using the following conditions. Chiral Column: ChiralPak IA, 20×250 mm, 5 μm (Chiral Technologies, Inc, Cat. No. 80345); Mobile Phase: 15% EtOH/85% Hexanes; Flow Rate: 15 mL/min; two peaks' retention time: Peak 1=13.3 min (corresponding to Enantiomer 1), Peak 2=18.0 min (corresponding to Enantiomer 2).

Both compounds of Peak 1 and Peak 2 were carried out for the follow up reactions. LCMS (M+H)+: m/z=417.1.

Example 49A

Enantiomer 1

5-{2-[2-amino-6-(4-methylpiperazin-1-yl)pyrimidin-4-yl]-3-methyl-1,2,3,4-tetrahydroisoquinolin-7-yl}-N-methylpyridine-2-carboxamide

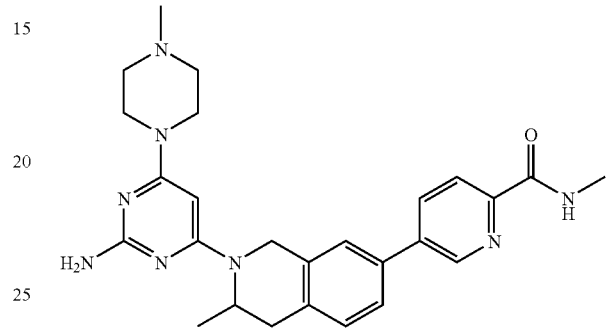

This compound was prepared by using procedures analogous to those described for the synthesis of Example 2 starting from 4-(7-bromo-3-methyl-3,4-dihydroisoquinolin-2(1H)-yl)-6-(4-methylpiperazin-1-yl)pyrimidin-2-amine (Peak 1, Example 49, Step 7) and N-methyl-5-(4,4,5,5-tetramethyl-1,3,2-dioxaborolan-2-yl)pyridine-2-carboxamide (Frontier, Cat. No. M10074). LCMS (M+H)+: m/z=473.4.

Example 49B

Enantiomer 2

5-{2-[2-amino-6-(4-methylpiperazin-1-yl)pyrimidin-4-yl]-3-methyl-1,2,3,4-tetrahydroisoquinolin-7-yl}-N-methylpyridine-2-carboxamide

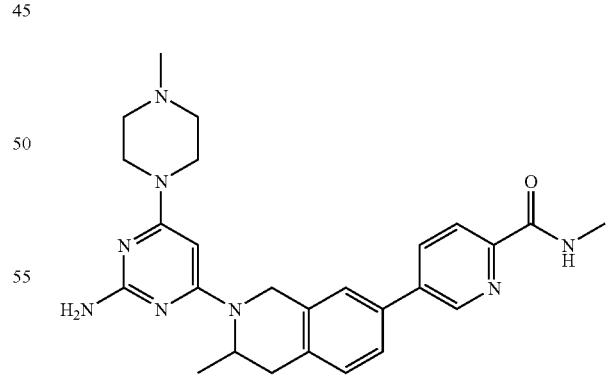

This compound was prepared by using procedures analogous to those described for the synthesis of Example 2 starting from 4-(7-bromo-3-methyl-3,4-dihydroisoquinolin-2(1H)-yl)-6-(4-methylpiperazin-1-yl)pyrimidin-2-amine (Peak 2, Example 49, Step 7) and N-methyl-5-(4,4,5,5-tetramethyl-1,3,2-dioxaborolan-2-yl)pyridine-2-carboxamide (Frontier, Cat. No. M10074). LCMS (M+H)+: m/z=473.4.

Example 50

5-(2-(2-Amino-6-(4-methylpiperazin-1-yl)pyrimidin-4-yl)-3-methyl-1,2,3,4-tetrahydroisoquinolin-7-yl)-N,N-dimethylpicolinamide

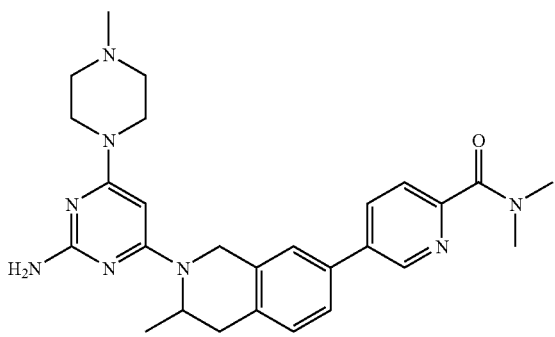 [SMILES: CC1Cc2ccc(-c3ccc(C(=O)N(C)C)nc3)cc2CN1c1cc(N2CCN(C)CC2)nc(N)n1]

Example 50A

Enantiomer 1

5-(2-(2-amino-6-(4-methylpiperazin-1-yl)pyrimidin-4-yl)-3-methyl-1,2,3,4-tetrahydroisoquinolin-7-yl)-N,N-dimethylpicolinamide

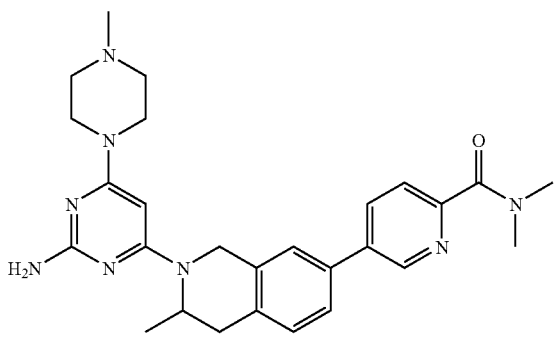 [SMILES: CC1Cc2ccc(-c3ccc(C(=O)N(C)C)nc3)cc2CN1c1cc(N2CCN(C)CC2)nc(N)n1]

Step 1: 5-{2-[2-amino-6-(4-methylpiperazin-1-yl)pyrimidin-4-yl]-3-methyl-1,2,3,4-tetrahydroisoquinolin-7-yl}pyridine-2-carboxylic acid

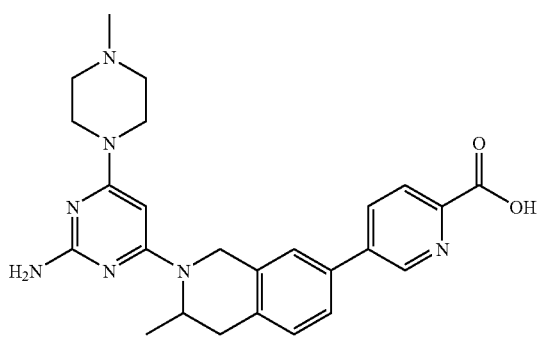 [SMILES: CC1Cc2ccc(-c3ccc(C(=O)O)nc3)cc2CN1c1cc(N2CCN(C)CC2)nc(N)n1]

A mixture of 4-(7-bromo-3-methyl-3,4-dihydroisoquinolin-2(1H)-yl)-6-(4-methylpiperazin-1-yl)pyrimidin-2-amine (100 mg, 0.2 mmol) (Peak 1, Example 49, Step 7), methyl 5-(4,4,5,5-tetramethyl-1,3,2-dioxaborolan-2-yl)pyridine-2-carboxylate (75.6 mg, 0.287 mmol, Frontier, Cat. No. M2012), [1,1'-bis(diphenylphosphino)ferrocene]dichloropalladium(II) complex with dichloromethane (1:1) (11.7 mg, 0.0144 mmol), and potassium phosphate (152.6 mg, 0.7188 mmol) in 1,4-dioxane (5 mL) and water (1 mL) was degassed with nitrogen and heated at 120° C. overnight. The reaction mixture was cooled to r.t. and filtered. The filtrate was concentrated to dryness. The residue was dissolved in MeOH and purified by RP-HPLC (pH=2) to afford the desired compound as TFA salt. LCMS (M+H)+: m/z=460.3.

Step 2: 5-(2-(2-amino-6-(4-methylpiperazin-1-yl)pyrimidin-4-yl)-3-methyl-1,2,3,4-tetrahydroisoquinolin-7-yl)-N,N-dimethylpicolinamide

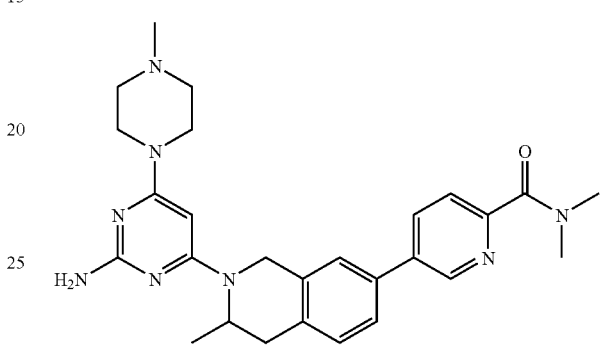

To a solution of 5-{2-[2-amino-6-(4-methylpiperazin-1-yl)pyrimidin-4-yl]-3-methyl-1,2,3,4-tetrahydroisoquinolin-7-yl}pyridine-2-carboxylic acid (20 mg, 0.04 mmol) and dimethylamine hydrochloride (6.9 mg, 0.084 mmol) in N,N-dimethylformamide (0.8 mL) was added (benzotriazol-1-yloxy)tripyrrolidinophosphonium hexafluorophosphate (28 mg, 0.053 mmol) and N,N-diisopropylethylamine (23 uL, 0.13 mmol). The solution was stirred at r.t. for 2 h. The reaction mixture was diluted with MeOH and purified by RP-HPLC (pH=2) to afford the desired compound as TFA salt. LCMS (M+H)+: m/z=487.2

Example 50 B

Enantiomer 2

5-(2-(2-amino-6-(4-methylpiperazin-1-yl)pyrimidin-4-yl)-3-methyl-1,2,3,4-tetrahydroisoquinolin-7-yl)-N,N-dimethylpicolinamide Step 1: 5-{2-[2-amino-6-(4-methylpiperazin-1-yl)pyrimidin-4-yl]-3-methyl-1,2,3,4-tetrahydroisoquinolin-7-yl}pyridine-2-carboxylic acid

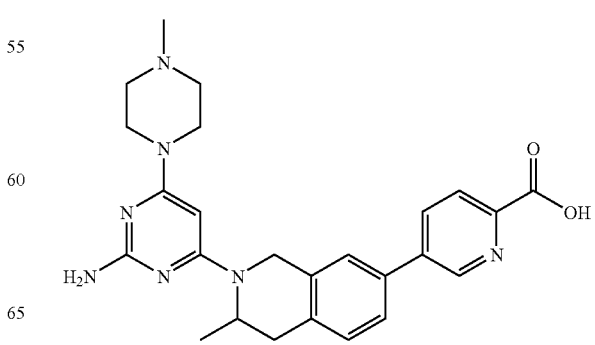

A mixture of 4-(7-bromo-3-methyl-3,4-dihydroisoquinolin-2(1H)-yl)-6-(4-methylpiperazin-1-yl)pyrimidin-2-amine (100 mg, 0.2 mmol) (Peak 2, Example 49, Step 7), methyl 5-(4,4,5,5-tetramethyl-1,3,2-dioxaborolan-2-yl)pyridine-2-carboxylate (75.6 mg, 0.287 mmol, Frontier, Cat. No. M2012), [1,1'-bis(diphenylphosphino)ferrocene]dichloropalladium(II) complex with dichloromethane (1:1) (11.7 mg, 0.0144 mmol), and potassium phosphate (152.6 mg, 0.7188 mmol) in 1,4-dioxane (5 mL) and water (1 mL) was degassed with nitrogen and heated at 120° C. overnight. The reaction mixture was cooled to r.t. and filtered. The filtrate was concentrated to dryness. The residue was dissolved in MeOH and purified by RP-HPLC (pH=2) to afford the desired compound as TFA salt. LCMS (M+H)$^+$: m/z=460.3.

Step 2: Enantiomer 2: 5-(2-(2-amino-6-(4-methylpiperazin-1-yl)pyrimidin-4-yl)-3-methyl-1,2,3,4-tetrahydroisoquinolin-7-yl)-N,N-dimethylpicolinamide

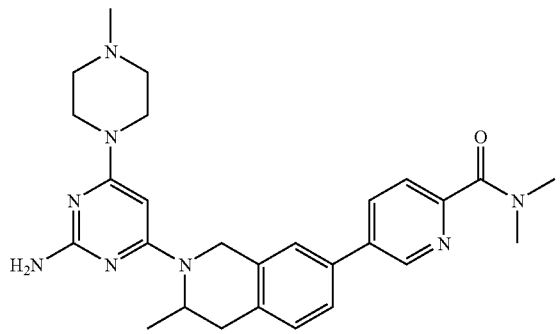 [SMILES: CC1Cc2ccc(-c3ccc(C(=O)N(C)C)nc3)cc2CN1c1cc(N2CCN(C)CC2)nc(N)n1]

To a solution of 5-{2-[2-amino-6-(4-methylpiperazin-1-yl)pyrimidin-4-yl]-3-methyl-1,2,3,4-tetrahydroisoquinolin-7-yl}pyridine-2-carboxylic acid (20 mg, 0.04 mmol) and dimethylamine hydrochloride (6.9 mg, 0.084 mmol) in N,N-dimethylformamide (0.8 mL) was added (benzotriazol-1-yloxy)tripyrrolidinophosphonium hexafluorophosphate (28 mg, 0.053 mmol) and N,N-diisopropylethylamine (23 uL, 0.13 mmol). The solution was stirred at r.t. for 2 h. The reaction mixture was diluted with MeOH and purified by RP-HPLC (pH=2) to afford the desired compound as TFA salt. LCMS (M+H)$^+$: m/z=487.2

Example 51

5-{2-[2-Amino-6-(4-methylpiperazin-1-yl)pyrimidin-4-yl]-3-methyl-1,2,3,4-tetrahydroisoquinolin-7-yl}-N-[(1R)-2-hydroxy-1-methylethyl]pyridine-2-carboxamide

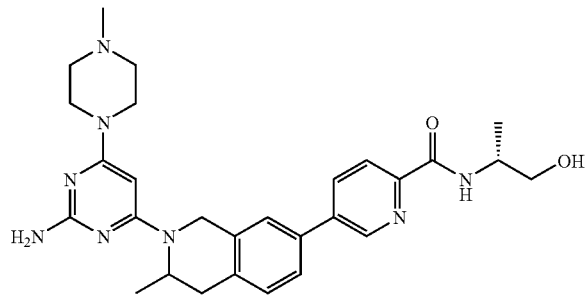 [SMILES: CC1Cc2ccc(-c3ccc(C(=O)N[C@H](C)CO)nc3)cc2CN1c1cc(N2CCN(C)CC2)nc(N)n1]

Example 51A

Enantiomer 1

5-{2-[2-amino-6-(4-methylpiperazin-1-yl)pyrimidin-4-yl]-3-methyl-1,2,3,4-tetrahydroisoquinolin-7-yl}-N-[(1R)-2-hydroxy-1-methylethyl]pyridine-2-carboxamide

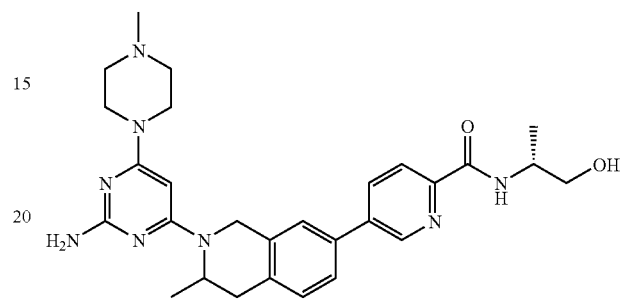

This compound was prepared by using procedures analogous to those described for the synthesis of Example 50A starting from 5-{2-[2-amino-6-(4-methylpiperazin-1-yl)pyrimidin-4-yl]-3-methyl-1,2,3,4-tetrahydroisoquinolin-7-yl}pyridine-2-carboxylic acid (Example 50A, Step 1) and (R)-(−)-1-Amino-2-propanol (Aldrich, Cat. No. 297682). LCMS (M+H)$^+$: m/z=517.3.

Example 51B

Enantiomer 2

5-{2-[2-amino-6-(4-methylpiperazin-1-yl)pyrimidin-4-yl]-3-methyl-1,2,3,4-tetrahydroisoquinolin-7-yl}-N-[(1R)-2-hydroxy-1-methylethyl]pyridine-2-carboxamide

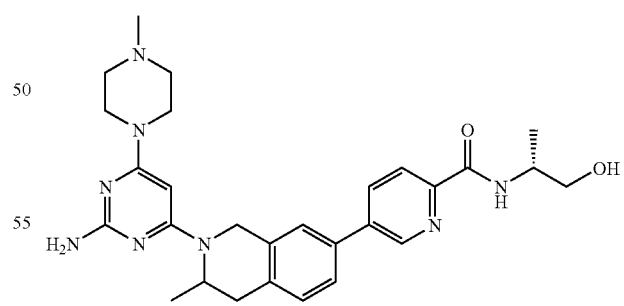

This compound was prepared by using procedures analogous to those described for the synthesis of Example 50B starting from 5-{2-[2-amino-6-(4-methylpiperazin-1-yl)pyrimidin-4-yl]-3-methyl-1,2,3,4-tetrahydroisoquinolin-7-yl}pyridine-2-carboxylic acid (Example 50B, Step 1) and (R)-(−)-1-Amino-2-propanol (Aldrich, Cat. No. 297682). LCMS (M+H)$^+$: m/z=517.3.

Example 52

5-{2-[2-Amino-6-(4-methylpiperazin-1-yl)pyrimidin-4-yl]-3-methyl-1,2,3,4-tetrahydroisoquinolin-7-yl}-N-[2-(dimethylamino)ethyl]-N-methylpyridine-2-carboxamide

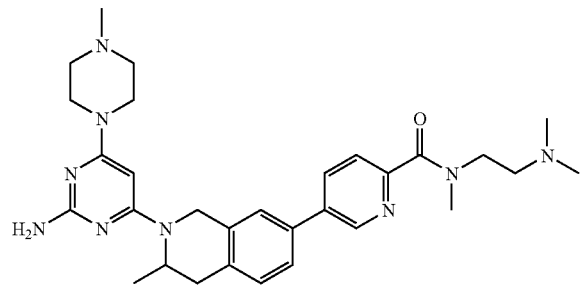

Example 52A

Enantiomer 1

5-{2-[2-amino-6-(4-methylpiperazin-1-yl)pyrimidin-4-yl]-3-methyl-1,2,3,4-tetrahydroisoquinolin-7-yl}-N-[2-(dimethylamino)ethyl]-N-methylpyridine-2-carboxamide

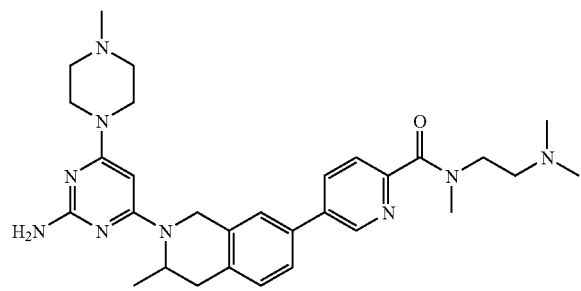 [SMILES: CC1Cc2ccc(-c3ccc(C(=O)N(C)CCN(C)C)nc3)cc2CN1c1cc(N2CCN(C)CC2)nc(N)n1]

This compound was prepared by using procedures analogous to those described for the synthesis of Example 50A starting from 5-{2-[2-amino-6-(4-methylpiperazin-1-yl)pyrimidin-4-yl]-3-methyl-1,2,3,4-tetrahydroisoquinolin-7-yl}pyridine-2-carboxylic acid (Example 50A, Step 1) and N,N,N'-trimethylethylenediamine (Aldrich, Cat. No. 127124). LCMS (M+H)$^+$: m/z=544.3.

Example 52B

Enantiomer 2

5-{2-[2-amino-6-(4-methylpiperazin-1-yl)pyrimidin-4-yl]-3-methyl-1,2,3,4-tetrahydroisoquinolin-7-yl}-N-[2-(dimethylamino)ethyl]-N-methylpyridine-2-carboxamide

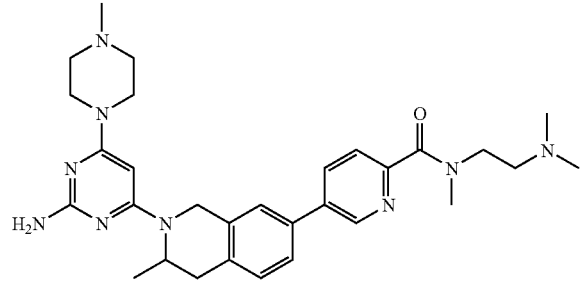 [SMILES: CC1Cc2ccc(-c3ccc(C(=O)N(C)CCN(C)C)nc3)cc2CN1c1cc(N2CCN(C)CC2)nc(N)n1]

This compound was prepared by using procedures analogous to those described for the synthesis of Example 50B starting from 5-{2-[2-amino-6-(4-methylpiperazin-1-yl)pyrimidin-4-yl]-3-methyl-1,2,3,4-tetrahydroisoquinolin-7-yl}pyridine-2-carboxylic acid (Example 50B, Step 1) and N,N,N'-trimethylethylenediamine (Aldrich, Cat. No. 127124). LCMS (M+H)$^+$: m/z=544.3.

Example 53

4-[7-[6-(Azetidin-1-ylcarbonyl)pyridin-3-yl]-3-methyl-3,4-dihydroisoquinolin-2(1H)-yl]-6-(4-methylpiperazin-1-yl)pyrimidin-2-amine

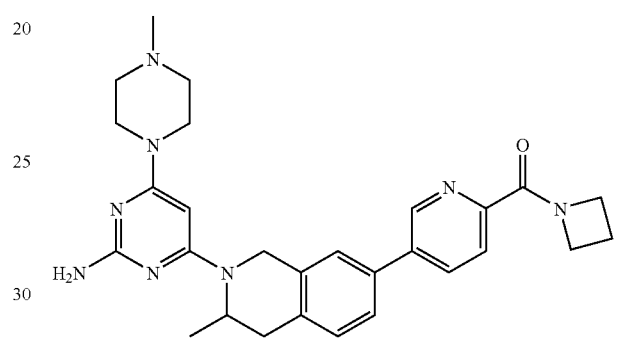

Example 53A

Enantiomer 1

4-[7-[6-(azetidin-1-ylcarbonyl)pyridin-3-yl]-3-methyl-3,4-dihydroisoquinolin-2(1H)-yl]-6-(4-methylpiperazin-1-yl)pyrimidin-2-amine

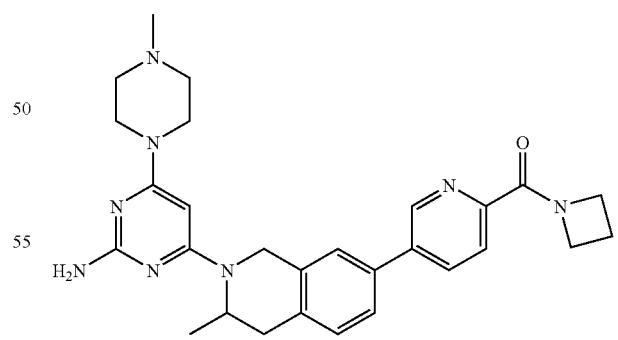

This compound was prepared by using procedures analogous to those described for the synthesis of Example 50A starting from 5-{2-[2-amino-6-(4-methylpiperazin-1-yl)pyrimidin-4-yl]-3-methyl-1,2,3,4-tetrahydroisoquinolin-7-yl}pyridine-2-carboxylic acid (Example 50A, Step 1) and azetidine hydrochloride (Aldrich, Cat. No. 414336). LCMS (M+H)$^+$: m/z=499.2.

Example 53B

Enantiomer 2

4-[7-[6-(azetidin-1-ylcarbonyl)pyridin-3-yl]-3-methyl-3,4-dihydroisoquinolin-2(1H)-yl]-6-(4-methylpiperazin-1-yl)pyrimidin-2-amine

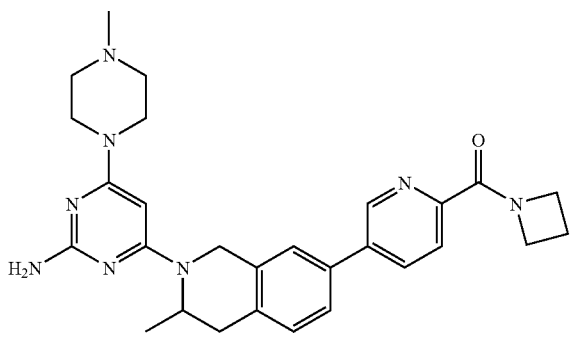 [SMILES: CC1Cc2ccc(-c3ccc(C(=O)N4CCC4)nc3)cc2CN1c1cc(N2CCN(C)CC2)nc(N)n1]

This compound was prepared by using procedures analogous to those described for the synthesis of Example 50B starting from 5-{2-[2-amino-6-(4-methylpiperazin-1-yl)pyrimidin-4-yl]-3-methyl-1,2,3,4-tetrahydroisoquinolin-7-yl}pyridine-2-carboxylic acid (Example 50B, Step 1) and azetidine hydrochloride (Aldrich, Cat. No. 414336). LCMS (M+H)$^+$: m/z=499.2.

Example 54

1-[(5-{2-[2-Amino-6-(4-methylpiperazin-1-yl)pyrimidin-4-yl]-3-methyl-1,2,3,4-tetrahydroisoquinolin-7-yl}-pyridin-2-yl)carbonyl]azetidine-3-carbonitrile

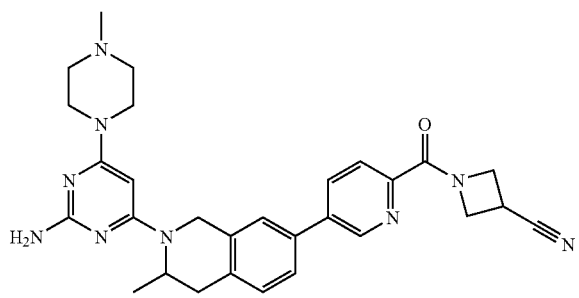 [SMILES: CC1Cc2ccc(-c3ccc(C(=O)N4CC(C#N)C4)nc3)cc2CN1c1cc(N2CCN(C)CC2)nc(N)n1]

Example 54A

Enantiomer 1

1-[(5-{2-[2-amino-6-(4-methylpiperazin-1-yl)pyrimidin-4-yl]-3-methyl-1,2,3,4-tetrahydroisoquinolin-7-yl}pyridin-2-yl)carbonyl]azetidine-3-carbonitrile

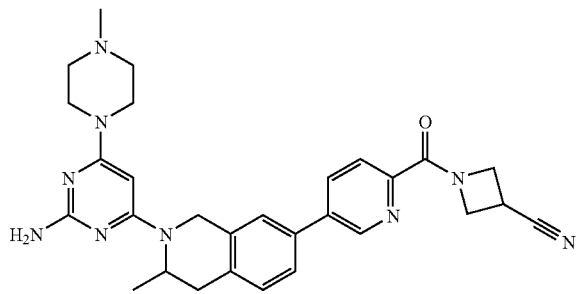 [SMILES: CC1Cc2ccc(-c3ccc(C(=O)N4CC(C#N)C4)nc3)cc2CN1c1cc(N2CCN(C)CC2)nc(N)n1]

This compound was prepared by using procedures analogous to those described for the synthesis of Example 50A starting from 5-{2-[2-amino-6-(4-methylpiperazin-1-yl)pyrimidin-4-yl]-3-methyl-1,2,3,4-tetrahydroisoquinolin-7-yl}pyridine-2-carboxylic acid (Example 50A, Step 1) and azetidine-3-carbonitrile hydrochloride (Astatech, Cat. No. 52028). LCMS (M+H)$^+$: m/z=524.3.

Example 54B

Enantiomer 2

1-[(5-{2-[2-amino-6-(4-methylpiperazin-1-yl)pyrimidin-4-yl]-3-methyl-1,2,3,4-tetrahydroisoquinolin-7-yl}pyridin-2-yl)carbonyl]azetidine-3-carbonitrile

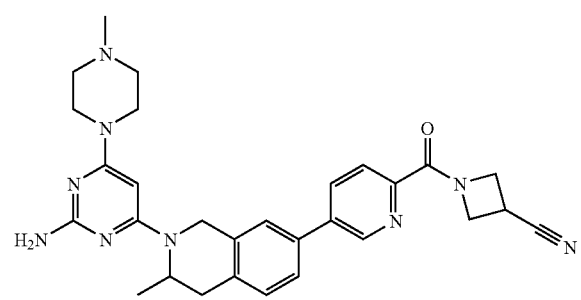 [SMILES: CC1Cc2ccc(-c3ccc(C(=O)N4CC(C#N)C4)nc3)cc2CN1c1cc(N2CCN(C)CC2)nc(N)n1]

This compound was prepared by using procedures analogous to those described for the synthesis of Example 50B starting from 5-{2-[2-amino-6-(4-methylpiperazin-1-yl)pyrimidin-4-yl]-3-methyl-1,2,3,4-tetrahydroisoquinolin-7-yl}pyridine-2-carboxylic acid (Example 50B, Step 1) and azetidine-3-carbonitrile hydrochloride (Astatech, Cat. No. 52028). LCMS (M+H)$^+$: m/z=524.3.

Example 55

4-(4-Methylpiperazin-1-yl)-6-[3-methyl-7-[6-(pyrrolidin-1-ylcarbonyl)pyridin-3-yl]-3,4-dihydroisoquinolin-2(1H)-yl]pyrimidin-2-amine

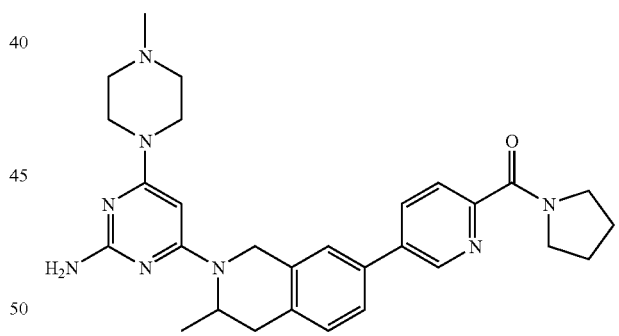

Example 55A

Enantiomer 1

4-(4-methylpiperazin-1-yl)-6-[3-methyl-7-[6-(pyrrolidin-1-ylcarbonyl)pyridin-3-yl]-3,4-dihydroisoquinolin-2(1H)-yl]pyrimidin-2-amine This compound was prepared by using procedures analogous to those described for the synthesis of Example 50A starting from 5-{2-[2-amino-6-(4-methylpiperazin-1-yl)pyrimidin-4-yl]-3-methyl-1,2,3,4-tetrahydroisoquinolin-7-yl}pyridine-2-carboxylic acid (Example 50A, Step 1) and pyrrolidine. LCMS (M+H)$^+$: m/z=513.3.

Example 55B

Enantiomer 2

4-(4-methylpiperazin-1-yl)-6-[3-methyl-7-[6-(pyrrolidin-1-ylcarbonyl)pyridin-3-yl]-3,4-dihydroisoquinolin-2(1H)-yl]pyrimidin-2-amine This compound was prepared by using procedures analogous to those described for the synthesis of Example 50B starting from 5-{2-[2-amino-6-(4-methylpiperazin-1-yl)pyrimidin-4-yl]-3-methyl-1,2,3,4-tetrahydroisoquinolin-7-yl}pyridine-2-carboxylic acid (Example 50B, Step 1) and pyrrolidine. LCMS (M+H)$^+$: m/z=513.3.

Example 56

(3R)-1-[(5-{2-[2-Amino-6-(4-methylpiperazin-1-yl)pyrimidin-4-yl]-3-methyl-1,2,3,4-tetrahydroisoquinolin-7-yl}-pyridin-2-yl)carbonyl]pyrrolidin-3-ol

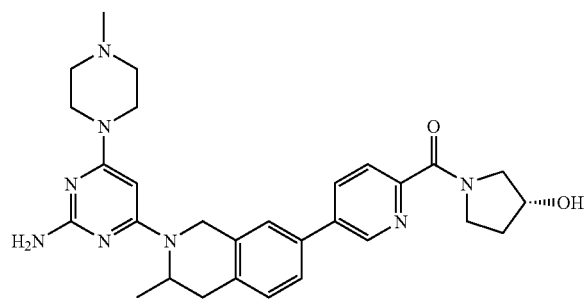 [SMILES: CC1Cc2ccc(-c3ccc(C(=O)N4CC[C@@H](O)C4)nc3)cc2CN1c1cc(N2CCN(C)CC2)nc(N)n1]

Example 56A

Enantiomer 1

(3R)-1-[(5-{2-[2-amino-6-(4-methylpiperazin-1-yl)pyrimidin-4-yl]-3-methyl-1,2,3,4-tetrahydroisoquinolin-7-yl}pyridin-2-yl)carbonyl]pyrrolidin-3-ol This compound was prepared by using procedures analogous to those described for the synthesis of Example 50A starting from 5-{2-[2-amino-6-(4-methylpiperazin-1-yl)pyrimidin-4-yl]-3-methyl-1,2,3,4-tetrahydroisoquinolin-7-yl}pyridine-2-carboxylic acid (Example 50A, Step 1) and (R)-3-hydroxypyrrolidine (Aldrich, Cat. No. 382981). LCMS (M+H)$^+$: m/z=529.3.

Example 56B

Enantiomer 2

(3R)-1-[(5-{2-[2-amino-6-(4-methylpiperazin-1-yl)pyrimidin-4-yl]-3-methyl-1,2,3,4-tetrahydroisoquinolin-7-yl}pyridin-2-yl)carbonyl]pyrrolidin-3-ol This compound was prepared by using procedures analogous to those described for the synthesis of Example 50B starting from 5-{2-[2-amino-6-(4-methylpiperazin-1-yl)pyrimidin-4-yl]-3-methyl-1,2,3,4-tetrahydroisoquinolin-7-yl}pyridine-2-carboxylic acid (Example 50B, Step 1) and (R)-3-hydroxypyrrolidine (Aldrich, Cat. No. 382981). LCMS (M+H)$^+$: m/z=529.3.

Example 57

4-[7-(6-{[3-(Dimethylamino)pyrrolidin-1-yl]carbonyl}pyridin-3-yl)-3-methyl-3,4-dihydroisoquinolin-2(1H)-yl]-6-(4-methylpiperazin-1-yl)pyrimidin-2-amine

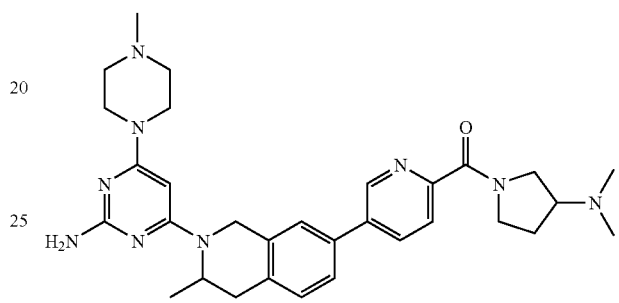

This compound was prepared by using procedures analogous to those described for the synthesis of Example 50A starting from 5-{2-[2-amino-6-(4-methylpiperazin-1-yl)pyrimidin-4-yl]-3-methyl-1,2,3,4-tetrahydroisoquinolin-7-yl}pyridine-2-carboxylic acid (Example 50A, Step 1) and 3-(dimethylamino)pyrrolidine (TCI, Cat. No. D1859). LCMS (M+H)$^+$: m/z=556.3.

Example 58

4-[3-Methyl-7-{6-[(4-methylpiperazin-1-yl)carbonyl]pyridin-3-yl}-3,4-dihydroisoquinolin-2(1H)-yl]-6-(4-methylpiperazin-1-yl)pyrimidin-2-amine

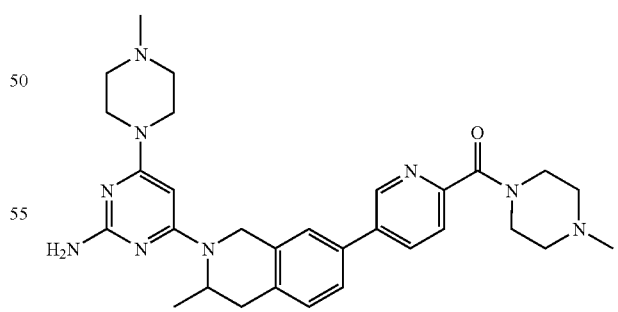

This compound was prepared by using procedures analogous to those described for the synthesis of Example 50A starting from 5-{2-[2-amino-6-(4-methylpiperazin-1-yl)pyrimidin-4-yl]-3-methyl-1,2,3,4-tetrahydroisoquinolin-7-yl}pyridine-2-carboxylic acid (Example 50A, Step 1) and 1-methylpiperazine (Aldrich, Cat. No. 130001). LCMS (M+H)$^+$: m/z=542.3.

Example 59

5-{2-[2-Amino-6-(4-methylpiperazin-1-yl)pyrimidin-4-yl]-3-methyl-1,2,3,4-tetrahydroisoquinolin-7-yl}-N-(2-hydroxyethyl)pyridine-2-carboxamide

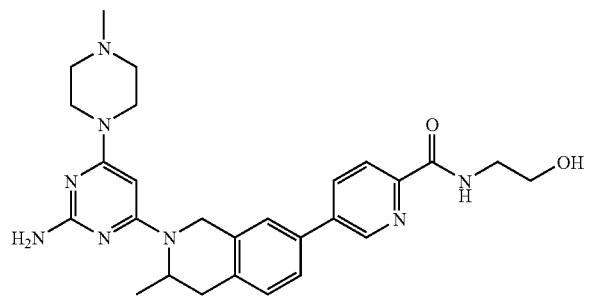

This compound was prepared by using procedures analogous to those described for the synthesis of Example 50B starting from 5-{2-[2-amino-6-(4-methylpiperazin-1-yl)pyrimidin-4-yl]-3-methyl-1,2,3,4-tetrahydroisoquinolin-7-yl}pyridine-2-carboxylic acid (Example 50B, Step 1) and ethanolamine (Aldrich, Cat. No. 411000). LCMS (M+H)$^+$: m/z=503.2.

Example 60

1-[(5-{2-[2-Amino-6-(4-methylpiperazin-1-yl)pyrimidin-4-yl]-3-methyl-1,2,3,4-tetrahydroisoquinolin-7-yl}pyridin-2-yl)carbonyl]azetidin-3-ol

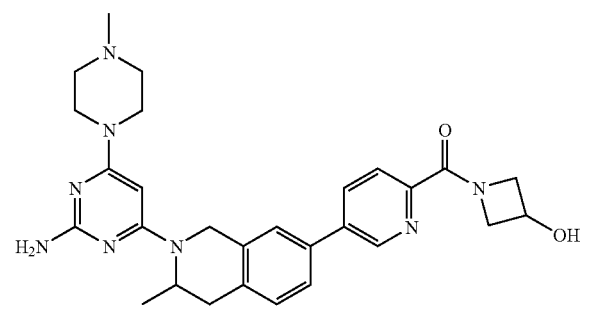

Enantiomer 2

This compound was prepared by using procedures analogous to those described for the synthesis of Example 50B starting from 5-{2-[2-amino-6-(4-methylpiperazin-1-yl)pyrimidin-4-yl]-3-methyl-1,2,3,4-tetrahydroisoquinolin-7-yl}pyridine-2-carboxylic acid (Example 50B, Step 1) and 3-hydroxyazetidine hydrochloride (Oakwood, Cat. No. 013898). LCMS (M+H)$^+$: m/z=515.2.

Example 61

4-{2-[2-amino-6-(4-methylpiperazin-1-yl)pyrimidin-4-yl]-3-methyl-1,2,3,4-tetrahydroisoquinolin-7-yl}-N,N-dimethylpyridine-2-carboxamide

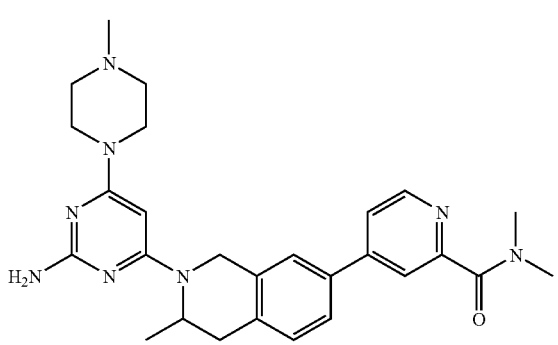 [SMILES: CC1Cc2ccc(-c3ccnc(C(=O)N(C)C)c3)cc2CN1c1cc(N2CCN(C)CC2)nc(N)n1]

Example 61A

Enantiomer 1

4-{2-[2-amino-6-(4-methylpiperazin-1-yl)pyrimidin-4-yl]-3-methyl-1,2,3,4-tetrahydroisoquinolin-7-yl}-N,N-dimethylpyridine-2-carboxamide Step 1: 4-(4-methylpiperazin-1-yl)-6-[3-methyl-7-(4,4,5,5-tetramethyl-1,3,2-dioxaborolan-2-yl)-3,4-dihydroisoquinolin-2(1H)-yl]pyrimidin-2-amine

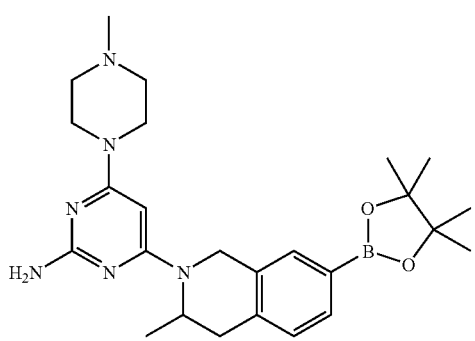 [SMILES: CC1Cc2ccc(B3OC(C)(C)C(C)(C)O3)cc2CN1c1cc(N2CCN(C)CC2)nc(N)n1]

This compound was prepared by using procedures analogous to those described for the synthesis of Example 43 starting from 4-(7-bromo-3-methyl-3,4-dihydroisoquinolin-2(1H)-yl)-6-(4-methylpiperazin-1-yl)pyrimidin-2-amine (Peak 1, Example 49, Step 7). LCMS (M+H)$^+$: m/z=465.3.

Step 2: 4-{2-[2-amino-6-(4-methylpiperazin-1-yl)
pyrimidin-4-yl]-3-methyl-1,2,3,4-tetrahydroiso-
quinolin-7-yl}pyridine-2-carboxylic acid

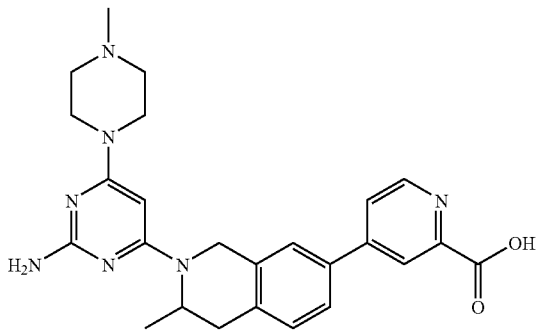 [SMILES: CC1Cc2ccc(-c3ccnc(C(=O)O)c3)cc2CN1c1cc(N2CCN(C)CC2)nc(N)n1]

This compound was prepared by using procedures analogous to those described for the synthesis of Example 50A, Step 1 starting from 4-(4-methylpiperazin-1-yl)-6-[3-methyl-7-(4,4,5,5-tetramethyl-1,3,2-dioxaborolan-2-yl)-3,4-dihydroisoquinolin-2(1H)-yl]pyrimidin-2-amine and methyl 4-iodopyridine-2-carboxylate (Combi-Blocks, Cat. No. CA-4128). LCMS (M+H)⁺: m/z=460.2.

Step 3: Enantiomer 1: 4-{2-[2-amino-6-(4-methylpiperazin-1-yl)pyrimidin-4-yl]-3-methyl-1,2,3,4-tetrahydroisoquinolin-7-yl}-N,N-dimethylpyridine-2-carboxamide

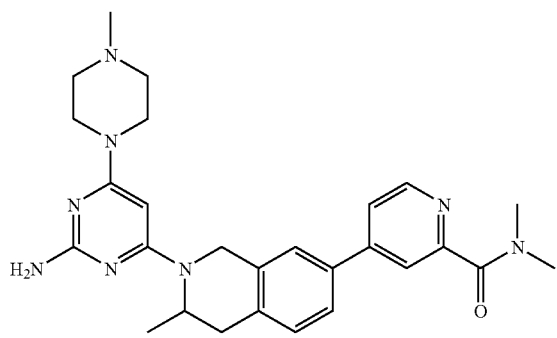 [SMILES: CC1Cc2ccc(-c3ccnc(C(=O)N(C)C)c3)cc2CN1c1cc(N2CCN(C)CC2)nc(N)n1]

This compound was prepared by using procedures analogous to those described for the synthesis of Example 50A starting from 4-{2-[2-amino-6-(4-methylpiperazin-1-yl)pyrimidin-4-yl]-3-methyl-1,2,3,4-tetrahydroisoquinolin-7-yl}pyridine-2-carboxylic acid and dimethylamine hydrochloride. LCMS (M+H)⁺: m/z=487.3.

Example 61B

Enantiomer 2

Step 1: 4-(4-methylpiperazin-1-yl)-6-[3-methyl-7-(4,4,5,5-tetramethyl-1,3,2-dioxaborolan-2-yl)-3,4-dihydroisoquinolin-2(1H)-yl]pyrimidin-2-amine This compound was prepared by using procedures analogous to those described for the synthesis of Example 43 starting from 4-(7-bromo-3-methyl-3,4-dihydroisoquinolin-2(1H)-yl)-6-(4-methylpiperazin-1-yl)pyrimidin-2-amine (Peak 2, Example 49, Step 7). LCMS (M+H)⁺: m/z=465.3.

Step 2: 4-{2-[2-amino-6-(4-methylpiperazin-1-yl)
pyrimidin-4-yl]-3-methyl-1,2,3,4-tetrahydroiso-
quinolin-7-yl}pyridine-2-carboxylic acid This compound was prepared by using procedures analogous to those described for the synthesis of Example 50B, Step 1 starting from 4-(4-methylpiperazin-1-yl)-6-[3-methyl-7-(4,4,5,5-tetramethyl-1,3,2-dioxaborolan-2-yl)-3,4-dihydroisoquinolin-2(1H)-yl]pyrimidin-2-amine and methyl 4-iodopyridine-2-carboxylate (Combi-Blocks, Cat. No. CA-4128). LCMS (M+H)⁺: m/z=460.2.

Step 3: Enantiomer 2: 4-{2-[2-amino-6-(4-methylpiperazin-1-yl)pyrimidin-4-yl]-3-methyl-1,2,3,4-tetrahydroisoquinolin-7-yl}-N,N-dimethylpyridine-2-carboxamide This compound was prepared by using procedures analogous to those described for the synthesis of Example 50B, Step 2 starting from 4-{2-[2-amino-6-(4-methylpiperazin-1-yl)pyrimidin-4-yl]-3-methyl-1,2,3,4-tetrahydroisoquinolin-7-yl}pyridine-2-carboxylic acid and dimethylamine hydrochloride. LCMS (M+H)⁺: m/z=487.3.

Example 62

4-[7-[2-(Azetidin-1-ylcarbonyl)pyridin-4-yl]-3-methyl-3,4-dihydroisoquinolin-2(1H)-yl]-6-(4-methylpiperazin-1-yl)pyrimidin-2-amine

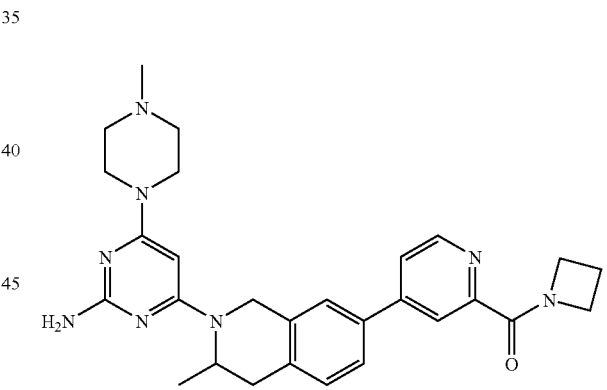

Example 62A

Enantiomer 1

4-[7-[2-(azetidin-1-ylcarbonyl)pyridin-4-yl]-3-methyl-3,4-dihydroisoquinolin-2(1H)-yl]-6-(4-methylpiperazin-1-yl)pyrimidin-2-amine This compound was prepared by using procedures analogous to those described for the synthesis of Example 61A starting from 4-{2-[2-amino-6-(4-methylpiperazin-1-yl)pyrimidin-4-yl]-3-methyl-1,2,3,4-tetrahydroisoquinolin-7-yl}pyridine-2-carboxylic acid (Example 61A, Step 2) and azetidine hydrochloride (Aldrich, Cat. No. 414336). LCMS (M+H)⁺: m/z=499.2.

Example 62B

Enantiomer 2

4-[7-[2-(azetidin-1-ylcarbonyl)pyridin-4-yl]-3-methyl-3,4-dihydroisoquinolin-2(1H)-yl]-6-(4-methylpiperazin-1-yl)pyrimidin-2-amine This compound was prepared by using procedures analogous to those described for the synthesis of Example 61B starting from 4-{2-[2-amino-6-(4-methylpiperazin-1-yl)pyrimidin-4-yl]-3-methyl-1,2,3,4-tetrahydroisoquinolin-7-yl}pyridine-2-carboxylic acid (Example 61B, Step 2) and azetidine hydrochloride (Aldrich, Cat. No. 414336). LCMS (M+H)$^+$: m/z=499.2.

Example 63

1-[(4-{2-[2-Amino-6-(4-methylpiperazin-1-yl)pyrimidin-4-yl]-3-methyl-1,2,3,4-tetrahydroisoquinolin-7-yl}pyridin-2-yl)carbonyl]azetidine-3-carbonitrile

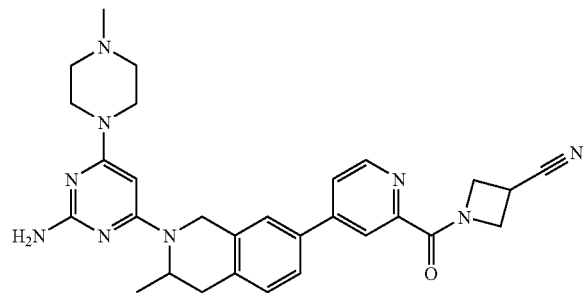 [SMILES: CC1Cc2ccc(-c3ccnc(C(=O)N4CC(C#N)C4)c3)cc2CN1c1cc(N2CCN(C)CC2)nc(N)n1]

Example 63A

Enantiomer 1

1-[(4-{2-[2-amino-6-(4-methylpiperazin-1-yl)pyrimidin-4-yl]-3-methyl-1,2,3,4-tetrahydroisoquinolin-7-yl}pyridin-2-yl)carbonyl]azetidine-3-carbonitrile This compound was prepared by using procedures analogous to those described for the synthesis of Example 61A starting from 4-{2-[2-amino-6-(4-methylpiperazin-1-yl)pyrimidin-4-yl]-3-methyl-1,2,3,4-tetrahydroisoquinolin-7-yl}pyridine-2-carboxylic acid (Example 61A, Step 2) and azetidine-3-carbonitrile hydrochloride (Astatech, Cat. No. 52028). (M+H)$^+$: m/z=524.3.

Example 63B

Enantiomer 2

1-[(4-{2-[2-amino-6-(4-methylpiperazin-1-yl)pyrimidin-4-yl]-3-methyl-1,2,3,4-tetrahydroisoquinolin-7-yl}pyridin-2-yl)carbonyl]azetidine-3-carbonitrile This compound was prepared by using procedures analogous to those described for the synthesis of Example 61B starting from 4-{2-[2-amino-6-(4-methylpiperazin-1-yl)pyrimidin-4-yl]-3-methyl-1,2,3,4-tetrahydroisoquinolin-7-yl}pyridine-2-carboxylic acid (Example 61B, Step 2) and azetidine-3-carbonitrile hydrochloride (Astatech, Cat. No. 52028). LCMS (M+H)$^+$: m/z=524.3.

Example 64

4-(4-Methylpiperazin-1-yl)-6-[3-methyl-7-[2-(pyrrolidin-1-ylcarbonyl)pyridin-4-yl]-3,4-dihydroisoquinolin-2(1H)-yl]pyrimidin-2-amine

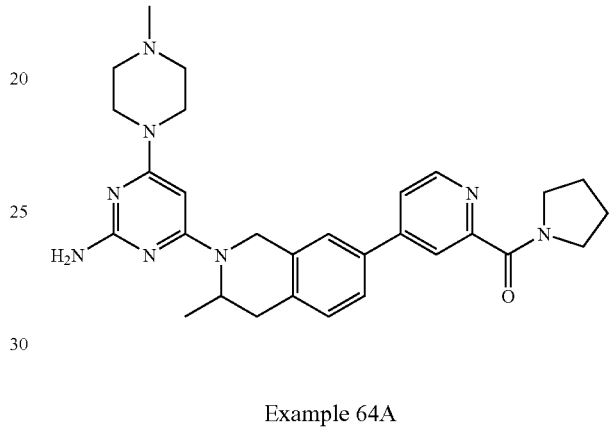

Example 64A

Enantiomer 1

4-(4-methylpiperazin-1-yl)-6-[3-methyl-7-[2-(pyrrolidin-1-ylcarbonyl)pyridin-4-yl]-3,4-dihydroisoquinolin-2(1H)-yl]pyrimidin-2-amine This compound was prepared by using procedures analogous to those described for the synthesis of Example 61A starting from 4-{2-[2-amino-6-(4-methylpiperazin-1-yl)pyrimidin-4-yl]-3-methyl-1,2,3,4-tetrahydroisoquinolin-7-yl}pyridine-2-carboxylic acid (Example 61A, Step 2) and pyrrolidine. LCMS (M+H)$^+$: m/z=513.3.

Example 64B

Enantiomer 2

4-(4-methylpiperazin-1-yl)-6-[3-methyl-7-[2-(pyrrolidin-1-ylcarbonyl)pyridin-4-yl]-3,4-dihydroisoquinolin-2(1H)-yl]pyrimidin-2-amine This compound was prepared by using procedures analogous to those described for the synthesis of Example 61B starting from 4-{2-[2-amino-6-(4-methylpiperazin-1-yl)pyrimidin-4-yl]-3-methyl-1,2,3,4-tetrahydroisoquinolin-7-yl}pyridine-2-carboxylic acid (Example 61B, Step 2) and pyrrolidine. LCMS (M+H)$^+$: m/z=513.3.

Example 65

(3S)-1-[(4-{2-[2-Amino-6-(4-methylpiperazin-1-yl)pyrimidin-4-yl]-3-methyl-1,2,3,4-tetrahydroisoquinolin-7-yl}pyridin-2-yl)carbonyl]pyrrolidin-3-ol

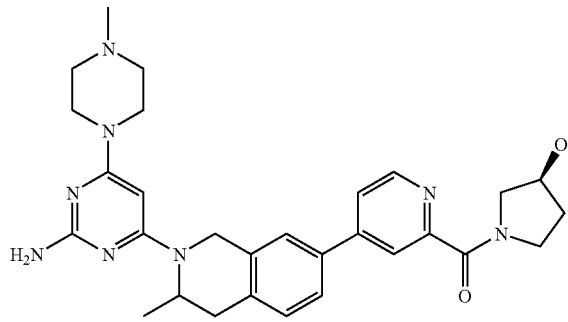 [SMILES: CC1Cc2ccc(-c3ccnc(C(=O)N4CC[C@H](F)C4)c3)cc2CN1c1cc(N2CCN(C)CC2)nc(N)n1]

Example 65A

Enantiomer 1

(3S)-1-[(4-{2-[2-amino-6-(4-methylpiperazin-1-yl)pyrimidin-4-yl]-3-methyl-1,2,3,4-tetrahydroisoquinolin-7-yl}pyridin-2-yl)carbonyl]pyrrolidin-3-ol This compound was prepared by using procedures analogous to those described for the synthesis of Example 61A starting from 4-{2-[2-amino-6-(4-methylpiperazin-1-yl)pyrimidin-4-yl]-3-methyl-1,2,3,4-tetrahydroisoquinolin-7-yl}pyridine-2-carboxylic acid (Example 61A, Step 2) and (S)-(−)-3-Hydroxypyrrolidine (Fluka, Cat. No. 56437). LCMS (M+H)$^+$: m/z=529.3.

Example 65B

Enantiomer 2

(3S)-1-[(4-{2-[2-amino-6-(4-methylpiperazin-1-yl)pyrimidin-4-yl]-3-methyl-1,2,3,4-tetrahydroisoquinolin-7-yl}pyridin-2-yl)carbonyl]pyrrolidin-3-ol This compound was prepared by using procedures analogous to those described for the synthesis of Example 61B starting from 4-{2-[2-amino-6-(4-methylpiperazin-1-yl)pyrimidin-4-yl]-3-methyl-1,2,3,4-tetrahydroisoquinolin-7-yl}pyridine-2-carboxylic acid (Example 61B, Step 2) and (S)-(−)-3-hydroxypyrrolidine (Fluka, Cat. No. 56437). LCMS (M+H)$^+$: m/z=529.3.

Example 66

4-[7-(2-{[(3S)-3-Fluoropyrrolidin-1-yl]carbonyl}pyridin-4-yl)-3-methyl-3,4-dihydroisoquinolin-2(1H)-yl]-6-(4-methylpiperazin-1-yl)pyrimidin-2-amine

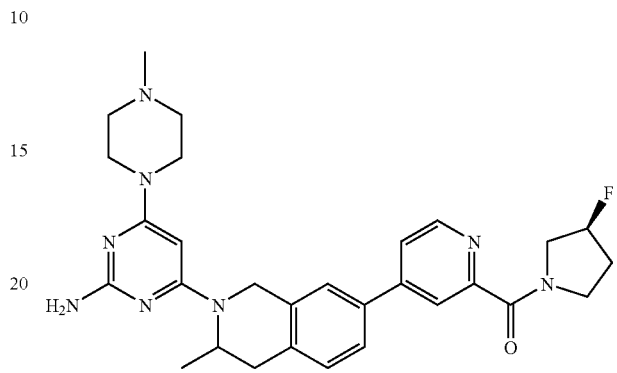

Example 66A

Enantiomer 1

4-[7-(2-{[(3S)-3-fluoropyrrolidin-1-yl]carbonyl}pyridin-4-yl)-3-methyl-3,4-dihydroisoquinolin-2(1H)-yl]-6-(4-methylpiperazin-1-yl)pyrimidin-2-amine This compound was prepared by using procedures analogous to those described for the synthesis of Example 61A starting from 4-{2-[2-amino-6-(4-methylpiperazin-1-yl)pyrimidin-4-yl]-3-methyl-1,2,3,4-tetrahydroisoquinolin-7-yl}pyridine-2-carboxylic acid (Example 61A, Step 2) and (S)-(+)-3-fluoropyrrolidine hydrochloride (Oakwood, Cat. No. 013157). LCMS (M+H)$^+$: m/z=531.2.

Example 66B

Enantiomer 2

4-[7-(2-{[3S)-3-fluoropyrrolidin-1-yl]carbonyl}pyridin-4-yl)-3-methyl-3,4-dihydroisoquinolin-2(1H)-yl]-6-(4-methylpiperazin-1-yl)pyrimidin-2-amine This compound was prepared by using procedures analogous to those described for the synthesis of Example 61B starting from 4-{2-[2-amino-6-(4-methylpiperazin-1-yl)pyrimidin-4-yl]-3-methyl-1,2,3,4-tetrahydroisoquinolin-7-yl}pyridine-2-carboxylic acid (Example 61B, Step 2) and (S)-(+)-3-fluoropyrrolidine hydrochloride (Oakwood, Cat. No. 013157). LCMS (M+H)$^+$: m/z=531.2.

Example 67

4-[7-(2-{[3-(Dimethylamino)pyrrolidin-1-yl]carbonyl}pyridin-4-yl)-3-methyl-3,4-dihydroisoquinolin-2(1H)-yl]-6-(4-methylpiperazin-1-yl)pyrimidin-2-amine

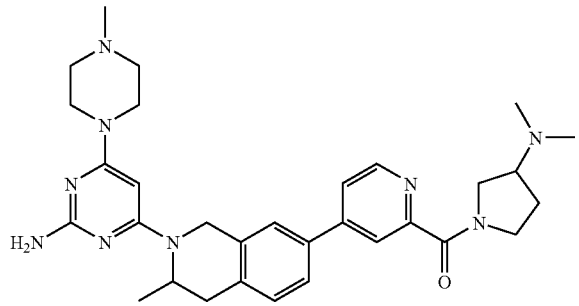 [SMILES: CC1Cc2ccc(-c3ccnc(C(=O)N4CCC(N(C)C)C4)c3)cc2CN1c1cc(N2CCN(C)CC2)nc(N)n1]

Example 68

4-{2-[2-Amino-6-(4-methylpiperazin-1-yl)pyrimidin-4-yl]-3-methyl-1,2,3,4-tetrahydroisoquinolin-7-yl}-N-[2-(dimethylamino)ethyl]-N-methylpyridine-2-carboxamide

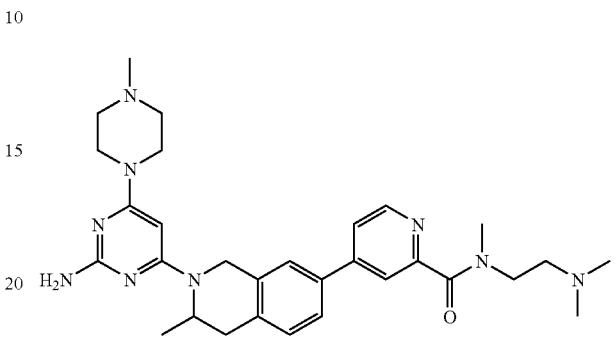

Example 67A

Enantiomer 1

4-[7(2-{[3-(dimethylamino)pyrrolidin-1-yl]carbonyl}pyridin-4-yl)-3-methyl-3,4-dihydroisoquinolin-2(1H)-yl]-6-(4-methylpiperazin-1-yl)pyrimidin-2-amine This compound was prepared by using procedures analogous to those described for the synthesis of Example 61A starting from 4-{2-[2-amino-6-(4-methylpiperazin-1-yl)pyrimidin-4-yl]-3-methyl-1,2,3,4-tetrahydroisoquinolin-7-yl}pyridine-2-carboxylic acid (Example 61A, Step 2) and 3-(dimethylamino)pyrrolidine (TCI, Cat. No. D1859). LCMS (M+H)$^+$: m/z=556.3.

Example 67B

Enantiomer 2

4-[7(2-{[3-(dimethylamino)pyrrolidin-1-yl]carbonyl}pyridin-4-yl)-3-methyl-3,4-dihydroisoquinolin-2(1H)-yl]-6-(4-methylpiperazin-1-yl)pyrimidin-2-amine This compound was prepared by using procedures analogous to those described for the synthesis of Example 61B starting from 4-{2-[2-amino-6-(4-methylpiperazin-1-yl)pyrimidin-4-yl]-3-methyl-1,2,3,4-tetrahydroisoquinolin-7-yl}pyridine-2-carboxylic acid (Example 61B, Step 2) and 3-(dimethylamino)pyrrolidine (TCI, Cat. No. D1859). LCMS (M+H)$^+$: m/z=556.3.

Example 68A

Enantiomer 1

4-{2-[2-amino-6-(4-methylpiperazin-1-yl)pyrimidin-4-yl]-3-methyl-1,2,3,4-tetrahydroisoquinolin-7-yl}-N-[2-(dimethylamino)ethyl]-N-methylpyridine-2-carboxamide This compound was prepared by using procedures analogous to those described for the synthesis of Example 61A starting from 4-{2-[2-amino-6-(4-methylpiperazin-1-yl)pyrimidin-4-yl]-3-methyl-1,2,3,4-tetrahydroisoquinolin-7-yl}pyridine-2-carboxylic acid (Example 61A, Step 2) and N,N,N'-trimethylethylenediamine (Aldrich, Cat. No. 127124). LCMS (M+H)$^+$: m/z=544.2.

Example 68B

Enantiomer 2

4-{2-[2-amino-6-(4-methylpiperazin-1-yl)pyrimidin-4-yl]-3-methyl-1,2,3,4-tetrahydroisoquinolin-7-yl}-N-[2-(dimethylamino)ethyl]-N-methylpyridine-2-carboxamide This compound was prepared by using procedures analogous to those described for the synthesis of Example 61B starting from 4-{2-[2-amino-6-(4-methylpiperazin-1-yl)pyrimidin-4-yl]-3-methyl-1,2,3,4-tetrahydroisoquinolin-7-yl}pyridine-2-carboxylic acid (Example 61B, Step 2) and N,N,N'-trimethylethylenediamine (Aldrich, Cat. No. 127124). LCMS (M+H)$^+$: m/z=544.2.

Example 69

4-{2-[2-Amino-6-(4-methylpiperazin-1-yl)pyrimidin-4-yl]-3-methyl-1,2,3,4-tetrahydroisoquinolin-7-yl}-N-[(1R)-2-hydroxy-1-methylethyl]pyridine-2-carboxamide

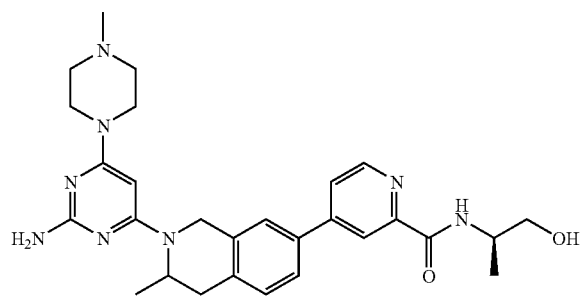 [SMILES: CC1Cc2ccc(-c3ccnc(C(=O)N[C@H](C)CO)c3)cc2CN1c1cc(N2CCN(C)CC2)nc(N)n1]

Enantiomer 1

This compound was prepared by using procedures analogous to those described for the synthesis of Example 61A starting from 4-{2-[2-amino-6-(4-methylpiperazin-1-yl)pyrimidin-4-yl]-3-methyl-1,2,3,4-tetrahydroisoquinolin-7-yl}pyridine-2-carboxylic acid (Example 61A, Step 2) and R-(−)-1-amino-2-propanol (Aldrich, Cat. No. 297682). LCMS (M+H)$^+$: m/z=517.3.

Example 70

4-[3-Methyl-7-{2-[(4-methylpiperazin-1-yl)carbonyl]pyridin-4-yl}-3,4-dihydroisoquinolin-2(1H)-yl]-6-(4-methylpiperazin-1-yl)pyrimidin-2-amine

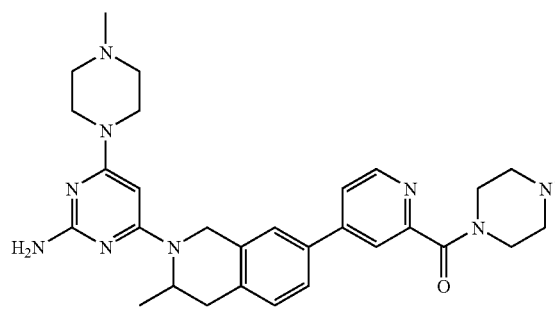

Enantiomer 1

This compound was prepared by using procedures analogous to those described for the synthesis of Example 61A starting from 4-{2-[2-amino-6-(4-methylpiperazin-1-yl)pyrimidin-4-yl]-3-methyl-1,2,3,4-tetrahydroisoquinolin-7-yl}pyridine-2-carboxylic acid (Example 61A, Step 2) and 1-methylpiperazine (Aldrich, Cat. No. 130001). LCMS (M+H)$^+$: m/z=542.3.

Example 71

6-{2-[2-Amino-6-(4-methylpiperazin-1-yl)pyrimidin-4-yl]-3-methyl-1,2,3,4-tetrahydroisoquinolin-7-yl}-N-ethylnicotinamide

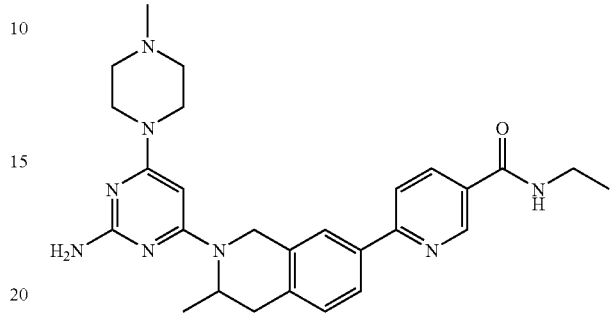

Enantiomer 2

This compound was prepared by using procedures analogous to those described for the synthesis of Example 61B starting from 4-(7-bromo-3-methyl-3,4-dihydroisoquinolin-2(1H)-yl)-6-(4-methylpiperazin-1-yl)pyrimidin-2-amine (Peak 2, Example 49, Step 7) and ethyl 6-chloronicotinate (Aldrich, Cat. No. 531197) and ethylamine in THF solution (2.0 M). LCMS (M+H)$^+$: m/z=487.3.

Example 72

6-{2-[2-Amino-6-(4-methylpiperazin-1-yl)pyrimidin-4-yl]-3-methyl-1,2,3,4-tetrahydroisoquinolin-7-yl}-N,N-dimethylnicotinamide

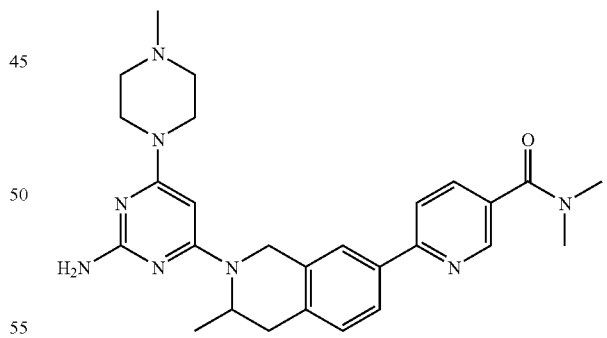

Enantiomer 2

This compound was prepared by using procedures analogous to those described for the synthesis of Example 61B starting from 4-(7-bromo-3-methyl-3,4-dihydroisoquinolin-2(1H)-yl)-6-(4-methylpiperazin-1-yl)pyrimidin-2-amine (Peak 2, Example 49, Step 7) and ethyl 6-chloronicotinate (Aldrich, Cat. No. 531197) and dimethylamine hydrochloride. LCMS (M+H)$^+$: m/z=487.3.

Example 73

1-[(6-{2-[2-Amino-6-(4-methylpiperazin-1-yl)pyrimidin-4-yl]-3-methyl-1,2,3,4-tetrahydroisoquinolin-7-yl}pyridin-3-yl)carbonyl]azetidin-3-ol

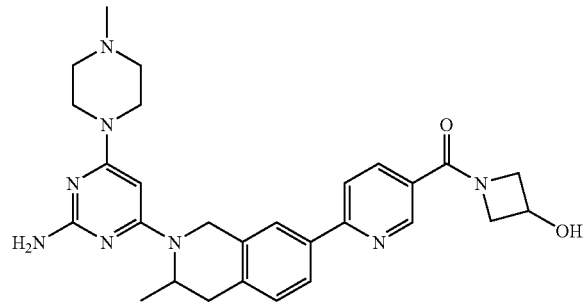 [SMILES: CC1Cc2ccc(-c3ccc(C(=O)N4CC(O)C4)cn3)cc2CN1c1cc(N2CCN(C)CC2)nc(N)n1]

Enantiomer 2

This compound was prepared by using procedures analogous to those described for the synthesis of Example 61B starting from 4-(7-bromo-3-methyl-3,4-dihydroisoquinolin-2(1H)-yl)-6-(4-methylpiperazin-1-yl)pyrimidin-2-amine (Peak 2, Example 49, Step 7) and ethyl 6-chloronicotinate (Aldrich, Cat. No. 531197) and 3-hydroxyazetidine hydrochloride. LCMS (M+H)$^+$: m/z=515.2.

Example 74

5-{2-[2-Amino-6-(4-methylpiperazin-1-yl)pyrimidin-4-yl]-3-methyl-1,2,3,4-tetrahydroisoquinolin-7-yl}-N,N-dimethylnicotinamide

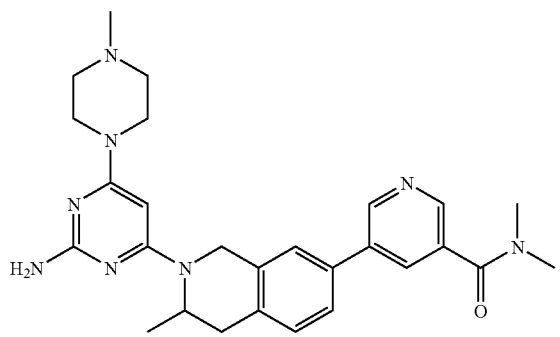 [SMILES: CC1Cc2ccc(-c3cncc(C(=O)N(C)C)c3)cc2CN1c1cc(N2CCN(C)CC2)nc(N)n1]

Enantiomer 2

This compound was prepared by using procedures analogous to those described for the synthesis of Example 50B starting from 4-(7-bromo-3-methyl-3,4-dihydroisoquinolin-2(1H)-yl)-6-(4-methylpiperazin-1-yl)pyrimidin-2-amine (Peak 2, Example 49, Step 7) and ethyl 5-(4,4,5,5-tetramethyl-1,3,2-dioxaborolan-2-yl)nicotinate (Frontier, Cat. No. C1083) and dimethylamine hydrochloride. LCMS (M+H)$^+$: m/z=487.2.

Example 75

1-[(5-{2-[2-Amino-6-(4-methylpiperazin-1-yl)pyrimidin-4-yl]-3-methyl-1,2,3,4-tetrahydroisoquinolin-7-yl}pyridin-3-yl)carbonyl]azetidin-3-ol

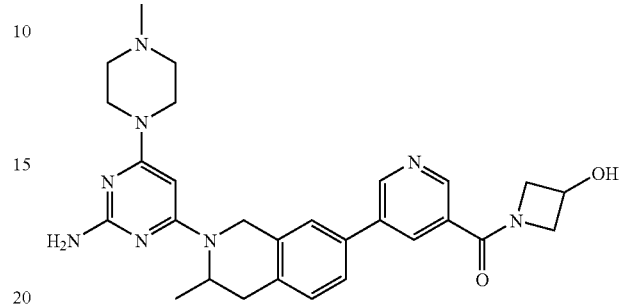

Enantiomer 2

This compound was prepared by using procedures analogous to those described for the synthesis of Example 50B starting from 4-(7-bromo-3-methyl-3,4-dihydroisoquinolin-2(1H)-yl)-6-(4-methylpiperazin-1-yl)pyrimidin-2-amine (Peak 2, Example 49, Step 7) and ethyl 5-(4,4,5,5-tetramethyl-1,3,2-dioxaborolan-2-yl)nicotinate (Frontier, Cat. No. C1083) and 3-hydroxyazetidine hydrochloride. LCMS (M+H)$^+$: m/z=515.2.

Example 76

6-{2-[2-Amino-6-(4-methylpiperazin-1-yl)pyrimidin-4-yl]-3-methyl-1,2,3,4-tetrahydroisoquinolin-7-yl}-N,N-dimethylpyridine-2-carboxamide

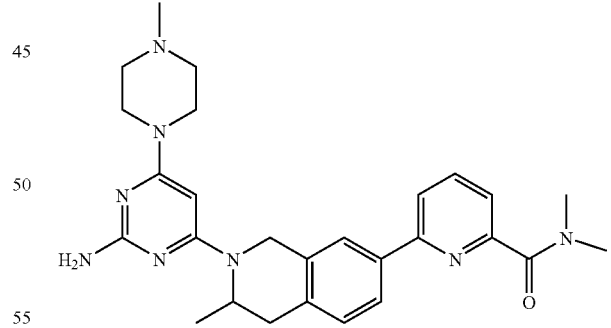

Enantiomer 2

This compound was prepared by using procedures analogous to those described for the synthesis of Example 61B starting from 4-(7-bromo-3-methyl-3,4-dihydroisoquinolin-2(1H)-yl)-6-(4-methylpiperazin-1-yl)pyrimidin-2-amine (Peak 2, Example 49, Step 7) and methyl 6-bromopyridine-2-carboxylate (Aldrich, Cat. No. 650110) and dimethylamine hydrochloride. LCMS (M+H)$^+$: m/z=487.3.

Example 77

5-{2-[2-Amino-6-(4-methylpiperazin-1-yl)pyrimidin-4-yl]-3-methyl-1,2,3,4-tetrahydroisoquinolin-7-yl}-N-ethylpyrimidine-2-carboxamide

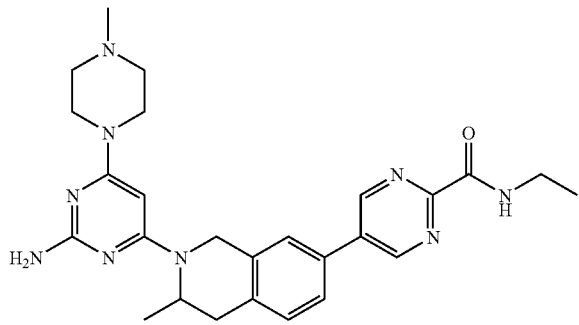 [SMILES: CCNC(=O)c1ncc(-c2ccc3c(c2)CN(c2cc(N4CCN(C)CC4)nc(N)n2)C(C)C3)cn1]

Enantiomer 2

Step 1: 5-{2-[2-amino-6-(4-methylpiperazin-1-yl)pyrimidin-4-yl]-3-methyl-1,2,3,4-tetrahydroisoquinolin-7-yl}pyrimidine-2-carbonitrile

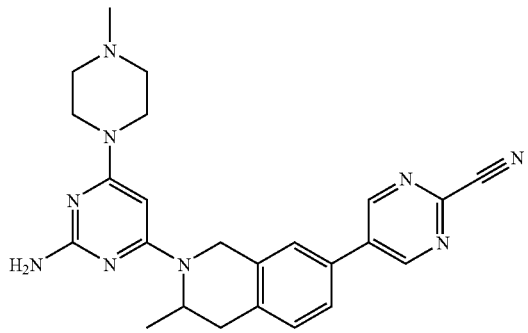 [SMILES: CC1Cc2ccc(-c3cnc(C#N)nc3)cc2CN1c1cc(N2CCN(C)CC2)nc(N)n1]

This compound was prepared by using procedures analogous to those described for the synthesis of Example 50A starting from 4-(7-bromo-3-methyl-3,4-dihydroisoquinolin-2(1H)-yl)-6-(4-methylpiperazin-1-yl)pyrimidin-2-amine (Peak 2, Example 49, Step 7) and 5-(4,4,5,5-tetramethyl-1,3,2-dioxaborolan-2-yl)pyrimidine-2-carbonitrile (Frontier, Cat. No. C2065). LCMS (M+H)$^+$: m/z=442.2.

Step 2: 5-{2-[2-amino-6-(4-methylpiperazin-1-yl)pyrimidin-4-yl]-3-methyl-1,2,3,4-tetrahydroisoquinolin-7-yl}-N-ethylpyrimidine-2-carboxamide

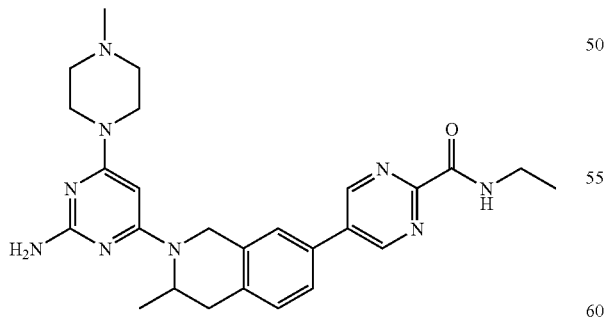

Enantiomer 2

This compound was prepared by using procedures analogous to those described for the synthesis of Example 24, Step 2 and 3 starting from 5-{2-[2-amino-6-(4-methylpiperazin-1-yl)pyrimidin-4-yl]-3-methyl-1,2,3,4-tetrahydroisoquinolin-7-yl}pyrimidine-2-carbonitrile and ethylamine in THF solution (2.0 M). LCMS (M+H)$^+$: m/z=488.2.

Example 78

1-[(5-{2-[2-Amino-6-(4-methylpiperazin-1-yl)pyrimidin-4-yl]-3-methyl-1,2,3,4-tetrahydroisoquinolin-7-yl}pyrimidin-2-yl)carbonyl]azetidin-3-ol

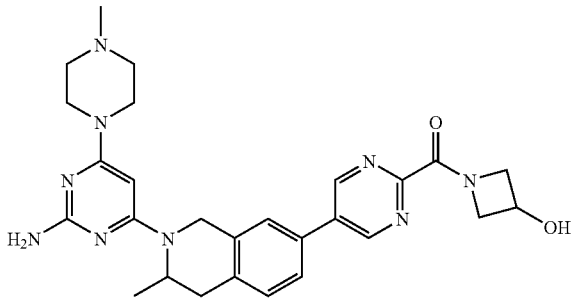 [SMILES: CC1Cc2ccc(-c3cnc(C(=O)N4CC(O)C4)nc3)cc2CN1c1cc(N2CCN(C)CC2)nc(N)n1]

Enantiomer 2

This compound was prepared by using procedures analogous to those described for the synthesis of Example 77 starting from 5-{2-[2-amino-6-(4-methylpiperazin-1-yl)pyrimidin-4-yl]-3-methyl-1,2,3,4-tetrahydroisoquinolin-7-yl}-N-ethylpyrimidine-2-carboxamide and then 3-hydroxyazetidine hydrochloride. LCMS (M+H)$^+$: m/z=516.2.

Example 79

2-(4-{2-[2-Amino-6-(4-methylpiperazin-1-yl)pyrimidin-4-yl]-3-methyl-1,2,3,4-tetrahydroisoquinolin-7-yl}-1H-pyrazol-1-yl)-N-methylacetamide

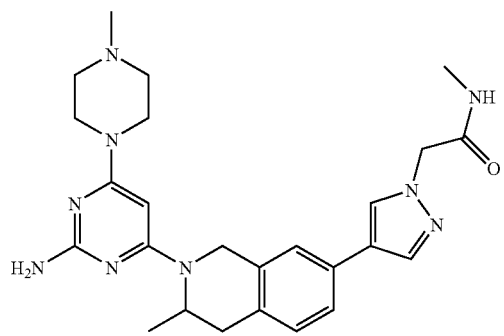 [SMILES: CNC(=O)Cn1cc(-c2ccc3c(c2)CN(c2cc(N4CCN(C)CC4)nc(N)n2)C(C)C3)cn1]

Step 1: tert-butyl [4-(4,4,5,5-tetramethyl-1,3,2-dioxaborolan-2-yl)-1H-pyrazol-1-yl]acetate

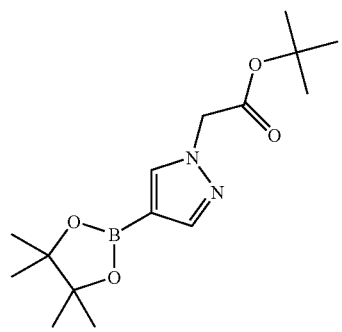 [SMILES: CC(C)(C)OC(=O)Cn1cc(B2OC(C)(C)C(C)(C)O2)cn1]

To a solution of 4-(4,4,5,5-tetramethyl-1,3,2-dioxaborolan-2-yl)-1H-pyrazole (400 mg, 0.002 mol, Aldrich, Cat. No. 525057) in acetonitrile (10 mL) was added tert-butyl 2-bromoacetate (0.36 mL, 0.0025 mol, Aldrich, Cat. No. 124230) and cesium carbonate (1.0 g, 0.0031 mol). The suspension was stirred at r.t. overnight. The reaction mixture was partitioned with AcOEt and water. The organic layer was separated, washed with water and brine, dried over MgSO$_4$. After filtration, the filtrate was concentrated to afford the desired compound which was directly used in the next step reaction without further purification. LCMS (M+H)$^+$: m/z=309.1.

Step 2: tert-butyl(4-{2-[2-amino-6-(4-methylpiperazin-1-yl)pyrimidin-4-yl]-3-methyl-1,2,3,4-tetrahydroisoquinolin-7-yl}-1H-pyrazol-1-yl)acetate

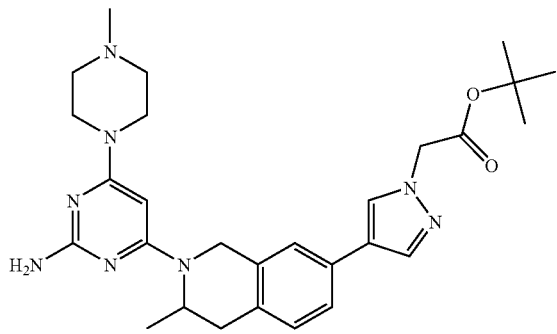 [SMILES: CC1Cc2ccc(-c3cnn(CC(=O)OC(C)(C)C)c3)cc2CN1c1cc(N2CCN(C)CC2)nc(N)n1]

This compound was prepared by using procedures analogous to those described for the synthesis of Example 50A starting from 4-(7-bromo-3-methyl-3,4-dihydroisoquinolin-2(1H)-yl)-6-(4-methylpiperazin-1-yl)pyrimidin-2-amine (Example 49, Step 6) and methyl tert-butyl [4-(4,4,5,5-tetramethyl-1,3,2-dioxaborolan-2-yl)-1H-pyrazol-1-yl]acetate. LCMS (M+H)$^+$: m/z=519.3.

Step 3: 2-(4-{2-[2-amino-6-(4-methylpiperazin-1-yl)pyrimidin-4-yl]-3-methyl-1,2,3,4-tetrahydroisoquinolin-7-yl}-1H-pyrazol-1-yl)-N-methylacetamide

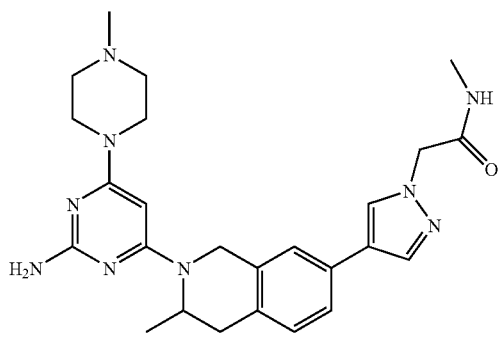 [SMILES: CNC(=O)Cn1cc(-c2ccc3c(c2)CN(c2cc(N4CCN(C)CC4)nc(N)n2)C(C)C3)cn1]

The mixture of tert-butyl(4-{2-[2-amino-6-(4-methylpiperazin-1-yl)pyrimidin-4-yl]-3-methyl-1,2,3,4-tetrahydroisoquinolin-7-yl}-1H-pyrazol-1-yl)acetate (66 mg, 0.13 mmol) and trifluoroacetic acid (1 mL, 10 mmol) in CH$_2$Cl$_2$ (1 mL) was stirred at r.t. for 1 h. The volatiles were removed under reduced pressure.

The residue (20 mg, 0.04 mmol) was dissolved in N,N-dimethylformamide (0.8 mL). To the solution was added 2.0 M of methylamine in tetrahydrofuran (44 uL, 0.088 mmol), (benzotriazol-1-yloxy)tripyrrolidinophosphonium hexafluorophosphate (28 mg, 0.053 mmol) and N,N-diisopropylethylamine (23 uL, 0.13 mmol). The mixture was stirred at r.t. for 2 h. The reaction solution was diluted with MeOH and purified by RP-HPLC (pH=10) to afford the desired compound. LCMS(M+H)$^+$: m/z=476.2.

Example 80

2-(4-{2-[2-Amino-6-(4-methylpiperazin-1-yl)pyrimidin-4-yl]-3-methyl-1,2,3,4-tetrahydroisoquinolin-7-yl}-1H-pyrazol-1-yl)-N,N-dimethylacetamide

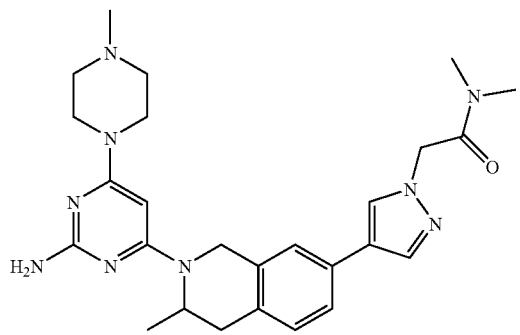 [SMILES: CC1Cc2ccc(-c3cnn(CC(=O)N(C)C)c3)cc2CN1c1cc(N2CCN(C)CC2)nc(N)n1]

This compound was prepared by using procedures analogous to those described for the synthesis of Example 79 starting from tert-butyl(4-{2-[2-amino-6-(4-methylpiperazin-1-yl)pyrimidin-4-yl]-3-methyl-1,2,3,4-tetrahydroisoquinolin-7-yl}-1H-pyrazol-1-yl)acetate and dimethylamine hydrochloride. LCMS (M+H)$^+$: m/z=490.3.

Example 81

5-[2-[2-Amino-6-(4-methylpiperazin-1-yl)pyrimidin-4-yl]-3-(hydroxymethyl)-1,2,3,4-tetrahydroisoquinolin-7-yl]-N-methylpyridine-2-carboxamide

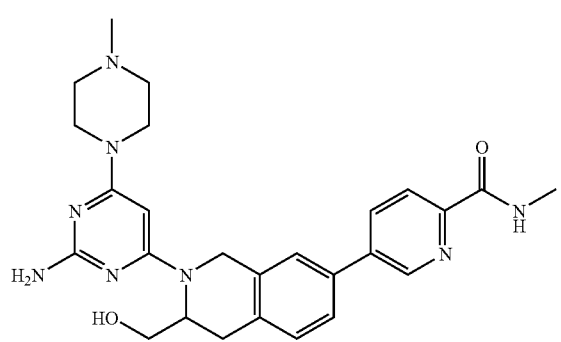 [SMILES: CNC(=O)c1ccc(-c2ccc3c(c2)CN(c2cc(N4CCN(C)CC4)nc(N)n2)C(CO)C3)cn1]

Step 1: methyl 2-amino-3-(4-bromophenyl)propanoate

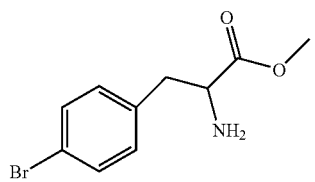

To a solution of 2-amino-3-(4-bromophenyl)propanoic acid (2.0 g, 8.2 mmol, Chem-Impex, Cat. No. 06163) in methanol (10 mL) was added thionyl chloride (1.2 mL, 16 mmol) dropwise. The mixture was stirred at r.t. overnight and then concentrated under reduced pressure. The residue was washed with ether and dried under vacuum to afford the desired compound which was directly used in the next step reaction without further purification. LCMS (M+H)$^+$: m/z=258.2.

Step 2: methyl 7-bromo-1,2,3,4-tetrahydroisoquinoline-3-carboxylate

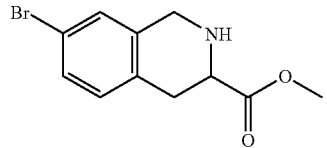

This compound was prepared by using procedures analogous to those described for the synthesis of Example 49 (Step 2 to 4) starting from methyl 2-amino-3-(4-bromophenyl)propanoate. LCMS (M+H)$^+$: m/z=270.2.

Step 3: (7-bromo-1,2,3,4-tetrahydroisoquinolin-3-yl)methanol

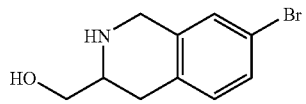

To a solution of methyl 7-bromo-1,2,3,4-tetrahydroisoquinoline-3-carboxylate (1.0 g, 3.7 mmol) in tetrahydrofuran (20 mL) was added 1.0 M of lithium tetrahydroaluminate in tetrahydrofuran (7.40 mL, 7.40 mmol, Aldrich Cat. No. 212776) dropwise at 0° C. The solution was stirred at 0° C. for 2 h. Water (0.3 mL), 15% NaOH aqueous solution (0.3 mL) and water (1.0 mL) were added dropwise in sequence to the reaction solution. The suspension was filtered through a pad of celite, and washed with ether. The filtrate was concentrated to afford the desired compound which was directly used in the next step reaction without further purification. LCMS (M+H)$^+$: m/z=242.2.

Step 4: 7-bromo-3-({[tert-butyl(dimethyl)silyl]oxy}methyl)-1,2,3,4-tetrahydroisoquinoline

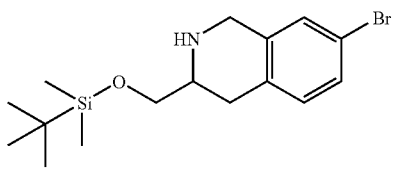 [SMILES: CC(C)(C)[Si](C)(C)OCC1Cc2ccc(Br)cc2CN1]

To a solution of (7-bromo-1,2,3,4-tetrahydroisoquinolin-3-yl)methanol (620 mg, 2.6 mmol) in N,N-dimethylformamide (5 mL) was added tert-butyldimethylsilyl chloride (580 mg, 3.8 mmol, Aldrich, Cat. No. 190550) and 1H-imidazole (260 mg, 3.8 mmol). The solution was stirred at r.t. overnight. The reaction solution was diluted with water, and extracted with AcOEt. The organic layer was washed with brine, dried over MgSO$_4$. After filtration, the filtrate was concentrated to afford the desired compound which was directly used in the next step reaction without further purification. LCMS (M+H)$^+$: m/z=356.3.

Step 5: 4-[7-bromo-3-({[tert-butyl(dimethyl)silyl]oxy}methyl)-3,4-dihydroisoquinolin-2(1H)-yl]-6-(4-methylpiperazin-1-yl)pyrimidin-2-amine

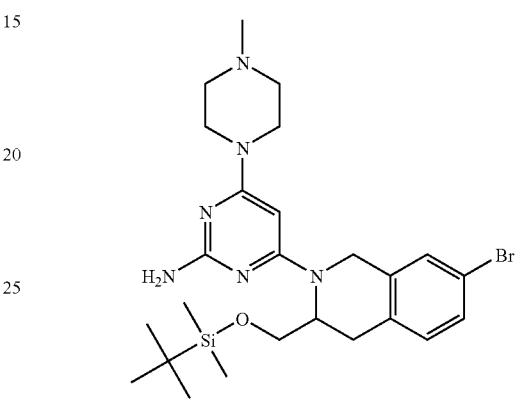

This compound was prepared by using procedures analogous to those described for the synthesis of Example 49, Step 5 and 6 starting from 7-bromo-3-({[tert-butyl(dimethyl)silyl]oxy}methyl)-1,2,3,4-tetrahydroisoquinoline, 2-amino-4,6-dichloropyrimidine and 1-methylpiperazine. LCMS (M+H)$^+$: m/z=547.2.

Step 6: {2-[2-amino-6-(4-methylpiperazin-1-yl)pyrimidin-4-yl]-7-bromo-1,2,3,4-tetrahydroisoquinolin-3-yl}methanol

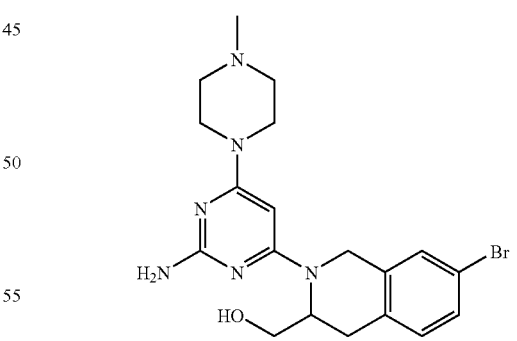

To a solution of 4-[7-bromo-3-({[tert-butyl(dimethyl)silyl]oxy}methyl)-3,4-dihydroisoquinolin-2(1H)-yl]-6-(4-methylpiperazin-1-yl)pyrimidin-2-amine (150 mg, 0.27 mmol) in 1,4-dioxane (3 mL) was added 1.7 M of fluorosilicic acid in water (480 uL). The reaction mixture was stirred at r.t. for 2 h., and then concentrated to remove dioxane. The residue was dissolved in MeOH and purified by RP-HPLC (pH=10) to afford the desired compound. LCMS(M+H)$^+$: m/z=433.2.

Step 7: 5-[2-[2-amino-6-(4-methylpiperazin-1-yl)pyrimidin-4-yl]-3-(hydroxymethyl)-1,2,3,4-tetrahydroisoquinolin-7-yl]-N-methylpyridine-2-carboxamide

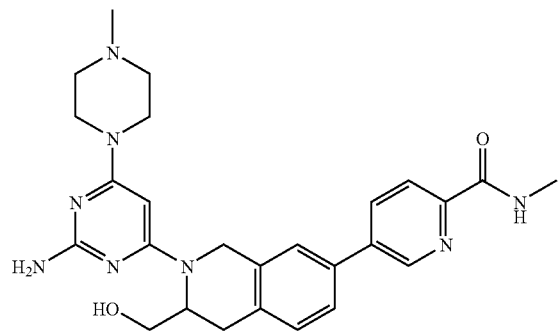 [SMILES: CNC(=O)c1ccc(-c2ccc3c(c2)CN(c2cc(N4CCN(C)CC4)nc(N)n2)C(CO)C3)cn1]

This compound was prepared by using procedures analogous to those described for the synthesis of Example 49A starting from {2-[2-amino-6-(4-methylpiperazin-1-yl)pyrimidin-4-yl]-7-bromo-1,2,3,4-tetrahydroisoquinolin-3-yl}methanol and N-methyl-5-(4,4,5,5-tetramethyl-1,3,2-dioxaborolan-2-yl)pyridine-2-carboxamide (Frontier, Cat. No. M10074). LCMS (M+H)$^+$: m/z=489.2.

Example 81A (Enantiomer 1) and Example 8B (Enantiomer 2)

5-[2-[2-amino-6-(4-methylpiperazin-1-yl)pyrimidin-4-yl]-3-(hydroxymethyl)-1,2,3,4-tetrahydroisoquinolin-7-yl]-N-methylpyridine-2-carboxamide

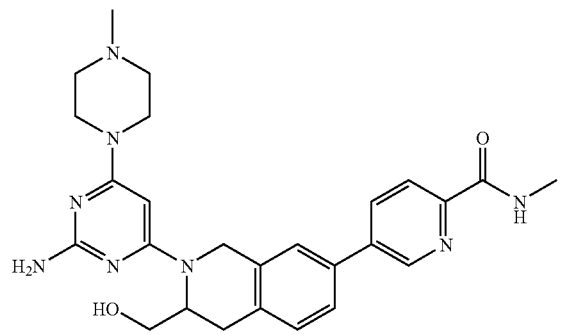 [SMILES: CNC(=O)c1ccc(-c2ccc3c(c2)CN(c2cc(N4CCN(C)CC4)nc(N)n2)C(CO)C3)cn1]

Compound 5-[2-[2-amino-6-(4-methylpiperazin-1-yl)pyrimidin-4-yl]-3-(hydroxymethyl)-1,2,3,4-tetrahydroisoquinolin-7-yl]-N-methylpyridine-2-carboxamide was separated into Enantiomer 1 and 2 by chiral column using the following conditions. Chiral Column: Cellulose-1, 21.2×250 mm, 5 μm (Phenomenex, Cat. No. 00G-4459-P0-AX); Mobile Phase: 60% EtOH/40% Hexanes; Flow Rate: 15 mL/min; two peaks, retention time: Peak 1=9.0 min (Enantiomer 1), Peak 2=10.8 min (Enantiomer 2). LCMS (M+H)$^+$: m/z=489.2.

Example 82

(3-{2-[2-Amino-6-(4-methylpiperazin-1-yl)pyrimidin-4-yl]-3-methyl-1,2,3,4-tetrahydroisoquinolin-7-yl}-1H-pyrazol-1-yl)acetonitrile

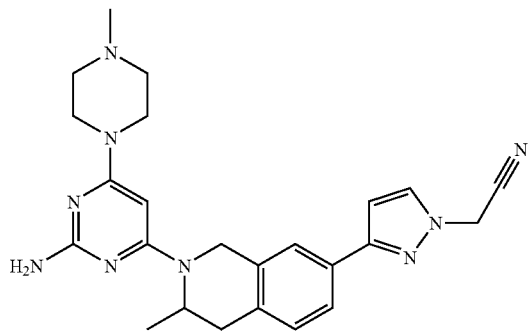 [SMILES: CC1Cc2ccc(-c3ccn(CC#N)n3)cc2CN1c1cc(N2CCN(C)CC2)nc(N)n1]

Example 82A

Enantiomer 1

Step 1: 4-(4-Ethylpiperazin-1-yl)-6-[3-methyl-7-(1H-pyrazol-3-yl)-3,4-dihydroisoquinolin-2(1H)-yl]pyrimidin-2-amine

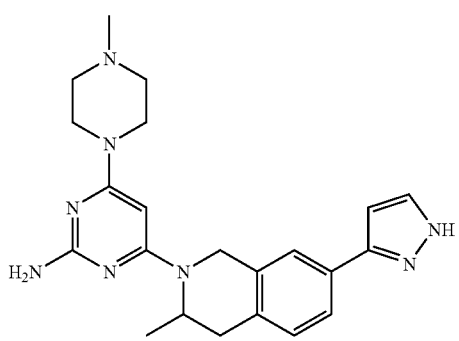 [SMILES: CC1Cc2ccc(-c3cc[nH]n3)cc2CN1c1cc(N2CCN(C)CC2)nc(N)n1]

A mixture of 1H-pyrazol-3-ylboronic acid (64.3 mg, 0.575 mmol, Frontier Scientific, Cat. No. P1638), 4-(7-bromo-3-methyl-3,4-dihydroisoquinolin-2(1H)-yl)-6-(4-methylpiperazin-1-yl)pyrimidin-2-amine (0.20 g, 0.48 mmol) (Peak 1, Example 49, Step 7), dichloro(bis{di-tert-butyl[4-(dimethylamino)phenyl]phosphoranyl})palladium (10.2 mg, 0.0144 mmol), and sodium carbonate (0.102 g, 0.958 mmol) in 1,4-dioxane (2.2 mL) and water (0.3 mL) was vacuumed and refilled with N$_2$ for 3 times and then stirred at 90° C. for overnight. The mixture was purified by RP-HPLC (pH=10) to afford the desired product. LCMS (M+H)$^+$: m/z=405.2.

Step 2: (3-{2-[2-Amino-6-(4-methylpiperazin-1-yl)pyrimidin-4-yl]-3-methyl-1,2,3,4-tetrahydroisoquinolin-7-yl}-1H-pyrazol-1-yl)acetonitrile Potassium tert-butoxide in THF (1.0 M, 74.2 uL, 0.0742 mmol) was added to a solution of 4-(4-methylpiperazin-1-yl)-6-[3-methyl-7-(1H-pyrazol-3-yl)-3,4-dihydroisoquinolin-2(1H)-yl]pyrimidin-2-amine (15.0 mg, 0.0371 mmol) in DMF (0.3 mL) and stirred at r.t. for 10 min, and then bromoacetonitrile (3.71 uL, 0.0556 mmol) was added. The mixture was stirred at r.t. for 1 h. LCMS showed the reaction was complete. The mixture was purified by RP-HPLC (pH=10) to afford the desired product. LCMS (M+H)$^+$: m/z=444.2.

Example 82B

Enantiomer 2

Step 1: 3-Bromo-1H-pyrazol-1-yl)acetonitrile

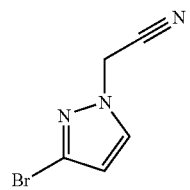

Potassium tert-butoxide in THF (0.510 mL, 1.0 M) was added to a solution of 3-bromo-1H-pyrazole (50.0 mg, 0.340 mmol, ChemPacific, Cat. No. 59726) in DMF (3 mL) and stirred at r.t. for 10 min, and then bromoacetonitrile (34.0 uL, 0.510 mmol) was added and then stirred at r.t. for 1 h. LCMS showed the reaction was complete. The mixture was diluted with ethyl acetate and then washed with water and brine, dried over $Na_2SO_4$, filtered and concentrated to give the crude product which was directly used in the next reaction without further purification. LCMS $(M+H)^+$: m/z=187.9.

Step 2: 4-(4-methylpiperazin-1-yl)-6-[3-methyl-7-(4,4,5,5-tetramethyl-1,3,2-dioxaborolan-2-yl)-3,4-dihydroisoquinolin-2(1H)-yl]pyrimidin-2-amine

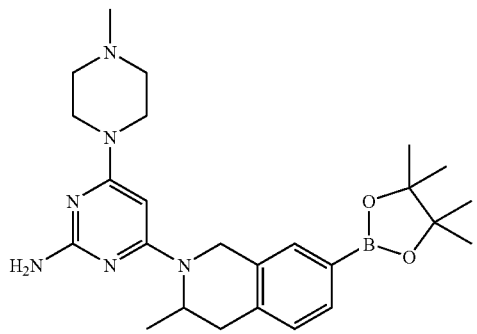 [SMILES: CC1Cc2ccc(B3OC(C)(C)C(C)(C)O3)cc2CN1c1cc(N2CCN(C)CC2)nc(N)n1]

A mixture of 4-(7-bromo-3-methyl-3,4-dihydroisoquinolin-2(1H)-yl)-6-(4-methylpiperazin-1-yl)pyrimidin-2-amine (300 mg, 0.7 mmol) (Peak 2, Example 49, Step 7), bis(pinacolato)diboron (274 mg, 1.08 mmol), [1,1'-bis(diphenylphosphino)-ferrocene]dichloropalladium(II), complex with dichloromethane (1:1) (17.6 mg, 0.0216 mmol), 1,1'-bis(diphenylphosphino)ferrocene (12.0 mg, 0.0216 mmol) and potassium acetate (212 mg, 2.16 mmol) in 1,4-dioxane (5.0 mL) was heated at 110° C. overnight. After cooling down to r.t., the mixture was diluted with ethyl acetate and filtered. The filtrate was concentrated under reduced pressure. The residue was purified by flash chromatography on a silica gel column with methanol in methylene chloride (0-10%) to afford the desired product. LCMS $(M+H)^+$: m/z=465.3.

Step 3: (3-{2-[2-Amino-6-(4-methylpiperazin-1-yl)pyrimidin-4-yl]-3-methyl-1,2,3,4-tetrahydroisoquinolin-7-yl}-1H-pyrazol-1-yl)acetonitrile A mixture of (3-bromo-1H-pyrazol-1-yl)acetonitrile (14.4 mg, 0.0775 mmol), 4-(4-methylpiperazin-1-yl)-6-[3-methyl-7-(4,4,5,5-tetramethyl-1,3,2-dioxaborolan-2-yl)-3,4-dihydroisoquinolin-2(1H)-yl]pyrimidin-2-amine (18.0 mg, 0.0388 mmol), dichloro(bis{di-tert-butyl[4-(dimethylamino)phenyl]phosphoranyl})palladium (1.0 mg, 0.0014 mmol), and sodium carbonate (8.22 mg, 0.0775 mmol) in 1,4-dioxane (0.5 mL) and water (0.1 mL) was vacuumed and refilled with $N_2$ for 3 times and then stirred at 90° C. overnight. The mixture was purified by RP-HPLC (pH=10) to afford the desired product. LCMS $(M+H)^+$: m/z=444.2.

Example 83

3-(3-{2-[2-Amino-6-(4-methylpiperazin-1-yl)pyrimidin-4-yl]-3-methyl-1,2,3,4-tetrahydroisoquinolin-7-yl}-1H-pyrazol-1-yl)propanenitrile

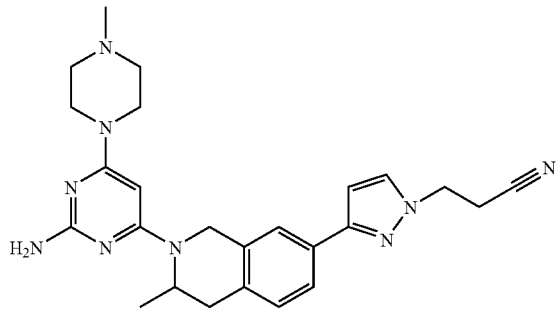 [SMILES: CC1Cc2ccc(-c3ccn(CCC#N)n3)cc2CN1c1cc(N2CCN(C)CC2)nc(N)n1]

Example 83A

Enantiomer 1

A mixture of 4-(4-methylpiperazin-1-yl)-6-[3-methyl-7-(1H-pyrazol-3-yl)-3,4-dihydroisoquinolin-2(1H)-yl]pyrimidin-2-amine (10.0 mg, 0.0247 mmol) (Example 82A, Step 1), 2-propenenitrile (50.0 uL, 0.761 mmol) and 1,8-diazabicyclo[5.4.0]undec-7-ene (5.0 uL, 0.033 mmol) in acetonitrile (0.15 mL) was heated at 50° C. for 2 h. The mixture was purified by RP-HPLC (pH=10) to afford the desired product. LCMS $(M+H)^+$: m/z=458.3.

Example 83B

Enantiomer 2

Step 1. 4-(4-Methylpiperazin-1-yl)-6-[3-methyl-7-(1H-pyrazol-3-yl)-3,4-dihydroisoquinolin-2(1H)-yl]pyrimidin-2-amine

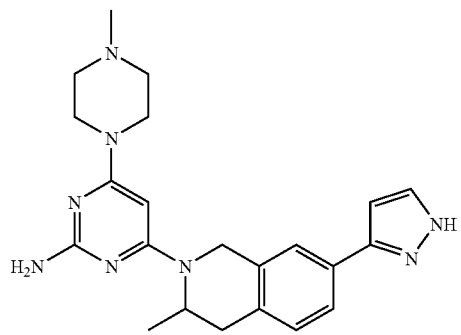 [SMILES: CC1Cc2ccc(-c3cc[nH]n3)cc2CN1c1cc(N2CCN(C)CC2)nc(N)n1]

A mixture of 1H-pyrazol-3-ylboronic acid (64.3 mg, 0.575 mmol, Frontier Scientific, Cat. No. P1638), 4-(7-bromo-3-methyl-3,4-dihydroisoquinolin-2(1H)-yl)-6-(4-methylpiperazin-1-yl)pyrimidin-2-amine (0.20 g, 0.48 mmol) (Peak 2, Example 49, Step 7), dichloro(bis{di-tert-butyl[4-(dimethylamino)phenyl]phosphoranyl})palladium (10.2 mg, 0.0144 mmol), and sodium carbonate (0.102 g, 0.958 mmol) in 1,4-dioxane (2.2 mL) and water (0.3 mL) was vacuumed and refilled with $N_2$ for 3 times and then stirred at 90° C. overnight. The mixture was purified by RP-HPLC (pH=10) to afford the desired product. LCMS $(M+H)^+$: m/z=405.2.

Step 2: 3-(3-{2-[2-Amino-6-(4-methylpiperazin-1-yl)pyrimidin-4-yl]-3-methyl-1,2,3,4-tetrahydroisoquinolin-7-yl)-1H-pyrazol-1-yl}propanenitrile A mixture of 4-(4-methylpiperazin-1-yl)-6-[3-methyl-7-(1H-pyrazol-3-yl)-3,4-dihydroisoquinolin-2(1H)-yl]pyrimidin-2-amine (10.0 mg, 0.0247 mmol), 2-propenenitrile (50.0 uL, 0.761 mmol) and 1,8-diazabicyclo[5.4.0]undec-7-ene (5.0 uL, 0.033 mmol) in acetonitrile (0.15 mL) was heated at 50° C. for 2 h. The mixture was purified by RP-HPLC (pH=10) to afford the desired product. LCMS (M+H)$^+$: m/z=458.3.

Example 84

2-(3-{2-[2-Amino-6-(4-methylpiperazin-1-yl)pyrimidin-4-yl]-3-methyl-1,2,3,4-tetrahydroisoquinolin-7-yl}-1H-pyrazol-1-yl)ethanol

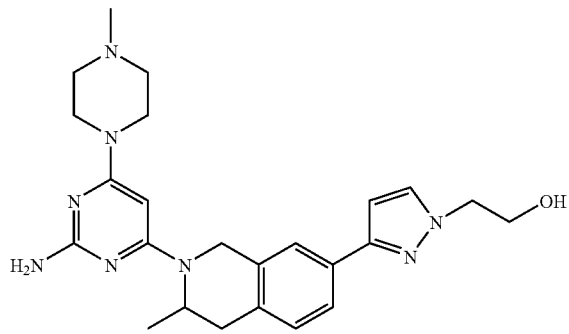 [SMILES: CC1Cc2ccc(-c3ccn(CCO)n3)cc2CN1c1cc(N2CCN(C)CC2)nc(N)n1]

Example 84A

Enantiomer 1

Step 1: 2-(3-Bromo-1H-pyrazol-1-yl)ethanol

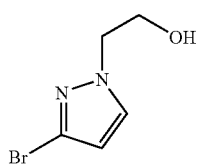

Potassium tert-butoxide in THF (0.510 mL, 0.510 mmol) was added to a solution of 3-bromo-1H-pyrazole (50.0 mg, 0.340 mmol) in DMF (3 mL) and stirred at r.t. for 10 min, and then 1,3,2-dioxathiolane 2,2-dioxide (0.0633 g, 0.510 mmol) was added and the stirred at r.t. for 1 h. At this time, conc. HCl (0.3 mL) was added to the above reaction mixture and then stirred at r.t. overnight. The mixture was diluted with ethyl acetate, washed with saturated NaHCO$_3$, water and brine, dried over Na$_2$SO$_4$, filtered, and concentrated to give the crude product which was directly used in the next reaction without further purification. LCMS (M+H)$^+$: m/z=191.0.

Step 2: 4-(4-methylpiperazin-1-yl)-6-[3-methyl-7-(4,4,5,5-tetramethyl-1,3,2-dioxaborolan-2-yl)-3,4-dihydroisoquinolin-2(1H)-yl]pyrimidin-2-amine

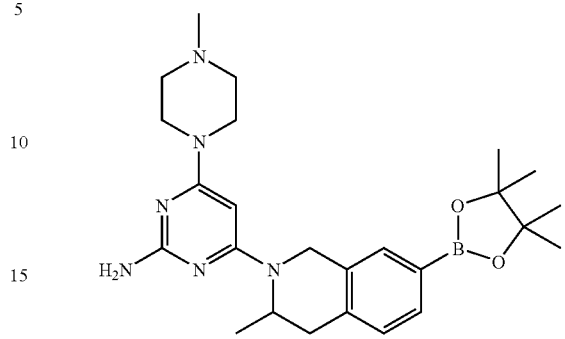

The compound was prepared by using procedure analogous to those described for the synthesis of Example 82B, Step 2 starting from 4-(7-bromo-3-methyl-3,4-dihydroisoquinolin-2(1H)-yl)-6-(4-methylpiperazin-1-yl)pyrimidin-2-amine (Peak 1, Example 49, Step 7). LCMS (M+H)$^+$: m/z=465.3.

Step 3: 2-(3-{2-[2-Amino-6-(4-methylpiperazin-1-yl)pyrimidin-4-yl]-3-methyl-1,2,3,4-tetrahydroisoquinolin-7-yl}-1H-pyrazol-1-yl)ethanol The compound was prepared by using procedure analogous to those described for the synthesis of Example 82B, Step 3 starting from 4-(4-methylpiperazin-1-yl)-6-[3-methyl-7-(4,4,5,5-tetramethyl-1,3,2-dioxaborolan-2-yl)-3,4-dihydroisoquinolin-2(1H)-yl]pyrimidin-2-amine and 2-(3-bromo-1H-pyrazol-1-yl)ethanol. LCMS (M+H)$^+$: m/z=449.3.

Example 84B

Enantiomer 2

The compound was prepared by using procedure analogous to those described for the synthesis of Example 82B, Step 3 starting from 4-(4-methylpiperazin-1-yl)-6-[3-methyl-7-(4,4,5,5-tetramethyl-1,3,2-dioxaborolan-2-yl)-3,4-dihydroisoquinolin-2(1H)-yl]pyrimidin-2-amine (Example 82B, Step2) and 2-(3-bromo-1H-pyrazol-1-yl)ethanol. LCMS (M+H)$^+$: m/z=449.3.

Example 85

4-[3-Methyl-7-(1-methyl-1H-pyrazol-3-yl)-3,4-dihydroisoquinolin-2(1H)-yl]-6-(4-methylpiperazin-1-yl)pyrimidin-2-amine

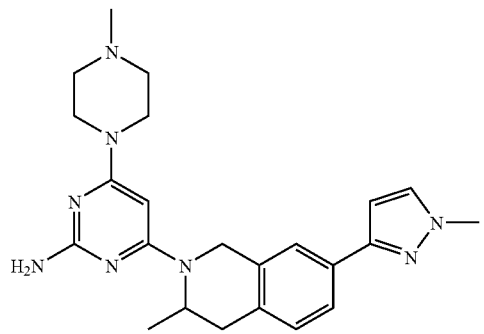 [SMILES: CC1Cc2ccc(-c3ccn(C)n3)cc2CN1c1cc(N2CCN(C)CC2)nc(N)n1]

Example 85A

Enantiomer 1

Step 1: 1-Methyl-3-(4,4,5,5-tetramethyl-1,3,2-dioxaborolan-2-yl)-1H-pyrazole

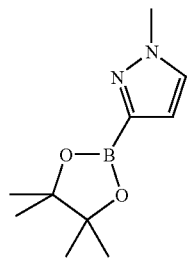

Potassium tert-butoxide in THF (1.0 M, 0.309 mL, 0.309 mmol) was added to a solution of 3-(4,4,5,5-tetramethyl-1,3,2-dioxaborolan-2-yl)-1H-pyrazole (30.0 mg, 0.155 mmol, Alfa Aesar, Cat. No. H27619) in DMF (0.5 mL) and stirred at r.t. for 10 min, and then methyl iodide (28.9 uL, 0.464 mmol) was added and the stirred at r.t. for 1 h. LCMS showed the reaction was complete. The mixture was diluted with ethyl acetate, washed with water and brine, dried over $Na_2SO_4$, filtered, and concentrated to give the crude product which was directly used in the next reaction without further purification. LCMS (M+H−82)$^+$: m/z=127.2.

Step 2: 4-[3-Methyl-7-(1-methyl-1H-pyrazol-3-yl)-3,4-dihydroisoquinolin-2(1H)-yl]-6-(4-methylpiperazin-1-yl)pyrimidin-2-amine A mixture of 1-methyl-3-(4,4,5,5-tetramethyl-1,3,2-dioxaborolan-2-yl)-1H-pyrazole (11.5 mg, 0.0518 mmol), 4-(7-bromo-3-methyl-3,4-dihydroisoquinolin-2(1H)-yl)-6-(4-methylpiperazin-1-yl)pyrimidin-2-amine (0.018 g, 0.043 mmol) (Peak 1, Example 49, Step 7), dichloro(bis{di-tert-butyl[4-(dimethylamino)phenyl]phosphoranyl})palladium (0.916 mg, 0.00129 mmol), and sodium carbonate (9.14 mg, 0.0862 mmol) in 1,4-dioxane (0.50 mL) and water (0.10 mL) was vacuumed and refilled with $N_2$ for 3 times and then stirred at 90° C. overnight. The mixture was purified by RP-HPLC (pH=10) to afford the desired product. LCMS (M+H)$^+$: m/z=419.3.

Example 85B

Enantiomer 2

This compound was prepared by using procedures analogous to those described for the synthesis of Example 85A, Step 2 starting from 4-(7-bromo-3-methyl-3,4-dihydroisoquinolin-2(1H)-yl)-6-(4-methylpiperazin-1-yl)pyrimidin-2-amine (Peak 2, Example 49, Step 7) and 1-methyl-3-(4,4,5,5-tetramethyl-1,3,2-dioxaborolan-2-yl)-1H-pyrazole. LCMS (M+H)$^+$: m/z=419.3.

Example 86

4-[7-(1-Ethyl-1H-pyrazol-3-yl)-3-methyl-3,4-dihydroisoquinolin-2(1H)-yl]-6-(4-methylpiperazin-1-yl)pyrimidin-2-amine

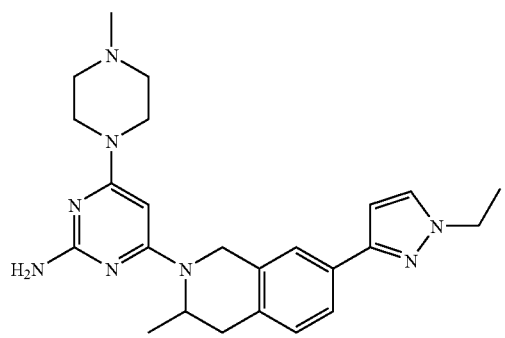 [SMILES: CCn1ccc(-c2ccc3c(c2)CN(c2cc(N4CCN(C)CC4)nc(N)n2)C(C)C3)n1]

Example 86A

Enantiomer 1

Step 1: 1-Ethyl-3-(4,4,5,5-tetramethyl-1,3,2-dioxaborolan-2-yl)-1H-pyrazole

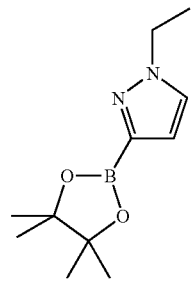 [SMILES: CCn1ccc(B2OC(C)(C)C(C)(C)O2)n1]

This compound was prepared by using procedure analogous to those described for the synthesis of Example 85A, Step 1 starting from 3-(4,4,5,5-tetramethyl-1,3,2-dioxaborolan-2-yl)-1H-pyrazole and ethyl iodide. LCMS (M+H−82)$^+$: m/z=141.1.

Step 2: 4-[3-Ethyl-7-(1-methyl-1H-pyrazol-3-yl)-3,4-dihydroisoquinolin-2(1H)-yl]-6-(4-methylpiperazin-1-yl)pyrimidin-2-amine This compound was prepared by using procedure analogous to those described for the synthesis of Example 85A, Step 2 starting from 4-(7-bromo-3-methyl-3,4-dihydroisoquinolin-2(1H)-yl)-6-(4-methylpiperazin-1-yl)pyrimidin-2-amine (Peak 1, Example 49, Step 7) and 1-ethyl-3-(4,4,5,5-tetramethyl-1,3,2-dioxaborolan-2-yl)-1H-pyrazole. LCMS (M+H)$^+$: m/z=433.3.

Example 86B

Enantiomer 2

This compound was prepared by using procedure analogous to those described for the synthesis of Example 85A, Step 2 starting from 4-(7-bromo-3-methyl-3,4-dihydroisoquinolin-2(1H)-yl)-6-(4-methylpiperazin-1-yl)pyrimidin-2-amine (Peak 2, Example 49, Step 7) and 1-ethyl-3-(4,4,5,5-tetramethyl-1,3,2-dioxaborolan-2-yl)-1H-pyrazole. LCMS (M+H)⁺: m/z=433.3.

Example 87

4-{2-[2-Amino-6-(4-methylpiperazin-1-yl)pyrimidin-4-yl]-3-methyl-1,2,3,4-tetrahydroisoquinolin-7-yl}-N,1-dimethyl-1H-pyrrole-2-carboxamide

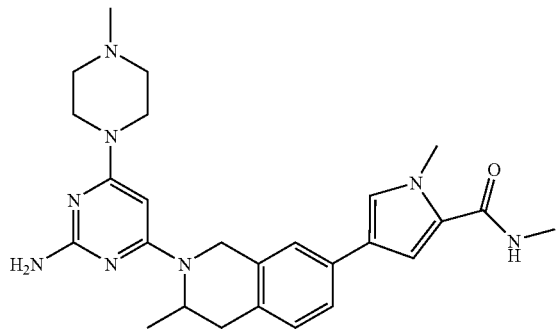 [SMILES: CNC(=O)c1cc(-c2ccc3c(c2)CN(c2cc(N4CCN(C)CC4)nc(N)n2)C(C)C3)cn1C]

Example 87A

Enantiomer 1

Step 1: 2,2,2-Trichloro-1-(4-iodo-1H-pyrrol-2-yl)ethanone

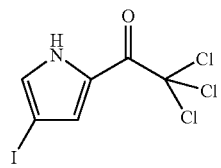 [SMILES: O=C(c1cc(I)c[nH]1)C(Cl)(Cl)Cl]

At r.t. to a solution of 2,2,2-trichloro-1-(1H-pyrrol-2-yl)ethanone (10.0 g, 47.1 mmol) in methylene chloride (80 mL) was added dropwise a solution of iodine monochloride (8.406 g, 51.77 mmol) in methylene chloride (40 mL) with stirring. After completion of addition the mixture was stirred at r.t. for additional 2 h. The mixture was diluted with methylene chloride, quenched with saturated Na₂S₂O₃ solution. After separation the organic solution was washed with water and brine, dried over Na₂SO₄, filtered, and concentrated to give the crude product which was directly used in the next reaction without further purification.

Step 2: Benzyl 4-iodo-1H-pyrrole-2-carboxylate

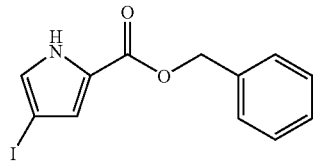 [SMILES: O=C(OCc1ccccc1)c1cc(I)c[nH]1]

A mixture of 2,2,2-trichloro-1-(4-iodo-1H-pyrrol-2-yl)ethanone (4.0 g, 12 mmol), benzyl alcohol (9.0 mL, 87 mmol), and triethylamine (2.5 mL, 18 mmol) in a round flask was heated at 60° C. with stirring for 2 h. After cooling, the volatiles were removed under reduced pressure to afford the crude product which was directly used in the next reaction without further purification.

Step 3: 2-Benzyl 1-ter.t-butyl 4-iodo-1H-pyrrole-1,2-dicarboxylate

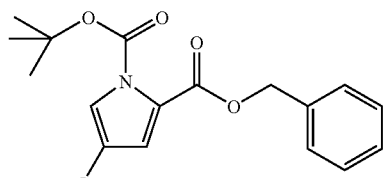

A mixture of benzyl 4-iodo-1H-pyrrole-2-carboxylate (3.9 g, 12 mmol), di-tert-butyldicarbonate (2.99 g, 13.7 mmol), 4-DMAP (0.146 g, 1.19 mmol), and triethylamine (1.83 mL, 13.1 mmol) in THF (40 mL) was stirred at r.t. for overnight. LCMS showed it worked well. The volatiles were removed under reduced pressure. The residue was taken up into ethyl acetate, and washed with 0.1 N HCl solution, water and brine, dried over Na₂SO₄, filtered, and concentrated. The residue was purified by flash chromatography on a silica gel column with ethyl acetate in hexane (0-10%) to afford the desired product. LCMS (M+H)⁺: m/z=449.8.

Step 4: 2-Benzyl 1-ter.t-butyl 4-(4,4,5,5-tetramethyl-1,3,2-dioxaborolan-2-yl)-1H-pyrrole-1,2-dicarboxylate

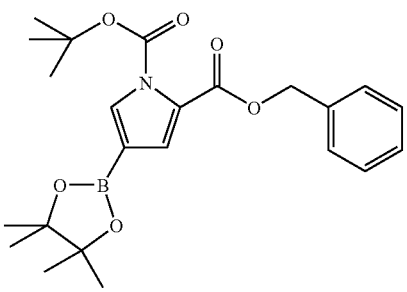 [SMILES: CC(C)(C)OC(=O)n1cc(B2OC(C)(C)C(C)(C)O2)cc1C(=O)OCc1ccccc1]

At −78° C. to a solution of 2-benzyl 1-tert-butyl 4-iodo-1H-pyrrole-1,2-dicarboxylate (6.49 g, 15.2 mmol), and 2—isopropoxy-4,4,5,5-tetramethyl-1,3,2-dioxaborolane (6.20 mL, 30.4 mmol) in THF (75 mL) was added dropwise a solution of 2.50 M of n-butyllithium in hexane (7.29 mL, 18.2 mmol) with stirring. After completion of addition the mixture was stirred at this temperature for 35 min. LCMS showed some SM left and then 2.50 M of n-butyllithium in hexane (0.80 mL, 2.0 mmol) was added and stirred for additional 30 min. It was quenched with saturated NH₄Cl solution and then diluted with ethyl acetate. After separation, the organic solution was washed with water twice and brine, dried over Na₂SO₄, filtered, and concentrated. The residue was purified by flash chromatography on a silica gel column with ethyl acetate in hexane (0-10%) to afford the desired product. LCMS (M+H)⁺: m/z=450.2.

Step 5: Benzyl 4-(4,4,5,5-tetramethyl-1,3,2-dioxaborolan-2-yl)-1H-pyrrole-2-carboxylate

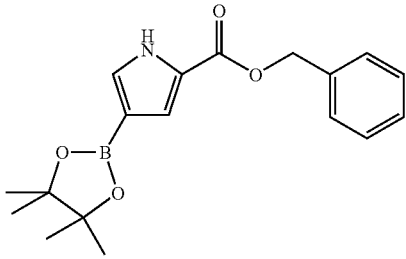 [SMILES: CC1(C)OB(c2c[nH]c(C(=O)OCc3ccccc3)c2)OC1(C)C]

Hydrogen chloride in 1,4-dioxane (4.0 M, 3.0 mL, 12 mmol) was added to a solution of 2-benzyl 1-tert-butyl 4-(4,4,5,5-tetramethyl-1,3,2-dioxaborolan-2-yl)-1H-pyrrole-1,2-dicarboxylate (0.80 g, 1.9 mmol) in methylene chloride (3.0 mL) at r.t. and the mixture was stirred for 0.5 h. The solvent was removed under reduced pressure to provide the desired product as an HCl salt. LCMS (M+H)$^+$: m/z=328.2.

Step 6: Benzyl 1-methyl-4-(4,4,5,5-tetramethyl-1,3,2-dioxaborolan-2-yl)-1H-pyrrole-2-carboxylate

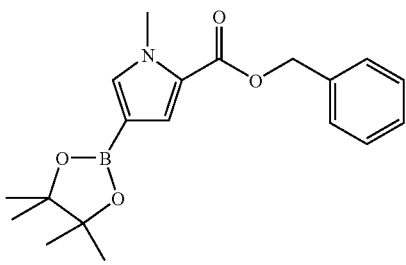 [SMILES: Cn1cc(B2OC(C)(C)C(C)(C)O2)cc1C(=O)OCc1ccccc1]

Methyl iodide (0.27 mL, 4.3 mmol) was added to a mixture of benzyl 4-(4,4,5,5-tetramethyl-1,3,2-dioxaborolan-2-yl)-1H-pyrrole-2-carboxylate (0.7 g, 2 mmol) and cesium carbonate (1.4 g, 4.3 mmol) in DMF (5.0 mL) and then the reaction was stirred at r.t. for 1 h. LCMS showed the reaction was complete. The mixture was diluted with ethyl acetate, washed with water and brine, dried over Na$_2$SO$_4$, filtered, and concentrated. The residue was purified by flash chromatography on a silica gel column with ethyl acetate in hexane (0-10%) to afford the desired product. LCMS (M+H)$^+$: m/z=342.2.

Step 7: Benzyl 4-{2-[2-amino-6-(4-methylpiperazin-1-yl)pyrimidin-4-yl]-3-methyl-1,2,3,4-tetrahydroisoquinolin-7-yl}-1-methyl-1H-pyrrole-2-carboxylate

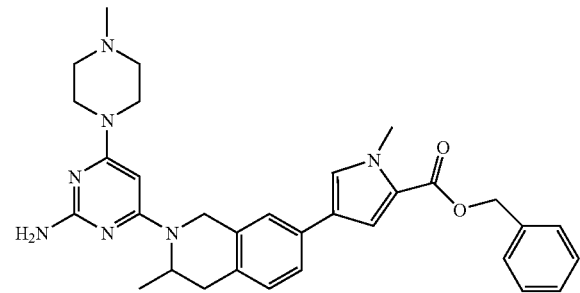 [SMILES: CC1Cc2ccc(-c3cc(C(=O)OCc4ccccc4)n(C)c3)cc2CN1c1cc(N2CCN(C)CC2)nc(N)n1]

A mixture of benzyl 1-methyl-4-(4,4,5,5-tetramethyl-1,3,2-dioxaborolan-2-yl)-1H-pyrrole-2-carboxylate (78.5 mg, 0.230 mmol), 4-(7-bromo-3-methyl-3,4-dihydroisoquinolin-2(1H)-yl)-6-(4-methylpiperazin-1-yl)pyrimidin-2-amine (0.080 g, 0.19 mmol) (Peak 1, Example 49, Step 7), dichloro(bis{di-tert-butyl[4-(dimethylamino)phenyl]phosphoranyl}) palladium (4.07 mg, 0.00575 mmol), and sodium carbonate (0.0406 g, 0.383 mmol) in 1,4-dioxane (0.88 mL) and water (0.1 mL) was vacuumed and refilled with N$_2$ for 3 times and then stirred at 90° C. overnight. LCMS monitored reaction. After cooling down to r.t., the mixture was diluted with ethyl acetate, washed with water and brine, dried over Na$_2$SO$_4$, filtered, and concentrated. The residue was purified by flash chromatography on a silica gel column with methanol in methylene chloride (0-10%) to afford the desired product. LCMS (M+H)$^+$: m/z=552.1.

Step 8: 4-{2-[2-Amino-6-(4-methylpiperazin-1-yl)pyrimidin-4-yl]-3-methyl-1,2,3,4-tetrahydroisoquinolin-7-yl}-1-methyl-1H-pyrrole-2-carboxylic acid

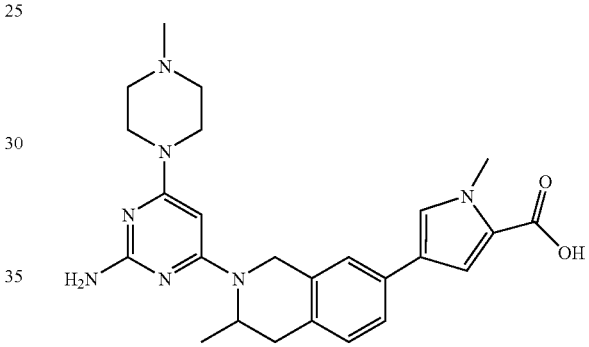

Pd/C (25.0 mg, 10 wt. % loading dry basis, matrix activated carbon, wet support, Degussa type E101 NE/W) was added to a solution of benzyl 4-{2-[2-amino-6-(4-methylpiperazin-1-yl)pyrimidin-4-yl]-3-methyl-1,2,3,4-tetrahydroisoquinolin-7-yl}-1-methyl-1H-pyrrole-2-carboxylate (0.10 g, 0.18 mmol) in methanol (2.0 mL) and then the reaction was stirred under hydrogen (balloon) for 2 h. LCMS showed the reaction was complete. The reaction mixture was filtered. The solvent was removed under reduced pressure to give the product which was directly used in the next step reaction without further purification. LCMS (M+H)$^+$: m/z=462.3.

Step 9: 4-{2-[2-Amino-6-(4-methylpiperazin-1-yl)pyrimidin-4-yl]-3-methyl-1,2,3,4-tetrahydroisoquinolin-7-yl}-N,1-dimethyl-1H-pyrrole-2-carboxamide 4-{2-[2-Amino-6-(4-methylpiperazin-1-yl)pyrimidin-4-yl]-3-methyl-1,2,3,4-tetrahydroisoquinolin-7-yl}-1-methyl-1H-pyrrole-2-carboxylic acid (12.0 mg, 0.0260 mmol) and benzotriazol-1-yloxytris(dimethylamino)phosphonium hexafluorophosphate (0.0192 g, 0.0433 mmol) in DMF (0.5 mL) was stirred at r.t. for 3 min. and then methylamine in THF (2.0M, 0.2 mL, 0.4 mmol) was added. To this mixture, triethylamine (15.4 uL, 0.110 mmol) was slowly added and the mixture was stirred for 1 h at r.t. The mixture was purified by RP-HPLC (pH=10) to afford the desired product. LCMS (M+H)$^+$: m/z=475.3.

Example 87B

Enantiomer 2

Step 1: Benzyl 4-{2-[2-amino-6-(4-methylpiperazin-1-yl)pyrimidin-4-yl]-3-methyl-1,2,3,4-tetrahydroisoquinolin-7-yl}-1-methyl-1H-pyrrole-2-carboxylate

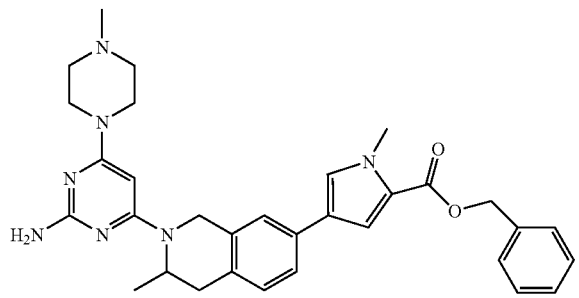 [SMILES: CC1Cc2ccc(-c3cc(C(=O)OCc4ccccc4)n(C)c3)cc2CN1c1cc(N2CCN(C)CC2)nc(N)n1]

The compound was prepared by using procedures analogous to those described for the synthesis of Example 87A, Step 7 starting from benzyl 1-methyl-4-(4,4,5,5-tetramethyl-1,3,2-dioxaborolan-2-yl)-1H-pyrrole-2-carboxylate (Example 87A, Step 6) and 4-(7-bromo-3-methyl-3,4-dihydroisoquinolin-2(1H)-yl)-6-(4-methylpiperazin-1-yl)pyrimidin-2-amine (Peak 2, Example 49, Step 7). LCMS (M+H)$^+$: m/z=552.1.

Step 2: 4-{2-[2-Amino-6-(4-methylpiperazin-1-yl)pyrimidin-4-yl]-3-methyl-1,2,3,4-tetrahydroisoquinolin-7-yl}-1-methyl-1H-pyrrole-2-carboxylic acid

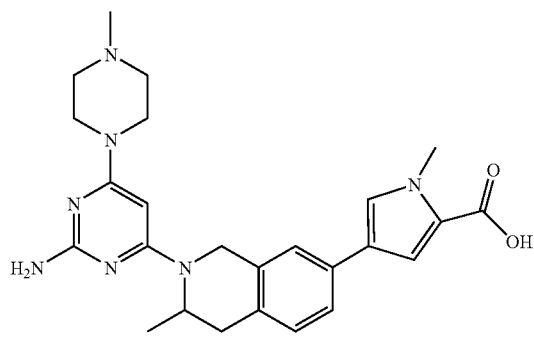 [SMILES: CC1Cc2ccc(-c3cc(C(=O)O)n(C)c3)cc2CN1c1cc(N2CCN(C)CC2)nc(N)n1]

The compound was prepared by using procedures analogous to those described for the synthesis of Example 87A, Step 8 starting from benzyl 4-{2-[2-amino-6-(4-methylpiperazin-1-yl)pyrimidin-4-yl]-3-methyl-1,2,3,4-tetrahydroisoquinolin-7-yl}-1-methyl-1H-pyrrole-2-carboxylate (Step 1). LCMS (M+H)$^+$: m/z=462.3.

Step 3: 4-{2-[2-Amino-6-(4-methylpiperazin-1-yl)pyrimidin-4-yl]-3-methyl-1,2,3,4-tetrahydroisoquinolin-7-yl}-N,1-dimethyl-1H-pyrrole-2-carboxamide The compound was prepared by using procedures analogous to those described for the synthesis of Example 87A, Step 9 starting from 4-{2-[2-Amino-6-(4-methylpiperazin-1-yl)pyrimidin-4-yl]-3-methyl-1,2,3,4-tetrahydroisoquinolin-7-yl}-1-methyl-1H-pyrrole-2-carboxylic acid (Step 2) and methylamine in THF solution (2.0 M). LCMS (M+H)$^+$: m/z=475.3.

Example 88

4-{2-[2-Amino-6-(4-methylpiperazin-1-yl)pyrimidin-4-yl]-3-methyl-1,2,3,4-tetrahydroisoquinolin-7-yl}-N-ethyl-1-methyl-1H-pyrrole-2-carboxamide

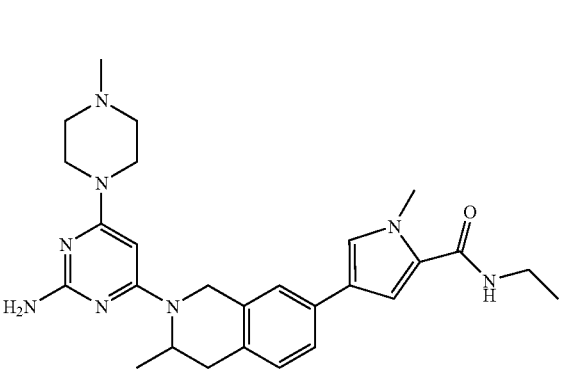 [SMILES: CCNC(=O)c1cc(-c2ccc3c(c2)CN(c2cc(N4CCN(C)CC4)nc(N)n2)C(C)C3)cn1C]

Example 88A

Enantiomer 1

The compound was prepared by using procedures analogous to those described for the synthesis of Example 87A, Step 9 starting from 4-{2-[2-Amino-6-(4-methylpiperazin-1-yl)pyrimidin-4-yl]-3-methyl-1,2,3,4-tetrahydroisoquinolin-7-yl}-1-methyl-1H-pyrrole-2-carboxylic acid (Example 87A, Step 8) and ethylamine in THF solution (2.0 M). LCMS (M+H)$^+$: m/z=489.3.

Example 88B

Enantiomer 2

The compound was prepared by using procedures analogous to those described for the synthesis of Example 87A, Step 9 starting from 4-{2-[2-Amino-6-(4-methylpiperazin-1-yl)pyrimidin-4-yl]-3-methyl-1,2,3,4-tetrahydroisoquinolin-7-yl}-1-methyl-1H-pyrrole-2-carboxylic acid (Example 87B, Step 2) and ethylamine in THF solution (2.0 M). LCMS (M+H)$^+$: m/z=489.3.

Example 89

4-{2-[2-Amino-6-(4-methylpiperazin-1-yl)pyrimidin-4-yl]-3-methyl-1,2,3,4-tetrahydroisoquinolin-7-yl}-N,N,1-trimethyl-1H-pyrrole-2-carboxamide

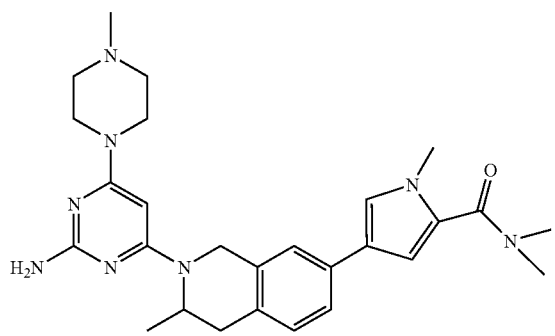 [SMILES: CC1Cc2ccc(-c3cc(C(=O)N(C)C)n(C)c3)cc2CN1c1cc(N2CCN(C)CC2)nc(N)n1]

Example 89A

Enantiomer 1

The compound was prepared by using procedures analogous to those described for the synthesis of Example 87A, Step 9 starting from 4-{2-[2-Amino-6-(4-methylpiperazin-1-yl)pyrimidin-4-yl]-3-methyl-1,2,3,4-tetrahydroisoquinolin-7-yl}-1-methyl-1H-pyrrole-2-carboxylic acid (Example 87A, Step 8) and N,N-dimethylamine in THF solution (2.0 M). LCMS (M+H)+: m/z=489.3.

Example 89B

Enantiomer 2

The compound was prepared by using procedures analogous to those described for the synthesis of Example 87A, Step 9 starting from 4-{2-[2-Amino-6-(4-methylpiperazin-1-yl)pyrimidin-4-yl]-3-methyl-1,2,3,4-tetrahydroisoquinolin-7-yl}-1-methyl-1H-pyrrole-2-carboxylic acid (Example 87B, Step 2) and N,N-dimethylamine in THF solution (2.0 M). LCMS (M+H)+: m/z=489.3.

Example 90

4-{2-[2-Amino-6-(4-methylpiperazin-1-yl)pyrimidin-4-yl]-3-methyl-1,2,3,4-tetrahydroisoquinolin-7-yl}-N-isopropyl-1-methyl-1H-pyrrole-2-carboxamide

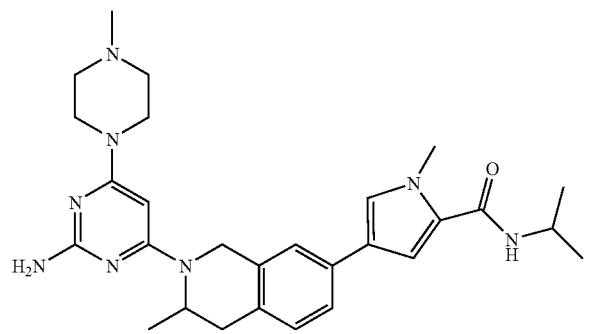 [SMILES: CC(C)NC(=O)c1cc(-c2ccc3c(c2)CN(c2cc(N4CCN(C)CC4)nc(N)n2)C(C)C3)cn1C]

Example 90A

Enantiomer 1

The compound was prepared by using procedures analogous to those described for the synthesis of Example 87A, Step 9 starting from 4-{2-[2-Amino-6-(4-methylpiperazin-1-yl)pyrimidin-4-yl]-3-methyl-1,2,3,4-tetrahydroisoquinolin-7-yl}-1-methyl-1H-pyrrole-2-carboxylic acid (Example 87A, Step 8) and isopropylamine. LCMS (M+H)+: m/z=503.4.

Example 90B

Enantiomer 2

The compound was prepared by using procedures analogous to those described for the synthesis of Example 87A, Step 9 starting from 4-{2-[2-Amino-6-(4-methylpiperazin-1-yl)pyrimidin-4-yl]-3-methyl-1,2,3,4-tetrahydroisoquinolin-7-yl}-1-methyl-1H-pyrrole-2-carboxylic acid (Example 87B, Step 2) and isopropylamine. LCMS (M+H)+: m/z=503.4.

Example 91

4-{2-[2-Amino-6-(4-methylpiperazin-1-yl)pyrimidin-4-yl]-3-methyl-1,2,3,4-tetrahydroisoquinolin-7-yl}-N-cyclopropyl-1-methyl-1H-pyrrole-2-carboxamide

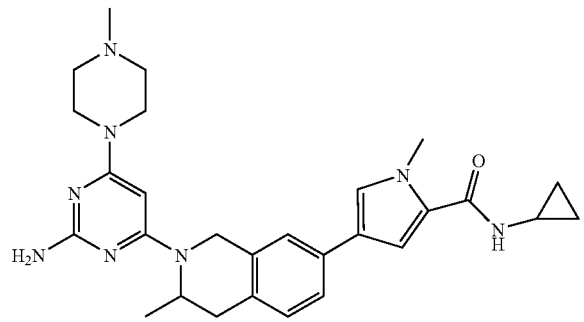 [SMILES: CC1Cc2ccc(-c3cc(C(=O)NC4CC4)n(C)c3)cc2CN1c1cc(N2CCN(C)CC2)nc(N)n1]

Example 91A

Enantiomer 1

The compound was prepared by using procedures analogous to those described for the synthesis of Example 87A, Step 9 starting from 4-{2-[2-Amino-6-(4-methylpiperazin-1-yl)pyrimidin-4-yl]-3-methyl-1,2,3,4-tetrahydroisoquinolin-7-yl}-1-methyl-1H-pyrrole-2-carboxylic acid (Example 87A, Step 8) and cyclopropylamine. LCMS (M+H)+: m/z=501.3.

Example 91B

Enantiomer 2

The compound was prepared by using procedures analogous to those described for the synthesis of Example 87A, Step 9 starting from 4-{2-[2-Amino-6-(4-methylpiperazin-1-yl)pyrimidin-4-yl]-3-methyl-1,2,3,4-tetrahydroisoquinolin-7-yl}-1-methyl-1H-pyrrole-2-carboxylic acid (Example 87B, Step 2) and cyclopropylamine. LCMS (M+H)+: m/z=501.3.

Example 92

4-[7-[5-(azetidin-1-ylcarbonyl)-1-methyl-1H-pyrrol-3-yl]-3-methyl-3,4-dihydroisoquinolin-2(1H)-yl]-6-(4-methylpiperazin-1-yl)pyrimidin-2-amine

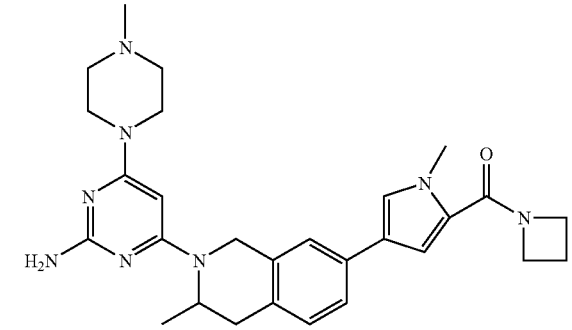 [SMILES: CC1Cc2ccc(-c3cc(C(=O)N4CCC4)n(C)c3)cc2CN1c1cc(N2CCN(C)CC2)nc(N)n1]

Example 92A

Enantiomer 1

The compound was prepared by using procedures analogous to those described for the synthesis of Example 87A, Step 9 starting from 4-{2-[2-Amino-6-(4-methylpiperazin-1-yl)pyrimidin-4-yl]-3-methyl-1,2,3,4-tetrahydroisoquinolin-7-yl}-1-methyl-1H-pyrrole-2-carboxylic acid (Example 87A, Step 8) and azetidine hydrochloride. LCMS (M+H)+: m/z=501.3.

Example 92B

Enantiomer 2

The compound was prepared by using procedures analogous to those described for the synthesis of Example 87A, Step 9 starting from 4-{2-[2-Amino-6-(4-methylpiperazin-1-yl)pyrimidin-4-yl]-3-methyl-1,2,3,4-tetrahydroisoquinolin-7-yl}-1-methyl-1H-pyrrole-2-carboxylic acid (Example 87B, Step 2) and azetidine hydrochloride. LCMS (M+H)+: m/z=501.3.

Example 93

4-{2-[2-Amino-6-(4-methylpiperazin-1-yl)pyrimidin-4-yl]-3-methyl-1,2,3,4-tetrahydroisoquinolin-7-yl}-N-[2-(dimethylamino)ethyl]-N,1-dimethyl-1H-pyrrole-2-carboxamide (Enantiomer 1)

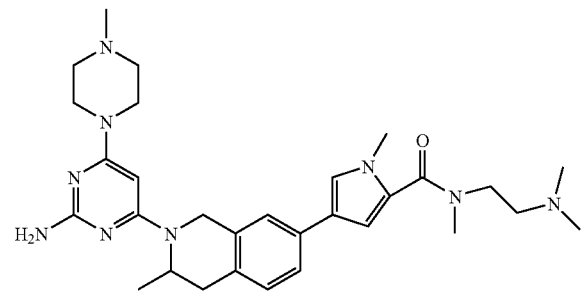 [SMILES: CC1Cc2ccc(-c3cc(C(=O)N(C)CCN(C)C)n(C)c3)cc2CN1c1cc(N2CCN(C)CC2)nc(N)n1]

This compound was prepared by using procedures analogous to those described for the synthesis of Example 87A, Step 9 starting from 4-{2-[2-Amino-6-(4-methylpiperazin-1-yl)pyrimidin-4-yl]-3-methyl-1,2,3,4-tetrahydroisoquinolin-7-yl}-1-methyl-1H-pyrrole-2-carboxylic acid (Example 87A, Step 8) and N,N,N'-trimethylethane-1,2-diamine. LCMS (M+H)+: m/z=546.4.

Example 94

4-[7-(5-{[3-(Dimethylamino)pyrrolidin-1-yl]carbonyl}-1-methyl-1H-pyrrol-3-yl)-3-methyl-3,4-dihydroisoquinolin-2(1H)-yl]-6-(4-methylpiperazin-1-yl)pyrimidin-2-amine (Enantiomer 1)

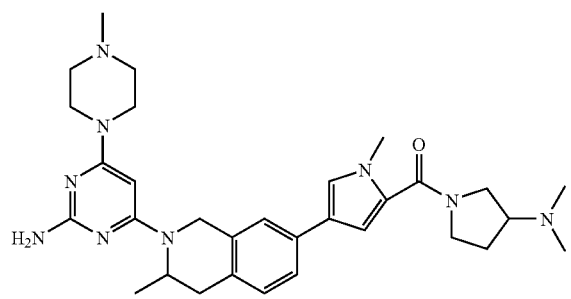 [SMILES: CC1Cc2ccc(-c3cc(C(=O)N4CCC(N(C)C)C4)n(C)c3)cc2CN1c1cc(N2CCN(C)CC2)nc(N)n1]

This compound was prepared by using procedures analogous to those described for the synthesis of Example 87A, Step 9 starting from 4-{2-[2-Amino-6-(4-methylpiperazin-1-yl)pyrimidin-4-yl]-3-methyl-1,2,3,4-tetrahydroisoquinolin-7-yl}-1-methyl-1H-pyrrole-2-carboxylic acid (Example 87A, Step 8) and N,N-dimethylpyrrolidin-3-amine. LCMS (M+H)+: m/z=558.3.

Example 95

4-(4-Methylpiperazin-1-yl)-6-[3-methyl-7-[1-(tetrahydro-2H-pyran-4-yl)-1H-pyrazol-4-yl]-3,4-dihydroisoquinolin-2(1H)-yl]pyrimidin-2-amine

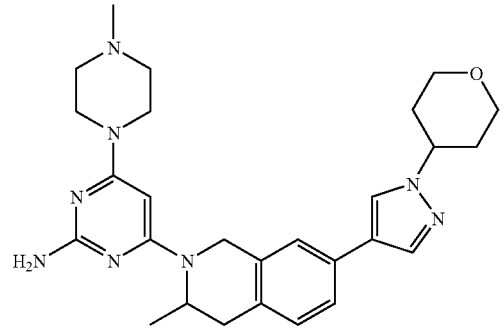 [SMILES: CC1Cc2ccc(-c3cnn(C4CCOCC4)c3)cc2CN1c1cc(N2CCN(C)CC2)nc(N)n1]

Example 95A

Enantiomer 1

Step 1: tetrahydro-2H-pyran-4-yl methanesulfonate

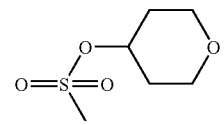

At r.t. to a solution of tetrahydro-4H-pyran-4-ol (90 uL, 1 mmol; Aldrich, Cat. No. 198234) in methylene chloride (3 mL) was added methanesulfonyl chloride (91 uL, 1.2 mmol), followed by triethylamine (0.20 mL, 1.5 mmol) and 4-dimethylaminopyridine (12 mg, 0.098 mmol). The mixture was stirred at r.t. for 3 h. It was diluted with methylene chloride. The solution was washed with water and brine, dried over Na2SO4. After filtration, the filtrate was concentrated to yield 0.21 g of the product (crude) which was directly used in the next step reaction without further purification.

Step2: 1-(tetrahydro-2H-pyran-4-yl)-4-(4,4,5,5-tetramethyl-1,3,2-dioxaborolan-2-yl)-1H-pyrazole

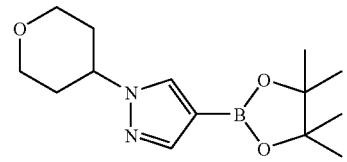 [SMILES: CC1(C)OB(c2cnn(C3CCOCC3)c2)OC1(C)C]

A mixture of 4-(4,4,5,5-tetramethyl-1,3,2-dioxaborolan-2-yl)-1H-pyrazole (0.1 g, 0.5 mmol; Aldrich, Cat. No. 525057), tetrahydro-2H-pyran-4-yl methanesulfonate (0.11 g, 0.62 mmol) and sodium hydride (31 mg, 0.77 mmol) in N,N-dimethylformamide (1 mL) was stirred at 110° C. for 2 h. After cooling, it was diluted with ethyl acetate, washed with water and brine, dried over Na2SO4. After filtration, the filtrate was concentrated to yield 0.15 g of the crude product which was directly used in the next step reaction without further purification.

Step 3: 4-(4-methylpiperazin-1-yl)-6-[3-methyl-7-[1-(tetrahydro-2H-pyran-4-yl)-1H-pyrazol-4-yl]-3,4-dihydroisoquinolin-2(1H)-yl]pyrimidin-2-amine A mixture of 4-(7-bromo-3-methyl-3,4-dihydroisoquinolin-2(1H)-yl)-6-(4-methylpiperazin-1-yl)pyrimidin-2-amine (10 mg, 0.02 mmol; Peak 1, Example 49, Step 7), 1-(tetrahydro-2H-pyran-4-yl)-4-(4,4,5,5-tetramethyl-1,3,2-dioxaborolan-2-yl)-1H-pyrazole (7.3 mg, 0.026 mmol), tetrakis(triphenylphosphine)palladium(0) (1.4 mg, 0.0012 mmol) and sodium bicarbonate (6.0 mg, 0.072 mmol) in a solution of 1,4-dioxane (0.2 mL) and water (0.1 mL) in a reaction vial was stirred at 90° C. overnight. After cooling, it was diluted with methanol. The solid was filtered off. The filtrate was purified with RP-HPLC (pH=10) to afford 0.9 mg of the desired product. LCMS (M+H)$^+$: m/z=489.4.

Example 95B

Enantiomer 2

A mixture of 4-(7-bromo-3-methyl-3,4-dihydroisoquinolin-2(1H)-yl)-6-(4-methylpiperazin-1-yl)pyrimidin-2-amine (10 mg, 0.02 mmol) (example 49, step 7, peak 2), 1-(tetrahydro-2H-pyran-4-yl)-4-(4,4,5,5-tetramethyl-1,3,2-dioxaborolan-2-yl)-1H-pyrazole (10 mg, 0.036 mmol), tetrakis(triphenylphosphine)palladium(0) (1.4 mg, 0.0012 mmol), and sodium bicarbonate (6.0 mg, 0.072 mmol) in 1,4-dioxane (0.2 mL) and water (0.1 mL) in a reaction vial was stirred at 90° C. for 2 h. After cooling, it was diluted with methanol, purified with RP-HPLC (pH=10) to afford 3.8 mg of the desired product. LCMS (M+H)$^+$: m/z=489.2.

Example 96

3-(4-{2-[2-Amino-6-(4-methylpiperazin-1-yl)pyrimidin-4-yl]-3-methyl-1,2,3,4-tetrahydroisoquinolin-7-yl}-1H-pyrazol-1-yl)propanenitrile

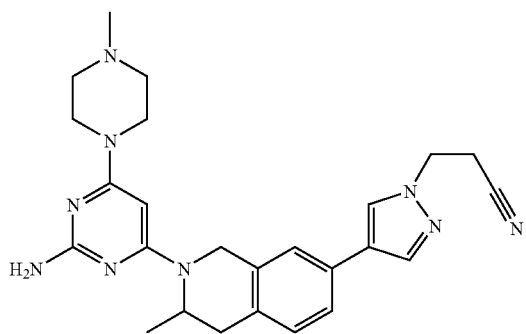 [SMILES: CC1Cc2ccc(-c3cnn(CCC#N)c3)cc2CN1c1cc(N2CCN(C)CC2)nc(N)n1]

Example 96A

Enantiomer 1

Step 1: 3-[4-(4,4,5,5-tetramethyl-1,3,2-dioxaborolan-2-yl)-1H-pyrazol-1-yl]propanenitrile

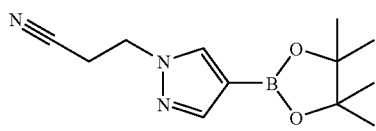 [SMILES: CC1(C)OB(c2cnn(CCC#N)c2)OC1(C)C]

A mixture of 4-(4,4,5,5-tetramethyl-1,3,2-dioxaborolan-2-yl)-1H-pyrazole (50 mg, 0.2 mmol), 3-bromopropionitrile (23 uL, 0.28 mmol, Aldrich, Cat. No. 109231) and cesium carbonate (250 mg, 0.77 mmol) in acetonitrile (1 mL) was stirred at 90° C. overnight. After cooling, it was diluted with ethyl acetate, washed with water twice and brine once, dried over Na$_2$SO$_4$. After filtration the filtrate was concentrated to yield 55 mg of the desired product.

Step 2: 3-(4-{2-[2-amino-6-(4-methylpiperazin-1-yl)pyrimidin-4-yl]-3-methyl-1,2,3,4-tetrahydroisoquinolin-7-yl}-1H-pyrazol-1-yl)propanenitrile A mixture of 4-(7-bromo-3-methyl-3,4-dihydroisoquinolin-2(1H)-yl)-6-(4-methylpiperazin-1-yl)pyrimidin-2-amine (15 mg, 0.036 mmol; Peak 1, Example 49, Step 7), 3-[4-(4,4,5,5-tetramethyl-1,3,2-dioxaborolan-2-yl)-1H-pyrazol-1-yl]propanenitrile (13 mg, 0.054 mmol), tetrakis(triphenylphosphine)palladium(0) (2.1 mg, 0.0018 mmol), and sodium bicarbonate (9.0 mg, 0.11 mmol) in a solution of 1,4-dioxane (0.2 mL) and water (0.1 mL) in a reaction vial was stirred at 90° C. overnight. After cooling it was diluted with methanol, purified with RP-HPLC (pH=10) to afford 12.1 mg of the desired product. LCMS (M+H)$^+$: m/z=458.3.

Example 96B

Enantiomer 2

A mixture of 4-(7-bromo-3-methyl-3,4-dihydroisoquinolin-2(1H)-yl)-6-(4-methylpiperazin-1-yl)pyrimidin-2-amine (10 mg, 0.02 mmol; Peak 2, Example 49, Step 7), 3-[4-(4,4,5,5-tetramethyl-1,3,2-dioxaborolan-2-yl)-1H-pyrazol-1-yl]propanenitrile (8.9 mg, 0.036 mmol), tetrakis(triphenylphosphine)palladium(0) (1.4 mg, 0.0012 mmol), and sodium bicarbonate (6.0 mg, 0.072 mmol) in 1,4-dioxane (0.2 mL) and water (0.1 mL) in a sealed reaction vial was stirred at 90° C. for 3 h. After cooling it was diluted with methanol. After filtration the filtrate was purified with RP-HPLC (using pH=10 conditions) to afford 6.0 mg of the desired product. LCMS (M+H)$^+$: m/z=458.3.

Example 97

1-[(4-{2-[2-Amino-6-(4-methylpiperazin-1-yl)pyrimidin-4-yl]-3-methyl-1,2,3,4-tetrahydroisoquinolin-7-yl}-1H-pyrazol-1-yl)methyl]cyclopropanecarbonitrile

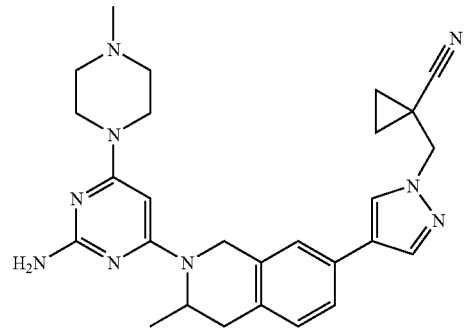 [SMILES: CC1Cc2ccc(-c3cnn(CC4(C#N)CC4)c3)cc2CN1c1cc(N2CCN(C)CC2)nc(N)n1]

Example 97A

Enantiomer 1

Step 1: 1-(hydroxymethyl)cyclopropanecarbonitrile

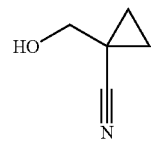

At r.t. to a solution of ethyl 1-cyanocyclopropanecarboxylate (1.0 g, 7.2 mmol; Aldrich, Cat. No. 543055) in tetrahydrofuran (15 mL) was added lithium tetrahydroborate (0.31 g, 14 mmol) portionwise with stirring. The resulting mixture was heated at reflux for 3 h. After cooling, it was quenched with water. The product was extracted with ethyl acetate. The extract was washed with water and brine, dried over $Na_2SO_4$. After filtration the filtrate was concentrated to yield 0.41 g of the product which was used directly in next step reaction without further purification.

Step 2: (1-cyanocyclopropyl)methyl methanesulfonate

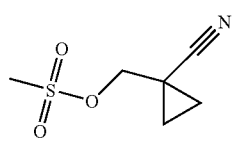

At r.t. to a solution of 1-(hydroxymethyl)cyclopropanecarbonitrile (0.41 g, 4.2 mmol) in methylene chloride (10 mL) was added methanesulfonyl chloride (490 uL, 6.3 mmol), followed by triethylamine (1.5 mL, 10.0 mmol) and 4-dimethylaminopyridine (18 mg, 0.15 mmol). The mixture was stirred at r.t. for 3 h. It was diluted with methylene chloride, washed with water and brine, dried over $Na_2SO_4$. After filtration the filtrate was concentrated to yield the crude product which was used in the next step reaction without further purification.

Step 3: {[4-(4,4,5,5-tetramethyl-1,3,2-dioxaborolan-2-yl)-1H-pyrazol-1-yl]methyl}cyclopropanecarbonitrile

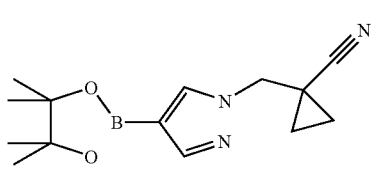

A mixture of 4-(4,4,5,5-tetramethyl-1,3,2-dioxaborolan-2-yl)-1H-pyrazole (0.1 g, 0.5 mmol), (1-cyanocyclopropyl)methyl methanesulfonate (0.14 g, 0.77 mmol), and sodium hydride (31 mg, 0.77 mmol) in N,N-dimethylformamide (1 mL) was stirred at 110° C. for 2 h. After cooling, it was diluted with ethyl acetate, washed with water and brine, dried over $Na_2SO_4$. After filtration the filtrate was concentrated to yield 0.15 g of the crude product which was used in the next step reaction without further purification.

Step 4: 1-[(4-{2-[2-amino-6-(4-methylpiperazin-1-yl)pyrimidin-4-yl]-3-methyl-1,2,3,4-tetrahydroisoquinolin-7-yl}-1H-pyrazol-1-yl)methyl]cyclopropanecarbonitrile A mixture of 4-(7-bromo-3-methyl-3,4-dihydroisoquinolin-2(1H)-yl)-6-(4-methylpiperazin-1-yl)pyrimidin-2-amine (10 mg, 0.02 mmol; Peak 1, Example 49, Step 7), 1-{[4-(4,4,5,5-tetramethyl-1,3,2-dioxaborolan-2-yl)-1H-pyrazol-1-yl]methyl}cyclopropanecarbonitrile (7.2 mg, 0.026 mmol), tetrakis(triphenylphosphine)palladium(0) (1.4 mg, 0.0012 mmol) and sodium bicarbonate (6.0 mg, 0.072 mmol) in a solution of 1,4-dioxane (0.2 mL) and water (0.1 mL) in a reaction vial was stirred at 90° C. overnight. After cooling, it was diluted with methanol. The solid was filtered off. The filtrate was purified with RP-HPLC (pH=10) to afford 5.3 mg of the desired product. LCMS $(M+H)^+$: m/z=484.2.

Example 97B

Enantiomer 2

A mixture of 4-(7-bromo-3-methyl-3,4-dihydroisoquinolin-2(1H)-yl)-6-(4-methylpiperazin-1-yl)pyrimidin-2-amine (10 mg, 0.02 mmol; Peak 2, Example 49, Step 7), 1-{[4-(4,4,5,5-tetramethyl-1,3,2-dioxaborolan-2-yl)-1H-pyrazol-1-yl]methyl}cyclopropanecarbonitrile (9.8 mg, 0.036 mmol), tetrakis(triphenylphosphine)palladium(0) (1.4 mg, 0.0012 mmol), and sodium bicarbonate (6.0 mg, 0.072 mmol) in a solution of 1,4-dioxane (0.2 mL) and water (0.1 mL) in a reaction vial was stirred at 90° C. for 2 h. After cooling, it was diluted with methanol, purified with RP-HPLC (pH=10). The fraction was lyophilized to yield 3.9 mg of the desired product. LCMS $(M+H)^+$: m/z=484.2.

Example 98

4-[7-[1-(1,1-Dioxidotetrahydro-3-thienyl)-1H-pyrazol-4-yl]-3-methyl-3,4-dihydroisoquinolin-2(1H)-yl]-6-(4-methylpiperazin-1-yl)pyrimidin-2-amine

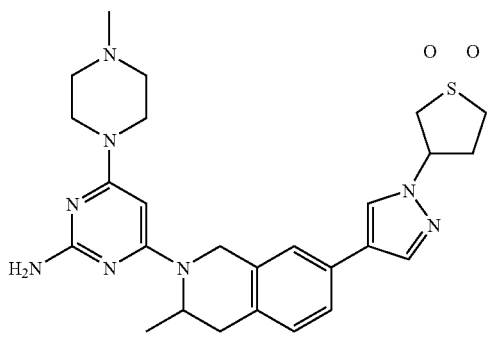

Example 98A

Enantiomer 1

Step 1: 1-(1,1-dioxidotetrahydro-3-thienyl)-4-(4,4,5,5-tetramethyl-1,3,2-dioxaborolan-2-yl)-1H-pyrazole

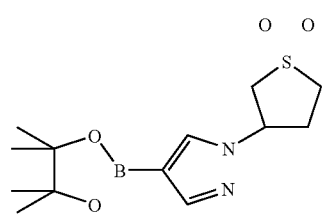

A mixture of 4-(4,4,5,5-tetramethyl-1,3,2-dioxaborolan-2-yl)-1H-pyrazole (50 mg, 0.2 mmol), 3-bromotetrahydrothiophene 1,1-dioxide (56 mg, 0.28 mmole; ChemBridge, Cat. No. 4011807), cesium carbonate (0.25 g, 0.77 mmol) in acetonitrile (1 mL) was stirred at 90° C. overnight. After cooling it was diluted with ethyl acetate, washed with water and brine, dried over $Na_2SO_4$. After filtration the filtrate was concentrated to yield 74 mg of the product. LCMS (M+H)+: m/z=313.1

Step 2: 4-[7-[1-(1,1-dioxidotetrahydro-3-thienyl)-1H-pyrazol-4-yl]-3-methyl-3,4-dihydroisoquinolin-2(1H)-yl]-6-(4-methylpiperazin-1-yl)pyrimidin-2-amine A mixture of 4-(7-bromo-3-methyl-3,4-dihydroisoquinolin-2(1H)-yl)-6-(4-methylpiperazin-1-yl)pyrimidin-2-amine (10 mg, 0.02 mmol; Peak 1, Example 49, Step 7), 1-(1,1-dioxidotetrahydro-3-thienyl)-4-(4,4,5,5-tetramethyl-1,3,2-dioxaborolan-2-yl)-1H-pyrazole (12.0 mg, 0.026 mmol), tetrakis(triphenylphosphine)palladium(0) (1.4 mg, 0.0012 mmol) and sodium bicarbonate (6.0 mg, 0.072 mmol) in a solution of 1,4-dioxane (0.2 mL) and water (0.1 mL) in a reaction vial was stirred at 90° C. overnight. After cooling, it was diluted with methanol. The solid was filtered off. The filtrate was purified with RP-HPLC (pH=10) to afford the desired product (2.8 mg). LCMS (M+H)$^+$: m/z=523.3.

Example 98B

Enantiomer 2

A mixture of 4-(7-bromo-3-methyl-3,4-dihydroisoquinolin-2(1H)-yl)-6-(4-methylpiperazin-1-yl)pyrimidin-2-amine (10 mg, 0.02 mmol; Peak 2, Example 49, Step 7), 1-(1,1-dioxidotetrahydro-3-thienyl)-4-(4,4,5,5-tetramethyl-1,3,2-dioxaborolan-2-yl)-1H-pyrazole (22 mg, 0.036 mmol), tetrakis(triphenylphosphine)palladium(0) (1.4 mg, 0.0012 mmol), and sodium bicarbonate (6.0 mg, 0.072 mmol) in a solution of 1,4-dioxane (0.2 mL) and water (0.1 mL) in a reaction vial was stirred at 90° C. for 2 h. After cooling, it was diluted with methanol, and purified with RP-HPLC (pH=10) to afford the desired product (2.4 mg). LCMS (M+H)$^+$: m/z=523.3.

Example 99

4-(4-Methylpiperazin-1-yl)-6-[3-methyl-7-[1-(tetrahydrofuran-2-ylmethyl)-1H-pyrazol-4-yl]-3,4-dihydroisoquinolin-2(1H)-yl]pyrimidin-2-amine

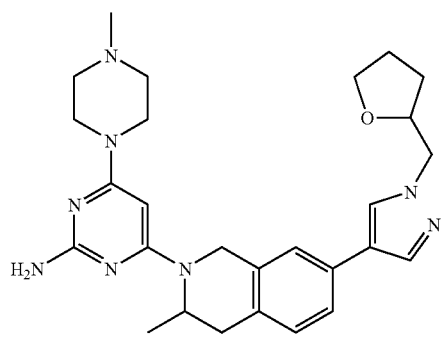 [SMILES: CC1Cc2ccc(/C(C=N)=C/NCC3CCCO3)cc2CN1c1cc(N2CCN(C)CC2)nc(N)n1]

Example 99A

Enantiomer 1

Step 1: 1-(tetrahydrofuran-2-ylmethyl)-4-(4,4,5,5-tetramethyl-1,3,2-dioxaborolan-2-yl)-1H-pyrazole

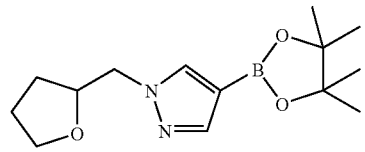 [SMILES: CC1(C)OB(c2cnn(CC3CCCO3)c2)OC1(C)C]

A mixture of 4-(4,4,5,5-tetramethyl-1,3,2-dioxaborolan-2-yl)-1H-pyrazole (50 mg, 0.2 mmol), tetrahydrofurfuryl bromide (51 mg, 0.31 mmol, Alfa Aesar, Cat. No. A15192), and cesium carbonate (250 mg, 0.77 mmol) in acetonitrile (1 mL) was stirred at 90° C. overnight. After cooling, it was diluted with ethyl acetate. The organic solution was washed with water and brine, and dried over $Na_2SO_4$. After filtration the filtrate was concentrated to yield 51 mg of the product.

Step 2: 4-(4-methylpiperazin-1-yl)-6-[3-methyl-7-[1-(tetrahydrofuran-2-ylmethyl)-1H-pyrazol-4-yl]-3,4-dihydroisoquinolin-2(1H)-yl]pyrimidin-2-amine A mixture of 4-(7-bromo-3-methyl-3,4-dihydroisoquinolin-2(1H)-yl)-6-(4-methylpiperazin-1-yl)pyrimidin-2-amine (10 mg, 0.02 mmol; Peak 1, Example 49, Step 7), 1-(tetrahydrofuran-2-ylmethyl)-4-(4,4,5,5-tetramethyl-1,3,2-dioxaborolan-2-yl)-1H-pyrazole (7.3 mg, 0.026 mmol), tetrakis(triphenylphosphine)palladium(0) (1.4 mg, 0.0012 mmol) and sodium bicarbonate (6.0 mg, 0.072 mmol) in a solution of 1,4-dioxane (0.2 mL) and water (0.1 mL) in a reaction vial was stirred at 90° C. overnight. After cooling it was diluted with methanol. The solid was filtered off. The filtrate was purified with RP-HPLC (pH=10) to afford the desired product (5.8 mg). LCMS (M+H)$^+$: m/z=489.4.

Example 99B

Enantiomer 2

A mixture of 4-(7-bromo-3-methyl-3,4-dihydroisoquinolin-2(1H)-yl)-6-(4-methylpiperazin-1-yl)pyrimidin-2-amine (10 mg, 0.02 mmol; Peak 2, Example 49, Step 7), 1-(tetrahydrofuran-2-ylmethyl)-4-(4,4,5,5-tetramethyl-1,3,2-dioxaborolan-2-yl)-1H-pyrazole (10 mg, 0.036 mmol), tetrakis(triphenylphosphine)palladium(0) (1.4 mg, 0.0012 mmol), and sodium bicarbonate (6.0 mg, 0.072 mmol) in a solution of 1,4-dioxane (0.2 mL) and water (0.1 mL) in a reaction vial was stirred at 90° C. overnight. After cooling it was diluted with methanol, purified with RP-HPLC (pH=10) to afford the desired product (8.4 mg). LCMS (M+H)$^+$: m/z=489.4.

Example 100

4-[7-[1-(2-Fluoroethyl)-1H-pyrazol-4-yl]-3-methyl-3,4-dihydroisoquinolin-2(1H)-yl]-6-(4-methylpiperazin-1-yl)pyrimidin-2-amine (Enantiomer 1)

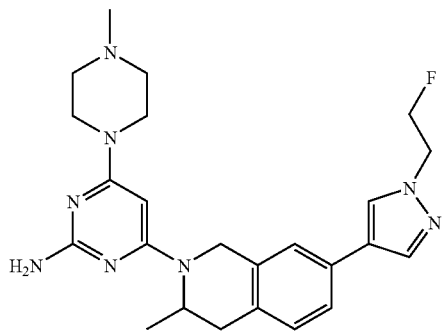 [SMILES: CC1Cc2ccc(-c3cnn(CCF)c3)cc2CN1c1cc(N2CCN(C)CC2)nc(N)n1]

Step 1: 1-(2-fluoroethyl)-4-(4,4,5,5-tetramethyl-1,3,2-dioxaborolan-2-yl)-1H-pyrazole

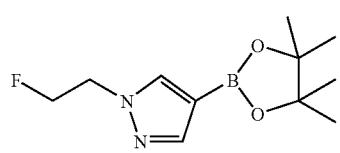 [SMILES: CC1(C)OB(c2cnn(CCF)c2)OC1(C)C]

A mixture of 4-(4,4,5,5-tetramethyl-1,3,2-dioxaborolan-2-yl)-1H-pyrazole (0.05 g, 0.2 mmol), 1-fluoro-2-iodoethane (0.049 g, 0.28 mmol, SynQuest Labs, Cat. No. 1100-k-18), and cesium carbonate (250 mg, 0.77 mmol) in acetonitrile (1.0 mL) in a sealed reaction vial was heated at 90° C. with stirring overnight. After cooling it was diluted with ethyl acetate. Then the organic solution was washed with water, brine; dried over Na$_2$SO$_4$. After filtration the filtrate was concentrated to yield 19 mg of the product which was directly used in the next step reaction without further purification.

Step 2: 4-[7-[1-(2-fluoroethyl)-1H-pyrazol-4-yl]-3-methyl-3,4-dihydroisoquinolin-2(1H)-yl]-6-(4-methylpiperazin-1-yl)pyrimidin-2-amine A mixture of 4-(7-bromo-3-methyl-3,4-dihydroisoquinolin-2(1H)-yl)-6-(4-methylpiperazin-1-yl)pyrimidin-2-amine (10 mg, 0.02 mmol; Peak 1, Example 49, Step 7), 1-(2-fluoroethyl)-4-(4,4,5,5-tetramethyl-1,3,2-dioxaborolan-2-yl)-1H-pyrazole (6.3 mg, 0.026 mmol), tetrakis(triphenylphosphine)palladium(0) (1.4 mg, 0.0012 mmol), and sodium bicarbonate (6.0 mg, 0.072 mmol) in a solution of 1,4-dioxane (0.2 mL) and water (0.1 mL) in a reaction vial was stirred at 90° C. overnight. After cooling it was diluted with methanol. After filtration the filtrate was purified with RP-HPLC (pH=10) to afford the desired product (2.1 mg). LCMS (M+H)$^+$: m/z=451.2.

Example 101

3-(4-{2-[2-Amino-6-(4-methylpiperazin-1-yl)pyrimidin-4-yl]-3-methyl-1,2,3,4-tetrahydroisoquinolin-7-yl}-1H-pyrazol-1-yl)-2-methylpropanenitrile (Enantiomer 1)

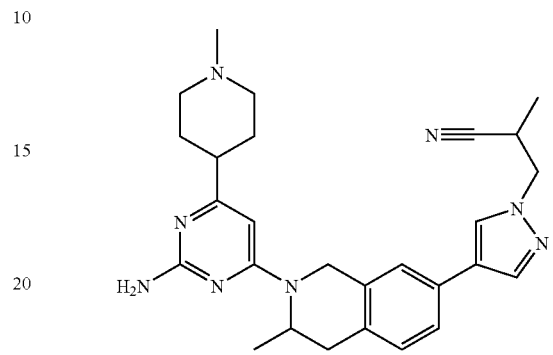

Step 1: 2-methyl-3-[4-(4,4,5,5-tetramethyl-1,3,2-dioxaborolan-2-yl)-1H-pyrazol-1-yl]propanenitrile

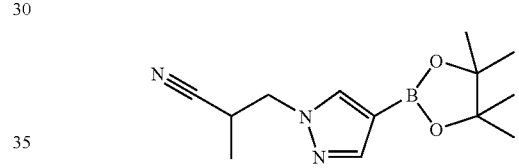

A mixture of 4-(4,4,5,5-tetramethyl-1,3,2-dioxaborolan-2-yl)-1H-pyrazole (0.050 g, 0.26 mmol), 3-chloro-2-methylpropanenitrile (27 uL, 0.28 mmol, Aldrich, Cat. No. 150428), and cesium carbonate (250 mg, 0.77 mmol) in acetonitrile (1 mL) in a sealed reaction vial was stirred at 90° C. overnight. After cooling it was diluted with ethyl acetate. Then the organic solution was washed with water, brine; dried over Na$_2$SO$_4$. After filtration the filtrate was concentrated to yield 41 mg product. It was directly used in the next step reaction without further purification.

Step 2: 3-(4-{2-[2-amino-6-(4-methylpiperazin-1-yl)pyrimidin-4-yl]-3-methyl-1,2,3,4-tetrahydroisoquinolin-7-yl}-1H-pyrazol-1-yl)-2-methylpropanenitrile A mixture of 4-(7-bromo-3-methyl-3,4-dihydroisoquinolin-2 (1H)-yl)-6-(4-methylpiperazin-1-yl)pyrimidin-2-amine (10 mg, 0.02 mmol; Peak 1, Example 49, Step 7), 2-methyl-3-[4-(4,4,5,5-tetramethyl-1,3,2-dioxaborolan-2-yl)-1H-pyrazol-1-yl]propanenitrile (7.5 mg, 0.029 mmol), tetrakis(triphenylphosphine)palladium(0) (1.4 mg, 0.0012 mmol), and sodium bicarbonate (6.0 mg, 0.072 mmol) in a solution of 1,4-dioxane (0.2 mL) and water (0.1 mL) in a reaction vial was stirred at 90° C. overnight. After cooling it was diluted with methanol. After filtration the filtrate was purified with RP-HPLC (pH=10) to afford the desired product (2.9 mg). LCMS (M+H)$^+$: m/z=472.3.

Example 102

4-[7-[1-(Cyclopropylmethyl)-1H-pyrazol-4-yl]-3-methyl-3,4-dihydroisoquinolin-2(1H)-yl]-6-(4-methylpiperazin-1-yl)pyrimidin-2-amine (Enantiomer 1)

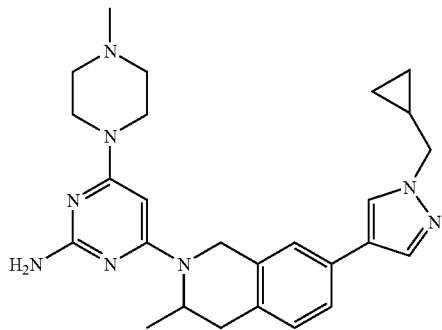 [SMILES: CC1Cc2ccc(-c3cnn(CC4CC4)c3)cc2CN1c1cc(N2CCN(C)CC2)nc(N)n1]

Step 1: 1-(cyclopropylmethyl)-4-(4,4,5,5-tetramethyl-1,3,2-dioxaborolan-2-yl)-1H-pyrazole

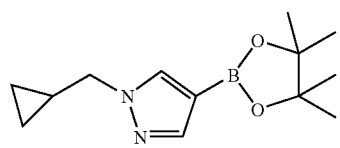 [SMILES: CC1(C)OB(c2cnn(CC3CC3)c2)OC1(C)C]

A mixture of 4-(4,4,5,5-tetramethyl-1,3,2-dioxaborolan-2-yl)-1H-pyrazole (0.1 g, 0.5 mmol), cyclopropylmethyl bromide (60.0 uL, 0.62 mmol, Aldrich, Cat. No. 242403), and cesium carbonate (500.0 mg, 1.5 mmol) in acetonitrile (1 mL) was stirred at 90° C. overnight. After cooling it was diluted with ethyl acetate. Then the organic solution was washed with water, brine; dried over $Na_2SO_4$. After filtration the filtrate was concentrated to yield 120 mg of the product which was directly used in the next step reaction without further purification.

Step 2: 4-[7-[1-(cyclopropylmethyl)-1H-pyrazol-4-yl]-3-methyl-3,4-dihydroisoquinolin-2(1H)-yl]-6-(4-methylpiperazin-1-yl)pyrimidin-2-amine A mixture of 4-(7-bromo-3-methyl-3,4-dihydroisoquinolin-2 (1H)-yl)-6-(4-methylpiperazin-1-yl)pyrimidin-2-amine (10 mg, 0.02 mmol; Peak 1, Example 49, Step 7), 1-(cyclopropylmethyl)-4-(4,4,5,5-tetramethyl-1,3,2-dioxaborolan-2-yl)-1H-pyrazole (7.1 mg, 0.029 mmol), tetrakis(triphenylphosphine)palladium(0) (1.4 mg, 0.0012 mmol), and sodium bicarbonate (6.0 mg, 0.072 mmol) in a solution of 1,4-dioxane (0.2 mL) and water (0.1 mL) in a reaction vial was stirred at 90° C. overnight. After cooling it was diluted with methanol. After filtration the filtrate was purified with RP-HPLC (pH=10) to afford the desired product (5.3 mg). LCMS $(M+H)^+$: m/z=459.3.

Example 103

3-(4-{2-[2-Amino-6-(4-methylpiperazin-1-yl)pyrimidin-4-yl]-3-methyl-1,2,3,4-tetrahydroisoquinolin-7-yl}-1H-pyrazol-1-yl)butanenitrile (Enantiomer 1)

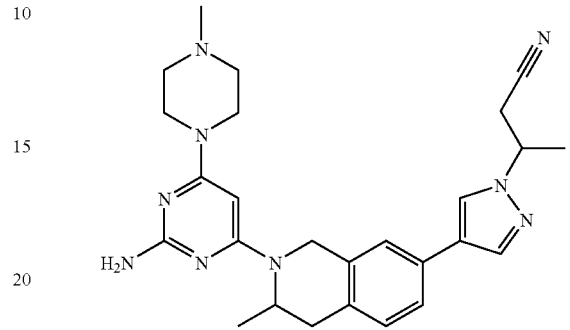

Step 1: 3-[4-(4,4,5,5-tetramethyl-1,3,2-dioxaborolan-2-yl)-1H-pyrazol-1-yl]butanenitrile

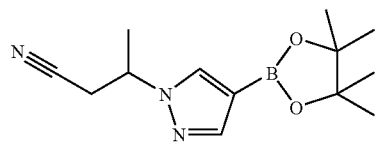 [SMILES: CC(CC#N)n1cc(B2OC(C)(C)C(C)(C)O2)cn1]

A mixture of 4-(4,4,5,5-tetramethyl-1,3,2-dioxaborolan-2-yl)-1H-pyrazole (50 mg, 0.2 mmol), 3-bromobutanenitrile (46 mg, 0.31 mmol, TCI America, Cat. No. B 1452), and cesium carbonate (250 mg, 0.77 mmol) in acetonitrile (1 mL) was stirred at 90° C. for 3 hours. After cooling it was quenched with water, extracted with ethyl acetate. The extract was washed with water twice, brine once; dried over $Na_2SO_4$. After filtration the filtrate was concentrated to yield 60 mg product. It was directly used in the next step reaction without further purification.

Step 2: 3-(4-{2-[2-amino-6-(4-methylpiperazin-1-yl)pyrimidin-4-yl]-3-methyl-1,2,3,4-tetrahydroisoquinolin-7-yl}-1H-pyrazol-1-yl)butanenitrile A mixture of 4-(7-bromo-3-methyl-3,4-dihydroisoquinolin-2(1H)-yl)-6-(4-methylpiperazin-1-yl)pyrimidin-2-amine (10 mg, 0.02 mmol; Peak 1, Example 49, Step 7), 3-[4-(4,4,5,5-tetramethyl-1,3,2-dioxaborolan-2-yl)-1H-pyrazol-1-yl]butanenitrile (7.5 mg, 0.029 mmol), tetrakis(triphenylphosphine)palladium(0) (1.4 mg, 0.0012 mmol), and sodium bicarbonate (6.0 mg, 0.072 mmol) in a solution of 1,4-dioxane (0.2 mL) and water (0.1 mL) in a reaction vial was stirred at 90° C. overnight. After cooling it was diluted with methanol. After filtration the filtrate was purified with RP-HPLC (pH=10) to afford the desired product (3.9 mg). LCMS $(M+H)^+$: m/z=472.3.

Example 104

4-[3-Methyl-7-[1-(2-morpholin-4-ylethyl)-1H-pyrazol-4-yl]-3,4-dihydroisoquinolin-2(1H)-yl]-6-(4-methylpiperazin-1-yl)pyrimidin-2-amine (Enantiomer 1)

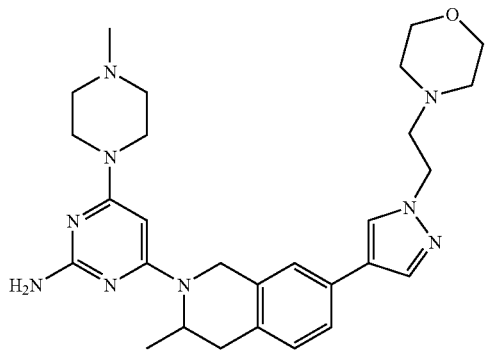 [SMILES: CC1Cc2ccc(-c3cnn(CCN4CCOCC4)c3)cc2CN1c1cc(N2CCN(C)CC2)nc(N)n1]

Step 1: 4-{2-[4-(4,4,5,5-tetramethyl-1,3,2-dioxaborolan-2-yl)-1H-pyrazol-1-yl]ethyl}morpholine

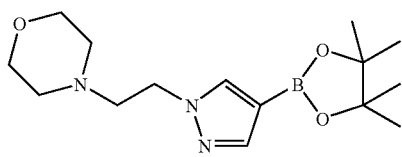 [SMILES: CC1(C)OB(c2cnn(CCN3CCOCC3)c2)OC1(C)C]

A mixture of 4-(4,4,5,5-tetramethyl-1,3,2-dioxaborolan-2-yl)-1H-pyrazole (50 mg, 0.2 mmol), 4-(2-chloroethyl)morpholine hydrochloride (252 mg, 0.28 mmole, Aldrich, Cat. No. C42203), cesium carbonate (250 mg, 0.77 mmol) in acetonitrile (1 mL) in a sealed reaction vial was stirred at 90° C. overnight. LC/MS showed it worked well. After cooling it was diluted with ethyl acetate. Then the organic solution was washed with water, brine; dried over $Na_2SO_4$. After filtration the filtrate was concentrated to yield 50 mg of the product which was directly used in the next step reaction without further purification.

Step 2: 4-[3-methyl-7-[1-(2-morpholin-4-ylethyl)-1H-pyrazol-4-yl]-3,4-dihydroisoquinolin-2(1H)-yl]-6-(4-methylpiperazin-1-yl)pyrimidin-2-amine A mixture of 4-(7-bromo-3-methyl-3,4-dihydroisoquinolin-2(1H)-yl)-6-(4-methylpiperazin-1-yl)pyrimidin-2-amine (10 mg, 0.02 mmol; Peak 1, Example 49, Step 7), 4-{2-[4-(4,4,5,5-tetramethyl-1,3,2-dioxaborolan-2-yl)-1H-pyrazol-1-yl]ethyl}morpholine (8.8 mg, 0.029 mmol), tetrakis(triphenylphosphine)palladium(0) (1.4 mg, 0.0012 mmol), and sodium bicarbonate (6.0 mg, 0.072 mmol) in a solution of 1,4-dioxane (0.2 mL) and water (0.1 mL) in a reaction vial was stirred at 90° C. overnight. After cooling, it was diluted with methanol. After filtration the filtrate was purified with RP-HPLC (pH=10) to afford the desired product (6.3 mg). LCMS $(M+H)^+$: m/z=518.4.

Example 105

4-[7-(1-Isopropyl-1H-pyrazol-4-yl)-3-methyl-3,4-dihydroisoquinolin-2(1H)-yl]-6-(4-methylpiperazin-1-yl)pyrimidin-2-amine (Enantiomer 1)

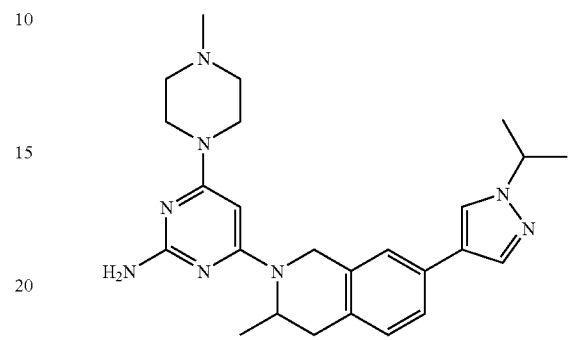

Step 1: 1-isopropyl-4-(4,4,5,5-tetramethyl-1,3,2-dioxaborolan-2-yl)-1H-pyrazole

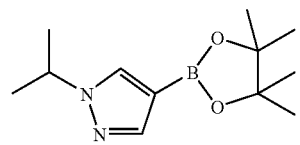 [SMILES: CC(C)n1cc(B2OC(C)(C)C(C)(C)O2)cn1]

A mixture of 4-(4,4,5,5-tetramethyl-1,3,2-dioxaborolan-2-yl)-1H-pyrazole (0.05 g, 0.2 mmol), 2-Bromopropane (36 uL, 0.39 mmol, Aldrich, Cat. No. 239909), and cesium carbonate (250 mg, 0.77 mmol) in acetonitrile (1 mL) was stirred at 90° C. for 2 h. After cooling it was quenched with water. The product was extracted with ethyl acetate. The extract was washed with water twice, brine once; dried over $Na_2SO_4$. After filtration the filtrate was concentrated to yield 53 mg of the product which was directly used in the next step reaction without further purification.

Step 2: 4-[7-(1-isopropyl-1H-pyrazol-4-yl)-3-methyl-3,4-dihydroisoquinolin-2(1H)-yl]-6-(4-methylpiperazin-1-yl)pyrimidin-2-amine A mixture of 4-(7-bromo-3-methyl-3,4-dihydroisoquinolin-2(1H)-yl)-6-(4-methylpiperazin-1-yl)pyrimidin-2-amine (10 mg, 0.02 mmol; Peak 1, Example 49, Step 7), 1-isopropyl-4-(4,4,5,5-tetramethyl-1,3,2-dioxaborolan-2-yl)-1H-pyrazole (6.2 mg, 0.026 mmol), tetrakis(triphenylphosphine)palladium(0) (1.4 mg, 0.0012 mmol), and sodium bicarbonate (6.0 mg, 0.072 mmol) in a solution of 1,4-dioxane (0.2 mL) and water (0.1 mL) in a reaction vial was stirred at 90° C. overnight. It was diluted with methanol. After filtration the filtrate was purified with RP-HPLC (pH=10) to afford the desired product (4.4 mg). LCMS $(M+H)^+$: m/z=447.4.

Example 106

4-[7-[1-(Cyclobutylmethyl)-1H-pyrazol-4-yl]-3-methyl-3,4-dihydroisoquinolin-2(1H)-yl]-6-(4-methylpiperazin-1-yl)pyrimidin-2-amine (Enantiomer 1)

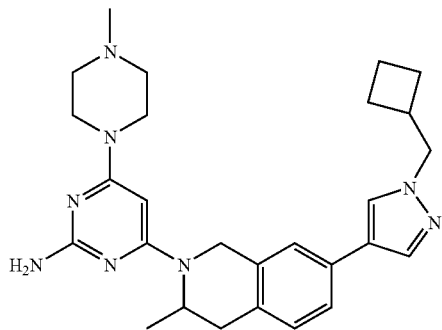 [SMILES: CC1Cc2ccc(-c3cnn(CC4CCC4)c3)cc2CN1c1cc(N2CCN(C)CC2)nc(N)n1]

Step 1: 1-(cyclobutylmethyl)-4-(4,4,5,5-tetramethyl-1,3,2-dioxaborolan-2-yl)-1H-pyrazole

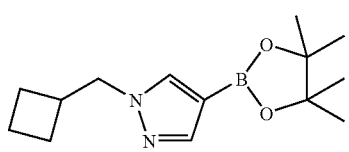 [SMILES: CC1(C)OB(c2cnn(CC3CCC3)c2)OC1(C)C]

A mixture of 4-(4,4,5,5-tetramethyl-1,3,2-dioxaborolan-2-yl)-1H-pyrazole (0.05 g, 0.2 mmol), (bromomethyl)cyclobutane (58 mg, 0.39 mmol, Aldrich, Cat. No. 226998), and cesium carbonate (250 mg, 0.77 mmol) in acetonitrile (1 mL) was stirred at 90° C. for 2 h. After cooling it was quenched with water. The product was extracted with ethyl acetate. The extract was washed with water twice, brine once; dried over $Na_2SO_4$. After filtration the filtrate was concentrated to yield 64 mg of the product which was directly used in the next step reaction without further purification.

Step 2: 4-[7-[1-(cyclobutylmethyl)-1H-pyrazol-4-yl]-3-methyl-3,4-dihydroisoquinolin-2(1H)-yl]-6-(4-methylpiperazin-1-yl)pyrimidin-2-amine A mixture of 4-(7-bromo-3-methyl-3,4-dihydroisoquinolin-2(1H)-yl)-6-(4-methylpiperazin-1-yl)pyrimidin-2-amine (10 mg, 0.02 mmol; Peak 1, Example 49, Step 7), 1-(cyclobutylmethyl)-4-(4,4,5,5-tetramethyl-1,3,2-dioxaborolan-2-yl)-1H-pyrazole (6.9 mg, 0.026 mmol), tetrakis(triphenylphosphine)palladium(0) (1.4 mg, 0.0012 mmol), and sodium bicarbonate (6.0 mg, 0.072 mmol) in a solution of 1,4-dioxane (0.2 mL) and water (0.1 mL) in a reaction vial was stirred at 90° C. overnight. It was diluted with methanol. After filtration the filtrate was purified with RP-HPLC (pH=10) to afford the desired product (6.2 mg). LCMS (M+H)$^+$: m/z=473.3.

Example 107

4-[7-(1-Ethyl-1H-pyrazol-4-yl)-3-methyl-3,4-dihydroisoquinolin-2(1H)-yl]-6-(4-methylpiperazin-1-yl)pyrimidin-2-amine (Enantiomer 1)

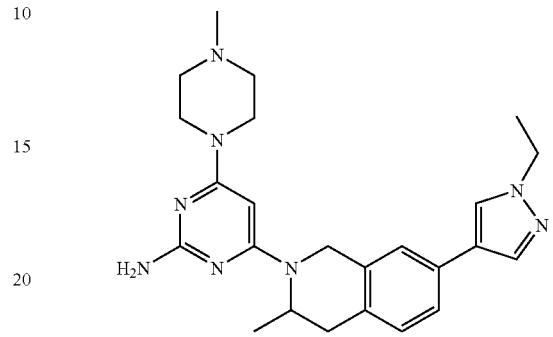

Step 1: 1-ethyl-4-(4,4,5,5-tetramethyl-1,3,2-dioxaborolan-2-yl)-1H-pyrazole

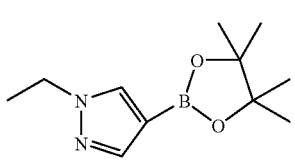 [SMILES: CCn1cc(B2OC(C)(C)C(C)(C)O2)cn1]

A mixture of 4-(4,4,5,5-tetramethyl-1,3,2-dioxaborolan-2-yl)-1H-pyrazole (0.05 g, 0.2 mmol), iodoethane (31 uL, 0.39 mmol, Sigma-Aldrich, Cat. No. 17780), and cesium carbonate (250 mg, 0.77 mmol) in acetonitrile (1 mL) was stirred at 90° C. for 2 h. After cooling it was quenched with water. The product was extracted with ethyl acetate. The extract was washed with water twice, brine once; dried over $Na_2SO_4$. After filtration the filtrate was concentrated to yield 34 mg of the product which was directly used in the next step reaction without further purification.

Step 2: 4-[7-(1-ethyl-1H-pyrazol-4-yl)-3-methyl-3,4-dihydroisoquinolin-2(1H)-yl]-6-(4-methylpiperazin-1-yl)pyrimidin-2-amine A mixture of 4-(7-bromo-3-methyl-3,4-dihydroisoquinolin-2(1H)-yl)-6-(4-methylpiperazin-1-yl)pyrimidin-2-amine (10 mg, 0.02 mmol; Peak 1, Example 49, Step 7), 1-ethyl-4-(4,4,5,5-tetramethyl-1,3,2-dioxaborolan-2-yl)-1H-pyrazole (5.8 mg, 0.026 mmol), tetrakis(triphenylphosphine)palladium(0) (1.4 mg, 0.0012 mmol), and sodium bicarbonate (6.0 mg, 0.072 mmol) in a solution of 1,4-dioxane (0.2 mL) and water (0.1 mL) in a reaction vial was stirred at 90° C. overnight. It was diluted with methanol. After filtration the filtrate was purified with RP-HPLC (pH=10) to afford the desired product (5.5 mg). LCMS (M+H)$^+$: m/z=433.3.

Example 108

4-(4-Methylpiperazin-1-yl)-6-[3-methyl-7-[1-(tetrahydrofuran-3-yl)-1H-pyrazol-4-yl]-3,4-dihydroisoquinolin-2(1H)-yl]pyrimidin-2-amine (Enantiomer 1)

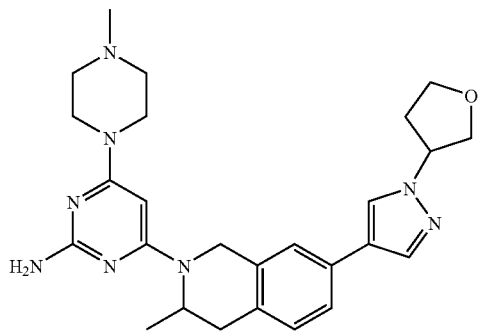 [SMILES: CC1Cc2ccc(-c3cnn(C4CCOC4)c3)cc2CN1c1cc(N2CCN(C)CC2)nc(N)n1]

Step 1: tetrahydrofuran-3-yl methanesulfonate

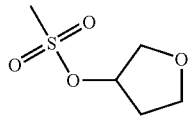

A mixture of 3-hydroxytetrahydrofuran (100 mg, 1 mmol, Aldrich, Cat. No. H59109), methanesulfonyl chloride (100.0 uL, 1.4 mmol), triethylamine (350 uL, 2.5 mmol) in methylene chloride (2 mL) was stirred at r.t. for 2 hours. It was diluted with methylene chloride, washed with water, brine; dried over $Na_2SO_4$. After filtration the filtrate was concentrated to yield 180 mg of the product which was directly used in the next step reaction without further purification.

Step 2: 1-(tetrahydrofuran-3-yl)-4-(4,4,5,5-tetramethyl-1,3,2-dioxaborolan-2-yl)-1H-pyrazole

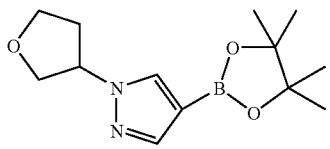 [SMILES: CC1(C)OB(c2cnn(C3CCOC3)c2)OC1(C)C]

A mixture of 4-(4,4,5,5-tetramethyl-1,3,2-dioxaborolan-2-yl)-1H-pyrazole (0.1 g, 0.5 mmol), sodium hydride (31 mg, 0.77 mmol) in N,N-dimethylformamide (1 mL, 10 mmol) was stirred at r.t. for 10 min, then, tetrahydrofuran-3-yl methanesulfonate (86 mg, 0.52 mmol) was added. The resulting mixture was stirred at 110° C. for 2 hours. After cooling it was diluted with ethyl acetate, washed with water twice, brine once; dried over $Na_2SO_4$. After filtration the filtrate was concentrated to yield 95 mg of product which was directly used in the next step reaction without further purification.

Step 3: 4-(4-methylpiperazin-1-yl)-6-[3-methyl-7-[1-(tetrahydrofuran-3-yl)-1H-pyrazol-4-yl]-3,4-dihydroisoquinolin-2(1H)-yl]pyrimidin-2-amine A mixture of 4-(7-bromo-3-methyl-3,4-dihydroisoquinolin-2(1H)-yl)-6-(4-methylpiperazin-1-yl)pyrimidin-2-amine (10 mg, 0.02 mmol; Peak 1, Example 49, Step 7), 1-(tetrahydrofuran-3-yl)-4-(4,4,5,5-tetramethyl-1,3,2-dioxaborolan-2-yl)-1H-pyrazole (7.0 mg, 0.026 mmol), tetrakis(triphenylphosphine)palladium(0) (1.4 mg, 0.0012 mmol), and sodium bicarbonate (6.0 mg, 0.072 mmol) in a solution of 1,4-dioxane (0.2 mL) and water (0.1 mL) in a reaction vial was stirred at 90° C. overnight. It was diluted with methanol. After filtration the filtrate was purified with RP-HPLC (pH=10) to afford the desired product (4.7 mg). LCMS $(M+H)^+$: m/z=475.2.

Example 109

4-[7-[1-(Cyclopentylmethyl)-1H-pyrazol-4-yl]-3-methyl-3,4-dihydroisoquinolin-2(1H)-yl]-6-(4-methylpiperazin-1-yl)pyrimidin-2-amine (Enantiomer 1)

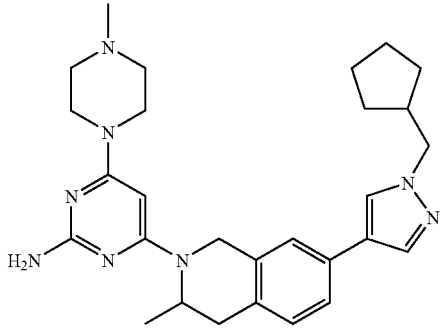 [SMILES: CC1Cc2ccc(-c3cnn(CC4CCCC4)c3)cc2CN1c1cc(N2CCN(C)CC2)nc(N)n1]

Step 1: cyclopentylmethyl methanesulfonate

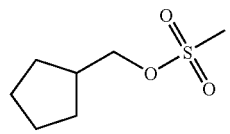

At room temperature (r.t.) to a solution of cyclopentanemethanol (0.2 g, 2 mmol, Aldrich, Cat. No. 103985) in methylene chloride (5 mL, 80 mmol) was added methanesulfonyl chloride (180 uL, 2.4 mmol), followed by triethylamine (330 uL, 2.4 mmol), and 4-dimethylaminopyridine (24 mg, 0.20 mmol). The mixture was stirred at r.t. overnight. It was diluted with methylene chloride, washed with water, brine; dried over $Na_2SO_4$. After filtration the filtrate was concentrated to yield 0.39 g of the product which was directly used in the next step reaction without further purification.

Step 2: 1-(cyclopentylmethyl)-4-(4,4,5,5-tetramethyl-1,3,2-dioxaborolan-2-yl)-1H-pyrazole

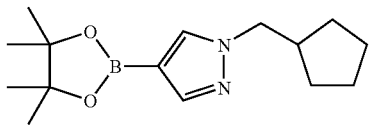 [SMILES: CC1(C)OB(c2cnn(CC3CCCC3)c2)OC1(C)C]

A mixture of 4-(4,4,5,5-tetramethyl-1,3,2-dioxaborolan-2-yl)-1H-pyrazole (0.1 g, 0.5 mmol), cyclopentylmethyl methanesulfonate (0.10 g, 0.58 mmol), and sodium hydride (31 mg, 0.77 mmol) in N,N-dimethylformamide (1 mL) was stirred at 110° C. for 2 h. After cooling it was diluted with ethyl acetate, washed with water twice, brine once; dried over Na$_2$SO$_4$. After filtration the filtrate was concentrated to yield 0.11 g of the product which was directly used in the next step reaction without further purification.

Step 3: 4-[7-[1-(cyclopentylmethyl)-1H-pyrazol-4-yl]-3-methyl-3,4-dihydroisoquinolin-2(1H)-yl]-6-(4-methylpiperazin-1-yl)pyrimidin-2-amine A mixture of 4-(7-bromo-3-methyl-3,4-dihydroisoquinolin-2(1H)-yl)-6-(4-methylpiperazin-1-yl)pyrimidin-2-amine (10 mg, 0.02 mmol; Peak 1, Example 49, Step 7), 1-(cyclopentylmethyl)-4-(4,4,5,5-tetramethyl-1,3,2-dioxaborolan-2-yl)-1H-pyrazole (7.3 mg, 0.026 mmol), tetrakis(triphenylphosphine)palladium(0) (1.4 mg, 0.0012 mmol), and sodium bicarbonate (6.0 mg, 0.072 mmol) in a solution of 1,4-dioxane (0.2 mL) and water (0.1 mL) in a reaction vial was stirred at 90° C. overnight. It was diluted with methanol. After filtration the filtrate was purified with RP-HPLC (pH=10) to afford the desired product (4.1 mg). LCMS (M+H)$^+$: m/z=487.3.

Example 110

2-(4-{2-[2-Amino-6-(4-methylpiperazin-1-yl)pyrimidin-4-yl]-3-methyl-1,2,3,4-tetrahydroisoquinolin-7-yl}-1H-pyrazol-1-yl)ethanol (Enantiomer 1)

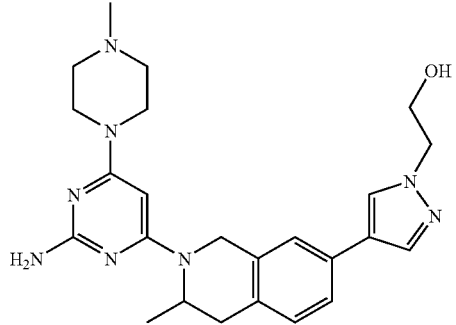 [SMILES: CC1Cc2ccc(-c3cnn(CCO)c3)cc2CN1c1cc(N2CCN(C)CC2)nc(N)n1]

Step 1: 1-(2-{[tert-butyl(dimethyl)silyl]oxy}ethyl)-4-(4,4,5,5-tetramethyl-1,3,2-dioxaborolan-2-yl)-1H-pyrazole

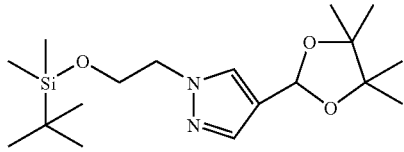

A mixture of 4-(4,4,5,5-tetramethyl-1,3,2-dioxaborolan-2-yl)-1H-pyrazole (0.05 g, 0.2 mmol), (2-bromoethoxy)(tert-butyl)dimethylsilane (61 uL, 0.28 mmol, Aldrich, Cat. No. 428426), and cesium carbonate (250 mg, 0.77 mmol) in acetonitrile (1 mL) was stirred at 90° C. overnight. After cooling it was diluted with ethyl acetate. Then the organic solution was washed with water, brine; dried over Na$_2$SO$_4$. After filtration the filtrate was concentrated to yield 74 mg of product which was directly used in the next step reaction without further purification.

Step 2: 2-(4-{2-[2-amino-6-(4-methylpiperazin-1-yl)pyrimidin-4-yl]-3-methyl-1,2,3,4-tetrahydroisoquinolin-7-yl}-1H-pyrazol-1-yl)ethanol A mixture of 4-(7-bromo-3-methyl-3,4-dihydroisoquinolin-2(1H)-yl)-6-(4-methylpiperazin-1-yl)pyrimidin-2-amine (10 mg, 0.02 mmol; Peak 1, Example 49, Step 7), 1-(2-{[tert-butyl(dimethyl)silyl]oxy}ethyl)-4-(4,4,5,5-tetramethyl-1,3,2-dioxaborolan-2-yl)-1H-pyrazole (10 mg, 0.029 mmol), tetrakis(triphenylphosphine)palladium(0) (1.4 mg, 0.0012 mmol), sodium bicarbonate (6.0 mg, 0.072 mmol) in a solution of 1,4-dioxane (0.2 mL) and water (0.1 mL) in a reaction vial was stirred at 90° C. overnight. After cooling it was concentrated. The residue was treated with methanol. The solid was filtered off. The filtrate was concentrated. The resulting residue was dissolved in 1.5 ml of 1% HCl ethanol solution, and stirred at r.t. overnight. Then it was purified with RP-HPLC (pH=10) to afford the desired product (4.6 mg). LCMS (M+H)$^+$: m/z=449.3.

Example 111

2-[4-(4-{2-[2-Amino-6-(4-methylpiperazin-1-yl)pyrimidin-4-yl]-3-methyl-1,2,3,4-tetrahydroisoquinolin-7-yl}-1H-pyrazol-1-yl)piperidin-1-yl]ethanol (Enantiomer 1)

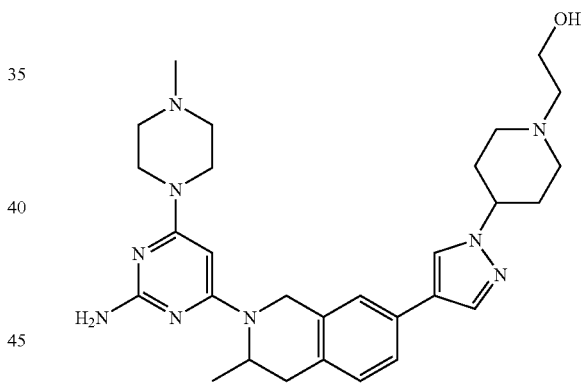

Step 1: 4-[4-(4,4,5,5-tetramethyl-1,3,2-dioxaborolan-2-yl)-1H-pyrazol-1-yl]piperidine

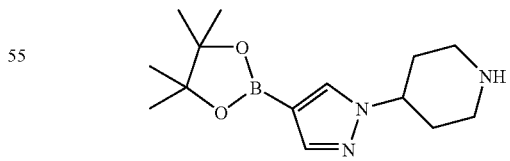

A mixture of tert-butyl 4-[4-(4,4,5,5-tetramethyl-1,3,2-dioxaborolan-2-yl)-1H-pyrazol-1-yl]piperidine-1-carboxylate (0.25 g, 0.66 mmol) in ethyl acetate (2 mL) and 4.0 M of hydrogen chloride in 1,4-dioxane (1 mL, 4 mmol) was stirred at r.t. overnight. It was concentrated to yield the product as HCl salt (quantitative) which was directly used in the next step reaction without further purification.

Step 2: 1-(2-{[tert-butyl(dimethyl)silyl]oxy}ethyl)-4-[4-(4,4,5,5-tetramethyl-1,3,2-dioxaborolan-2-yl)-1H-pyrazol-1-yl]piperidine

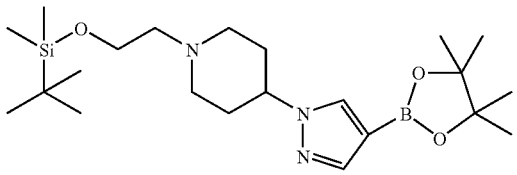

A mixture of 4-[4-(4,4,5,5-tetramethyl-1,3,2-dioxaborolan-2-yl)-1H-pyrazol-1-yl]piperidine HCl salt (0.040 g, 0.13 mmol), (2-bromoethoxy)(tert-butyl)dimethylsilane (55 uL, 0.26 mmol), and cesium carbonate (120 mg, 0.38 mmol) in acetonitrile (1 mL) was stirred at 90° C. overnight. After cooling it was diluted with ethyl acetate. Then the organic solution was washed with water, brine; dried over $Na_2SO_4$. After filtration the filtrate was concentrated to yield 50 mg of the product which was directly used in the next step reaction without further purification.

Step 3: 2-[4-(4-{2-[2-amino-6-(4-methylpiperazin-1-yl)pyrimidin-4-yl]-3-methyl-1,2,3,4-tetrahydroisoquinolin-7-yl}-1H-pyrazol-1-yl)piperidin-1-yl]ethanol A mixture of 4-(7-bromo-3-methyl-3,4-dihydroisoquinolin-2(1H)-yl)-6-(4-methylpiperazin-1-yl)pyrimidin-2-amine (10 mg, 0.02 mmol; Peak 1, Example 49, Step 7), 1-(2-{[tert-butyl(dimethyl)silyl]oxy}ethyl)-4-[4-(4,4,5,5-tetramethyl-1,3,2-dioxaborolan-2-yl)-1H-pyrazol-1-yl]piperidine (12 mg, 0.029 mmol), tetrakis(triphenylphosphine)palladium(0) (1.4 mg, 0.0012 mmol), and sodium bicarbonate (6.0 mg, 0.072 mmol) in a solution of 1,4-dioxane (0.2 mL) and water (0.1 mL) in a reaction vial was stirred at 90° C. overnight. After cooling it was concentrated. The residue was treated with methanol. After solid was filtered off the filtrate was concentrated. The resulting residue was dissolved in 1.5 ml of 1% HCl ethanol solution and stirred at r.t. overnight. Then it was purified with RP-HPLC (pH=10) to afford the desired product (2.5 mg). LCMS $(M+H)^+$:m/z=532.3.

Example 112

4-[7-[1-(2-Methoxyethyl)-1H-pyrazol-4-yl]-3-methyl-3,4-dihydroisoquinolin-2(1H)-yl]-6-(4-methylpiperazin-1-yl)pyrimidin-2-amine (Enantiomer 1)

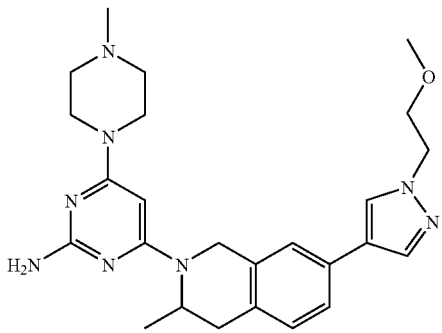 [SMILES: COCCn1cc(-c2ccc3c(c2)CN(c2cc(N4CCN(C)CC4)nc(N)n2)C(C)C3)cn1]

Step 1: 1-(2-methoxyethyl)-4-(4,4,5,5-tetramethyl-1,3,2-dioxaborolan-2-yl)-1H-pyrazole

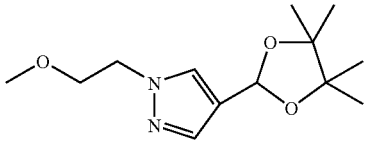

A mixture of [A] 4-(4,4,5,5-tetramethyl-1,3,2-dioxaborolan-2-yl)-1H-pyrazole (100 mg, 0.5 mmol), 2-bromoethyl methyl ether (58 uL, 0.62 mmol, Aldrich, Cat. No. 238155), and cesium carbonate (500.0 mg, 1.5 mmol) in acetonitrile (1 mL) was stirred at 90° C. overnight. After cooling it was quenched with water, extracted with ethyl acetate. The extract was washed with water twice, brine once; dried over $Na_2SO_4$. After filtration the filtrate was concentrated to yield 90 mg of the product. LCMS $(M+H)^+$: m/z=253.1

Step 2: 4-[7-[1-(2-methoxyethyl)-1H-pyrazol-4-yl]-3-methyl-3,4-dihydroisoquinolin-2(1H)-yl]-6-(4-methylpiperazin-1-yl)pyrimidin-2-amine A mixture of 4-(7-bromo-3-methyl-3,4-dihydroisoquinolin-2(1H)-yl)-6-(4-methylpiperazin-1-yl)pyrimidin-2-amine (10 mg, 0.02 mmol; Peak 1, Example 49, Step 7), 1-(2-methoxyethyl)-4-(4,4,5,5-tetramethyl-1,3,2-dioxaborolan-2-yl)-1H-pyrazole (9.1 mg, 0.036 mmol), tetrakis(triphenylphosphine)palladium(0) (1.4 mg, 0.0012 mmol), and sodium bicarbonate (6.0 mg, 0.072 mmol) in 1,4-dioxane (0.2 mL) and water (0.1 mL) was stirred at 90° C. for 2 h. After cooling, it was diluted with methanol, and purified with RP-HPLC (pH=10). to afford the desired product (4.7 mg). LCMS $(M+H)^+$: m/z=463.3.

Example 113

2-(4-{2-[2-Amino-6-(4-methylpiperazin-1-yl)pyrimidin-4-yl]-3-methyl-1,2,3,4-tetrahydroisoquinolin-7-yl}-1H-pyrazol-1-yl)acetamide (Enantiomer 1)

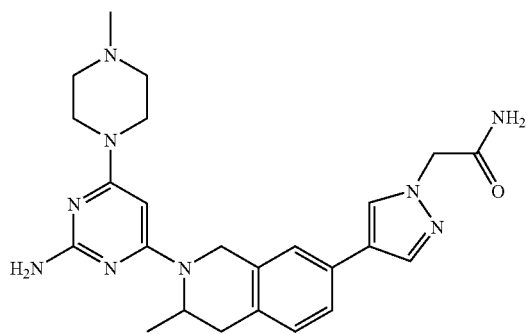 [SMILES: CC1Cc2ccc(-c3cnn(CC(N)=O)c3)cc2CN1c1cc(N2CCN(C)CC2)nc(N)n1]

Step 1: 2-[4-(4,4,5,5-tetramethyl-1,3,2-dioxaborolan-2-yl)-1H-pyrazol-1-yl]acetamide

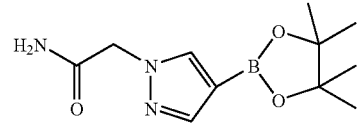

A mixture of 4-(4,4,5,5-tetramethyl-1,3,2-dioxaborolan-2-yl)-1H-pyrazole (50 mg, 0.2 mmol), 2-Bromoacetamide (43 mg, 0.31 mmol, Aldrich, Cat. No. 301272), and cesium carbonate (250 mg, 0.77 mmol) in acetonitrile (1 mL) was stirred at 90° C. for 2 h. After cooling it was quenched with water, extracted with ethyl acetate. The extract was washed with water twice, brine once; dried over $Na_2SO_4$. After filtration the filtrate was concentrated to yield 45 mg of the product which was directly used in the next step reaction without further purification. LCMS (M+H)+: m/z=252.1

Step 2: 2-(4-{2-[2-amino-6-(4-methylpiperazin-1-yl) pyrimidin-4-yl]-3-methyl-1,2,3,4-tetrahydroisoquinolin-7-yl}-1H-pyrazol-1-yl)acetamide A mixture of 4-(7-bromo-3-methyl-3,4-dihydroisoquinolin-2(1H)-yl)-6-(4-methylpiperazin-1-yl)pyrimidin-2-amine (10 mg, 0.02 mmol; Peak 1, Example 49, Step 7), 2-[4-(4,4,5,5-tetramethyl-1,3,2-dioxaborolan-2-yl)-1H-pyrazol-1-yl] acetamide (7.2 mg, 0.029 mmol), tetrakis(triphenylphosphine)palladium(0) (1.4 mg, 0.0012 mmol), and sodium bicarbonate (6.0 mg, 0.072 mmol) in 1,4-dioxane (0.2 mL) and water (0.1 mL) was stirred at 90° C. overnight. After cooling, it was diluted with methanol, and purified with RP-HPLC (pH=10 to afford the desired product (1.5 mg). LCMS (M+H)+: m/z=462.3.

Example 114

3-(4-{2-[2-Amino-6-(4-methylpiperazin-1-yl)pyrimidin-4-yl]-3-methyl-1,2,3,4-tetrahydroisoquinolin-7-yl}-1H-pyrazol-1-yl)propanamide (Enantiomer 1)

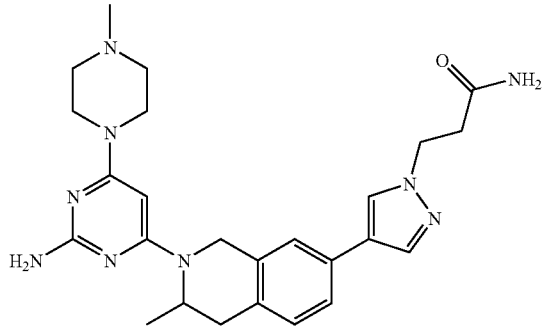 [SMILES: CC1Cc2ccc(-c3cnn(CCC(N)=O)c3)cc2CN1c1cc(N2CCN(C)CC2)nc(N)n1]

Step 1: 3-[4-(4,4,5,5-tetramethyl-1,3,2-dioxaborolan-2-yl)-1H-pyrazol-1-yl]propanamide

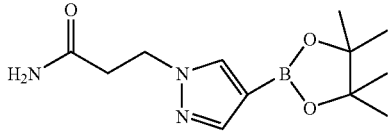 [SMILES: CC1(C)OB(c2cnn(CCC(N)=O)c2)OC1(C)C]

A mixture of 4-(4,4,5,5-tetramethyl-1,3,2-dioxaborolan-2-yl)-1H-pyrazole (50 mg, 0.2 mmol), 3-bromopropanamide (47 mg, 0.31 mmol, TCI-EP, Cat. No. B1410), and cesium carbonate (250 mg, 0.77 mmol) in acetonitrile (1 mL) was stirred at 90° C. for 2 hours. After cooling it was quenched with water, extracted with ethyl acetate. The extract was washed with water, brine; dried over $Na_2SO_4$. After filtration the filtrate was concentrated to yield 45 mg of the product which was directly used in the next step reaction without further purification. LCMS (M+H)+: m/z=266.2

Step 2: 3-(4-{2-[2-amino-6-(4-methylpiperazin-1-yl) pyrimidin-4-yl]-3-methyl-1,2,3,4-tetrahydroisoquinolin-7-yl}-1H-pyrazol-1-yl)propanamide A mixture of 4-(7-bromo-3-methyl-3,4-dihydroisoquinolin-2(1H)-yl)-6-(4-methylpiperazin-1-yl)pyrimidin-2-amine (10 mg, 0.02 mmol; Peak 1, Example 49, Step 7), 3-[4-(4,4,5,5-tetramethyl-1,3,2-dioxaborolan-2-yl)-1H-pyrazol-1-yl] propanamide (7.6 mg, 0.029 mmol), tetrakis(triphenylphosphine)palladium(0) (1.4 mg, 0.0012 mmol), and sodium bicarbonate (6.0 mg, 0.072 mmol) in 1,4-dioxane (0.2 mL) and water (0.1 mL) was stirred at 90° C. overnight. After cooling, it was diluted with methanol, and purified with RP-HPLC (pH=10) to afford the desired product (3.2 mg). LCMS (M+H)+: m/z=476.2.

Example 115

4-[7-(1-Cyclopentyl-1H-pyrazol-4-yl)-3-methyl-3,4-dihydroisoquinolin-2(1 H)-yl]-6-(4-methylpiperazin-1-yl)pyrimidin-2-amine (Enantiomer 1)

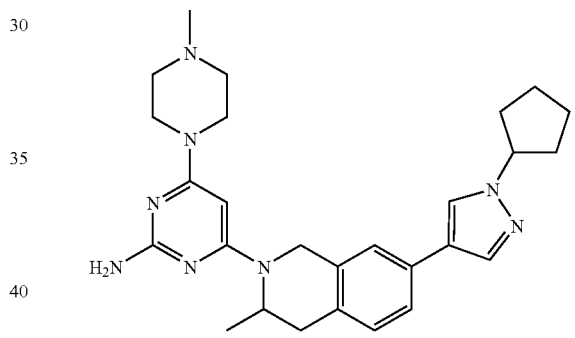

Step 1: 1-cyclopentyl-4-(4,4,5,5-tetramethyl-1,3,2-dioxaborolan-2-yl)-1H-pyrazole

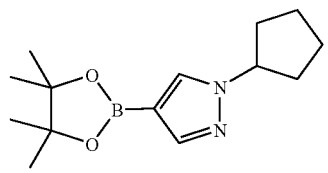 [SMILES: CC1(C)OB(c2cnn(C3CCCC3)c2)OC1(C)C]

A mixture of 4-(4,4,5,5-tetramethyl-1,3,2-dioxaborolan-2-yl)-1H-pyrazole (50 mg, 0.2 mmol), cyclopentyl bromide (46 mg, 0.31 mmol, Aldrich, Cat. No. C115207), and cesium carbonate (250 mg, 0.77 mmol) in acetonitrile (1 mL) was stirred at 90° C. for 2 hours. After cooling it was quenched with water, extracted with ethyl acetate. The extract was washed with water, brine; dried over $Na_2SO_4$. After filtration the filtrate was concentrated to yield 40 mg of the product which was directly used in the next step reaction without further purification. LCMS (M+H)+: m/z=263.3

Step 2: 4-[7-(1-cyclopentyl-1H-pyrazol-4-yl)-3-methyl-3,4-dihydroisoquinolin-2(1 H)-yl]-6-(4-methylpiperazin-1-yl)pyrimidin-2-amine A mixture of 4-(7-bromo-3-methyl-3,4-dihydroisoquinolin-2(1H)-yl)-6-(4-methylpiperazin-1-yl)pyrimidin-2-amine (10 mg, 0.02 mmol; Peak 1, Example 49, Step 7), 1-cyclopentyl-4-(4,4,5,5-tetramethyl-1,3,2-dioxaborolan-2-yl)-1H-pyrazole (7.5 mg, 0.029 mmol), tetrakis(triphenylphosphine)palladium(0) (1.4 mg, 0.0012 mmol), and sodium bicarbonate (6.0 mg, 0.072 mmol) in 1,4-dioxane (0.2 mL) and water (0.1 mL) was stirred at 90° C. overnight. After cooling, it was diluted with methanol, and purified with RP-HPLC (pH=10) to afford the desired product (4.7 mg). LCMS (M+H)+: m/z=473.2.

Example 116

4-[3-Methyl-7-(2-methyl-1,3-thiazol-4-yl)-3,4-dihydroisoquinolin-2(1H)-yl]-6-(4-methylpiperazin-1-yl)pyrimidin-2-amine

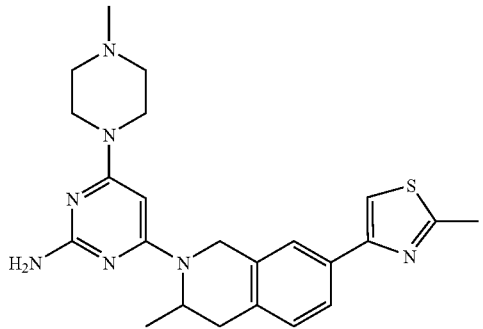 [SMILES: Cc1nc(-c2ccc3c(c2)CN(c2cc(N4CCN(C)CC4)nc(N)n2)C(C)C3)cs1]

Step 1: 4-(4-methylpiperazin-1-yl)-6-[3-methyl-7-(4,4,5,5-tetramethyl-1,3,2-dioxaborolan-2-yl)-3,4-dihydroisoquinolin-2(1H)-yl]pyrimidin-2-amine

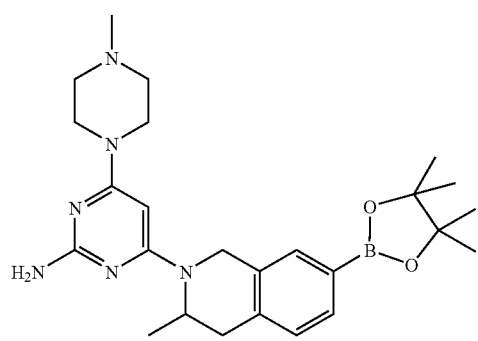 [SMILES: CC1Cc2ccc(B3OC(C)(C)C(C)(C)O3)cc2CN1c1cc(N2CCN(C)CC2)nc(N)n1]

To a solution of 4-(7-bromo-3-methyl-3,4-dihydroisoquinolin-2(1H)-yl)-6-(4-methylpiperazin-1-yl)pyrimidin-2-amine (0.390 g, 0.934 mmol) (Example 49, Step 6) and 4,4,5,5,4',4',5',5'-octamethyl-[2,2']bi[[1,3,2]dioxaborolanyl] (0.356 g, 1.40 mmol, Aldrich, Cat. No. 473294) in dioxane (5 mL) was added [1,1'-bis(diphenylphosphino)ferrocene]dichloropalladium(II) complex with dichloromethane (1:1) (22.9 mg, 0.0280 mmol, Aldrich, Cat. No. 379270), potassium acetate (0.275 g, 2.80 mmol), and 1,1'-bis(diphenylphosphino)ferrocene (15.5 mg, 0.0280 mmol, Aldrich, Cat. No. 177261) under nitrogen. The reaction mixture was stirred at 120° C. for 3 h. After cooled to r.t., the mixture was filtered through a pad of celite, washed with ethyl acetate, and concentrated under reduced pressure to afford the crude product which was directly used in next step reaction without further purification. LCMS (M+H)+: m/z=465.4.

Step 2: 4-[3-methyl-7-(2-methyl-1,3-thiazol-4-yl)-3,4-dihydroisoquinolin-2(1 H)-yl]-6-(4-methylpiperazin-1-yl)pyrimidin-2-amine A mixture of 4-(4-methylpiperazin-1-yl)-6-[3-methyl-7-(4,4,5,5-tetramethyl-1,3,2-dioxaborolan-2-yl)-3,4-dihydroisoquinolin-2(1H)-yl]pyrimidin-2-amine (0.0464 g, 0.100 mmol), 4-bromo-2-methyl-1,3-thiazole (0.0231 g, 0.130 mmol, Frontier, Cat. No. B4559) in 1,4-dioxane (1.0 mL) was stirred at r.t. for 10 min. Potassium carbonate (63.0 mg, 0.456 mmol) in water (0.50 mL) was added to give a deep red solution. The mixture was degassed and refilled with nitrogen three times. [1,1'-Bis(diphenylphosphino)ferrocene]dichloropalladium(II) complex with dichloromethane (1:1) (5.0 mg, 0.0061 mmol) was added and the mixture was degassed and refilled with nitrogen three times and then heated at 120° C.) (oil bath temperature) for 3 h. After cooling, the mixture was diluted with methanol, and filtered. The filtrate was purified on RP-HPLC (pH=10) to afford the desired product. LCMS (M+H)+: m/z=436.1.

Example 117

4-[7-(2-Ethoxy-1,3-thiazol-4-yl)-3-methyl-3,4-dihydroisoquinolin-2(1H)-yl]-6-(4-methylpiperazin-1-yl)pyrimidin-2-amine

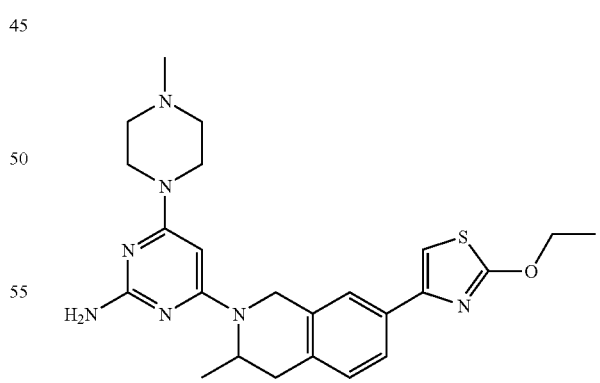

This compound was prepared by using procedures analogous to those described for the synthesis of Example 116 starting from 4-(4-methylpiperazin-1-yl)-6-[3-methyl-7-(4,4,5,5-tetramethyl-1,3,2-dioxaborolan-2-yl)-3,4-dihydroisoquinolin-2(1H)-yl]pyrimidin-2-amine and 4-bromo-2-ethoxy-1,3-thiazole (Indofine, Cat. No. 08-932). LCMS (M+H)+: m/z=466.2.

Example 118

4-[(3R)-3-Aminopyrrolidin-1-yl]-6-[3-methyl-7-(1-methyl-1H-pyrazol-4-yl)-3,4-dihydroisoquinolin-2(1H)-yl]pyrimidin-2-amine

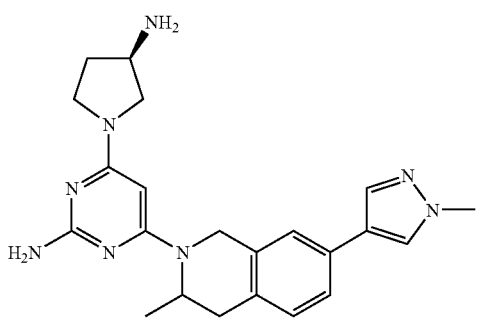 [SMILES: CC1Cc2ccc(-c3cnn(C)c3)cc2CN1c1cc(N2CC[C@@H](N)C2)nc(N)n1]

Step 1: tert-butyl 7-bromo-3-methyl-3,4-dihydroisoquinoline-2(1H)-carboxylate

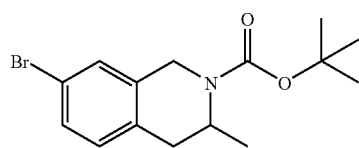 [SMILES: CC1Cc2ccc(Br)cc2CN1C(=O)OC(C)(C)C]

To a solution of 7-bromo-3-methyl-1,2,3,4-tetrahydroisoquinoline hydroiodide (1.00 g, 2.82 mmol, Example 49, Step 4) in tetrahydrofuran (9 mL) was added di-tert-butyldicarbonate (0.925 g, 4.24 mmol) and sodium carbonate (0.599 g, 5.65 mmol) in water (4 mL). The mixture was stirred at r.t. 3 h. The mixture was diluted with ethyl acetate, washed with water and brine, dried over Na$_2$SO$_4$, filtered, and concentrated under reduced pressure to afford the crude product which was directly used in next step reaction without further purification. LCMS (M−56)$^+$: m/z=270.0/272.0.

Step 2: tert-butyl 3-methyl-7-(1-methyl-1H-pyrazol-4-yl)-3,4-dihydroisoquinoline-2(1H)-carboxylate

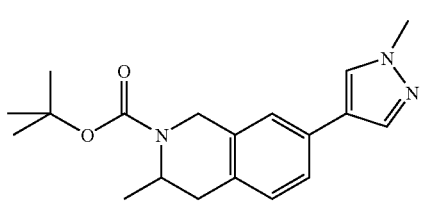 [SMILES: CC1Cc2ccc(-c3cnn(C)c3)cc2CN1C(=O)OC(C)(C)C]

A mixture of tert-butyl 7-bromo-3-methyl-3,4-dihydroisoquinoline-2(1H)-carboxylate (0.326 g, 1.00 mmol), 1-methyl-4-(4,4,5,5-tetramethyl-1,3,2-dioxaborolan-2-yl)-1H-pyrazole (0.31 g, 1.50 mmol, Aldrich, Cat. No. 595314), in 1,4-dioxane (4.0 mL) was stirred at r.t. for 10 min. Potassium carbonate (415 mg, 3.00 mmol) in water (2.0 mL) was added to give a deep red solution. The mixture was degassed and refilled with nitrogen three times. [1,1'-Bis(diphenylphosphino)ferrocene]dichloropalladium(II) complex with dichloromethane (1:1) (35.0 mg, 0.0424 mmol) was added and the mixture was degassed and refilled with nitrogen three times and then heated at 120° C.)(oil bath temperature) for 3 h. After cooling, the mixture was diluted with ethyl acetate, washed with water and brine, dried over Na$_2$SO$_4$, filtered and concentrated under reduced pressure. The residue was purified by flash chromatography on a silica gel column with methanol in DCM (0-10%) to give the desired product (320 mg, 97.7%). LCMS (M+H)$^+$: m/z=328.1.

Step 3: 6-chloro-4-[3-methyl-7-(1-methyl-1H-pyrazol-4-yl)-3,4-dihydroisoquinolin-2(1H)-yl]pyrimidin-2-amine

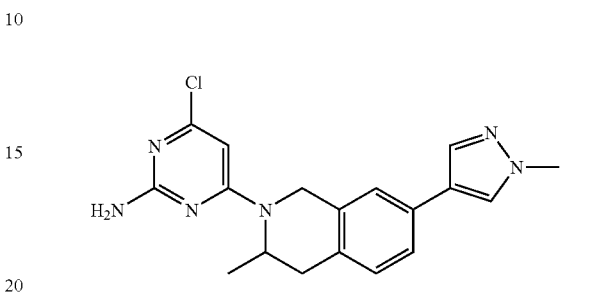

tert-butyl 3-methyl-7-(1-methyl-1H-pyrazol-4-yl)-3,4-dihydroisoquinoline-2(1H)-carboxylate (0.320 g, 0.977 mmol) in ethyl acetate (1 mL) was treated with 4.0 M of hydrogen chloride in 1,4-dioxane (1.00 mL, 4.00 mmol) at r.t. for 1 h. The mixture was diluted with ether (5 mL), and was centrifugalized. The solvents were decanted. The residue was dried in-vacuo, and dissolved in tert-butanol (10 mL). To the solution was added 2-amino-4,6-dichloropyrimidine (0.246 g, 1.50 mmol) and N,N-diisopropylethylamine (522 uL, 3.00 mmol). The mixture was heated and stirred at 120° C. overnight. The solvent was removed under reduced pressure. The residue was purified by flash chromatography on a silica gel column with methanol in DCM (0-10%) to give the desired product (303 mg, 87.6%). LCMS (M+H)$^+$: m/z=355.1/357.1.

Step 4: 4-[(3R)-3-aminopyrrolidin-1-yl]-6-[3-methyl-7-(1-methyl-1H-pyrazol-4-yl)-3,4-dihydroisoquinolin-2(1H)-yl]pyrimidin-2-amine A mixture of 4-chloro-6-[3-methyl-7-(1-methyl-1H-pyrazol-4-yl)-3,4-dihydroisoquinolin-2(1H)-yl]pyrimidin-2-amine (18 mg, 0.050 mmol), tert-butyl(3R)-pyrrolidin-3-yl-carbamate (27.9 mg, 0.150 mmol, TCI, Cat. No. A1171) and N,N-diisopropylethylamine (20.0 L, 0.115 mmol) in tert-butyl alcohol (0.5 mL) was heated at 120° C. overnight. After cooling, the mixture was diluted with methanol. To the solution was added 4N HCl in dioxane (0.3 mL). The mixture was stirred at r.t. for 2 h., and purified by RP-HPLC (pH=2) to afford the desired product as TFA salt. LCMS (M+H)$^+$: m/z=405.2.

Example 119

4-[(3S)-3-Aminopiperidin-1-yl]-6-[3-methyl-7-(1-methyl-1H-pyrazol-4-yl)-3,4-dihydroisoquinolin-2(1H)-yl]pyrimidin-2-amine

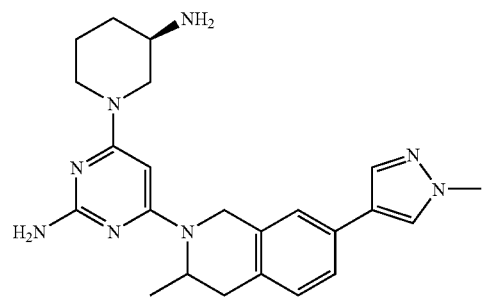 [SMILES: CC1Cc2ccc(-c3cnn(C)c3)cc2CN1c1cc(N2CCC[C@@H](N)C2)nc(N)n1]

This compound was prepared as TFA salt by using procedures analogous to those described for the synthesis of Example 118 starting from 4-chloro-6-[3-methyl-7-(1-methyl-1H-pyrazol-4-yl)-3,4-dihydroisoquinolin-2(1H)-yl]pyrimidin-2-amine and tert-butyl(3S)-piperidin-3-ylcarbamate (CNH Technologies, Cat. No. C-3102S). LCMS (M+H)+: m/z=419.2.

Example 120

4-(4-Aminopiperidin-1-yl)-6-[3-methyl-7-(1-methyl-1H-pyrazol-4-yl)-3,4-dihydroisoquinolin-2(1H)-yl]pyrimidin-2-amine

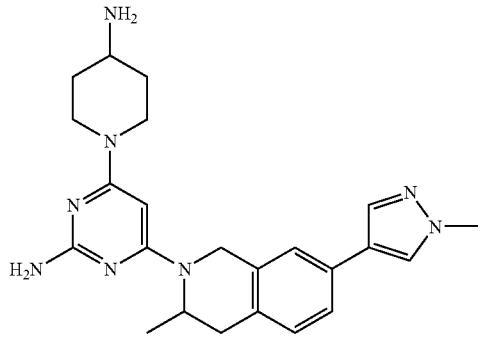 [SMILES: CC1Cc2ccc(-c3cnn(C)c3)cc2CN1c1cc(N2CCC(N)CC2)nc(N)n1]

This compound was prepared as TFA salt by using procedures analogous to those described for the synthesis of Example 118 starting from 4-chloro-6-[3-methyl-7-(1-methyl-1H-pyrazol-4-yl)-3,4-dihydroisoquinolin-2(1H)-yl]pyrimidin-2-amine and tert-butyl piperidin-4-ylcarbamate (Aldrich, Cat. No. 540935). LCMS (M+H)+: m/z=419.2.

Example 121

4-[3-Methyl-7-(1-methyl-1H-pyrazol-4-yl)-3,4-dihydroisoquinolin-2(1H)-yl]-6-piperazin-1-ylpyrimidin-2-amine

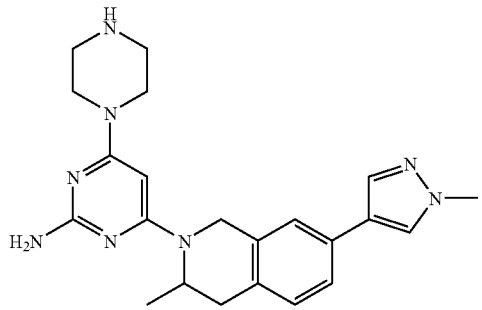 [SMILES: CC1Cc2ccc(-c3cnn(C)c3)cc2CN1c1cc(N2CCNCC2)nc(N)n1]

This compound was prepared as TFA salt by using procedures analogous to those described for the synthesis of Example 118 starting from 4-chloro-6-[3-methyl-7-(1-methyl-1H-pyrazol-4-yl)-3,4-dihydroisoquinolin-2(1H)-yl]pyrimidin-2-amine and tert-butyl piperazine-1-carboxylate (Aldrich, Cat. No. 343536). LCMS (M+H)+: m/z=405.2.

Example 122

4-(1,4-Diazepan-1-yl)-6-[3-methyl-7-(1-methyl-1H-pyrazol-4-yl)-3,4-dihydroisoquinolin-2(1H)-yl]pyrimidin-2-amine

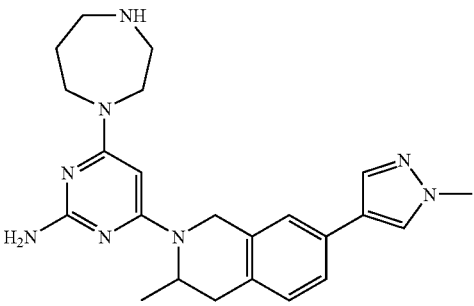 [SMILES: CC1Cc2ccc(-c3cnn(C)c3)cc2CN1c1cc(N2CCCNCC2)nc(N)n1]

A mixture of 4-chloro-6-[3-methyl-7-(1-methyl-1H-pyrazol-4-yl)-3,4-dihydroisoquinolin-2(1H)-yl]pyrimidin-2-amine (18 mg, 0.050 mmol), 1,4-diazepane (15.0 mg, 0.150 mmol, Aldrich, Cat. No. H16604)) and N,N-diisopropylethylamine (20.0 uL, 0.115 mmol) in tert-butyl alcohol (0.5 mL, 5 mmol) was heated at 120° C. overnight. After cooling, the mixture was diluted with methanol, and purified by RP-HPLC (pH=10) to afford the desired product. (M+H)+: m/z=419.2.

Example 123

4-(2,5-Diazabicyclo[2.2.1]hept-2-yl)-6-[3-methyl-7-(1-methyl-1H-pyrazol-4-yl)-3,4-dihydroisoquinolin-2(1H)-yl]pyrimidin-2-amine

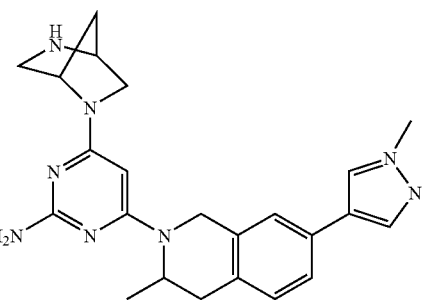

This compound was prepared as TFA salt by using procedures analogous to those described for the synthesis of Example 118 starting from 4-chloro-6-[3-methyl-7-(1-methyl-1H-pyrazol-4-yl)-3,4-dihydroisoquinolin-2(1H)-yl]pyrimidin-2-amine and tert-butyl 2,5-diazabicyclo[2.2.1]heptane-2-carboxylate (Alfa Aesar, Cat. No. L20131). LCMS (M+H)+: m/z=417.2.

Example 124

4-[(3R)-3-(Methylamino)pyrrolidin-1-yl]-6-[3-methyl-7-(1-methyl-1H-pyrazol-4-yl)-3,4-dihydroisoquinolin-2(1H)-yl]pyrimidin-2-amine

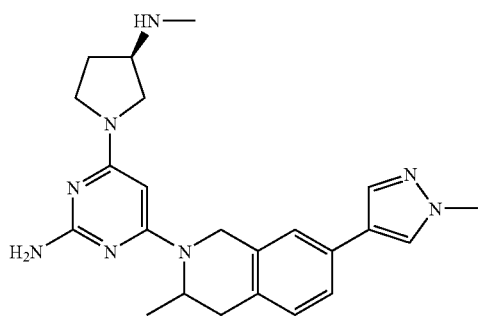 [SMILES: CN[C@@H]1CCN(c2cc(N3Cc4cc(-c5cnn(C)c5)ccc4CC3C)nc(N)n2)C1]

Step 1: benzyl(3R)-3-[(tert-butoxycarbonyl)(methyl)amino]pyrrolidine-1-carboxylate

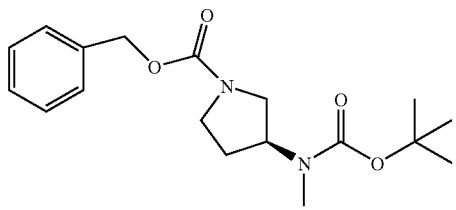 [SMILES: CN(C(=O)OC(C)(C)C)[C@H]1CCN(C(=O)OCc2ccccc2)C1]

Benzyl chloroformate (0.749 mL, 5.25 mmol) was added to a solution of tert-butyl(3R)-pyrrolidin-3-ylcarbamate (0.93 g, 5.0 mmol, TCI, Cat. No. A1171) and triethylamine (1.39 mL, 10.0 mmol) in methylene chloride (15.0 mL) at 0° C. The mixture was stirred at r.t. for 1 h. The mixture was diluted with CH$_2$Cl$_2$, washed with 0.5 N aqueous HCl, water and brine, dried over Na$_2$SO$_4$, filtered, and concentrated under reduced pressure. The residue was dissolved in N,N-dimethylformamide (10.0 mL), and cooled with ice-water. To the solution was added sodium hydride (0.300 g, 7.50 mmol) in small portions. The mixture was stirred for 15 min at r.t., and then methyl iodide (1.42 g, 10.0 mmol) was added. The mixture was stirred for additional 30 min., then diluted with ether, washed with water and brine, over Na$_2$SO$_4$, filtered, and concentrated under reduced pressure to give the desired product which was directly used in the next step reaction without further purification. LCMS (M+Na)$^+$: m/z=357.3.

Step 2: tert-butyl methyl[(3R)-pyrrolidin-3-yl]carbamate

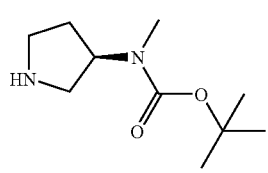

Pd/C (wt. 10%, 400 mg) was added to a solution of benzyl (3R)-3-[tert-butoxycarbonyl)(methyl)amino]pyrrolidine-1-carboxylate (1.4 g, 4.2 mmol) in methanol (10.0 mL) under nitrogen. The mixture was stirred under hydrogen balloon for 2 h., and filtered. The filtrate was concentrated under reduced pressure to give the desired product which was directly used in the next step reaction without further purification. LCMS (M+Na)$^+$: m/z=201.3.

Step 3: 4-[(3R)-3-(Methylamino)pyrrolidin-1-yl]-6-[3-methyl-7-(1-methyl-1H-pyrazol-4-yl)-3,4-dihydroisoquinolin-2(1H)-yl]pyrimidin-2-amine This compound was prepared as TFA salt by using procedures analogous to those described for the synthesis of Example 118 starting from 4-chloro-6-[3-methyl-7-(1-methyl-1H-pyrazol-4-yl)-3,4-dihydroisoquinolin-2(1H)-yl]pyrimidin-2-amine and tert-butyl methyl[(3R)-pyrrolidin-3-yl]carbamate. LCMS (M+H)$^+$: m/z=419.2.

Example 125

4-(4-Methyl-1,4-diazepan-1-yl)-6-[3-methyl-7-(1-methyl-1H-pyrazol-4-yl)-3,4-dihydroisoquinolin-2(1H)-yl]pyrimidin-2-amine

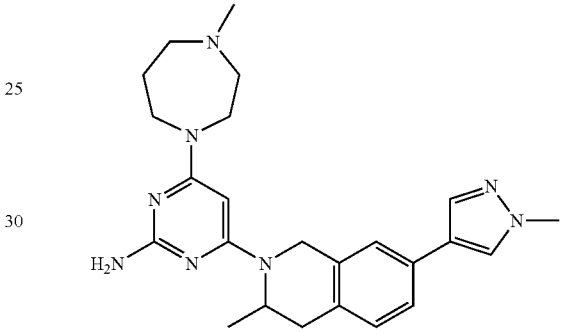

This compound was prepared by using procedures analogous to those described for the synthesis of Example 118 starting from 4-chloro-6-[3-methyl-7-(1-methyl-1H-pyrazol-4-yl)-3,4-dihydroisoquinolin-2(1H)-yl]pyrimidin-2-amine and 1-methyl-1,4-diazepane (Aldrich, Cat. No. 186090). LCMS (M+H)$^+$: m/z=433.3.

Example 126

4-(Hexahydropyrrolo[1,2-a]pyrazin-2(1H)-yl)-6-[3-methyl-7-(1-methyl-1H-pyrazol-4-yl)-3,4-dihydroisoquinolin-2(1H)-yl]pyrimidin-2-amine

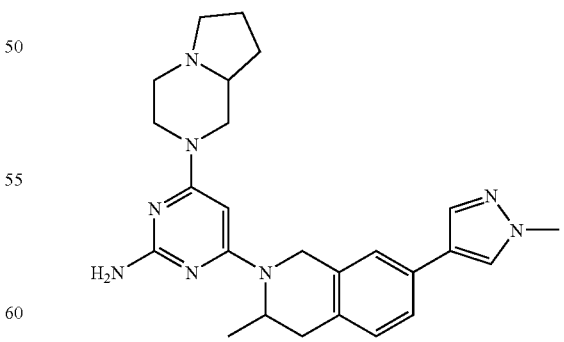

This compound was prepared by using procedures analogous to those described for the synthesis of Example 118 starting from 4-chloro-6-[3-methyl-7-(1-methyl-1H-pyrazol-4-yl)-3,4-dihydroisoquinolin-2(1H)-yl]pyrimidin-2-amine and octahydropyrrolo[1,2-a]pyrazine (Oakwood, Cat. No. 032034). LCMS (M+H)$^+$: m/z=445.2.

Example 127

5-{2-[2-Amino-6-(4-methylpiperazin-1-yl)pyrimidin-4-yl]-6-fluoro-1,2,3,4-tetrahydroisoquinolin-7-yl}-N-methylpyridine-2-carboxamide

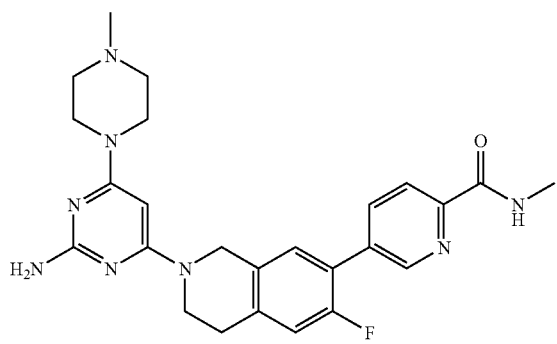 [SMILES: CNC(=O)c1ccc(-c2cc3c(cc2F)CCN(c2cc(N4CCN(C)CC4)nc(N)n2)C3)cn1]

Step 1: 7-bromo-6-fluoroisoquinoline

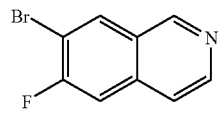

A reaction mixture of 3-bromo-4-fluorobenzaldehyde (1.70 g, 8.37 mmol) and aminoacetaldehyde dimethyl acetal (0.917 mL, 8.37 mmol) in toluene (17.0 mL) was stirred at r.t. overnight. Then sulfuric acid (10 mL) and phosphorus pentoxide (2.38 g, 8.37 mmol) were added. The mixture was stirred at 160° C. for 1 h. After cooled, the mixture was poured into crushed ice. The acidic mixture was carefully adjusted to pH=8 by the addition of aqueous NaOH solution (1 N) with stirring and external cooling. The mixture was extracted with ethyl acetate (3×200 mL). The combined organic layers were washed with brine, dried over MgSO$_4$, filtered, and concentrated under reduced pressure. The residue was purified by flash chromatography on a silica gel column with 40% ethyl acetate in hexanes to afford the desired product (0.35 g, 18.5%). LCMS (M+H)$^+$: m/z=225.9/227.9.

Step 2: tert-butyl 7-bromo-6-fluoro-3,4-dihydroisoquinoline-2(1H)-carboxylate

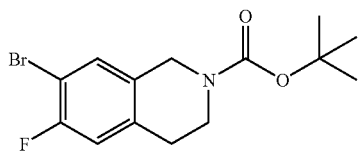 [SMILES: CC(C)(C)OC(=O)N1CCc2cc(F)c(Br)cc2C1]

To a solution of 7-bromo-6-fluoroisoquinoline (0.50 g, 2.2 mmol) in THF (10 mL) was added 1.0 M of lithium triethylborohydride in THF (9.7 mL, 9.7 mmol) dropwise under N$_2$ at r.t. The reaction mixture was stirred for 2 h. The mixture was adjusted to pH=2 with aqueous HCl, then adjusted to pH=10 with aqueous Na$_2$CO$_3$. LCMS (M+H)$^+$: m/z=229.9/232.0.

A solution of di-tert-butyldicarbonate (0.53 g, 2.4 mmol) in THF (4.0 mL) was added to the above mixture at r.t. The reaction mixture was stirred at r.t. for 30 min, extracted with ethyl acetate (3×20 mL). The combined organic layers were dried over MgSO$_4$, filtered and concentrated. The residue was purified by flash chromatography on a silica gel column with 20% ethyl acetate in hexanes to afford the desired product. LCMS (M+H)$^+$: m/z=272.0/273.9.

Step 3: 7-bromo-6-fluoro-1,2,3,4-tetrahydroisoquinoline

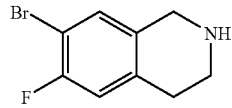

tert-Butyl 7-bromo-6-fluoro-3,4-dihydroisoquinoline-2(1H)-carboxylate (0.272 g, 1.0 mmol) in ethyl acetate (1 mL) was treated with 4.0 M of hydrogen chloride in 1,4-dioxane (1.0 mL, 4.0 mmol) at r.t. for 2 h. The mixture was diluted with ethyl ether, and centrifugalized. The solvents were decanted. The residue was dried in-vacuo to afford the desired product as HCl salt which was directly used in next step reaction without further purification.

Step 4: 4-(7-bromo-6-fluoro-3,4-dihydroisoquinolin-2(1H)-yl)-6-(4-methylpiperazin-1-yl)pyrimidin-2-amine

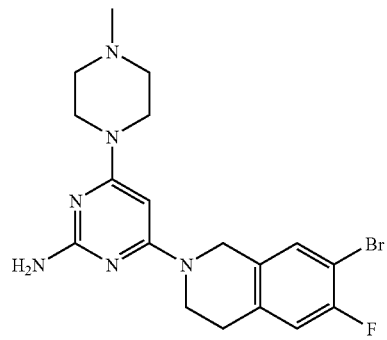 [SMILES: CN1CCN(c2cc(N3CCc4cc(F)c(Br)cc4C3)nc(N)n2)CC1]

A mixture of 2-amino-4,6-dichloropyrimidine (0.149 g, 0.908 mmol), 7-bromo-6-fluoro-1,2,3,4-tetrahydroisoquinoline hydrochloride (0.242 g, 0.908 mmol) and, 1,4-dimethylpiperazine (487 uL, 3.63 mmol) in tert-butyl alcohol (2.00 mL, 20.9 mmol) was heated at 90° C. for 2 h. After cooling, 1-methylpiperazine (202 uL, 1.82 mmol) was added. The mixture was heated at 120° C. overnight. After cooling, the volatiles were removed under reduced pressure. The residue was purified by flash chromatography on a silica gel column with methanol in DCM (0-10%) to give the desired product (215 mg, 56.2%). LCMS (M+H)$^+$: m/z=421.1/423.1.

Step 5: 5-{2-[2-amino-6-(4-methylpiperazin-1-yl)pyrimidin-4-yl]-6-fluoro-1,2,3,4-tetrahydroisoquinolin-7-yl}-N-methylpyridine-2-carboxamide

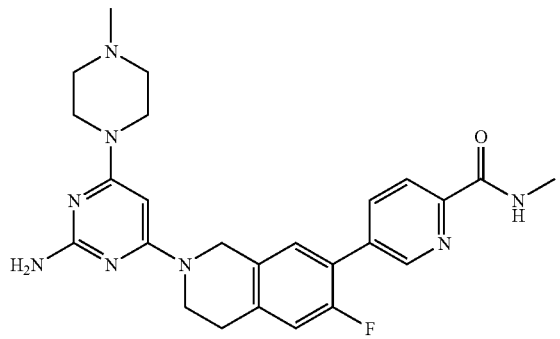 [SMILES: CNC(=O)c1ccc(-c2cc3c(cc2F)CCN(c2cc(N4CCN(C)CC4)nc(N)n2)C3)cn1]

A mixture of 4-(7-bromo-6-fluoro-3,4-dihydroisoquinolin-2(1H)-yl)-6-(4-methylpiperazin-1-yl)pyrimidin-2-amine (0.025 g, 0.060 mmol), N-methyl-5-(4,4,5,5-tetramethyl-1,3,2-dioxaborolan-2-yl)pyridine-2-carboxamide (0.0140 g, Frontier, Cat. No. M10074) in 1,4-dioxane (0.36 mL) was stirred at r.t. for 10 min. Potassium carbonate (37.8 mg, 0.274 mmol) in water (0.18 mL) was added. The mixture was degassed and refilled with nitrogen three times [1,1'-bis(diphenylphosphino)ferrocene]dichloropalladium(II) complex with dichloromethane (1:1) (3.0 mg, 0.0036 mmol) was added and the mixture was degassed and refilled with nitrogen three times and then heated at 120° C.) (oil bath temperature) for 3 h. After cooling, the mixture was diluted with methanol, and filtered. The filtrate was purified on RP-HPLC (pH=10) to afford the desired product. LCMS (M+H)$^+$: m/z=477.2.

Example 128

3-{2-[2-Amino-6-(4-methylpiperazin-1-yl)pyrimidin-4-yl]-6-fluoro-1,2,3,4-tetrahydroisoquinolin-7-yl}-N,N-dimethylbenzamide

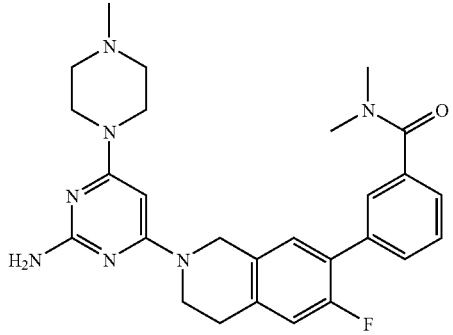 [SMILES: CN1CCN(c2cc(N3CCc4cc(F)c(-c5cccc(C(=O)N(C)C)c5)cc4C3)nc(N)n2)CC1]

This compound was prepared by using procedures analogous to those described for the synthesis of Example 127 starting from 4-(7-bromo-6-fluoro-3,4-dihydroisoquinolin-2(1H)-yl)-6-(4-methylpiperazin-1-yl)pyrimidin-2-amine and {3-[(dimethylamino)carbonyl]phenyl}boronic acid (Frontier, Cat. No. D4088). LCMS (M+H)$^+$: m/z=490.2.

Example 129

5-{2-[2-Amino-6-(4-methylpiperazin-1-yl)pyrimidin-4-yl]-3-methyl-1,2,3,4-tetrahydroisoquinolin-7-yl}-2-cyclopropylisoindolin-1-one

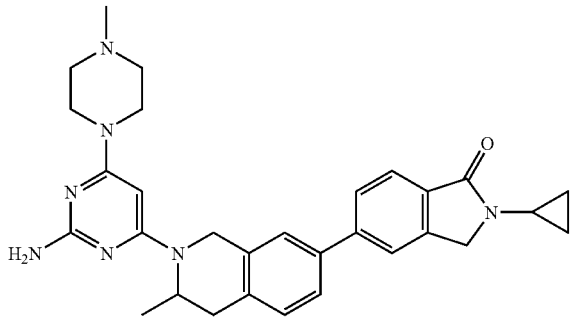 [SMILES: CC1Cc2ccc(-c3ccc4c(c3)CN(C3CC3)C4=O)cc2CN1c1cc(N2CCN(C)CC2)nc(N)n1]

Step 1. methyl 4-bromo-2-(bromomethyl)benzoate

A mixture of methyl 4-bromo-2-methylbenzoate (0.7 g, 0.003 mol), N-bromosuccinimide (0.65 g, 0.0037 mol) and benzoyl peroxide (0.038 g, 0.00016 mol) in carbon tetrachloride (30 mL) was refluxed under an atmosphere of nitrogen for 2 h. The mixture was cooled to RT, and filtered through silica gel eluting with dichloromethane followed by diethyl ether. The mixture was concentrated and the residue was purified by chromatography on silica gel with 30% EtOAc in hexanes to afford the desired product (0.86 g, 90%).

Step 2: 5-bromo-2-cyclopropylisoindolin-1-one

A mixture of methyl 4-bromo-2-(bromomethyl)benzoate (0.13 g, 0.42 mmol), cyclopropylamine (0.034 mL, 0.49 mmol) and potassium carbonate (0.090 g, 0.65 mmol) in ethanol (0.9 mL) was stirred at 40° C. for 3 h. The reaction mixture was quenched with saturated sodium bicarbonate and extracted with EtOAc (3×20 mL). The combined organic layers were washed with brine, dried over anhydrous Na$_2$SO$_4$, filtered, and concentrated. The residue was purified by chromatography on silica gel with 30% EtOAc in hexanes to afford the desired product (0.10 g, 94%). LCMS (M+H)$^+$: m/z=252.0/254.0.

Step 3: 2-cyclopropyl-5-(4,4,5,5-tetramethyl-1,3,2-dioxaborolan-2-yl)isoindolin-1-one

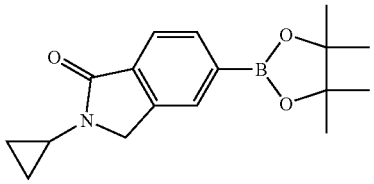 [SMILES: CC1(C)OB(c2ccc3c(c2)CN(C2CC2)C3=O)OC1(C)C]

To a solution of 5-bromo-2-cyclopropylisoindolin-1-one (0.51 g, 2.0 mmol) and 4,4,5,5,4',4',5',5'-octamethyl-[2,2']bi[[1,3,2]dioxaborolanyl] (0.56 g, 2.2 mmol) in 1,4-dioxane (4.88 mL) was added [1,1'-bis(diphenylphosphino)ferrocene]dichloropalladium(II) complex with dichloromethane (1:1) (0.08 g, 0.1 mmol), potassium acetate (0.60 g, 6.1 mmol), and 1,1'-bis(diphenylphosphino)ferrocene (0.06 g, 0.1 mmol) under an atmosphere of nitrogen. The reaction mixture was stirred at 80° C. overnight. After cooled to room temperature, the mixture was filtered through a pad of celite, washed with ethyl acetate, and concentrated under reduced pressure. The residue was purified by flash chromatography on a silica gel column with ethyl acetate in hexanes (40%) to afford the desired product. LCMS (M+H)$^+$: m/z=300.2.

Step 4: 5-{2-[2-amino-6-(4-methylpiperazin-1-yl)pyrimidin-4-yl]-3-methyl-1,2,3,4-tetrahydroisoquinolin-7-yl}-2-cyclopropylisoindolin-1-one

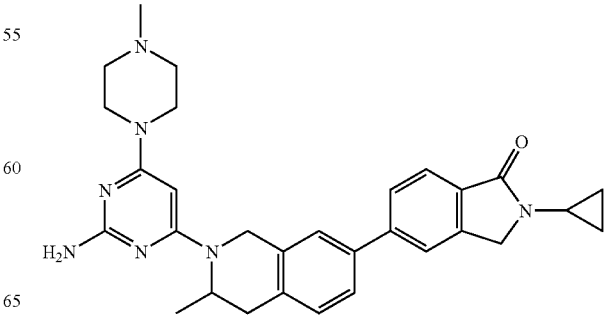

A mixture of 4-(7-bromo-3-methyl-3,4-dihydroisoquinolin-2(1H)-yl)-6-(4-methylpiperazin-1-yl)pyrimidin-2-amine (0.0209 g, 0.0500 mmol), 2-cyclopropyl-5-(4,4,5,5-tetramethyl-1,3,2-dioxaborolan-2-yl)isoindolin-1-one (0.0194 g, 0.0650 mmol), in 1,4-dioxane (0.30 mL) was stirred at r.t. for 10 min. Potassium carbonate (27.6 mg, 0.200 mmol) in water (0.15 mL) was added. The mixture was degassed and refilled with nitrogen three times. [1,1'-Bis(diphenylphosphino)ferrocene]dichloropalladium(II) complex with dichloromethane (1:1) (2.5 mg, 0.0030 mmol) was added The mixture was degassed and refilled with nitrogen three times, and heated at 120° C.) (oil bath temperature) for 1 h. After cooling, the mixture was diluted with methanol, and filtered. The filtrate was purified on RP-HPLC (pH=10) to afford the desired product. LCMS (M+H)$^+$: m/z=510.2.

Example 130

4-{2-[2-Amino-6-(4-methylpiperazin-1-yl)pyrimidin-4-yl]-3-methyl-1,2,3,4-tetrahydroisoquinolin-7-yl}-N,2-dimethylbenzamide

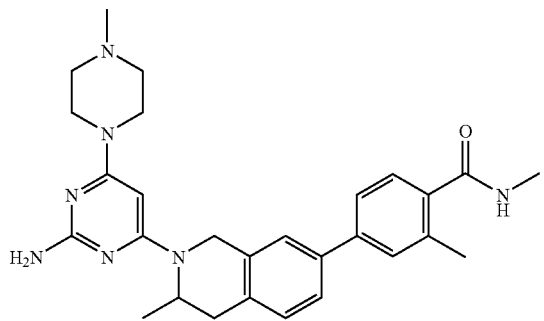 [SMILES: CNC(=O)c1ccc(-c2ccc3c(c2)CN(c2cc(N4CCN(C)CC4)nc(N)n2)C(C)C3)cc1C]

Step 1: 4-bromo-N,2-dimethylbenzamide

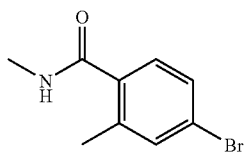

N,N-Dimethylformamide (10 uL) was added to a mixture of 4-bromo-2-methylbenzoic acid (1.0 g, 0.0046 mol) in oxalyl chloride (2.0 mL, 0.023 mol). The mixture was stirred at r.t. overnight. The volatiles were removed under reduced pressure. The residue was dissolved in methylene chloride (2 mL). To the solution was added to a mixture of methylamine (0.41 mL, 0.0093 mol) and triethylamine (1.3 mL, 0.0093 mol) in DCM (10 ml). After 30 min, the reaction mixture was quenched with aqueous sodium carbonate (10 mL) and extracted with DCM (3×20 mL). The organic layers were washed with brine, dried over Na$_2$SO$_4$, filtered. The solvents were removed under reduced pressure to give a crude product (980 mg, 92.4%). LCMS (M+H)$^+$: m/z=228.1/230.2.

Step 2: N,2-dimethyl-4-(4,4,5,5-tetramethyl-1,3,2-dioxaborolan-2-yl)benzamide

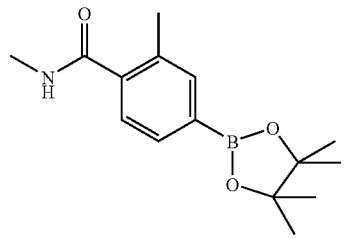

To a solution of 4-bromo-N,2-dimethylbenzamide (0.50 g, 0.0022 mol) and 4,4,5,5,4',4',5',5'-octamethyl-[2,2']bi[[1,3,2]dioxaborolanyl] (0.67 g, 0.0026 mol) in 1,4-dioxane (5.28 mL, 0.0677 mol) was added [1,1'-bis(diphenylphosphino)ferrocene]dichloropalladium(II) complex with dichloromethane (1:1) (0.09 g, 0.0001 mol), potassium acetate (0.64 g, 0.0066 mol), and 1,1'-bis(diphenylphosphino)ferrocene (0.06 g, 0.0001 mol) under an atmosphere of nitrogen. The reaction mixture was stirred at 80° C. overnight. After cooled to room temperature, the mixture was filtered, and concentrated under reduced pressure. The residue was purified by flash chromatography on a silica gel column with 30% EA in dichloromethane to afford the desired product (620 mg). LCMS (M+H)$^+$: m/z=276.4.

Step 3: 4-{2-[2-amino-6-(4-methylpiperazin-1-yl)pyrimidin-4-yl]-3-methyl-1,2,3,4-tetrahydroisoquinolin-7-yl}-N,2-dimethylbenzamide This compound was prepared by using procedures analogous to those described for the synthesis of Example 129, Step 4 starting from 4-(7-bromo-3-methyl-3,4-dihydroisoquinolin-2(1H)-yl)-6-(4-methylpiperazin-1-yl)pyrimidin-2-amine and N,2-dimethyl-4-(4,4,5,5-tetramethyl-1,3,2-dioxaborolan-2-yl)benzamide. LCMS (M+H)$^+$: m/z=486.298.

Example 131

6-{2-[2-Amino-6-(4-methylpiperazin-1-yl)pyrimidin-4-yl]-3-methyl-1,2,3,4-tetrahydroisoquinolin-7-yl}-2H-1,4-benzoxazin-3(4H)-one

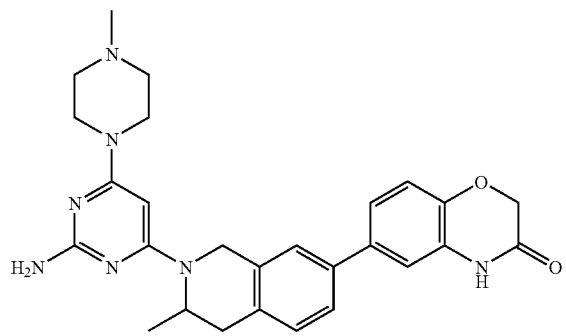 [SMILES: CC1Cc2ccc(-c3ccc4c(c3)NC(=O)CO4)cc2CN1c1cc(N2CCN(C)CC2)nc(N)n1]

Step 1: 6-(4,4,5,5-tetramethyl-1,3,2-dioxaborolan-2-yl)-2H-1,4-benzoxazin-3(4H)-one

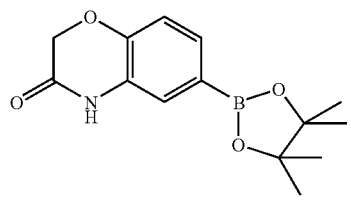 [SMILES: CC1(C)OB(c2ccc3c(c2)NC(=O)CO3)OC1(C)C]

This compound was prepared by using procedures analogous to those described for the synthesis of Example 129, Step 3 starting from 6-bromo-2H-1,4-benzoxazin-3(4H)-one (0.50 g, 0.0022 mol, Aldrich, Cat. No. 662348) and 4,4,5,5,4',4',5',5'-Octamethyl-[2,2']bi[[1,3,2]dioxaborolanyl] (0.67 g, 0.0026 mol). LCMS (M+H)+: m/z=276.3.

Step 2: 6-{2-[2-amino-6-(4-methylpiperazin-1-yl)pyrimidin-4-yl]-3-methyl-1,2,3,4-tetrahydroisoquinolin-7-yl}-2H-1,4-benzoxazin-3(4H)-one This compound was prepared by using procedures analogous to those described for the synthesis of Example 129, Step 4 starting from 4-(7-bromo-3-methyl-3,4-dihydroisoquinolin-2(1H)-yl)-6-(4-methylpiperazin-1-yl)pyrimidin-2-amine (0.0209 g, 0.0500 mmol) and 6-(4,4,5,5-tetramethyl-1,3,2-dioxaborolan-2-yl)-2H-1,4-benzoxazin-3(4H)-one. LCMS (M+H)+: m/z=486.2.

Example 132

6-{2-[2-Amino-6-(4-methylpiperazin-1-yl)pyrimidin-4-yl]-3-methyl-1,2,3,4-tetrahydroisoquinolin-7-yl}-4-methyl-2H-1,4-benzoxazin-3(4H)-one

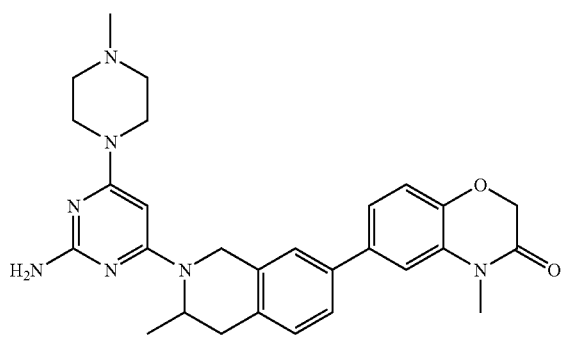 [SMILES: CC1Cc2ccc(-c3ccc4c(c3)N(C)C(=O)CO4)cc2CN1c1cc(N2CCN(C)CC2)nc(N)n1]

Step 1: 4-methyl-6-(4,4,5,5-tetramethyl-1,3,2-dioxaborolan-2-yl)-2H-1,4-benzoxazin-3(4H)-one

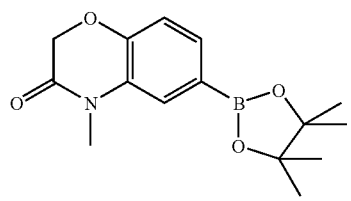 [SMILES: CN1C(=O)COc2ccc(B3OC(C)(C)C(C)(C)O3)cc21]

This compound was prepared by using procedures analogous to those described for the synthesis of Example 129, Step 3 starting from 6-bromo-4-methyl-2H-1,4-benzoxazin-3(4H)-one and 4,4,5,5,4',4',5',5'-Octamethyl-[2,2']bi[[1,3,2]dioxaborolanyl]. LCMS (M+H)+: m/z=290.3.

Step 2: 6-(2-(2-amino-6-(4-methylpiperazin-1-yl)pyrimidin-4-yl)-3-methyl-1,2,3,4-tetrahydroisoquinolin-7-yl)-4-methyl-2H-benzo[b][1,4]oxazin-3(4H)-one This compound was prepared by using procedures analogous to those described for the synthesis of Example 129, Step 4 starting from 4-(7-bromo-3-methyl-3,4-dihydroisoquinolin-2(1H)-yl)-6-(4-methylpiperazin-1-yl)pyrimidin-2-amine and 4-methyl-6-(4,4,5,5-tetramethyl-1,3,2-dioxaborolan-2-yl)-2H-1,4-benzoxazin-3(4H)-one. LCMS (M+H)+: m/z=500.2.

Example 133

2-{2-[2-amino-6-(4-methylpiperazin-1-yl)pyrimidin-4-yl]-3-methyl-1,2,3,4-tetrahydroisoquinolin-7-yl}-N-methyl-1,3-thiazole-5-carboxamide

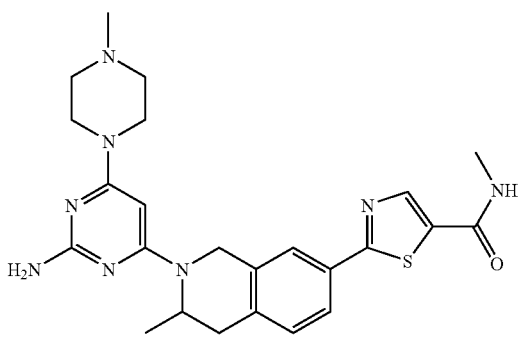 [SMILES: CNC(=O)c1cnc(-c2ccc3c(c2)CN(c2cc(N4CCN(C)CC4)nc(N)n2)C(C)C3)s1]

Step 1: ethyl 2-{2-[2-amino-6-(4-methylpiperazin-1-yl)pyrimidin-4-yl]-3-methyl-1,2,3,4-tetrahydroisoquinolin-7-yl}-1,3-thiazole-5-carboxylate and 2-(2-(2-amino-6-(4-methylpiperazin-1-yl)pyrimidin-4-yl)-3-methyl-1,2,3,4-tetrahydroisoquinolin-7-yl)thiazole-5-carboxylic acid

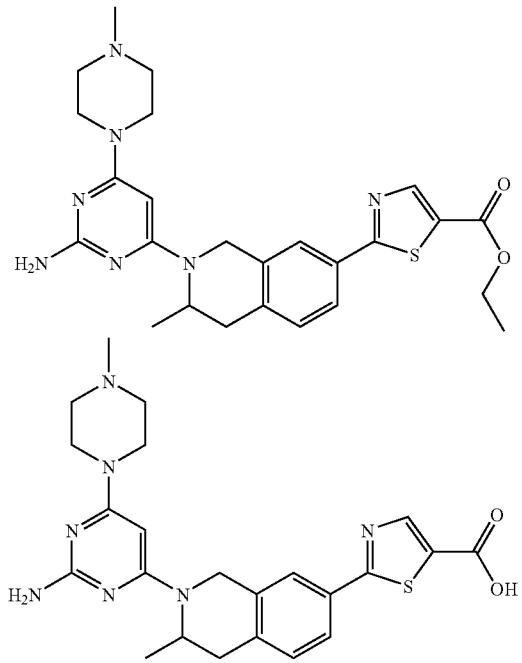

A mixture of 4-(4-methylpiperazin-1-yl)-6-[3-methyl-7-(4,4,5,5-tetramethyl-1,3,2-dioxaborolan-2-yl)-3,4-dihydroisoquinolin-2(1H)-yl]pyrimidin-2-amine (0.0464 g, 0.100 mmol, Example 116, Step 1), ethyl 2-bromo-1,3-thiazole-5-carboxylate (0.0307 g, 0.130 mmol, Aldrich, Cat. No. 642495) in 1,4-dioxane (0.60 mL) was stirred at r.t. for 10 min. Potassium phosphate (63.7 mg, 0.300 mmol) in water (0.30 mL) was added. The mixture was degassed and refilled with nitrogen three times. [1,1'-Bis(diphenylphosphino)ferrocene]dichloropalladium(II) complex with dichloromethane (1:1) (5.0 mg, 0.0061 mmol) was added and the mixture was degassed and refilled with nitrogen three times and then heated at 120° C.) (oil bath temperature) for 3 h. After cooling, the mixture was diluted with methanol, and filtered. The filtrate was purified on RP-HPLC (pH=10) to afford the two products: the ester [LCMS (M+H)$^+$: m/z=466.2] and the corresponding acid [LCMS (M+H)$^+$: m/z=494.1] in a ratio of about 1:2.

Step 2: 2-{2-[2-amino-6-(4-methylpiperazin-1-yl)pyrimidin-4-yl]-3-methyl-1,2,3,4-tetrahydroisoquinolin-7-yl}-N-methyl-1,3-thiazole-5-carboxamide

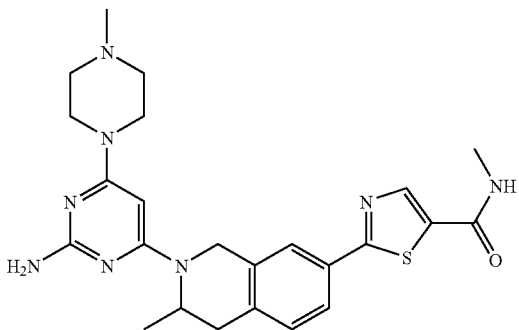 [SMILES: CNC(=O)c1cnc(-c2ccc3c(c2)CN(c2cc(N4CCN(C)CC4)nc(N)n2)C(C)C3)s1]

A mixture of 2-{2-[2-amino-6-(4-methylpiperazin-1-yl)pyrimidin-4-yl]-3-methyl-1,2,3,4-tetrahydroisoquinolin-7-yl}-1,3-thiazole-5-carboxylic acid (15.0 mg, 0.0322 mmol), benzotriazol-1-yloxytris(dimethylamino)phosphonium hexafluorophosphate (14.2 mg, 0.0322 mmol) and 2.0 M of methylamine in tetrahydrofuran (0.100 mL, 0.200 mmol) in DMF (1.0 mL) was stirred at r.t. for 2 h., and was diluted with methanol (0.8 mL). The resulting solution was purified by RP-HPLC (pH=10) to afford the desired product. LCMS (M+H)$^+$: m/z=479.1.

Example 134

2-{2-[2-Amino-6-(4-methylpiperazin-1-yl)pyrimidin-4-yl]-3-methyl-1,2,3,4-tetrahydroisoquinolin-7-yl}-N,N-dimethyl-1,3-thiazole-5-carboxamide

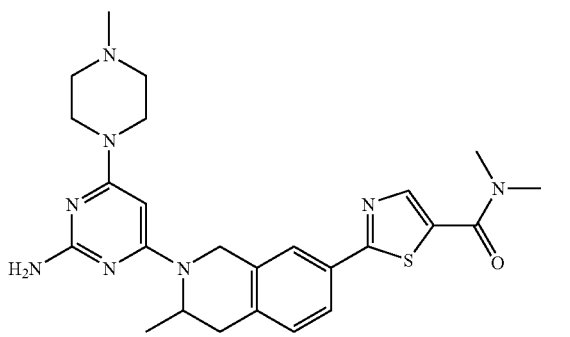 [SMILES: CC1Cc2ccc(-c3ncc(C(=O)N(C)C)s3)cc2CN1c1cc(N2CCN(C)CC2)nc(N)n1]

This compound was prepared by using procedures analogous to those described for the synthesis of Example 133 starting from 2-{2-[2-amino-6-(4-methylpiperazin-1-yl)pyrimidin-4-yl]-3-methyl-1,2,3,4-tetrahydroisoquinolin-7-yl}-1,3-thiazole-5-carboxylic acid and 2.0 M of dimethylamine in tetrahydrofuran solution. LCMS (M+H)$^+$: m/z=493.2.

Example 135

4-[7-(3H-Imidazo[4,5-b]pyridin-6-yl)-3-methyl-3,4-dihydroisoquinolin-2(1H)-yl]-6-(4-methylpiperazin-1-yl)pyrimidin-2-amine

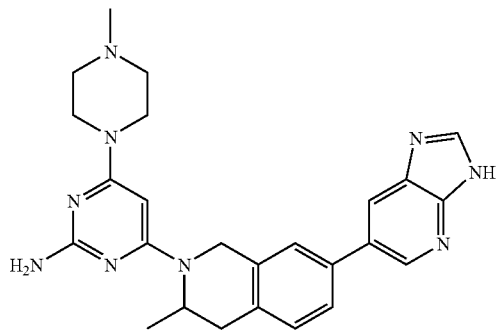 [SMILES: CC1Cc2ccc(-c3cnc4[nH]cnc4c3)cc2CN1c1cc(N2CCN(C)CC2)nc(N)n1]

This compound was prepared by using procedures analogous to those described for the synthesis of Example 116 starting from 4-(4-methylpiperazin-1-yl)-6-[3-methyl-7-(4,4,5,5-tetramethyl-1,3,2-dioxaborolan-2-yl)-3,4-dihydroisoquinolin-2(1H)-yl]pyrimidin-2-amine (Example 116, Step 1) and 6-bromo-3H-imidazo[4,5-b]pyridine (Focus synthesis, Cat. No. FS000626). LCMS (M+H)$^+$: m/z=456.2.

Example 136

4-{2-[2-Amino-6-(4-methylpiperazin-1-yl)pyrimidin-4-yl]-3-methyl-1,2,3,4-tetrahydroisoquinolin-7-yl}-N-cyclopentyl-3,6-dihydropyridine-1(2H)-carboxamide

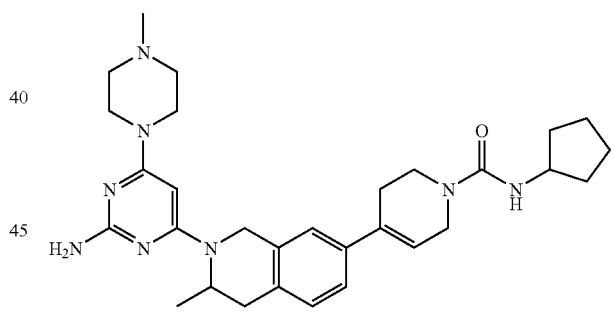

Step 1: tert-butyl 4-{2-[2-amino-6-(4-methylpiperazin-1-yl)pyrimidin-4-yl]-3-methyl-1,2,3,4-tetrahydroisoquinolin-7-yl}-3,6-dihydropyridine-1(2H)-carboxylate

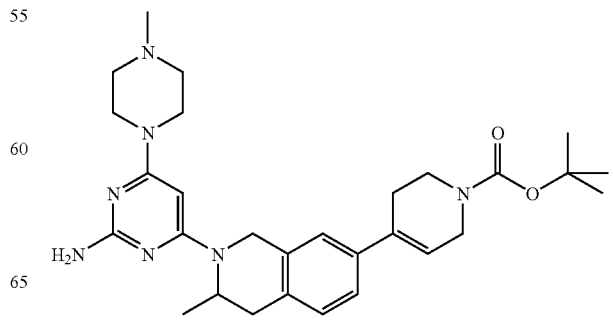

A mixture of 4-(7-bromo-3-methyl-3,4-dihydroisoquinolin-2(1H)-yl)-6-(4-methylpiperazin-1-yl)pyrimidin-2-amine (0.313 g, 0.750 mmol, Example 49, Step 6), tert-butyl 4-(4,4,5,5-tetramethyl-1,3,2-dioxaborolan-2-yl)-3,6-dihydropyridine-1(2H)-carboxylate (0.301 g, 0.975 mmol, Boron Molecular, Cat. No. BM550), [1,1'-bis(diphenylphosphino)ferrocene]dichloropalladium(II) complex with dichloromethane (1:1) (38 mg, 0.045 mmol), potassium carbonate (415 mg, 3.00 mmol) in water (2.2 mL, 120 mmol) and 1,4-dioxane (4.5 mL) was degassed and recharged with nitrogen three times, and then heated at 120° C.) (oil bath temperature) for 2 h. After cooling, the mixture was diluted with ethyl acetate, washed with water and brine, dried over $Na_2SO_4$, filtered and concentrated under reduced pressure. The residue was purified by flash chromatography on a silica gel column with ethyl acetate in haxene (0-50%) to give the desired product (380 mg, 97.5%). LCMS $(M+H)^+$: m/z=520.3.

Step 2: 4-(4-methylpiperazin-1-yl)-6-[3-methyl-7-(1,2,3,6-tetrahydropyridin-4-yl)-3,4-dihydroisoquinolin-2(1H)-yl]pyrimidin-2-amine

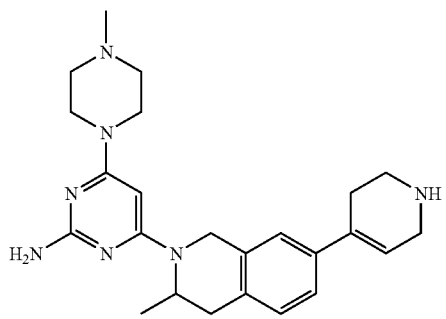 [SMILES: CC1Cc2ccc(C3=CCNCC3)cc2CN1c1cc(N2CCN(C)CC2)nc(N)n1]

tert-Butyl 4-{2-[2-amino-6-(4-methylpiperazin-1-yl)pyrimidin-4-yl]-3-methyl-1,2,3,4-tetrahydroisoquinolin-7-yl}-3,6-dihydropyridine-1(2H)-carboxylate (0.20 g, 0.38 mmol) in ethyl acetate (1.0 mL) was treated with 4.0 M of hydrogen chloride in 1,4-dioxane (1.0 mL, 4.0 mmol) at r.t. for 2 h. The mixture was diluted with ethyl ether, and centrifugalized. The solvents were decanted. The residue was dried in-vacuo to afford the desired product as HCl salt which was directly used in next step reaction without further purification. LCMS $(M+H)^+$: m/z=420.2.

Step 3: 4-{2-[2-amino-6-(4-methylpiperazin-1-yl)pyrimidin-4-yl]-3-methyl-1,2,3,4-tetrahydroisoquinolin-7-yl}-N-cyclopentyl-3,6-dihydropyridine-1(2H)-carboxamide

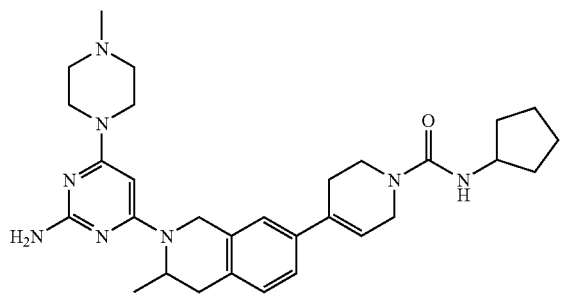 [SMILES: CC1Cc2ccc(C3=CCN(C(=O)NC4CCCC4)CC3)cc2CN1c1cc(N2CCN(C)CC2)nc(N)n1]

4-(4-Methylpiperazin-1-yl)-6-[3-methyl-7-(1,2,3,6-tetrahydropyridin-4-yl)-3,4-dihydroisoquinolin-2(1H)-yl]pyrimidin-2-amine (21.0 mg) HCl salt in N,N-dimethylformamide (1.0 mL) was treated with N,N-diisopropylethylamine (0.070 mL, 0.40 mmol). To the solution was added isocyanatocyclopentane (11.1 mg, 0.100 mmol). The mixture was stirred at r.t. for 2 h. The mixture was diluted with methanol, and purified by RP-HPLC (pH=10) to afford the desired product. LCMS $(M+H)^+$: m/z=531.2.

Example 137

4-{2-[2-Amino-6-(4-methylpiperazin-1-yl)pyrimidin-4-yl]-3-methyl-1,2,3,4-tetrahydroisoquinolin-7-yl}-3,6-dihydro-2H-1,2'-bipyridine-4'-carbonitrite

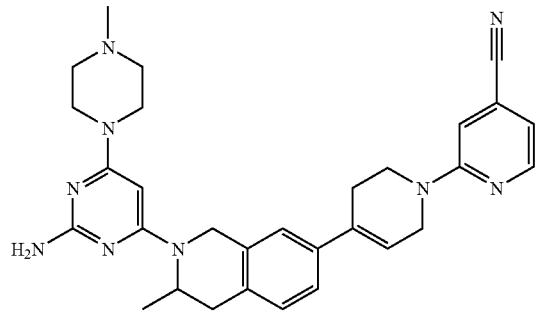 [SMILES: CC1Cc2ccc(C3=CCN(c4cc(C#N)ccn4)CC3)cc2CN1c1cc(N2CCN(C)CC2)nc(N)n1]

4-(4-Methylpiperazin-1-yl)-6-[3-methyl-7-(1,2,3,6-tetrahydropyridin-4-yl)-3,4-dihydroisoquinolin-2(1H)-yl]pyrimidin-2-amine (21.0 mg) HCl salt in N,N-dimethylformamide (1.0 mL) was treated with N,N-diisopropylethylamine (0.070 mL, 0.40 mmol). To the solution was added 2-chloroisonicotinonitrile (13.8 mg, 0.10 mmol). The mixture was stirred and heated at 150° C. for 2 h. The mixture was diluted with methanol, and purified by RP-HPLC (pH=10) to afford the desired product. LCMS $(M+H)^+$: m/z=522.3.

Example 138

4-[7-[1-(Cyclopentylacetyl)piperidin-4-yl]-3-methyl-3,4-dihydroisoquinolin-2(1 H)-yl]-6-(4-methylpiperazin-1-yl)pyrimidin-2-amine

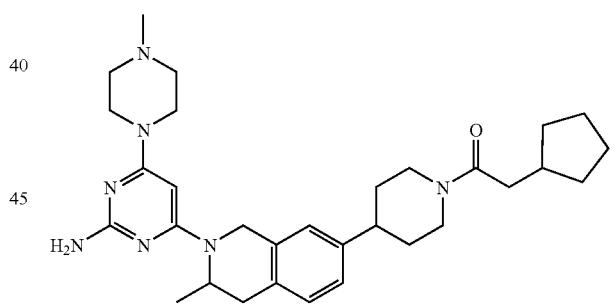

Step 1: tert-butyl 4-{2-[2-amino-6-(4-methylpiperazin-1-yl)pyrimidin-4-yl]-3-methyl-1,2,3,4-tetrahydroisoquinolin-7-yl}piperidine-1-carboxylate

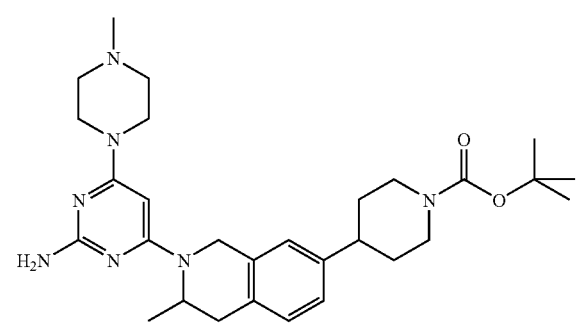

To a solution of tert-butyl 4-{2-[2-amino-6-(4-methylpiperazin-1-yl)pyrimidin-4-yl]-3-methyl-1,2,3,4-tetrahydroisoquinolin-7-yl}-3,6-dihydropyridine-1(2H)-carboxylate (Example 43, Step 1) (0.20 g, 0.38 mmol) in methanol (5 mL) was added palladium on carbon 10% wt. (20 mg) under an atmosphere of nitrogen. The mixture was vacuumed and re-charged with hydrogen three times, and stirred at r.t. for 48 h. The mixture was filtered. The filtrate was concentrated to afford the desired product which was directly used in next step reaction without further purification (200 mg, 99.61%). LCMS (M+H)$^+$: m/z=522.3.

Step 2: 4-(4-methylpiperazin-1-yl)-6-(3-methyl-7-piperidin-4-yl-3,4-dihydroisoquinolin-2(1H)-yl)pyrimidin-2-amine

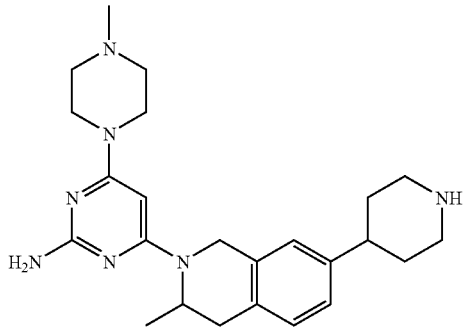 [SMILES: CC1Cc2ccc(C3CCNCC3)cc2CN1c1cc(N2CCN(C)CC2)nc(N)n1]

tert-Butyl 4-{2-[2-amino-6-(4-methylpiperazin-1-yl)pyrimidin-4-yl]-3-methyl-1,2,3,4-tetrahydroisoquinolin-7-yl}piperidine-1-carboxylate (0.20 g, 0.38 mmol) in ethyl acetate (1.0 mL) was treated with 4.0 M of Hydrogen chloride in 1,4-dioxane (1.0 mL, 4.0 mmol) at r.t. for 2 h. The mixture was diluted with ethyl ether, and centrifugalized. The solvents were decanted. The residue was dried in-vacuo to afford the desired product as HCl salt which was directly used in next step reaction without further purification. LCMS (M+H)$^+$: m/z=422.2.

Step 3: 4-[7-[1-(cyclopentylacetyl)piperidin-4-yl]-3-methyl-3,4-dihydroisoquinolin-2(1H)-yl]-6-(4-methylpiperazin-1-yl)pyrimidin-2-amine

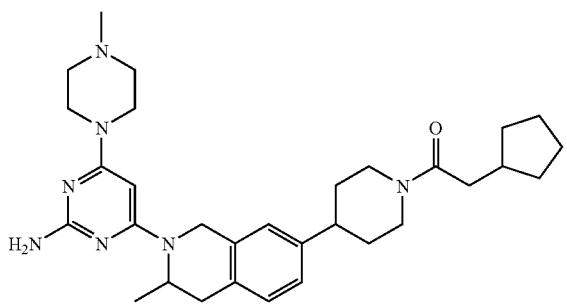 [SMILES: CC1Cc2ccc(C3CCN(C(=O)CC4CCCC4)CC3)cc2CN1c1cc(N2CCN(C)CC2)nc(N)n1]

4-(4-Methylpiperazin-1-yl)-6-(3-methyl-7-piperidin-4-yl-3,4-dihydroisoquinolin-2(1H)-yl)pyrimidin-2-amine HCl salt (21.1 mg) in acetonitrile (0.50 mL) was treated with N,N-diisopropylethylamine (0.070 mL, 0.40 mmol). To the solution was added cyclopentylacetyl chloride (10.0 mg). The mixture was stirred at r.t. for 2 h. The mixture was diluted with methanol, and purified by RP-HPLC (pH=10) to afford the desired product. LCMS (M+H)$^+$: m/z=532.3.

Example 139

Isopropyl 4-{2-[2-amino-6-(4-methylpiperazin-1-yl)pyrimidin-4-yl]-3-methyl-1,2,3,4-tetrahydroisoquinolin-7-yl}piperidine-1-carboxylate

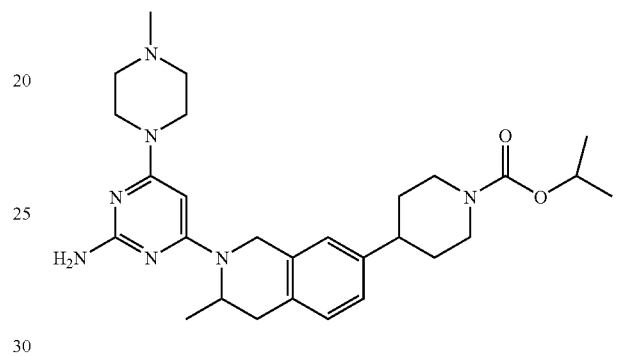

This compound was prepared by using procedures analogous to those described for the synthesis of Example 138 starting from 4-(4-methylpiperazin-1-yl)-6-(3-methyl-7-piperidin-4-yl-3,4-dihydroisoquinolin-2(1H)-yl)pyrimidin-2-amine HCl salt and isopropyl chloroformate. LCMS (M+H)$^+$: m/z=508.3.

Example 140

4-{2-[2-Amino-6-(4-methylpiperazin-1-yl)pyrimidin-4-yl]-3-methyl-1,2,3,4-tetrahydroisoquinolin-7-yl}-N-isopropylpiperidine-1-carboxamide

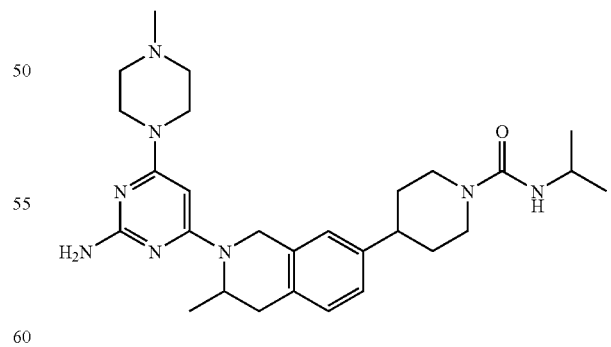

This compound was prepared by using procedures analogous to those described for the synthesis of Example 138 starting from 4-(4-methylpiperazin-1-yl)-6-(3-methyl-7-piperidin-4-yl-3,4-dihydroisoquinolin-2(1H)-yl)pyrimidin-2-amine HCl salt and 2— isocyanatopropane. LCMS (M+H)$^+$: m/z=507.3.

Example 141

4-{2-[2-Amino-6-(4-methylpiperazin-1-yl)pyrimidin-4-yl]-3-methyl-1,2,3,4-tetrahydroisoquinolin-7-yl}-N,N-dimethylpiperidine-1-carboxamide

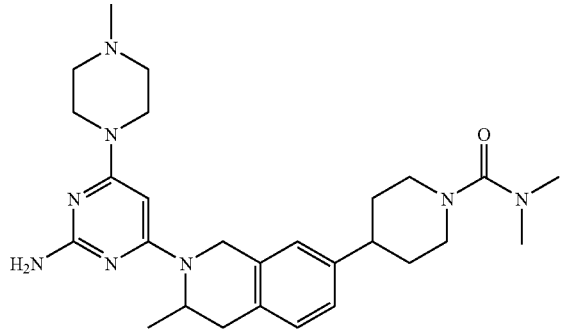

This compound was prepared by using procedures analogous to those described for the synthesis of Example 138 starting from 4-(4-methylpiperazin-1-yl)-6-(3-methyl-7-piperidin-4-yl-3,4-dihydroisoquinolin-2(1H)-yl)pyrimidin-2-amine HCl salt and N,N-dimethylcarbamoyl chloride. LCMS (M+H)⁺: m/z=493.2.

Example 142

4-(4-Methylpiperazin-1-yl)-6-[3-methyl-7-[1-(pyrrolidin-1-ylcarbonyl)piperidin-4-yl]-3,4-dihydroisoquinolin-2(1H)-yl]pyrimidin-2-amine

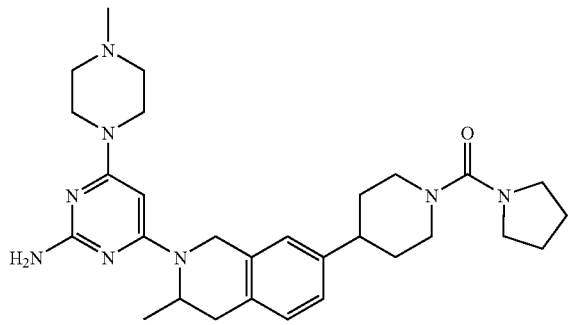 [SMILES: CC1Cc2ccc(C3CCN(C(=O)N4CCCC4)CC3)cc2CN1c1cc(N2CCN(C)CC2)nc(N)n1]

This compound was prepared by using procedures analogous to those described for the synthesis of Example 138 starting from 4-(4-methylpiperazin-1-yl)-6-(3-methyl-7-piperidin-4-yl-3,4-dihydroisoquinolin-2(1H)-yl)pyrimidin-2-amine HCl salt and 1-pyrrolidinecarbonyl chloride. LCMS (M+H)⁺: m/z=519.2.

Example 143

4-[7-[1-(Isopropylsulfonyl)piperidin-4-yl]-3-methyl-3,4-dihydroisoquinolin-2(1H)-yl]-6-(4-methylpiperazin-1-yl)pyrimidin-2-amine

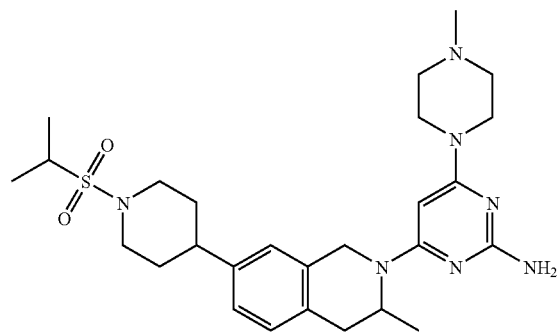 [SMILES: CC1Cc2ccc(C3CCN(S(=O)(=O)C(C)C)CC3)cc2CN1c1cc(N2CCN(C)CC2)nc(N)n1]

This compound was prepared by using procedures analogous to those described for the synthesis of Example 138 starting from 4-(4-methylpiperazin-1-yl)-6-(3-methyl-7-piperidin-4-yl-3,4-dihydroisoquinolin-2(1H)-yl)pyrimidin-2-amine HCl salt and propane-2-sulfonyl chloride. LCMS (M+H)⁺: m/z=528.3.

Example 144

4-{2-[2-Amino-6-(4-methylpiperazin-1-yl)pyrimidin-4-yl]-3-methyl-1,2,3,4-tetrahydroisoquinolin-7-yl}-N,N-dimethylpiperidine-1-carboxamide

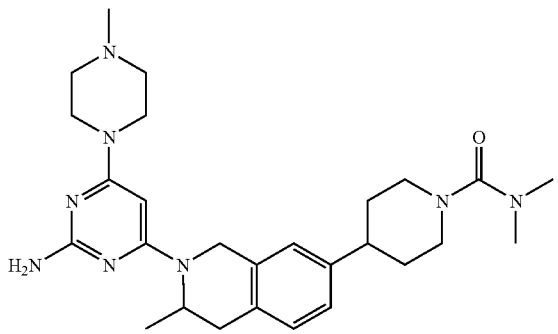

Step 1: tert-butyl 4-{2-[2-amino-6-(4-methylpiperazin-1-yl)pyrimidin-4-yl]-3-methyl-1,2,3,4-tetrahydroisoquinolin-7-yl}-3,6-dihydropyridine-1(2H)-carboxylate

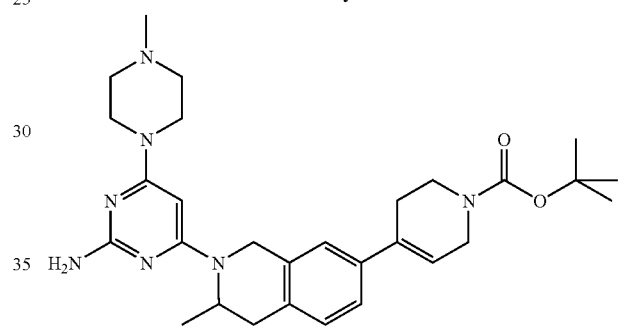

A mixture of 4-(7-bromo-3-methyl-3,4-dihydroisoquinolin-2(1H)-yl)-6-(4-methylpiperazin-1-yl)pyrimidin-2-amine (0.350 g, 0.839 mmol) (Peak 1, Example 49, Step 7), tert-butyl 4-(4,4,5,5-tetramethyl-1,3,2-dioxaborolan-2-yl)-3,6-dihydropyridine-1(2H)-carboxylate (0.311 g, 1.01 mmol), [1,1'-bis(diphenylphosphino)ferrocene]dichloropalladium (II) complex with dichloromethane (1:1) (41.1 mg, 0.0503 mmol), potassium carbonate (0.464 g, 3.35 mmol) in 1,4-dioxane (5.0 mL) and water (2.5 mL) was degassed and recharged with nitrogen three times, and heated at 120° C. for 2 h. The reaction was diluted with ethyl acetate and then washed with water and brine, dried over NaSO₄, filtered and concentrated under reduced pressure. The residue was purified by flash chromatography on a silica gel column eluted with methanol in DCM (0-10%) to afford the desired product (260 mg, 59.7%). LCMS (M+H)⁺: m/z=520.4.

Step 2: tert-butyl 4-{2-[2-amino-6-(4-methylpiperazin-1-yl)pyrimidin-4-yl]-3-methyl-1,2,3,4-tetrahydroisoquinolin-7-yl}piperidine-1-carboxylate

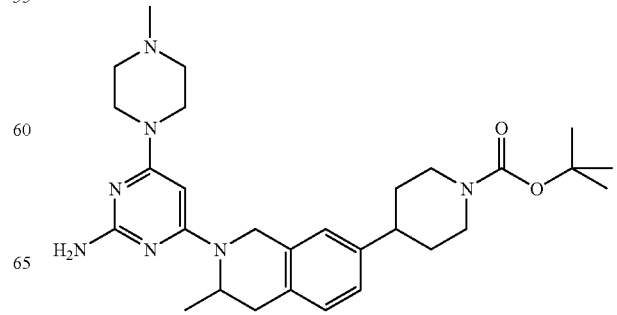

To a solution of tert-butyl 4-{2-[2-amino-6-(4-methylpiperazin-1-yl)pyrimidin-4-yl]-3-methyl-1,2,3,4-tetrahydroisoquinolin-7-yl}-3,6-dihydropyridine-1(2H)-carboxylate (0.26 g, 0.50 mmol) in methanol (5 mL) was added palladium on carbon 10% wt. (52 mg) under an atmosphere of nitrogen. The mixture was vacuumed and re-charged with hydrogen three times, and stirred at r.t. for 48 h. The mixture was filtered. The filtrate was concentrated to afford the desired product which was directly used in next step reaction without further purification. LCMS (M+H)⁺: m/z=522.4.

Step 3: 4-(4-methylpiperazin-1-yl)-6-(3-methyl-7-piperidin-4-yl-3,4-dihydroisoquinolin-2(1H)-yl)pyrimidin-2-amine

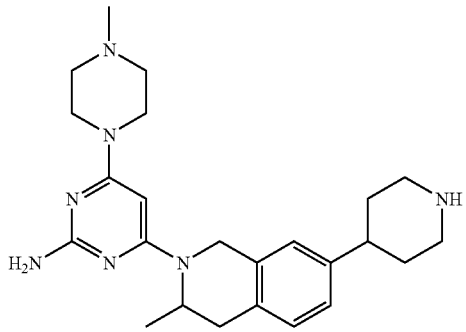

tert-Butyl 4-{2-[2-amino-6-(4-methylpiperazin-1-yl)pyrimidin-4-yl]-3-methyl-1,2,3,4-tetrahydroisoquinolin-7-yl}piperidine-1-carboxylate (0.26 g, 0.50 mmol) in ethyl acetate (1 mL) was treated with 4.0 M of hydrogen chloride in 1,4-dioxane (1.00 mL, 4.00 mmol) at r.t. for 1 h. The mixture was diluted with ether (3 mL), and centrifugalized. The solvents were decanted. The residue was dried in-vacuo to afford the desired product as HCl salt which was directly used in next step reaction without further purification. LCMS (M+H)⁺: m/z=422.2.

Step 4: 4-{2-[2-amino-6-(4-methylpiperazin-1-yl)pyrimidin-4-yl]-3-methyl-1,2,3,4-tetrahydroisoquinolin-7-yl}-N,N-dimethylpiperidine-1-carboxamide 4-(4-Methylpiperazin-1-yl)-6-(3-methyl-7-piperidin-4-yl-3,4-dihydroisoquinolin-2(1H)-yl)pyrimidin-2-amine tetrahydrochloride (17 mg) HCl salt in acetonitrile (0.50 mL) was treated with N,N-diisopropylethylamine (42 uL, 0.24 mmol). To the solution was added N,N-Dimethylcarbamoyl chloride (3.59 uL, 0.0390 mmol). The mixture was stirred at r.t. for 2 h. The mixture was diluted with methanol, and purified by RP-HPLC (pH=10) to afford the desired product. LCMS:(M+H)⁺=493.4.

Example 144

4-{2-[2-Amino-6-(4-methylpiperazin-1-yl)pyrimidin-4-yl]-3-methyl-1,2,3,4-tetrahydroisoquinolin-7-yl}-N,N-dimethylpiperidine-1-carboxamide

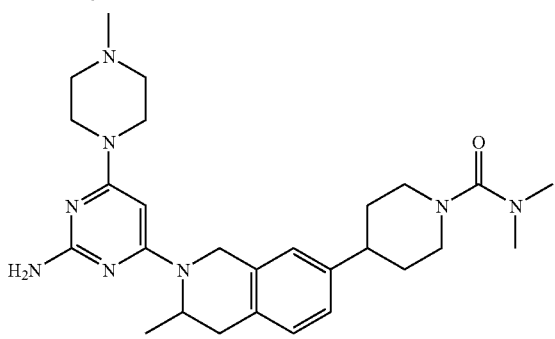 [SMILES: CC1Cc2ccc(C3CCN(C(=O)N(C)C)CC3)cc2CN1c1cc(N2CCN(C)CC2)nc(N)n1]

Step 1: tert-butyl 4-{2-[2-amino-6-(4-methylpiperazin-1-yl)pyrimidin-4-yl]-3-methyl-1,2,3,4-tetrahydroisoquinolin-7-yl}-3,6-dihydropyridine-1(2H)-carboxylate

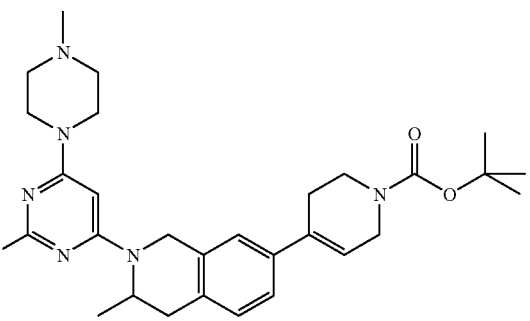

A mixture of 4-(7-bromo-3-methyl-3,4-dihydroisoquinolin-2(1H)-yl)-6-(4-methylpiperazin-1-yl)pyrimidin-2-amine (0.350 g, 0.839 mmol) (Peak 1, Example 49, Step 7), tert-butyl 4-(4,4,5,5-tetramethyl-1,3,2-dioxaborolan-2-yl)-3,6-dihydropyridine-1(2H)-carboxylate (0.311 g, 1.01 mmol), [1,1'-bis(diphenylphosphino)ferrocene]dichloropalladium (II) complex with dichloromethane (1:1) (41.1 mg, 0.0503 mmol), potassium carbonate (0.464 g, 3.35 mmol) in 1,4-dioxane (5.0 mL) and water (2.5 mL) was degassed and recharged with nitrogen three times, and heated at 120° C. for 2 h. The reaction was diluted with ethyl acetate and then washed with water and brine, dried over NaSO₄, filtered and concentrated under reduced pressure. The residue was purified by flash chromatography on a silica gel column eluted with methanol in DCM (0-10%) to afford the desired product (260 mg, 59.7%). LCMS (M+H)⁺: m/z=520.4.

Step 2: tert-butyl 4-{2-[2-amino-6-(4-methylpiperazin-1-yl)pyrimidin-4-yl]-3-methyl-1,2,3,4-tetrahydroisoquinolin-7-yl}piperidine-1-carboxylate

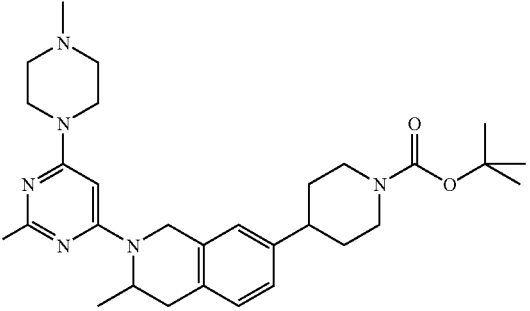

To a solution of tert-butyl 4-{2-[2-amino-6-(4-methylpiperazin-1-yl)pyrimidin-4-yl]-3-methyl-1,2,3,4-tetrahydroisoquinolin-7-yl}-3,6-dihydropyridine-1(2H)-carboxylate (0.26 g, 0.50 mmol) in methanol (5 mL) was added palladium on carbon 10% wt. (52 mg) under an atmosphere of nitrogen. The mixture was vacuumed and re-charged with hydrogen three times, and stirred at r.t. for 48 h. The mixture was filtered. The filtrate was concentrated to afford the desired product which was directly used in next step reaction without further purification. LCMS (M+H)⁺: m/z=522.4.

Step 3: 4-(4-methylpiperazin-1-yl)-6-(3-methyl-7-piperidin-4-yl-3,4-dihydroisoquinolin-2(1H)-yl)pyrimidin-2-amine

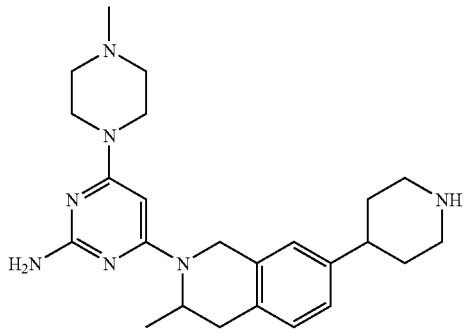 [SMILES: CC1Cc2ccc(C3CCNCC3)cc2CN1c1cc(N2CCN(C)CC2)nc(N)n1]

tert-Butyl 4-{2-[2-amino-6-(4-methylpiperazin-1-yl)pyrimidin-4-yl]-3-methyl-1,2,3,4-tetrahydroisoquinolin-7-yl}piperidine-1-carboxylate (0.26 g, 0.50 mmol) in ethyl acetate (1 mL) was treated with 4.0 M of hydrogen chloride in 1,4-dioxane (1.00 mL, 4.00 mmol) at r.t. for 1 h. The mixture was diluted with ether (3 mL), and centrifugalized. The solvents were decanted. The residue was dried in-vacuo to afford the desired product as HCl salt which was directly used in next step reaction without further purification. (M+H)$^+$: m/z=422.2.

Step 4: 4-{2-[2-amino-6-(4-methylpiperazin-1-yl)pyrimidin-4-yl]-3-methyl-1,2,3,4-tetrahydroisoquinolin-7-yl}-N,N-dimethylpiperidine-1-carboxamide 4-(4-Methylpiperazin-1-yl)-6-(3-methyl-7-piperidin-4-yl-3,4-dihydroisoquinolin-2(1H)-yl)pyrimidin-2-amine tetrahydrochloride (17 mg) HCl salt in acetonitrile (0.50 mL) was treated with N,N-diisopropylethylamine (42 uL, 0.24 mmol). To the solution was added N,N-Dimethylcarbamoyl chloride (3.59 uL, 0.0390 mmol). The mixture was stirred at r.t. for 2 h. The mixture was diluted with methanol, and purified by RP-HPLC (pH=10) to afford the desired product. LCMS (M+H)$^+$: m/z=493.4.

Example 145

4-{2-[2-Amino-6-(4-methylpiperazin-1-yl)pyrimidin-4-yl]-3-methyl-1,2,3,4-tetrahydroisoquinolin-7-yl}-N-ethylpiperidine-1-carboxamide

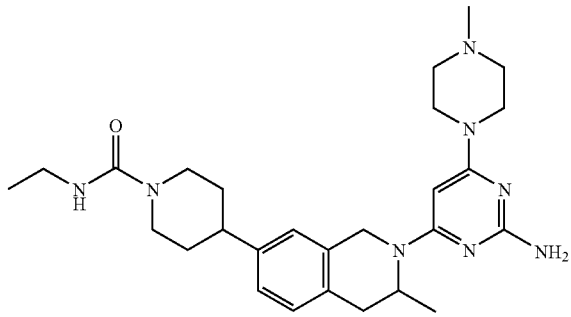 [SMILES: CCNC(=O)N1CCC(c2ccc3c(c2)CN(c2cc(N4CCN(C)CC4)nc(N)n2)C(C)C3)CC1]

This compound was prepared by using procedures analogous to those described for the synthesis of Example 144 starting from 4-(4-methylpiperazin-1-yl)-6-(3-methyl-7-piperidin-4-yl-3,4-dihydroisoquinolin-2(1H)-yl)pyrimidin-2-amine tetrahydrochloride HCl salt (Example 144, Step 3) and isocyanatoethane. LCMS (M+H)$^+$: m/z=493.4.

Example 146

4-[7-(1-Acetylpiperidin-4-yl)-3-methyl-3,4-dihydroisoquinolin-2(1H)-yl]-6-(4-methylpiperazin-1-yl)pyrimidin-2-amine

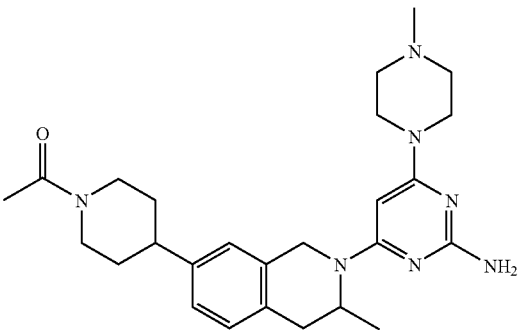 [SMILES: CC(=O)N1CCC(c2ccc3c(c2)CN(c2cc(N4CCN(C)CC4)nc(N)n2)C(C)C3)CC1]

This compound was prepared by using procedures analogous to those described for the synthesis of Example 144 starting from 4-(4-methylpiperazin-1-yl)-6-(3-methyl-7-piperidin-4-yl-3,4-dihydroisoquinolin-2(1H)-yl)pyrimidin-2-amine tetrahydrochloride HCl salt (Example 144, Step 3) and acetyl chloride. LCMS (M+H)$^+$: m/z=464.4.

Example 147

Methyl 4-{2-[2-amino-6-(4-methylpiperazin-1-yl)pyrimidin-4-yl]-3-methyl-1,2,3,4-tetrahydroisoquinolin-7-yl}piperidine-1-carboxylate

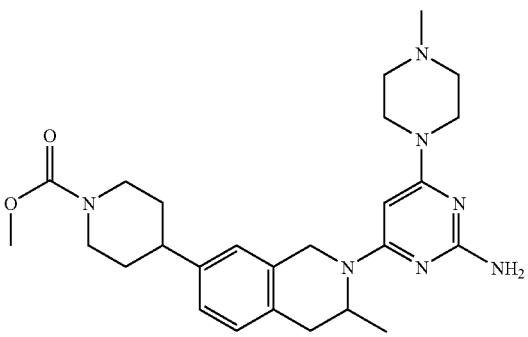 [SMILES: COC(=O)N1CCC(c2ccc3c(c2)CN(c2cc(N4CCN(C)CC4)nc(N)n2)C(C)C3)CC1]

This compound was prepared by using procedures analogous to those described for the synthesis of Example 144 starting from 4-(4-methylpiperazin-1-yl)-6-(3-methyl-7-piperidin-4-yl-3,4-dihydroisoquinolin-2(1H)-yl)pyrimidin-2-amine tetrahydrochloride HCl salt (Example 144, Step 3) and methyl chloroformate. LCMS (M+H)$^+$: m/z=480.3.

Example 148

4-[3-Methyl-7-[1-(methylsulfonyl)piperidin-4-yl]-3,4-dihydroisoquinolin-2(1H)-yl]-6-(4-methylpiperazin-1-yl)pyrimidin-2-amine

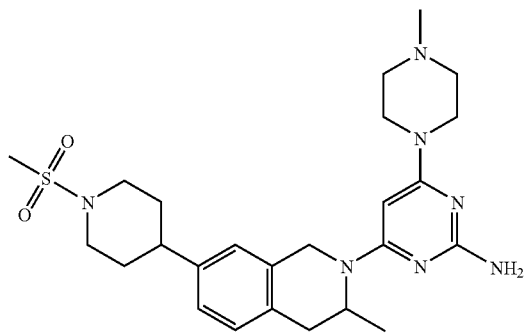 [SMILES: CC1Cc2ccc(C3CCN(S(C)(=O)=O)CC3)cc2CN1c1cc(N2CCN(C)CC2)nc(N)n1]

This compound was prepared by using procedures analogous to those described for the synthesis of Example 144 starting from 4-(4-methylpiperazin-1-yl)-6-(3-methyl-7-piperidin-4-yl-3,4-dihydroisoquinolin-2(1H)-yl)pyrimidin-2-amine tetrahydrochloride HCl salt (Example 144, Step 3) and methanesulfonyl chloride. LCMS (M+H)$^+$: m/z=500.3.

Example 149

4-(4-Methylpiperazin-1-yl)-6-[3-methyl-7-(1-propionylpiperidin-4-yl)-3,4-dihydroisoquinolin-2(1H)-yl]pyrimidin-2-amine

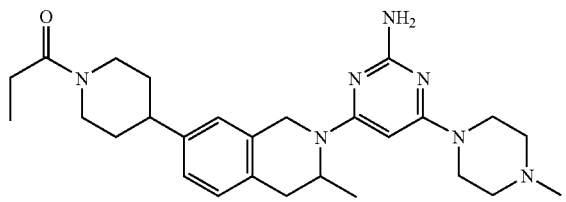 [SMILES: CCC(=O)N1CCC(c2ccc3c(c2)CN(c2cc(N4CCN(C)CC4)nc(N)n2)C(C)C3)CC1]

This compound was prepared by using procedures analogous to those described for the synthesis of Example 144 starting from 4-(4-methylpiperazin-1-yl)-6-(3-methyl-7-piperidin-4-yl-3,4-dihydroisoquinolin-2(1H)-yl)pyrimidin-2-amine tetrahydrochloride HCl salt (Example 144, Step 3) and propanoyl chloride. LCMS (M+H)$^+$: m/z=478.3.

Example 150

4-[7-[1-(Cyclopropylcarbonyl)piperidin-4-yl]-3-methyl-3,4-dihydroisoquinolin-2(1H)-yl]-6-(4-methylpiperazin-1-yl)pyrimidin-2-amine

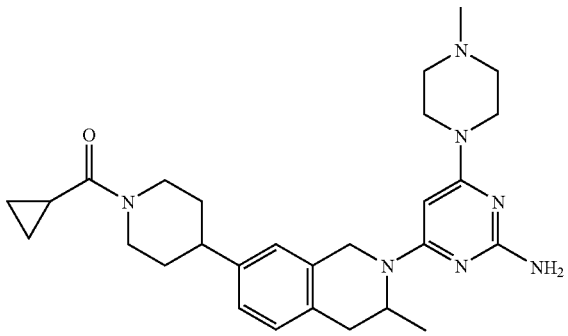 [SMILES: CC1Cc2ccc(C3CCN(C(=O)C4CC4)CC3)cc2CN1c1cc(N2CCN(C)CC2)nc(N)n1]

This compound was prepared by using procedures analogous to those described for the synthesis of Example 144 starting from 4-(4-methylpiperazin-1-yl)-6-(3-methyl-7-piperidin-4-yl-3,4-dihydroisoquinolin-2(1H)-yl)pyrimidin-2-amine tetrahydrochloride HCl salt (Example 144, Step 3) and cyclopropanecarbonyl chloride. LCMS (M+H)$^+$: m/z=490.2.

Example 151

4-{2-[2-Amino-6-(4-methylpiperazin-1-yl)pyrimidin-4-yl]-3-methyl-1,2,3,4-tetrahydroisoquinolin-7-yl}-N-methylpiperidine-1-carboxamide

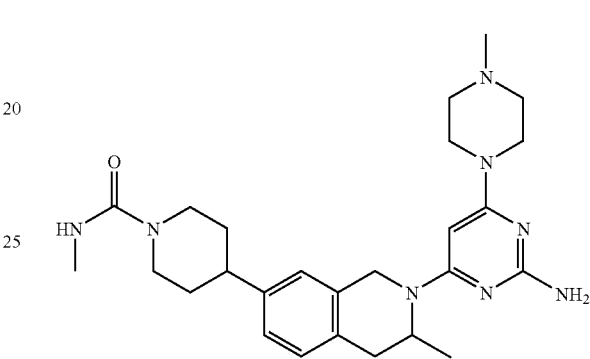

This compound was prepared by using procedures analogous to those described for the synthesis of Example 144 starting from 4-(4-methylpiperazin-1-yl)-6-(3-methyl-7-piperidin-4-yl-3,4-dihydroisoquinolin-2(1H)-yl)pyrimidin-2-amine tetrahydrochloride HCl salt (Example 144, Step 3) and methyl isocyanate. LCMS (M+H)$^+$: m/z=479.2.

Example 152

4-[7-[1-(Ethylsulfonyl)piperidin-4-yl]-3-methyl-3,4-dihydroisoquinolin-2(1H)-yl]-6-(4-methylpiperazin-1-yl)pyrimidin-2-amine

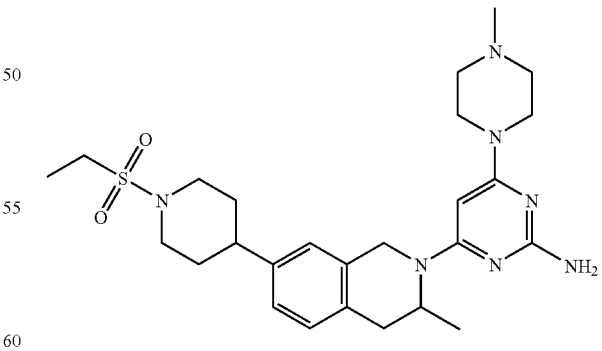

This compound was prepared by using procedures analogous to those described for the synthesis of Example 144 starting from 4-(4-methylpiperazin-1-yl)-6-(3-methyl-7-piperidin-4-yl-3,4-dihydroisoquinolin-2(1H)-yl)pyrimidin-2-amine tetrahydrochloride HCl salt (Example 144, Step 3) and ethanesulfonyl chloride. LCMS (M+H)$^+$: m/z=514.2.

Example 153

1-[(4-{2-[2-Amino-6-(4-methylpiperazin-1-yl)pyrimidin-4-yl]-3-methyl-1,2,3,4-tetrahydroisoquinolin-7-yl}pyridin-2-yl)carbonyl]azetidin-3-ol

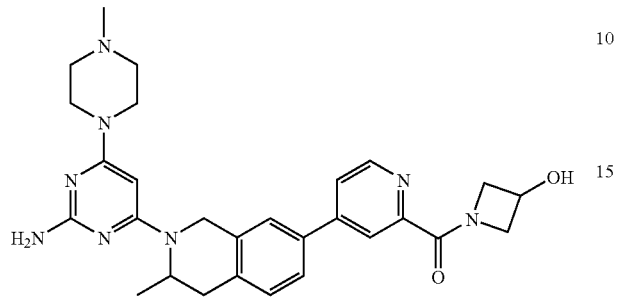

This compound was prepared by using procedures analogous to those described for the synthesis of Example 61B starting from 4-{2-[2-amino-6-(4-methylpiperazin-1-yl)pyrimidin-4-yl]-3-methyl-1,2,3,4-tetrahydroisoquinolin-7-yl}pyridine-2-carboxylic acid (Example 61B, Step 2) and 3-hydroxyazetidine hydrochloride (Oakwood, Cat. No. 013898). LCMS (M+H)$^+$: m/z=515.2.

Example 154

4-[7-(6-{[(3S)-3-Fluoropyrrolidin-1-yl]carbonyl}pyridin-3-yl)-3-methyl-3,4-dihydroisoquinolin-2(1H)-yl]-6-(4-methylpiperazin-1-yl)pyrimidin-2-amine

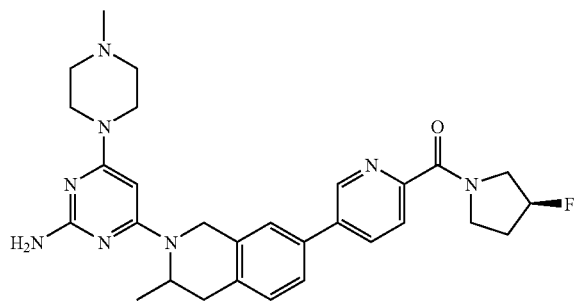 [SMILES: CC1Cc2ccc(-c3ccc(C(=O)N4CC[C@H](F)C4)nc3)cc2CN1c1cc(N2CCN(C)CC2)nc(N)n1]

Example 154A

Enantiomer 1

4-[7-(6-{[(3S)-3-fluoropyrrolidin-1-yl]carbonyl}pyridin-3-yl)-3-methyl-3,4-dihydroisoquinolin-2(1H)-yl]-6-(4-methylpiperazin-1-yl)pyrimidin-2-amine This compound was prepared by using procedures analogous to those described for the synthesis of Example 50A starting from 5-{2-[2-amino-6-(4-methylpiperazin-1-yl)pyrimidin-4-yl]-3-methyl-1,2,3,4-tetrahydroisoquinolin-7-yl}pyridine-2-carboxylic acid (Example 50A, Step 1) and (S)-(+)-3-fluoropyrrolidine hydrochloride (Oakwood, Cat. No. 013157). LCMS (M+H)$^+$: m/z=531.2.

Example 154B

Enantiomer 2

4-[7-(6-{[(3S)-3-fluoropyrrolidin-1-yl]carbonyl}pyridin-3-yl)-3-methyl-3,4-dihydroisoquinolin-2(1H)-yl]-6-(4-methylpiperazin-1-yl)pyrimidin-2-amine

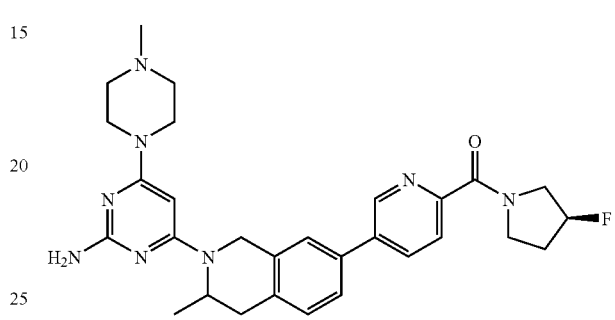

This compound was prepared by using procedures analogous to those described for the synthesis of Example 50B starting from 5-{2-[2-amino-6-(4-methylpiperazin-1-yl)pyrimidin-4-yl]-3-methyl-1,2,3,4-tetrahydroisoquinolin-7-yl}pyridine-2-carboxylic acid (Example 50B, Step 1) and (S)-(+)-3-fluoropyrrolidine hydrochloride (Oakwood, Cat. No. 013157). LCMS (M+H)$^+$: m/z=531.2.

Example 155

4-(4-Methylpiperazin-1-yl)-6-[3-methyl-7-[1-(pyridin-2-ylmethyl)-1H-pyrazol-3-yl]-3,4-dihydroisoquinolin-2(1H)-yl]pyrimidin-2-amine (Enantiomer 1)

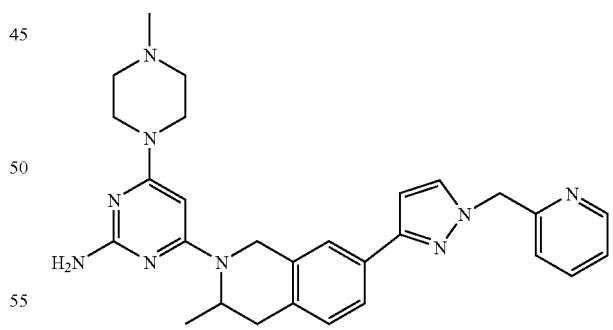

A mixture of 3-(4,4,5,5-tetramethyl-1,3,2-dioxaborolan-2-yl)-1H-pyrazole (39.6 mg, 0.204 mmol, Alfa Aesar, Cat. No. H27619), 2-(bromomethyl)pyridine hydrobromide (0.0620 g, 0.245 mmol) and cesium carbonate (0.200 g, 0.612 mmol) in DMF (0.5 mL) was stirred at 50° C. overnight. The reaction mixture was diluted with 1,4-dioxane and then filtered, the filtrate was concentrated under reduced pressure.

The residue was dissolved in 1,4-dioxane (0.50 mL) and water (0.10 mL). To the solution was added 4-(7-bromo-3-methyl-3,4-dihydroisoquinolin-2(1H)-yl)-6-(4-methylpiperazin-1-yl)pyrimidin-2-amine (0.018 g, 0.043 mmol, Peak 1, Example 49, Step 7), dichloro(bis{di-tert-butyl[4-(dimethylamino)phenyl]phosphoranyl})palladium (0.916 mg, 0.00129 mmol), sodium carbonate (9.14 mg, 0.0862 mmol). and the mixture was vacuumed and refilled with $N_2$ for 3 times. The reaction was stirred at 90° C. overnight. The mixture was purified by RP-HPLC (pH=10) to afford the desired product. LCMS (M+H)$^+$: m/z=496.3.

Example 156

4-(4-Methylpiperazin-1-yl)-6-[3-methyl-7-[1-(pyridin-3-ylmethyl)-1H-pyrazol-3-yl]-3,4-dihydroisoquinolin-2(1H)-yl]pyrimidin-2-amine (Enantiomer 1)

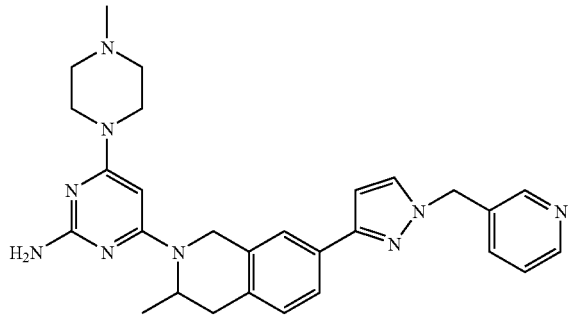

A mixture of 3-(4,4,5,5-tetramethyl-1,3,2-dioxaborolan-2-yl)-1H-pyrazole (39.6 mg, 0.204 mmol, Alfa Aesar, Cat. No. H27619), 3-(bromomethyl)pyridine hydrobromide (0.0620 g, 0.245 mmol) and cesium carbonate (0.200 g, 0.612 mmol) in DMF (0.5 mL) was stirred at 50° C. overnight. The reaction mixture was diluted with 1,4-dioxane and then filtered, the filtrate was concentrated under reduced pressure.

The residue was dissolved in 1,4-dioxane (0.50 mL) and water (0.10 mL), to this solution was added 4-(7-bromo-3-methyl-3,4-dihydroisoquinolin-2(1H)-yl)-6-(4-methylpiperazin-1-yl)pyrimidin-2-amine (0.018 g, 0.043 mmol, Peak 1, Example 49, Step 7), [1,1'-bis(diphenylphosphino)ferrocene]dichloropalladium(II) complex with dichloromethane (1:1) (1.76 mg, 0.00216 mmol), potassium carbonate (11.9 mg, 0.0862 mmol) and the mixture was vacuumed and refilled with $N_2$ for 3 times. The reaction was stirred at 110° C. overnight. The mixture was purified by RP-HPLC (pH=10) to afford the desired product. LCMS (M+H)$^+$: m/z=496.3.

Example 157

4-(4-Methylpiperazin-1-yl)-6-[3-methyl-7-[1-(pyridin-4-ylmethyl)-1H-pyrazol-3-yl]-3,4-dihydroisoquinolin-2(1H)-yl]pyrimidin-2-amine (Enantiomer 1)

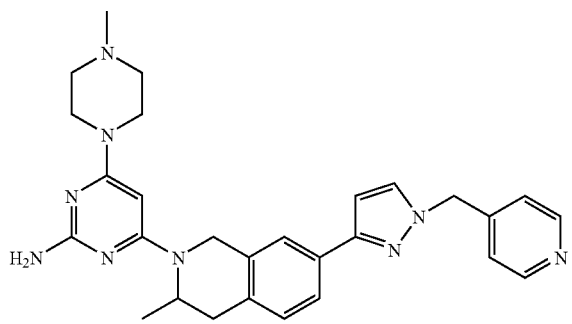 [SMILES: CC1Cc2ccc(-c3ccn(Cc4ccncc4)n3)cc2CN1c1cc(N2CCN(C)CC2)nc(N)n1]

This compound was prepared by using procedures analogous to those described for the synthesis of Example 156 starting from 3-(4,4,5,5-tetramethyl-1,3,2-dioxaborolan-2-yl)-1H-pyrazole (Alfa Aesar, Cat. No. H27619), 4-(bromomethyl)-pyridine hydrobromide and 4-(7-bromo-3-methyl-3,4-dihydroisoquinolin-2(1H)-yl)-6-(4-methylpiperazin-1-yl)pyrimidin-2-amine (Peak 1, Example 49, Step 7). LCMS (M+H)$^+$: m/z=496.3.

Example 158

6-{2-[2-Amino-6-(4-methylpiperazin-1-yl)pyrimidin-4-yl]-3-methyl-1,2,3,4-tetrahydroisoquinolin-7-yl}-N-ethylpyridine-2-carboxamide

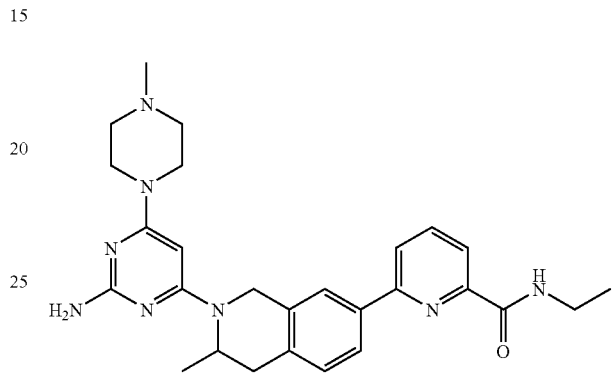

Enantiomer 2

This compound was prepared by using procedures analogous to those described for the synthesis of Example 61B starting from 4-(7-bromo-3-methyl-3,4-dihydroisoquinolin-2(1H)-yl)-6-(4-methylpiperazin-1-yl)pyrimidin-2-amine (Peak 2, Example 49, Step 7) and methyl 6-bromopyridine-2-carboxylate (Aldrich, Cat. No. 650110) and ethylamine in THF solution (2.0 M). LCMS (M+H)$^+$: m/z=487.3.

Example AA

H4 Membrane Binding Assay

Recombinant HEK293SFM cells expressing human H1, H2, H3, H4 or mouse H4 were harvested (Packard Filtermate Harvester) in ice-cold Tris-HCl, (50 mM, pH 7.5, Sigma) with protease inhibitors (Roche) and homogenized with a Polytron homogenizer. The homogenate was centrifuged for 5 minutes at 1000 g to remove nuclei and unbroken cells. The supernatant was centrifuged at 50000 g for 30 minutes, and the resulting pellet was re-suspended in ice-cold Tris-HCl (50 mM, pH 7.5). For binding displacement assays, the H1, H2, H3 and H4 membrane preparations (20-40 μg) were incubated in a total volume of 150 μL of Tris-HCl (50 mM, pH 7.5), with 2.5 nM $^3$H-Pyrilamine (Amersham), 2.5 nM $^3$H-Tiotidine (Perkin Elmer), 1 nM R(−)-α-Methy[$^3$H]histamine (Amersham) or 10 nM $^3$H-Histamine (Amersham) respectively, in the presence or absence of different amounts of test compounds for 1.5 hr at room temperature. Nonspecific binding was determined by inclusion of 1000× unlabeled ligands. The bound radioactivity was separated by filtration through polyethyleneimine-treated GF/B filters (Perkin Elmer). The filters were washed eight times with ice-cold Tris-HCl (50 mM, pH 7.5), and radioactivity retained on the filters was measured by liquid scintillation counting. The binding data were evaluated with Prism.

Example BB

Ca²⁺ Flux Assay

HEK-293 cells were transiently cotransfected in DMEM and 10% FCS with human H4 and $G_{\alpha 16}$ cDNAs using lipofectAMINE 2000 reagent. Twenty-four hours after transfection, the cells were harvested and reseeded at $5 \times 10^4$ cells/50 µL/well in DMEM and 10% FCS in poly(D-lysine)-treated, 384, clear-bottomed black plates. Forty eight hours after transfection, the cells were washed with Hank's balanced salt solution and loaded for 1 hr at 37° C. with Ca3 dye. Test compounds were then evaluated for their inhibitory activity against histamine-induced intracellular $Ca^{2+}$ mobilization using a florescence imaging plate reader. All experiments were performed in duplicate. The data (relative fluorescent unit change) was analyzed with Prizm.

Example CC

H4 Eosinophil Chemotaxis Assay

Human Whole Blood (Incyte Corp, Wilmington Del., or Biological Specialty, Colmar, Pa.) was obtained from normal, drug free donors. Polymorphnuclear leukocytes (PMNs) were isolated via density gradient centrifugation, using ficoll (Amersham Biologicals, Uppsala, Sweden) to make the gradient. Eosinophils are further isolated via MACS separation column (Miltenyi Biotec, Germany) and rested overnight at 4° C. 2e5 cells in 200 µL RPMI Media (Vitrogen/Gibco, Carlsbad, Calif.) with or without various concentrations of compound were loaded in the wells on top of an 8 micron polycarbonate filter in a 96 well modified Boyden chamber (Neuroprobe, Gaithersburg, Md.). Beneath the filter, 10 nM histamine (R&D Systems, Minneapolis, Minn.) with or without compound, or media was placed in a corresponding 96-well plate. The sealed chambers were incubated for 2 hours at 37° C., 5% $CO_2$. Filters were washed, Geimsa (Sigma, St Louis, Mo.) stained, and the number of eosinophils that migrated toward the histamine in the bottom chamber was counted by microscopy. The ability of the compound to antagonize H4-mediated chemotaxis was reported as the inhibitor/antagonist concentration required for 50% inhibition ($IC_{50}$ values) of specific migration to histamine. Specific migration is defined as the total migration minus the background migration.

The $IC_{50}$ values (or percentage of inhibition at a concentration of 1 µM) for the example compounds of invention with respect histamine H4 receptor are provided in Table A1 as follows.

TABLE A1

| Compound Example number | % INH (1 µM) | IC50 (nM) |
|---|---|---|
| Example 1 | | 39 |
| Example 2 | | 20 |
| Example 3 | | 31 |
| Example 4 | | 80 |
| Example 5 | | 128 |
| Example 6 | | 61 |
| Example 7 | | 76 |
| Example 8 | 35 | >1000 |
| Example 9 | | 89 |
| Example 10 | | 102 |
| Example 11 | | 110 |
| Example 12 | | 489 |
| Example 13 | | 35 |

TABLE A1-continued

| Compound Example number | % INH (1 µM) | IC50 (nM) |
|---|---|---|
| Example 14 | | 223 |
| Example 15 | | 145 |
| Example 16 | | 543 |
| Example 17 | | 285 |
| Example 18 | | 65 |
| Example 19 | | 110 |
| Example 20 | | 113 |
| Example 21 | | 181 |
| Example 22 | | 367 |
| Example 23 | | 158 |
| Example 24 | | 966 |
| Example 25 | | 260 |
| Example 26 | | 244 |
| Example 27 | | 670 |
| Example 28 | | 754 |
| Example 29 | | 229 |
| Example 30 | | 282 |
| Example 31 | | 299 |
| Example 32 | | 178 |
| Example 33 | | 266 |
| Example 34 | 69 | |
| Example 35 | 66 | |
| Example 36 | | 393 |
| Example 37 | | 579 |
| Example 38 | | 186 |
| Example 39 | | 51 |
| Example 40 | | 39 |
| Example 41 | | 38 |
| Example 42 | | 81 |
| Example 43 | | 99 |
| Example 44 | | 93 |
| Example 45 | | 106 |
| Example 46 | | 173 |
| Example 47 | | 127 |
| Example 48 | | 200 |
| Example 49 | | 42 |
| Example 49A | | 45 |
| Example 49B | | 38 |
| Example 50B | 78 | |
| Example 50A | | 88.7 |
| Example 51A | | 75 |
| Example 51B | | 63 |
| Example 52A | | 46 |
| Example 53A | | 201 |
| Example 53B | | 176 |
| Example 54A | | 99 |
| Example 54B | | 48 |
| Example 55A | | 95 |
| Example 55B | 65 | |
| Example 56A | | 85 |
| Example 56B | | 172 |
| Example 57 | | 119 |
| Example 58 | | 144 |
| Example 59 | | 54 |
| Example 60 | | 130 |
| Example 61A | | 110 |
| Example 61B | | 64 |
| Example 62A | | 46 |
| Example 62B | | 49 |
| Example 63A | | 44 |
| Example 63B | | 47 |
| Example 64A | | 116 |
| Example 64B | | 86 |
| Example 65A | | 107 |
| Example 65B | | 79 |
| Example 66A | | 64 |
| Example 66B | | 57 |
| Example 67A | | 56 |
| Example 67B | | 50 |
| Example 68A | | 30 |
| Example 68B | | 32 |
| Example 69 | | 66 |
| Example 70 | | 86 |
| Example 71 | | 153 |
| Example 72 | | 269 |
| Example 73 | | 195 |
| Example 74 | | 148 |

TABLE A1-continued

| Compound Example number | % INH (1 μM) | IC50 (nM) |
|---|---|---|
| Example 75 | | 100 |
| Example 76 | 66 | |
| Example 77 | | 149 |
| Example 78 | | 135 |
| Example 79 | | 108 |
| Example 80 | | 106 |
| Example 81A | | 75 |
| Example 81B | | 34 |
| Example 82A | | 22 |
| Example 82B | 66 | |
| Example 83A | | 33 |
| Example 83B | 61 | |
| Example 84A | | 30 |
| Example 84B | 52 | |
| Example 85A | | 20 |
| Example 85B | | 104 |
| Example 86A | | 40 |
| Example 86B | | 231 |
| Example 87A | | 26 |
| Example 87B | 69 | |
| Example 88A | | 25 |
| Example 88B | 74 | |
| Example 89A | | 26 |
| Example 89B | 67 | |
| Example 90A | | 66 |
| Example 90B | 72 | |
| Example 91A | | 49 |
| Example 91B | 76 | |
| Example 92A | | 25 |
| Example 92B | | 127 |
| Example 93 | | 24 |
| Example 94 | | 30 |
| Example 95A | | 35 |
| Example 95B | 79 | |
| Example 96A | | 26 |
| Example 96B | | 352 |
| Example 97A | | 44 |
| Example 97B | 72 | |
| Example 98A | | 24 |
| Example 98B | 56 | |
| Example 99B | | 172 |
| Example 99A | | 83 |
| Example 100 | | 20 |
| Example 101 | | 34 |
| Example 102 | | 42 |
| Example 103 | | 24 |
| Example 104 | | 45 |
| Example 105 | | 53 |
| Example 106 | | 63 |
| Example 107 | | 42 |
| Example 108 | | 46 |
| Example 109 | | 100 |
| Example 110 | | 35 |
| Example 111 | | 22 |
| Example 112 | | 40 |
| Example 113 | | 72 |
| Example 114 | | 34 |
| Example 115 | | 40 |
| Example 116 | | 20 |
| Example 117 | | 43 |
| Example 118 | | 255 |
| Example 119 | | 91 |
| Example 120 | | 40 |
| Example 121 | | 24 |
| Example 122 | | 51 |
| Example 123 | | 124 |
| Example 124 | | 121 |
| Example 125 | | 56 |
| Example 126 | | 66 |
| Example 127 | | 104 |
| Example 128 | | 148 |
| Example 129 | | 112 |
| Example 130 | | 69 |
| Example 131 | | 30 |
| Example 132 | | 39 |
| Example 133 | | 59 |
| Example 134 | | 38 |
| Example 135 | | 48 |
| Example 136 | | 68 |
| Example 137 | | 84 |
| Example 138 | | 64 |
| Example 139 | | 54 |
| Example 140 | | 80 |
| Example 141 | | 40 |
| Example 144 | | 24 |
| Example 145 | | 36 |
| Example 146 | | 22.8 |
| Example 147 | | 12.1 |
| Example 148 | | 30.6 |
| Example 149 | | 26.1 |
| Example 150 | | 22.5 |
| Example 151 | | 42.1 |
| Example 152 | | 17.6 |
| Example 153 | | 27 |
| Example 154A | | 85 |
| Example 154B | | 355 |
| Example 155 | | 15.3 |
| Example 156 | | 8.7 |
| Example 157 | | 8.7 |
| Example 158 | 70 | | a. when the experiment limit is set as "a" and the $IC_{50}$ measurement of the example compound exceeds the limit, then the $IC_{50}$ data is shown as ">a"

Various modifications of the invention, in addition to those described herein, will be apparent to those skilled in the art from the foregoing description. Such modifications are also intended to fall within the scope of the appended claims. Each reference cited in the present application is herein incorporated by reference in its entirety.

What is claimed is:

1. A compound selected from:
   4-(7-Bromo-3,4-dihydroisoquinolin-2(1H)-yl)-6-(4-methylpiperazin-1-yl)pyrimidin-2-amine;
   5-{2-[2-Amino-6-(4-methylpiperazin-1-yl)pyrimidin-4-yl]-1,2,3,4-tetrahydroisoquinolin-7-yl}-N-methylpyridine-2-carboxamide;
   N-(5-{2-[2-Amino-6-(4-methylpiperazin-1-yl)pyrimidin-4-yl]-1,2,3,4-tetrahydroisoquinolin-7-yl}pyridin-2-yl)acetamide;
   4-(4-Methylpiperazin-1-yl)-6-[7(1-methyl-1H-pyrazol-4-yl)-3,4-dihydroisoquinolin-2(1H)-yl]pyrimidin-2-amine;
   4-(4-Methylpiperazin-1-yl)-6-[7-[2-(4-methylpiperazin-1-yl)pyridin-4-yl]-3,4-dihydroisoquinolin-2(1H)-yl]pyrimidin-2-amine;
   4-[7-(6-Chloro-5-fluoropyridin-3-yl)-3,4-dihydroisoquinolin-2(1H)-yl]-6-(4-methylpiperazin-1-yl)pyrimidin-2-amine;
   5-{2-[2-Amino-6-(4-methylpiperazin-1-yl)pyrimidin-4-yl]-1,2,3,4-tetrahydroisoquinolin-7-yl}-3-fluoropyridine-2-carbonitrile;
   tert-Butyl 4-(5-{2-[2-amino-6-(4-methylpiperazin-1-yl)pyrimidin-4-yl]-1,2,3,4-tetrahydroisoquinolin-7-yl}pyrimidin-2-yl)piperazine-1-carboxylate;
   4-(4-Methylpiperazin-1-yl)-6-[7-(2-piperazin-1-ylpyrimidin-5-yl)-3,4-dihydroisoquinolin-2(1H)-yl]pyrimidin-2-amine;
   4-[7-{1-[(6-Ethoxypyridin-3-yl)methyl]-1H-pyrazol-4-yl}-3,4-dihydroisoquinolin-2(1H)-yl]-6-(4-methylpiperazin-1-yl)pyrimidin-2-amine;
   [1-(4-{2-[2-Amino-6-(4-methylpiperazin-1-yl)pyrimidin-4-yl]-1,2,3,4-tetrahydroisoquinolin-7-yl}-1H-pyrazol-1-yl)cyclopentyl]acetonitrile;

tert-Butyl 4-(4-{2-[2-amino-6-(4-methylpiperazin-1-yl)pyrimidin-4-yl]-1,2,3,4-tetrahydroisoquinolin-7-yl}-1H-pyrazol-1-yl)piperidine-1-carboxylate;

4-(4-Methylpiperazin-1-yl)-6-[7-piperidin-4-yl-1H-pyrazol-4-yl)-3,4-dihydroisoquinolin-2(1H)-yl]pyrimidin-2-amine;

4-[7-(4-Chloro-1H-pyrazol-1-yl)-3,4-dihydroisoquinolin-2(1H)-yl]-6-(4-methylpiperazin-1-yl)pyrimidin-2-amine;

{(3S)-2-[2-Amino-6-(4-methylpiperazin-1-yl)pyrimidin-4-yl]-1,2,3,4-tetrahydroisoquinolin-3-yl}methanol;

2-[2-Amino-6-(4-methylpiperazin-1-yl)pyrimidin-4-yl]-N-(6-methylpyridin-2-yl)-1,2,3,4-tetrahydroisoquinolin-7-amine;

4-[7-(2-Chlorophenoxy)-3,4-dihydroisoquinolin-2(1H)-yl]-6-(4-methylpiperazin-1-yl)pyrimidin-2-amine;

5-{2-[2-Amino-6-(4-methylpiperazin-1-yl)pyrimidin-4-yl]-1,2,3,4-tetrahydroisoquinolin-7-yl}-N-(pyridin-2-ylmethyl)pyridine-2-carboxamide;

5-{2-[2-Amino-6-(4-methylpiperazin-1-yl)pyrimidin-4-yl]-1,2,3,4-tetrahydroisoquinolin-7-yl}-N-(2-hydroxy-2-methylpropyl)pyridine-2-carboxamide;

5-{2-[2-Amino-6-(4-methylpiperazin-1-yl)pyrimidin-4-yl]-1,2,3,4-tetrahydroisoquinolin-7-yl}-N-(trans-4-hydroxycyclohexyl)pyridine-2-carboxamide;

1-[2-Amino-6-(4-methylpiperazin-1-yl)pyrimidin-4-yl]-1,2,3,4-tetrahydroquinolin-7-ol;

4-({2-[2-Amino-6-(4-methylpiperazin-1-yl)pyrimidin-4-yl]-1,2,3,4-tetrahydroisoquinolin-7-yl}oxy)-2-chlorobenzonitrile;

2-[2-Amino-6-(4-methylpiperazin-1-yl)pyrimidin-4-yl]-1,4-dihydroisoquinolin-3(2H)-one;

4-(4-Methylpiperazin-1-yl)-6-[7-[(3-phenylpyrrolidin-1-yl)carbonyl]-3,4-dihydroisoquinolin-2(1H)-yl]pyrimidin-2-amine;

2-[2-Amino-6-(4-methylpiperazin-1-yl)pyrimidin-4-yl]-N-(3-fluorobenzyl)-N-methyl-1,2,3,4-tetrahydroisoquinoline-7-carboxamide;

4-[7-(1,3-Dihydro-2H-isoindol-2-ylcarbonyl)-3,4-dihydroisoquinolin-2(1H)-yl]-6-(4-methylpiperazin-1-yl)pyrimidin-2-amine;

2-[2-Amino-6-(4-methylpiperazin-1-yl)pyrimidin-4-yl]-N,N-dimethyl-1,2,3,4-tetrahydroisoquinoline-7-carboxamide;

2-[2-Amino-6-(4-methylpiperazin-1-yl)pyrimidin-4-yl]-N-cyclopentyl-1,2,3,4-tetrahydroisoquinoline-7-carboxamide;

4-(4-Methylpiperazin-1-yl)-6-[7-(pyrrolidin-1-ylcarbonyl)-3,4-dihydroisoquinolin-2(1H)-yl]pyrimidin-2-amine;

Ethyl 4-{2-[2-amino-6-(4-methylpiperazin-1-yl)pyrimidin-4-yl]-1,2,3,4-tetrahydroisoquinolin-7-yl}piperazine-1-carboxylate;

4-[7-(4-Acetylpiperazin-1-yl)-3,4-dihydroisoquinolin-2(1H)-yl]-6-(4-methylpiperazin-1-yl)pyrimidin-2-amine;

4-{7-[4-(2-Furoyl)piperazin-1-yl]-3,4-dihydroisoquinolin-2(1H)-yl}-6-(4-methylpiperazin-1-yl)pyrimidin-2-amine;

4-{2-[2-Amino-6-(4-methylpiperazin-1-yl)pyrimidin-4-yl]-1,2,3,4-tetrahydroisoquinolin-7-yl}-N-(4-chlorophenyl)piperazine-1-carboxamide;

Ethyl {2-[2-amino-6-(4-methylpiperazin-1-yl)pyrimidin-4-yl]-1,2,3,4-tetrahydro isoquinolin-7-yl}carbamate;

N-{2-[2-Amino-6-(4-methylpiperazin-1-yl)pyrimidin-4-yl]-1,2,3,4-tetrahydroisoquinolin-7-yl}piperidine-1-carboxamide;

1-{2-[2-Amino-6-(4-methylpiperazin-1-yl)pyrimidin-4-yl]-1,2,3,4-tetrahydroisoquinolin-7-yl}piperidine-4-carbonitrile;

1-{2-[2-Amino-6-(4-methylpiperazin-1-yl)pyrimidin-4-yl]-1,2,3,4-tetrahydroisoquinolin-7-yl}-4-phenylpiperidin-4-ol;

4-(4-Methylpiperazin-1-yl)-6-[7-(4-pyridin-4-ylpiperidin-1-yl)-3,4-dihydroisoquinolin-2(1H)-yl]pyrimidin-2-amine;

4-(1-{2-[2-Amino-6-(4-methylpiperazin-1-yl)pyrimidin-4-yl]-1,2,3,4-tetrahydroisoquinolin-7-yl}piperidin-4-yl)-N-methylbenzamide;

4-(1-{2-[2-Amino-6-(4-methylpiperazin-1-yl)pyrimidin-4-yl]-1,2,3,4-tetrahydroisoquinolin-7-yl}piperidin-4-yl)benzamide;

4-(1-{2-[2-Amino-6-(4-methylpiperazin-1-yl)pyrimidin-4-yl]-1,2,3,4-tetrahydroisoquinolin-7-yl}piperidin-4-yl)-1-methylpyridin-2(1H)-one;

5-(1-{2-[2-Amino-6-(4-methylpiperazin-1-yl)pyrimidin-4-yl]-1,2,3,4-tetrahydroisoquinolin-7-yl}piperidin-4-yl)-1-methylpyridin-2(1H)-one;

4-{2-[2-Amino-6-(4-methylpiperazin-1-yl)pyrimidin-4-yl]-1,2,3,4-tetrahydroisoquinolin-7-yl}-1-methylpyridin-2(1H)-one;

6-(4-{2-[2-Amino-6-(4-methylpiperazin-1-yl)pyrimidin-4-yl]-1,2,3,4-tetrahydroisoquinolin-7-yl}-3-oxopiperazin-1-yl)-N-methylnicotinamide;

5-{2-[2-Amino-6-(4-methylpiperazin-1-yl)pyrimidin-4-yl]-1,2,3,4-tetrahydroisoquinolin-7-yl}-N,3-dimethylpyridine-2-carboxamide;

5-{2-[2-Amino-6-(4-methylpiperazin-1-yl)pyrimidin-4-yl]-1,2,3,4-tetrahydroisoquinolin-7-yl}-N,N,3-trimethylpyridine-2-carboxamide;

2-{2-[2-Amino-6-(4-methylpiperazin-1-yl)pyrimidin-4-yl]-1,2,3,4-tetrahydroisoquinolin-7-yl}-N-methyl-1,3-thiazole-4-carboxamide;

4-(4-Methylpiperazin-1-yl)-6-[7-[4-(pyrrolidin-1-ylcarbonyl)-1,3-thiazol-2-yl]-3,4-dihydroisoquinolin-2(1H)-yl]pyrimidin-2-amine;

5-{2-[2-Amino-6-(4-methylpiperazin-1-yl)pyrimidin-4-yl]-3-methyl-1,2,3,4-tetrahydroisoquinolin-7-yl}-N-methylpyridine-2-carboxamide;

5-(2-[2-Amino-6-(4-methylpiperazin-1-yl)pyrimidin-4-yl]-3-methyl-1,2,3,4-tetrahydroisoquinolin-7-yl)-N,N-dimethylpicolinamide;

5-{2-[2-Amino-6-(4-methylpiperazin-1-yl)pyrimidin-4-yl]-3-methyl-1,2,3,4-tetrahydroisoquinolin-7-yl}-N-[(1R)-2-hydroxy-1-methylethyl]pyridine-2-carboxamide;

5-{2-[2-Amino-6-(4-methylpiperazin-1-yl)pyrimidin-4-yl]-3-methyl-1,2,3,4-tetrahydroisoquinolin-7-yl}-N-[2-(dimethylamino)ethyl]-N-methylpyridine-2-carboxamide;

4-[7-[6-(Azetidin-1-ylcarbonyl)pyridin-3-yl]-3-methyl-3,4-dihydroisoquinolin-2(1H)-yl]-6-(4-methylpiperazin-1-yl)pyrimidin-2-amine;

1-[(5-{2-[2-Amino-6-(4-methylpiperazin-1-yl)pyrimidin-4-yl]-3-methyl-1,2,3,4-tetrahydroisoquinolin-7-yl}pyridin-2-yl)carbonyl]azetidine-3-carbonitrile;

4-(4-Methylpiperazin-1-yl)-6-[3-methyl-7-[6-(pyrrolidin-1-ylcarbonyl)pyridin-3-yl]-3,4-dihydroisoquinolin-2(1H)-yl]pyrimidin-2-amine;

(3R)-1-[(5-{2-[2-Amino-6-(4-methylpiperazin-1-yl)pyrimidin-4-yl]-3-methyl-1,2,3,4-tetrahydroisoquinolin-7-yl}pyridin-2-yl)carbonyl]pyrrolidin-3-ol;

4-[7-(6-{[3-(Dimethylamino)pyrrolidin-1-yl]carbonyl}pyridin-3-yl)-3-methyl-3,4-dihydroisoquinolin-2(1H)-yl]-6-(4-methylpiperazin-1-yl)pyrimidin-2-amine;

4-[3-Methyl-7-{6-[(4-methylpiperazin-1-yl)carbonyl]pyridin-3-yl}-3,4-dihydroisoquinolin-2(1H)-yl]-6-(4-methylpiperazin-1-yl)pyrimidin-2-amine;

5-{2-[2-Amino-6-(4-methylpiperazin-1-yl)pyrimidin-4-yl]-3-methyl-1,2,3,4-tetrahydroisoquinolin-7-yl}-N-(2-hydroxyethyl)pyridine-2-carboxamide;

1-[(5-{2-[2-Amino-6-(4-methylpiperazin-1-yl)pyrimidin-4-yl]-3-methyl-1,2,3,4-tetrahydroisoquinolin-7-yl}pyridin-2-yl)carbonyl]azetidin-3-ol;

4-{2-[2-amino-6-(4-methylpiperazin-1-yl)pyrimidin-4-yl]-3-methyl-1,2,3,4-tetrahydroisoquinolin-7-yl}-N,N-dimethylpyridine-2-carboxamide;

4-[7-2-(Azetidin-1-ylcarbonyl)pyridin-4-yl]-3-methyl-3,4-dihydroisoquinolin-2(1H)-yl]-6-(4-methylpiperazin-1-yl)pyrimidin-2-amine;

1-[(4-{2-[2-Amino-6-(4-methylpiperazin-1-yl)pyrimidin-4-yl]-3-methyl-1,2,3,4-tetrahydroisoquinolin-7-yl}pyridin-2-yl)carbonyl]azetidine-3-carbonitrile;

4-(4-Methylpiperazin-1-yl)-6-[3-methyl-7-[2-(pyrrolidin-1-ylcarbonyl)pyridin-4-yl]-3,4-dihydroisoquinolin-2(1H)-yl]pyrimidin-2-amine;

(3S)-1-[(4-{2-[2-Amino-6-(4-methylpiperazin-1-yl)pyrimidin-4-yl]-3-methyl-1,2,3,4-tetrahydroisoquinolin-7-yl}pyridin-2-yl)carbonyl]pyrrolidin-3-ol;

4-[7-(2-{[(3S)-3-Fluoropyrrolidin-1-yl]carbonyl}pyridin-4-yl)-3-methyl-3,4-dihydroisoquinolin-2(1H)-yl]-6-(4-methylpiperazin-1-yl)pyrimidin-2-amine;

4-[7-(2-{[3-(Dimethylamino)pyrrolidin-1-yl]carbonyl}pyridin-4-yl)-3-methyl-3,4-dihydroisoquinolin-2(1H)-yl]-6-(4-methylpiperazin-1-yl)pyrimidin-2-amine;

4-{2-[2-Amino-6-(4-methylpiperazin-1-yl)pyrimidin-4-yl]-3-methyl-1,2,3,4-tetrahydroisoquinolin-7-yl}-N-[2-(dimethylamino)ethyl]-N-methylpyridine-2-carboxamide;

4-{2-[2-Amino-6-(4-methylpiperazin-1-yl)pyrimidin-4-yl]-3-methyl-1,2,3,4-tetrahydroisoquinolin-7-yl}-N-[(1R)-2-hydroxy-1-methylethyl]pyridine-2-carboxamide;

4-[3-Methyl-7-{2-[(4-methylpiperazin-1-yl)carbonyl]pyridin-4-yl}-3,4-dihydroisoquinolin-2(1H)-yl]-6-(4-methylpiperazin-1-yl)pyrimidin-2-amine;

6-{2-[2-Amino-6-(4-methylpiperazin-1-yl)pyrimidin-4-yl]-3-methyl-1,2,3,4-tetrahydroisoquinolin-7-yl}-N-ethylnicotinamide;

6-{2-[2-Amino-6-(4-methylpiperazin-1-yl)pyrimidin-4-yl]-3-methyl-1,2,3,4-tetrahydroisoquinolin-7-yl}-N,N-dimethylnicotinamide;

1-[(6-{2-[2-Amino-6-(4-methylpiperazin-1-yl)pyrimidin-4-yl]-3-methyl-1,2,3,4-tetrahydroisoquinolin-7-yl}pyridin-3-yl)carbonyl]azetidin-3-ol;

5-{2-[2-Amino-6-(4-methylpiperazin-1-yl)pyrimidin-4-yl]-3-methyl-1,2,3,4-tetrahydroisoquinolin-7-yl}-N,N-dimethylnicotinamide;

1-[(5-{2-[2-Amino-6-(4-methylpiperazin-1-yl)pyrimidin-4-yl]-3-methyl-1,2,3,4-tetrahydroisoquinolin-7-yl}pyridin-3-yl)carbonyl]azetidin-3-ol;

6-{2-[2-Amino-6-(4-methylpiperazin-1-yl)pyrimidin-4-yl]-3-methyl-1,2,3,4-tetrahydroisoquinolin-7-yl}-N,N-dimethylpyridine-2-carboxamide;

5-{2-[2-Amino-6-(4-methylpiperazin-1-yl)pyrimidin-4-yl]-3-methyl-1,2,3,4-tetrahydroisoquinolin-7-yl}-N-ethylpyrimidine-2-carboxamide;

1-[(5-{2-[2-Amino-6-(4-methylpiperazin-1-yl)pyrimidin-4-yl]-3-methyl-1,2,3,4-tetrahydroisoquinolin-7-yl}pyrimidin-2-yl)carbonyl]azetidin-3-ol;

2-(4-{2-[2-Amino-6-(4-methylpiperazin-1-yl)pyrimidin-4-yl]-3-methyl-1,2,3,4-tetrahydroisoquinolin-7-yl}-1H-pyrazol-1-yl)-N-methylacetamide;

2-(4-{2-[2-Amino-6-(4-methylpiperazin-1-yl)pyrimidin-4-yl]-3-methyl-1,2,3,4-tetrahydroisoquinolin-7-yl}-1H-pyrazol-1-yl)-N,N-dimethylacetamide;

5-[2-[2-Amino-6-(4-methylpiperazin-1-yl)pyrimidin-4-yl]-3-(hydroxymethyl)-1,2,3,4-tetrahydroisoquinolin-7-yl]-N-methylpyridine-2-carboxamide;

(3-{2-[2-Amino-6-(4-methylpiperazin-1-yl)pyrimidin-4-yl]-3-methyl-1,2,3,4-tetrahydroisoquinolin-7-yl}-1H-pyrazol-1-yl)acetonitrile;

3-(3-{2-[2-Amino-6-(4-methylpiperazin-1-yl)pyrimidin-4-yl]-3-methyl-1,2,3,4-tetrahydroisoquinolin-7-yl}-1H-pyrazol-1-yl)propanenitrile;

2-(3-{2-[2-Amino-6-(4-methylpiperazin-1-yl)pyrimidin-4-yl]-3-methyl-1,2,3,4-tetrahydroisoquinolin-7-yl}-1H-pyrazol-1-yl)ethanol;

4-[3-Methyl-7-(1-methyl-1H-pyrazol-3-yl)-3,4-dihydroisoquinolin-2(1H)-yl]-6-(4-methylpiperazin-1-yl)pyrimidin-2-amine;

4-[7-(1-Ethyl-1H-pyrazol-3-yl)-3-methyl-3,4-dihydroisoquinolin-2(1H)-yl]-6-(4-methylpiperazin-1-yl)pyrimidin-2-amine;

4-{2-[2-Amino-6-(4-methylpiperazin-1-yl)pyrimidin-4-yl]-3-methyl-1,2,3,4-tetrahydroisoquinolin-7-yl}-N,1-dimethyl-1H-pyrrole-2-carboxamide;

4-{2-[2-Amino-6-(4-methylpiperazin-1-yl)pyrimidin-4-yl]-3-methyl-1,2,3,4-tetrahydroisoquinolin-7-yl}-N-ethyl-1-methyl-1H-pyrrole-2-carboxamide;

4-{2-[2-Amino-6-(4-methylpiperazin-1-yl)pyrimidin-4-yl]-3-methyl-1,2,3,4-tetrahydroisoquinolin-7-yl}-N,N,1-trimethyl-1H-pyrrole-2-carboxamide;

4-{2-[2-Amino-6-(4-methylpiperazin-1-yl)pyrimidin-4-yl]-3-methyl-1,2,3,4-tetrahydroisoquinolin-7-yl}-N-isopropyl-1-methyl-1H-pyrrole-2-carboxamide;

4-{2-[2-Amino-6-(4-methylpiperazin-1-yl)pyrimidin-4-yl]-3-methyl-1,2,3,4-tetrahydroisoquinolin-7-yl}-N-cyclopropyl-1-methyl-1H-pyrrole-2-carboxamide;

4-[7-[5-(azetidin-1-ylcarbonyl)-1-methyl-1H-pyrrol-3-yl]-3-methyl-3,4-dihydroisoquinolin-2(1H)-yl]-6-(4-methylpiperazin-1-yl)pyrimidin-2-amine;

4-{2-[2-Amino-6-(4-methylpiperazin-1-yl)pyrimidin-4-yl]-3-methyl-1,2,3,4-tetrahydroisoquinolin-7-yl}-N-[2-(dimethylamino)ethyl]-N,1-dimethyl-1H-pyrrole-2-carboxamide;

4-[7-(5-{[3-(Dimethylamino)pyrrolidin-1-yl]carbonyl}-1-methyl-1H-pyrrol-3-yl)-3-methyl-3,4-dihydroisoquinolin-2(1H)-yl]-6-(4-methylpiperazin-1-yl)pyrimidin-2-amine;

4-(4-Methylpiperazin-1-yl)-6-[3-methyl-7-[1-(tetrahydro-2H-pyran-4-yl)-1H-pyrazol-4-yl]-3,4-dihydroisoquinolin-2(1H)-yl]pyrimidin-2-amine;

3-(4-{2-[2-Amino-6-(4-methylpiperazin-1-yl)pyrimidin-4-yl]-3-methyl-1,2,3,4-tetrahydroisoquinolin-7-yl}-1H-pyrazol-1-yl)propanenitrile;

1-[(4-{2-[2-Amino-6-(4-methylpiperazin-1-yl)pyrimidin-4-yl]-3-methyl-1,2,3,4-tetrahydroisoquinolin-7-yl}-1H-pyrazol-1-yl)methyl]cyclopropanecarbonitrile;

4-[7-[1-(1,1-Dioxidotetrahydro-3-thienyl)-1H-pyrazol-4-yl]-3-methyl-3,4-dihydroisoquinolin-2(1H)-yl]-6-(4-methylpiperazin-1-yl)pyrimidin-2-amine;

4-(4-Methylpiperazin-1-yl)-6-[3-methyl-7-[1-(tetrahydrofuran-2-ylmethyl)-1H-pyrazol-4-yl]-3,4-dihydroisoquinolin-2(1H)-yl]pyrimidin-2-amine;
4-[7-[1-(2-Fluoroethyl)-1H-pyrazol-4-yl]-3-methyl-3,4-dihydroisoquinolin-2(1H)-yl]-6-(4-methylpiperazin-1-yl)pyrimidin-2-amine;
3-(4-{2-[2-Amino-6-(4-methylpiperazin-1-yl)pyrimidin-4-yl]-3-methyl-1,2,3,4-tetrahydroisoquinolin-7-yl}-1H-pyrazol-1-yl)-2-methylpropanenitrile;
4-[7-[1-(Cyclopropylmethyl)-1H-pyrazol-4-yl]-3-methyl-3,4-dihydroisoquinolin-2(1H)-yl]-6-(4-methylpiperazin-1-yl)pyrimidin-2-amine;
3-(4-{2-[2-Amino-6-(4-methylpiperazin-1-yl)pyrimidin-4-yl]-3-methyl-1,2,3,4-tetrahydroisoquinolin-7-yl}-1H-pyrazol-1-yl)butanenitrile;
4-[3-Methyl-7-[1-(2-morpholin-4-ylethyl)-1H-pyrazol-4-yl]-3,4-dihydroisoquinolin-2(1H)-yl]-6-(4-methylpiperazin-1-yl)pyrimidin-2-amine;
4-[7-(1-Isopropyl-1H-pyrazol-4-yl)-3-methyl-3,4-dihydroisoquinolin-2(1H)-yl]-6-(4-methylpiperazin-1-yl)pyrimidin-2-amine;
4-[7-[1-(Cyclobutylmethyl)-1H-pyrazol-4-yl]-3-methyl-3,4-dihydroisoquinolin-2(1H)-yl]-6-(4-methylpiperazin-1-yl)pyrimidin-2-amine;
4-[7-(1-Ethyl-1H-pyrazol-4-yl)-3-methyl-3,4-dihydroisoquinolin-2(1H)-yl]-6-(4-methylpiperazin-1-yl)pyrimidin-2-amine;
4-(4-Methylpiperazin-1-yl)-6-[3-methyl-7-[1-(tetrahydrofuran-3-yl)-1H-pyrazol-4-yl]-3,4-dihydroisoquinolin-2(1H)-yl]pyrimidin-2-amine;
4-[7-[1-(Cyclopentylmethyl)-1H-pyrazol-4-yl]-3-methyl-3,4-dihydroisoquinolin-2(1H)-yl]-6-(4-methylpiperazin-1-yl)pyrimidin-2-amine;
2-(4-{2-[2-Amino-6-(4-methylpiperazin-1-yl)pyrimidin-4-yl]-3-methyl-1,2,3,4-tetrahydroisoquinolin-7-yl}-1H-pyrazol-1-yl)ethanol;
2-[4-(4-{2-[2-Amino-6-(4-methylpiperazin-1-yl)pyrimidin-4-yl]-3-methyl-1,2,3,4-tetrahydroisoquinolin-7-yl}-1H-pyrazol-1-yl)piperidin-1-yl]ethanol;
4-[7-[1-(2-Methoxyethyl)-1H-pyrazol-4-yl]-3-methyl-3,4-dihydroisoquinolin-2(1H)-yl]-6-(4-methylpiperazin-1-yl)pyrimidin-2-amine;
2-(4-{2-[2-Amino-6-(4-methylpiperazin-1-yl)pyrimidin-4-yl]-3-methyl-1,2,3,4-tetrahydroisoquinolin-7-yl}-1H-pyrazol-1-yl)acetamide;
3-(4-{2-[2-Amino-6-(4-methylpiperazin-1-yl)pyrimidin-4-yl]-3-methyl-1,2,3,4-tetrahydroisoquinolin-7-yl}-1H-pyrazol-1-yl)propanamide;
4-[7-(1-Cyclopentyl-1H-pyrazol-4-yl)-3-methyl-3,4-dihydroisoquinolin-2(1H)-yl]-6-(4-methylpiperazin-1-yl)pyrimidin-2-amine;
4-[3-Methyl-7-(2-methyl-1,3-thiazol-4-yl)-3,4-dihydroisoquinolin-2(1H)-yl]-6-(4-methylpiperazin-1-yl)pyrimidin-2-amine;
4-[7-(2-Ethoxy-1,3-thiazol-4-yl)-3-methyl-3,4-dihydroisoquinolin-2(1H)-yl]-6-(4-methylpiperazin-1-yl)pyrimidin-2-amine;
4-[(3R)-3-Aminopyrrolidin-1-yl]-6-[3-methyl-7-(1-methyl-1H-pyrazol-4-yl)-3,4-dihydroisoquinolin-2(1H)-yl]pyrimidin-2-amine;
4-[(3S)-3-Aminopiperidin-1-yl]-6-[3-methyl-7-(1-methyl-1H-pyrazol-4-yl)-3,4-dihydroisoquinolin-2(1H)-yl]pyrimidin-2-amine;
4-(4-Aminopiperidin-1-yl)-6-[3-methyl-7-(1-methyl-1H-pyrazol-4-yl)-3,4-dihydroisoquinolin-2(1H)-yl]pyrimidin-2-amine;
4-[3-Methyl-7-(1-methyl-1H-pyrazol-4-yl)-3,4-dihydroisoquinolin-2(1H)-yl]-6-piperazin-1-ylpyrimidin-2-amine;
4-(1,4-Diazepan-1-yl)-6-[3-methyl-7-(1-methyl-1H-pyrazol-4-yl)-3,4-dihydroisoquinolin-2(1H)-yl]pyrimidin-2-amine;
4-(2,5-Diazabicyclo [2.2.1]hept-2-yl)-6-[3-methyl-7-(1-methyl-1H-pyrazol-4-yl)-3,4-dihydroisoquinolin-2(1H)-yl]pyrimidin-2-amine;
4-[(3R)-3-(Methylamino)pyrrolidin-1-yl]-6-[3-methyl-7-(1-methyl-1H-pyrazol-4-yl)-3,4-dihydroisoquinolin-2(1H)-yl]pyrimidin-2-amine;
4-(4-Methyl-1,4-diazepan-1-yl)-6-[3-methyl-7-(1-methyl-1H-pyrazol-4-yl)-3,4-dihydroisoquinolin-2(1H)-yl]pyrimidin-2-amine;
4-(Hexahydropyrrolo[1,2-a]pyrazin-2(1H)-yl)-6-[3-methyl-7-(1-methyl-1H-pyrazol-4-yl)-3,4-dihydroisoquinolin-2(1H)-yl]pyrimidin-2-amine;
5-{2-[2-Amino-6-(4-methylpiperazin-1-yl)pyrimidin-4-yl]-6-fluoro-1,2,3,4-tetrahydroisoquinolin-7-yl}-N-methylpyridine-2-carboxamide;
3-{2-[2-Amino-6-(4-methylpiperazin-1-yl)pyrimidin-4-yl]-6-fluoro-1,2,3,4-tetrahydroisoquinolin-7-yl}-N,N-dimethylbenzamide;
5-{2-[2-Amino-6-(4-methylpiperazin-1-yl)pyrimidin-4-yl]-3-methyl-1,2,3,4-tetrahydroisoquinolin-7-yl}-2-cyclopropylisoindolin-1-one;
4-{2-[2-Amino-6-(4-methylpiperazin-1-yl)pyrimidin-4-yl]-3-methyl-1,2,3,4-tetrahydroisoquinolin-7-yl}-N,2-dimethylbenzamide;
6-{2-[2-Amino-6-(4-methylpiperazin-1-yl)pyrimidin-4-yl]-3-methyl-1,2,3,4-tetrahydroisoquinolin-7-yl}-2H-1,4-benzoxazin-3(4H)-one;
6-{2-[2-Amino-6-(4-methylpiperazin-1-yl)pyrimidin-4-yl]-3-methyl-1,2,3,4-tetrahydroisoquinolin-7-yl}-4-methyl-2H-1,4-benzoxazin-3(4H)-one;
2-{2-[2-amino-6-(4-methylpiperazin-1-yl)pyrimidin-4-yl]-3-methyl-1,2,3,4-tetrahydroisoquinolin-7-yl}-N-methyl-1,3-thiazole-5-carboxamide;
2-{2-[2-Amino-6-(4-methylpiperazin-1-yl)pyrimidin-4-yl]-3-methyl-1,2,3,4-tetrahydroisoquinolin-7-yl}-N,N-dimethyl-1,3-thiazole-5-carboxamide;
4-[7-(3H-Imidazo[4,5-b]pyridin-6-yl)-3-methyl-3,4-dihydroisoquinolin-2(1H)-yl]-6-(4-methylpiperazin-1-yl)pyrimidin-2-amine;
4-{2-[2-Amino-6-(4-methylpiperazin-1-yl)pyrimidin-4-yl]-3-methyl-1,2,3,4-tetrahydroisoquinolin-7-yl}-N-cyclopentyl-3,6-dihydropyridine-1(2H)-carboxamide;
4-{2-[2-Amino-6-(4-methylpiperazin-1-yl)pyrimidin-4-yl]-3-methyl-1,2,3,4-tetrahydroisoquinolin-7-yl}-3,6-dihydro-2H-1,2'-bipyridine-4'-carbonitrile;
4-[7-[1-(Cyclopentylacetyl)piperidin-4-yl]-3-methyl-3,4-dihydroisoquinolin-2(1H)-yl]-6-(4-methylpiperazin-1-yl)pyrimidin-2-amine;
Isopropyl 4-{2-[2-amino-6-(4-methylpiperazin-1-yl)pyrimidin-4-yl]-3-methyl-1,2,3,4-tetrahydroisoquinolin-7-yl}piperidine-1-carboxylate;
4-{2-[2-Amino-6-(4-methylpiperazin-1-yl)pyrimidin-4-yl]-3-methyl-1,2,3,4-tetrahydroisoquinolin-7-yl}-N-isopropylpiperidine-1-carboxamide;
4-{2-[2-Amino-6-(4-methylpiperazin-1-yl)pyrimidin-4-yl]-3-methyl-1,2,3,4-tetrahydroisoquinolin-7-yl}-N,N-dimethylpiperidine-1-carboxamide;
4-(4-Methylpiperazin-1-yl)-6-[3-methyl-7-[1-(pyrrolidin-1-ylcarbonyl)piperidin-4-yl]-3,4-dihydroisoquinolin-2(1H)-yl]pyrimidin-2-amine;

4-[7-[1-(Isopropylsulfonyl)piperidin-4-yl]-3-methyl-3,4-dihydroisoquinolin-2(1H)-yl]-6-(4-methylpiperazin-1-yl)pyrimidin-2-amine;

4-{2-[2-Amino-6-(4-methylpiperazin-1-yl)pyrimidin-4-yl]-3-methyl-1,2,3,4-tetrahydroisoquinolin-7-yl}-N,N-dimethylpiperidine-1-carboxamide;

4-{2-[2-Amino-6-(4-methylpiperazin-1-yl)pyrimidin-4-yl]-3-methyl-1,2,3,4-tetrahydroisoquinolin-7-yl}-N-ethylpiperidine-1-carboxamide;

4-[7-(1-Acetylpiperidin-4-yl)-3-methyl-3,4-dihydroisoquinolin-2(1H)-yl]-6-(4-methylpiperazin-1-yl)pyrimidin-2-amine;

Methyl 4-{2-[2-amino-6-(4-methylpiperazin-1-yl)pyrimidin-4-yl]-3-methyl-1,2,3,4-tetrahydroisoquinolin-7-yl}piperidine-1-carboxylate;

4-[3-Methyl-7-[1-(methylsulfonyl)piperidin-4-yl]-3,4-dihydroisoquinolin-2(1H)-yl]-6-(4-methylpiperazin-1-yl)pyrimidin-2-amine;

4-(4-Methylpiperazin-1-yl)-6-[3-methyl-7-(1-propionylpiperidin-4-yl)-3,4-dihydroisoquinolin-2(1H)-yl]pyrimidin-2-amine;

4-[7-[1-(Cyclopropylcarbonyl)piperidin-4-yl]-3-methyl-3,4-dihydroisoquinolin-2(1H)-yl]-6-(4-methylpiperazin-1-yl)pyrimidin-2-amine;

4-{2-[2-Amino-6-(4-methylpiperazin-1-yl)pyrimidin-4-yl]-3-methyl-1,2,3,4-tetrahydroisoquinolin-7-yl}-N-methylpiperidine-1-carboxamide;

4-[7-[1-(Ethylsulfonyl)piperidin-4-yl]-3-methyl-3,4-dihydroisoquinolin-2(1H)-yl]-6-(4-methylpiperazin-1-yl)pyrimidin-2-amine;

1-[(4-{2-[2-Amino-6-(4-methylpiperazin-1-yl)pyrimidin-4-yl]-3-methyl-1,2,3,4-tetrahydroisoquinolin-7-yl}pyridin-2-yl)carbonyl]azetidin-3-ol;

4-[7-(6-{[(3S)-3-Fluoropyrrolidin-1-yl]carbonyl}pyridin-3-yl)-3-methyl-3,4-dihydroisoquinolin-2(1H)-yl]-6-(4-methylpiperazin-1-yl)pyrimidin-2-amine;

4-(4-Methylpiperazin-1-yl)-6-[3-methyl-7-[1-(pyridin-2-ylmethyl)-1H-pyrazol-3-yl]-3,4-dihydroisoquinolin-2(1H)-yl]pyrimidin-2-amine;

4-(4-Methylpiperazin-1-yl)-6-[3-methyl-7-[1-(pyridin-3-ylmethyl)-1H-pyrazol-3-yl]-3,4-dihydroisoquinolin-2(1H)-yl]pyrimidin-2-amine;

4-(4-Methylpiperazin-1-yl)-6-[3-methyl-7-[1-(pyridin-4-ylmethyl)-1H-pyrazol-3-yl]-3,4-dihydroisoquinolin-2(1H)-yl]pyrimidin-2-amine; and 6-{2-[2-Amino-6-(4-methylpiperazin-1-yl)pyrimidin-4-yl]-3-methyl-1,2,3,4-tetrahydroisoquinolin-7-yl}-N-ethylpyridine-2-carboxamide;

or pharmaceutically acceptable salt or N-oxide or quaternary ammonium salt thereof.

2. A composition comprising a compound of claim 1 or pharmaceutically acceptable salt or N-oxide or quaternary ammonium salt thereof, and a pharmaceutically acceptable carrier.

3. The composition of claim 2 further comprising one or more therapeutic agents.

4. The composition of claim 2 further comprising one or more other histamine H1, H2, H3, and/or H4 receptor inhibitors/antagonists.

5. The composition of claim 2 further comprising one or more other histamine H4 receptor inhibitors/antagonists selected from N-Cyclohexyl-4-(1H-imidazol-4-yl)piperidine-1-carbothioamide, 5-chloro-2-[(4-methylpiperazin-1-yl)carbonyl]-1H-indole, and 5-Chloro-2-[(4-methylpiperazin-1-yl)carbonyl]-1H-benzimidazole.

\* \* \* \* \*